US011264575B2

(12) United States Patent
Brocke et al.

(10) Patent No.: US 11,264,575 B2
(45) Date of Patent: Mar. 1, 2022

(54) COMPOUNDS FOR ELECTRONIC DEVICES

(71) Applicant: Merck Patent GmbH, Darmstadt (DE)

(72) Inventors: Constanze Brocke, Gross-Gerau (DE);
Christof Pflumm, Darmstadt (DE);
Amir Hossain Parham, Frankfurt am Main (DE); Rocco Fortte, Frankfurt am Main (DE)

(73) Assignee: MERCK PATENT GMBH, Darmstadt (DE)

(*) Notice: Subject to any disclaimer, the term of this patent is extended or adjusted under 35 U.S.C. 154(b) by 315 days.

(21) Appl. No.: 15/427,713

(22) Filed: Feb. 8, 2017

(65) Prior Publication Data

US 2017/0155062 A1     Jun. 1, 2017

Related U.S. Application Data

(63) Continuation of application No. 13/581,543, filed as application No. PCT/EP2011/000235 on Jan. 21, 2011, now Pat. No. 10,008,673.

(30) Foreign Application Priority Data

Mar. 2, 2010  (DE) .......................... 102010009903.1

(51) Int. Cl.
| | |
|---|---|
| *H01L 51/54* | (2006.01) |
| *H01L 51/00* | (2006.01) |
| *C07D 401/04* | (2006.01) |
| *C07D 401/10* | (2006.01) |
| *C07D 471/06* | (2006.01) |
| *C07D 471/16* | (2006.01) |
| *C07D 519/00* | (2006.01) |
| *C09B 19/00* | (2006.01) |
| *C09B 57/00* | (2006.01) |
| *C07D 498/06* | (2006.01) |
| *C07D 513/06* | (2006.01) |
| *C09K 11/02* | (2006.01) |
| *H01L 51/50* | (2006.01) |

(52) U.S. Cl.
CPC ........ *H01L 51/0072* (2013.01); *C07D 401/04* (2013.01); *C07D 401/10* (2013.01); *C07D 471/06* (2013.01); *C07D 471/16* (2013.01); *C07D 498/06* (2013.01); *C07D 513/06* (2013.01); *C07D 519/00* (2013.01); *C09B 19/00* (2013.01); *C09B 57/00* (2013.01); *C09K 11/025* (2013.01); *H01L 51/0061* (2013.01); *H01L 51/0071* (2013.01); *H01L 51/5012* (2013.01); *H01L 51/5016* (2013.01); *H01L 51/5048* (2013.01); *H01L 51/5056* (2013.01); *H01L 51/5088* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 5,256,945 A | 10/1993 | Imai | |
| 5,891,587 A | 4/1999 | Hu | |
| 2003/0091862 A1* | 5/2003 | Tokito | C08G 61/02 428/690 |
| 2004/0110031 A1* | 6/2004 | Fukuda | C09K 11/06 428/690 |
| 2006/0051613 A1* | 3/2006 | Tomita | H05B 33/14 428/690 |
| 2006/0134823 A1 | 6/2006 | Shukla et al. | |
| 2008/0124572 A1 | 5/2008 | Mizuki et al. | |
| 2009/0066224 A1 | 3/2009 | Yu et al. | |
| 2009/0066226 A1 | 3/2009 | Sugita et al. | |
| 2009/0295275 A1* | 12/2009 | Parham | C07D 471/16 313/504 |
| 2010/0032658 A1 | 2/2010 | Lee et al. | |
| 2010/0171417 A1 | 7/2010 | Kitamura | |
| 2010/0219406 A1* | 9/2010 | Kahle | H01L 51/0061 257/40 |
| 2012/0168730 A1 | 7/2012 | Kim | |

FOREIGN PATENT DOCUMENTS

| | | |
|---|---|---|
| CN | 101495534 A | 7/2009 |
| CN | 101525335 A | 9/2009 |
| EP | 2182040 A2 | 5/2010 |
| GB | 2439030 A | 12/2007 |
| JP | 08003547 A | 1/1996 |
| JP | 2000-021574 A | 1/2000 |
| JP | 2003133075 A | 5/2003 |

(Continued)

OTHER PUBLICATIONS

Vezzu et al., "Acridinone/Amine(carbazole)-Based Bipolar Molecules: Efficient Hosts for Fluorescent and Phosphorescent Emitters" Organic Letters (2009) vol. 11, pp. 4310-4313. (Year: 2009).*

Yasukawa et al., Machine Translation of JP 2009-016718 (2009) pp. 1-76. (Year: 2009).*

Okamoto et al., "Facile Synthesis of 5,10-Diaryl-5,10-dihydrophenazines and Application to EL Devices", Organic Letters, 2003, vol. 5, No. 3, pp. 373-376. (Year: 2003).*

Kuwabara, Advanced Materials, 1994, 6, No. 9, pp. 677-679. (Year: 1994).*

Blazys et al., "Phenothiazinyl-containing aromatic amines as novel amorphous molecular materials for optoelectronics", Journal of Photochemistry and Photobiology A: Chemistry, vol. 174, pp. 1-6 (2005).

(Continued)

*Primary Examiner* — Dylan C Kershner

(74) *Attorney, Agent, or Firm* — Faegre Drinker Biddle & Reath LLP

(57) ABSTRACT

The present invention relates to compounds of the formula (1), (17) 18) or (20) and to the use thereof in electronic devices, and to electronic devices which contain these compounds. The invention furthermore relates to the preparation of the compounds of the formula (1), (17) 18) or (20) and to formulations contains one or more compounds of the formula (1), (17) 18) or (20).

23 Claims, No Drawings

(56) References Cited

FOREIGN PATENT DOCUMENTS

| | | | | |
|---|---|---|---|---|
| JP | 2008531822 A | | 8/2008 | |
| JP | 2009016718 A | * | 1/2009 | |
| JP | 2009170815 A | | 7/2009 | |
| JP | 2011501878 A | | 1/2011 | |
| JP | 2012-507507 A | | 3/2012 | |
| JP | 2012530696 A | | 12/2012 | |
| KR | 10-2010-0007780 A | | 1/2010 | |
| TW | 201114770 A | | 5/2011 | |
| WO | WO-2006033563 A1 | * | 3/2006 | ........... C07D 219/14 |
| WO | WO-2006/096399 A2 | | 9/2006 | |
| WO | WO-2006/114966 A1 | | 11/2006 | |
| WO | 2008/127057 A1 | | 10/2008 | |
| WO | WO-2009047147 A1 | * | 4/2009 | ......... H01L 51/0061 |
| WO | WO-2010/050778 A1 | | 5/2010 | |
| WO | WO-2010050778 A1 | * | 5/2010 | ............. C09K 11/06 |
| WO | WO-2010147319 A2 | | 12/2010 | |

OTHER PUBLICATIONS

Grigalevicius et al., "Photoconductive Molecular Glasses Consisting of Twin Molecules", Journal of Photochemistry and Photobiology A: Chemistry, vol. 154, pp. 161-167 (2003).

Jiang, et al., "Diarylmethylene-bridged 4,4'-(bis(9-carbazolyl))biphenyl: morphological stable host material for highly efficient electrophosphorescence" J. Mater. Chem., 2009, 12 pp. 7661-7665.

Koene et al., "Asymmetric Triaryldiamines as Thermally Stable Hole Transporting Layers for Organic Light-Emitting Devices", Chem. Materials 10, pp. 2235-2250 (1998).

Kuwabara et al., Thermally Stable Multilayered Organic Electroluminescent Devices Using Novel Starburst Kuwabara et al., "Molecules 4,4',4"-Tri(N-carbazolyl)triphenylamine (TCTA) and 4,4',4"-Tris(3-methylphenylphenylamino) triphenylamine (m-MTDATA), as Hole-Transport Materials", 1994, Advanced Materials, vol. 6, No. 9, pp. 677-679.

International Search Report for PCT/EP2011/000235 dated Aug. 31, 2011.

Lengvinaite et al., "Indolo[3,2-b]carbazole-based functional derivatives as materials for light emitting diodes", Dyes and Pigments, vol. 85, pp. 183-188 (2010).

Machine translation of JP 08003547 A.

Machine translation of JP 2003133075 A.

Simokaitiene et al., "Synthesis and properties of glass-forming phenothiazine and carbazole adducts", Dyes and Pigments, vol. 79, pp. 40-47 (2008).

Vezzu, et al., "Acridinone/Amine(carbazole)-Based Bipolar Molecules: Efficient Hosts for Fluorescent and Phosphorescent Emitters" Organic Letters, 2009, vol. 11, No. 19, pp. 4310-4313.

Lee et al., "Synthesis and Hole-Transporting Properties of Various Bicarbazyl Derivatives", Journal of Nanoscience and Nanotechnology, 2008, vol. 8, pp. 4797-4802.

Zhang et al., "Synthesis, characterization, and electroluminescent properties of star shaped donor-acceptor dendrimers with carbazole dendrons as peripheral branches and heterotriangulene as central core", Tetrahedron, vol. 65, 2009, pp. 4455-4463.

\* cited by examiner

COMPOUNDS FOR ELECTRONIC DEVICES

CROSS-REFERENCE TO RELATED APPLICATIONS

This application is a continuation application of U.S. application Ser. No. 13/581,543, filed Aug. 28, 2012, which is incorporated by reference in its entirety. U.S. application Ser. No. 13/581,543 is a national stage application (under 35 U.S.C. § 371) of PCT/EP2011/000235, filed Jan. 21, 2011, which claims benefit of German Patent Application No. 10 2010 009 903.1, filed Mar. 2, 2010.

The present invention relates to compounds of the formula (1) or (2) and to the use thereof in electronic devices, and to electronic devices which comprise these compounds. The invention furthermore relates to the preparation of the compounds of the formula (1) or (2) and to formulations comprising one or more compounds of the formula (1) or (2).

The compounds of the formula (1) or (2) are used in accordance with the invention in electronic devices, preferably in organic electroluminescent devices (OLEDs). The general structure of these devices is described, for example, in U.S. Pat. Nos. 4,539,507, 5,151,629, EP 0676461 and WO 98/27136.

Hole-transport and -injection materials which are known from the prior art for organic electroluminescent devices are, inter alia, arylamine compounds. Materials of this type based on an indenofluorene skeleton are disclosed, for example, in WO 2006/100896 and WO 2006/122630.

However, the hole-transport materials known from the prior art frequently have low electron stability, which reduces the lifetime of electronic devices comprising these compounds. Overall, further improvements are desirable with respect to the efficiency of fluorescent organic electroluminescent devices and the lifetime, especially in the case of blue-fluorescent devices. There is also potential for improvement in the operating voltage of the electronic devices.

There is therefore a demand for alternative compounds which can be used, inter alia, as hole-transport materials in organic electroluminescent devices and which preferably effect an improvement in the above-mentioned performance data of the devices.

Matrix materials which are known from the prior art for phosphorescent dopants are, inter alia, carbazole derivatives, for example bis(carbazolyl)biphenyl. The use of ketones (WO 2004/093207), phosphine oxides and sulfones (WO 2005/003253) as matrix materials for phosphorescent dopants is furthermore known. Metal complexes, for example BAlq or zinc(II) bis[2-(2-benzothiazolyl)phenolate], are also used as matrix materials for phosphorescent dopants.

However, there continues to be a demand for alternative matrix materials for phosphorescent dopants, in particular those which effect an improvement in the performance data of the electronic devices.

Also of particular interest is the provision of alternative materials as matrix components of mixed-matrix systems. A mixed-matrix system in the sense of this application is taken to mean a system in which two or more different matrix compounds are used as a mixture together with one (or more) dopant compounds in an emitting layer. These systems are, in particular, of interest in the case of phosphorescent organic electroluminescent devices. For more detailed information, reference is made to the application WO 2010/108579.

Compounds known from the prior art which may be mentioned as matrix components in mixed-matrix systems are, inter alia, CBP (biscarbazolylbiphenyl) and TCTA (tris-carbazolyltriphenylamine) (first component). Suitable as the second component are compounds such as, for example, benzophenone derivatives, diazaphospholes (see the application WO 2010/054730) and triazines. However, there continues to be a demand for alternative compounds for use as matrix components in mixed-matrix systems. In particular, there is a demand for compounds which effect an improvement in the operating voltage and lifetime of the electronic devices.

The applications WO 2007/031165 and WO 2006/033563 disclose triarylamine derivatives for use as functional materials in electronic devices. In the triarylamine compounds, the individual aryl groups are bridged to one another in a defined manner and are additionally substituted by carbazole derivatives. However, the compounds disclosed therein contain three carbazole groups, which are arranged symmetrically around the central triarylamine group.

Bridged triarylamine derivatives are furthermore disclosed in the application WO 2010/083871.

However, there continues to be a demand for functional materials for use in OLEDs which preferably effect improvements in relation to the performance data of the electronic devices, in particular in relation to the lifetime and efficiency of the devices.

In particular, there is a demand for compounds which have high hole mobility. This facilitates a low dependence of the operating voltage on the thickness of the hole-transport layer, which represents a highly desirable property. Furthermore, there is a demand for oxidation- and temperature-stable compounds, since this improves the processability on use in electronic devices.

The present invention provides compounds of the formula (1) and (2) in order to achieve the technical object described above.

The invention thus relates to a compound of the formula (1) or (2)

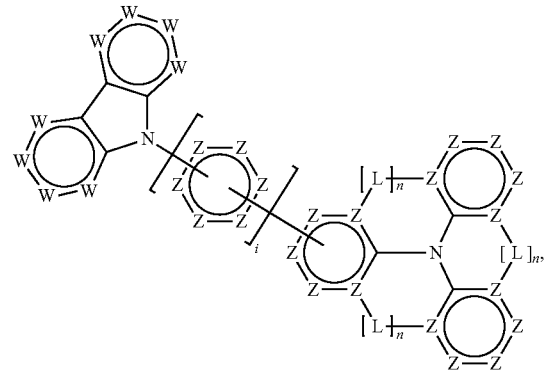

formula (1)

formula (2)

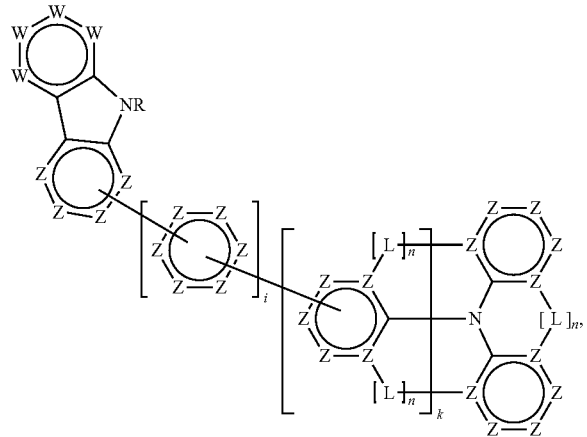

where the following applies to the symbols and indices occurring:

W is on each occurrence equal to Z,
where a unit comprising two adjacent groups W may optionally be replaced by a group of the formula (3)

formula (3)

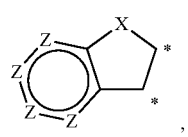

where the group of the formula (3) is arranged in such a way that the bond between the C atoms labelled with * is condensed onto the six-membered ring of the carbazole derivative;

X is a divalent group selected from $C(R)_2$, $Si(R)_2$, NR, PR, P(=O)R, BR, O, S, C=O, C=S, C=NR, S=O and $S(=O)_2$;

Z is selected on each occurrence, identically or differently, from CR and N, or is equal to C if a substituent is bonded to the group Z;

L is on each occurrence, identically or differently, a divalent group selected from $C(R)_2$, $Si(R)_2$, NR, PR, P(=O)R, BR, O, S, C=O, C=S, C=NR, $C=C(R)_2$, S=O, $S(=O)_2$ and CR=CR;

R is, identically or differently on each occurrence, H, D, F, Cl, Br, I, CHO, $N(R^1)_2$, $C(=O)R^1$, $P(=O)(R^1)_2$, $S(=O)R^1$, $S(=O)_2R^1$, $CR^1=C(R^1)_2$, CN, $NO_2$, $Si(R^1)_3$, $B(OR^1)_2$, $OSO_2R^1$, OH, $COOR^1$, $CON(R^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $-R^1C=CR^1-$, $-C\equiv C-$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, —O—, —S—, —COO— or $-CONR^1-$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, or a combination of these systems, where two or more radicals R may be linked to one another and may form a ring;

$R^1$ is, identically or differently on each occurrence, H, D, F, Cl, Br, I, CHO, $N(R^2)_2$, $C(=O)R^2$, $P(=O)(R^2)_2$, $S(=O)R^2$, $S(=O)_2R^2$, $CR^2=C(R^2)_2$, CN, $NO_2$, $Si(R^2)_3$, $B(OR^2)_2$, $OSO_2R^2$, OH, $COOR^2$, $CON(R^2)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $-R^2C=CR^2-$, $-C\equiv C-$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, —O—, —S—, —COO— or $-CONR^2-$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems, where two or more radicals $R^1$ may be linked to one another and may form a ring;

$R^2$ is, identically or differently on each occurrence, H, D, F or an aliphatic, aromatic and/or heteroaromatic organic radical having 1 to 20 C atoms, in which, in addition, one or more H atoms may be replaced by D or F; two or more substituents $R^2$ here may also be linked to one another and may form a ring;

i is equal to 0, 1 or 2, where, for i=0, the two groups which are bonded to the group with the index i are connected directly to one another;

j is equal to 0, 1 or 2, where, for j=0, the two groups which are bonded to the group with the index j are connected directly to one another;

k is equal to 0 or 1, where, for k=0, the nitrogen atom and the aromatic or heteroaromatic ring which are bonded to the group with the index k are connected directly to one another;

n is on each occurrence, identically or differently, 0 or 1, where the sum of the values of the indices n can be equal to 1, 2 or 3;

and where furthermore a maximum of one substituent R may represent a carbazole derivative, and where the following structures are excluded:
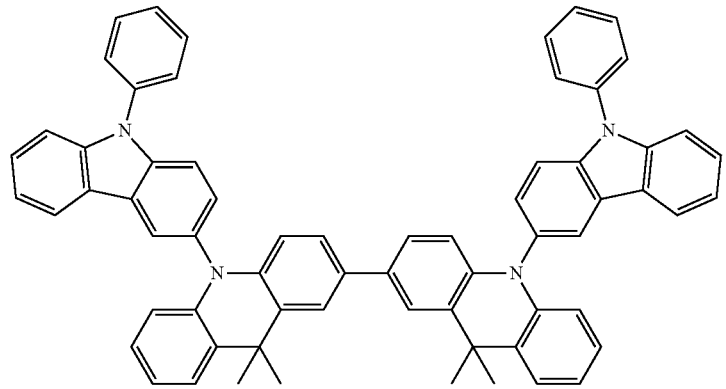
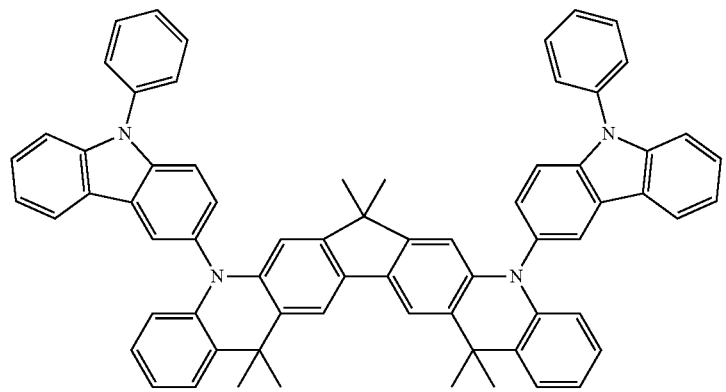
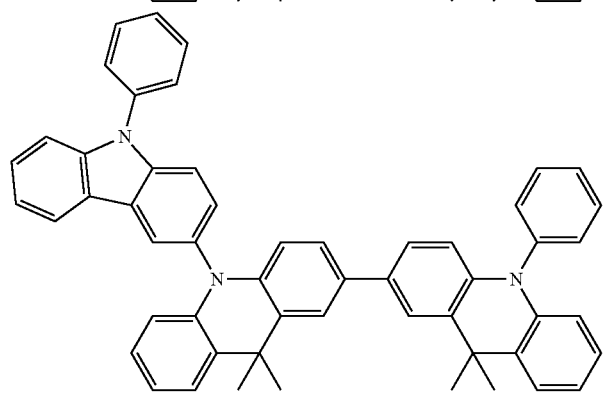
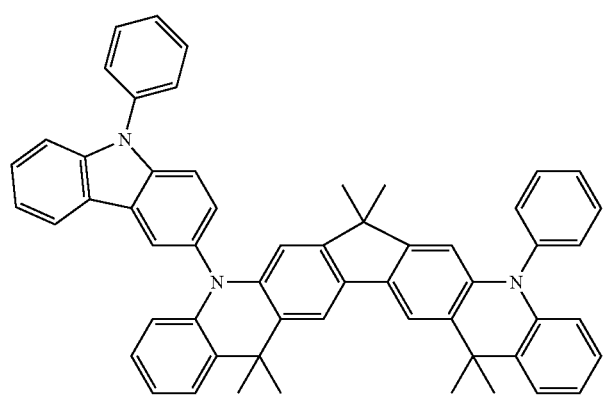

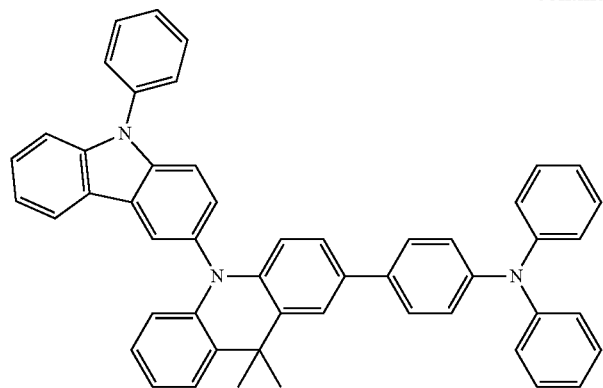
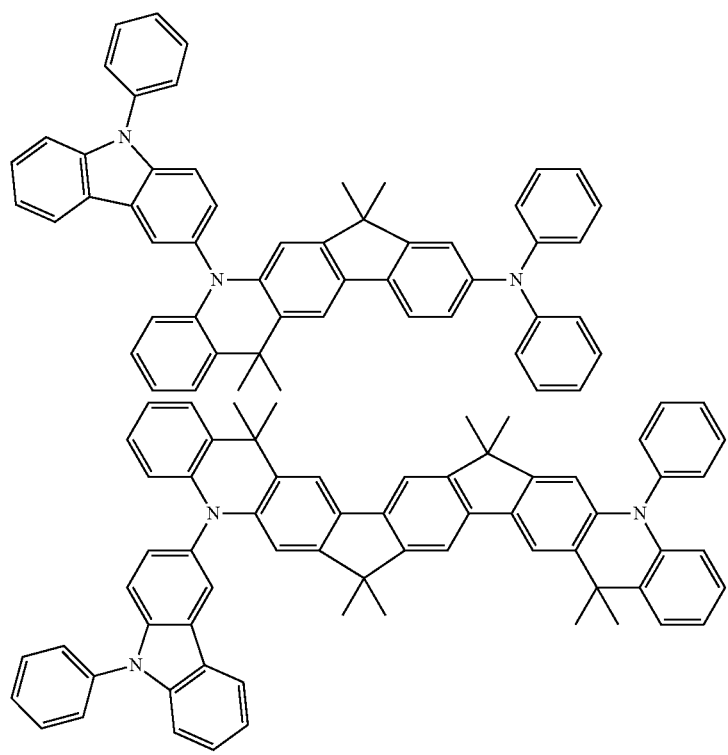
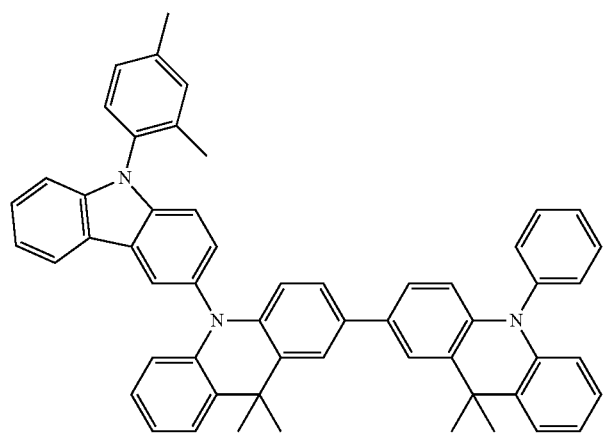

-continued
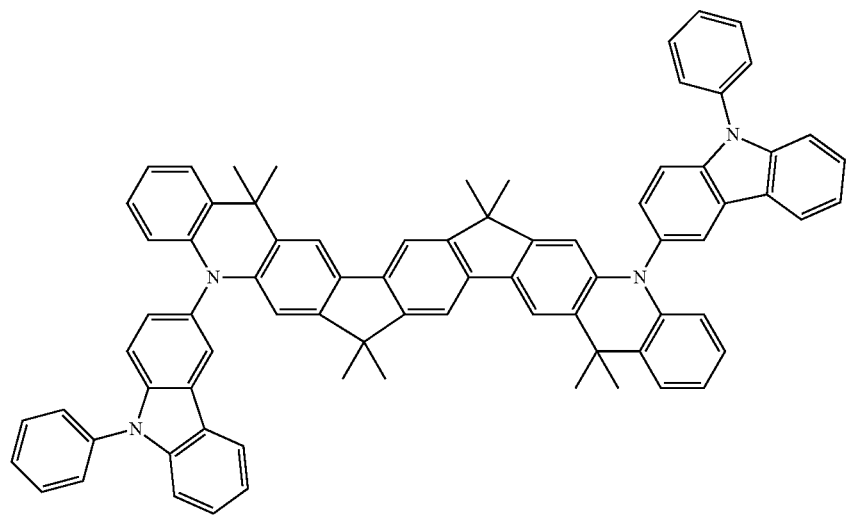
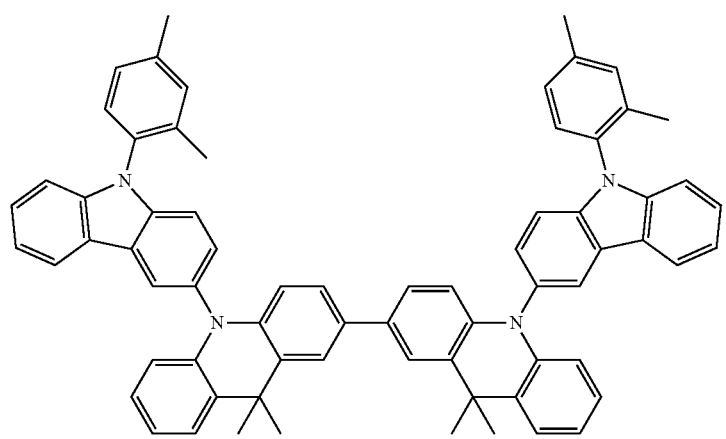
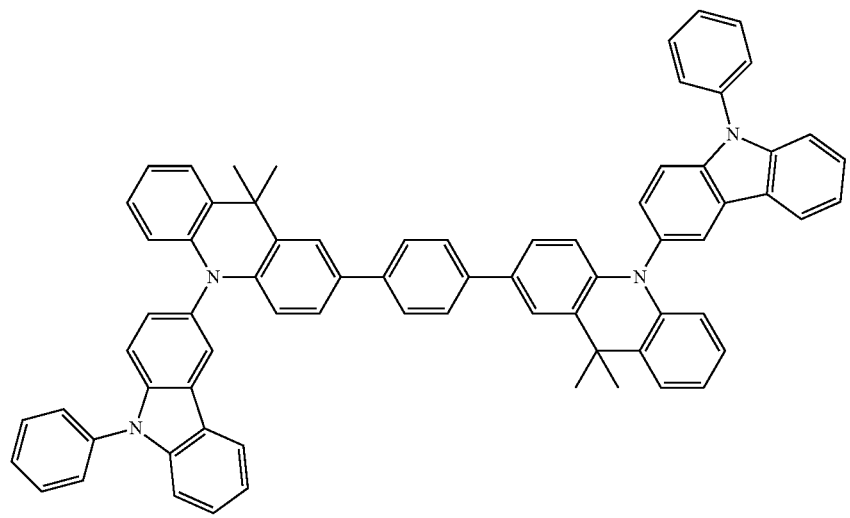

-continued
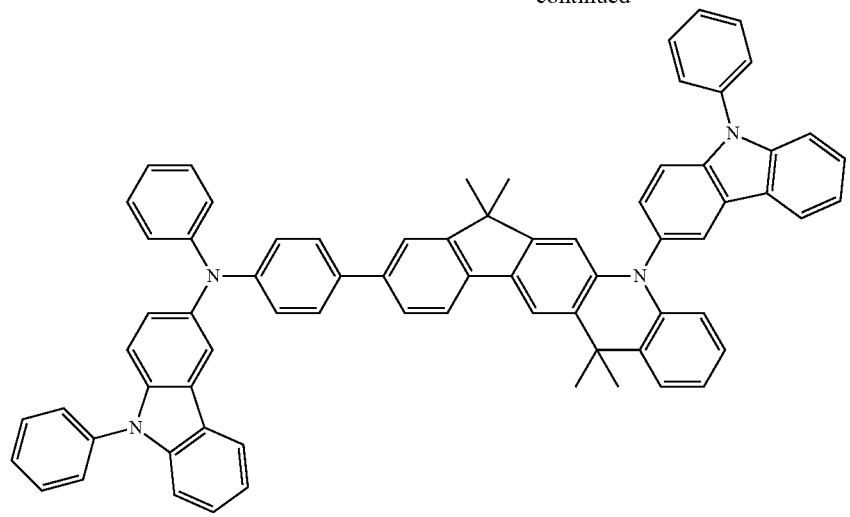
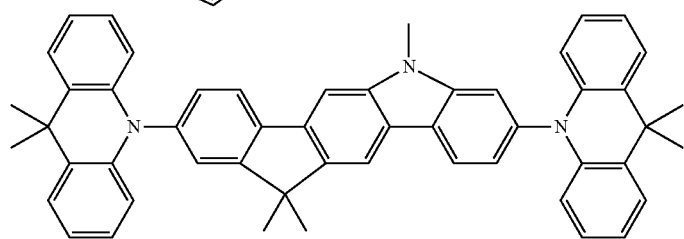
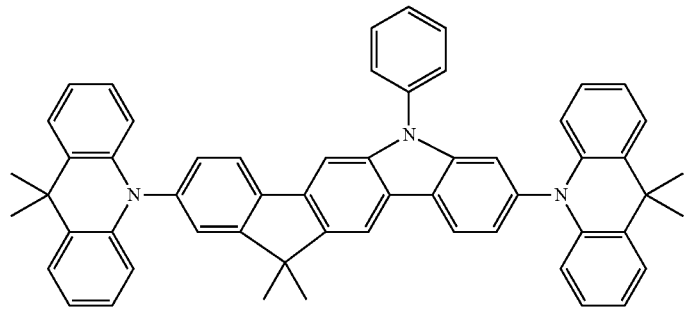
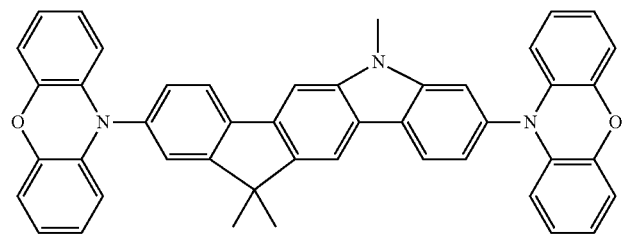
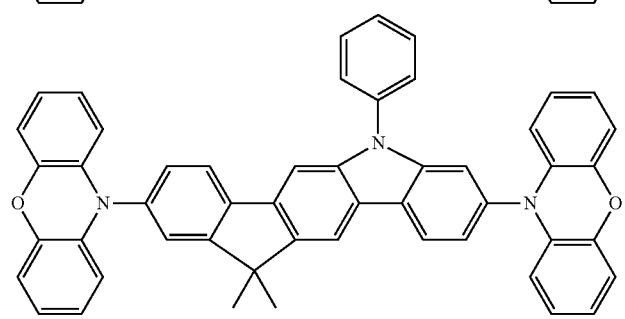

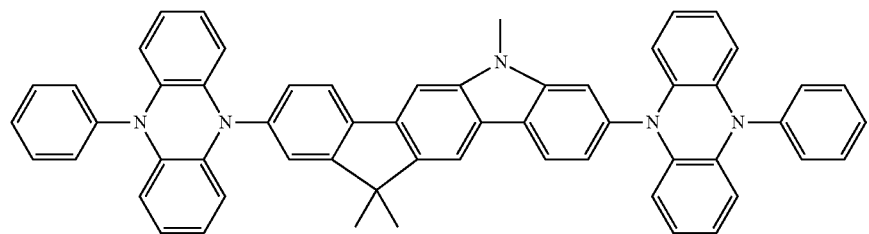
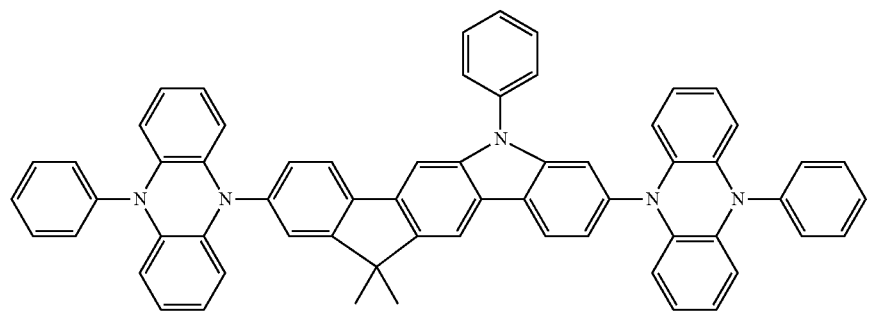
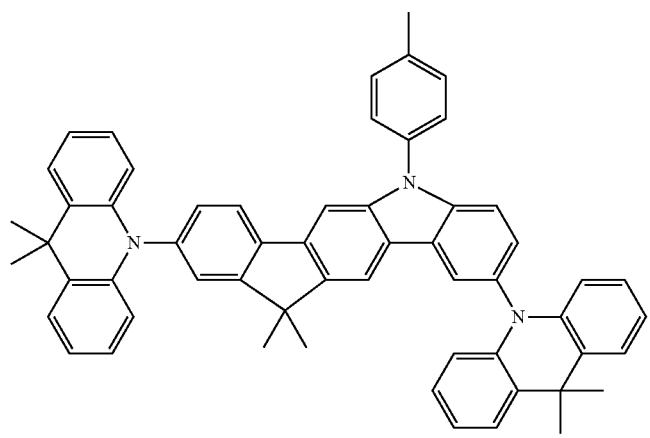
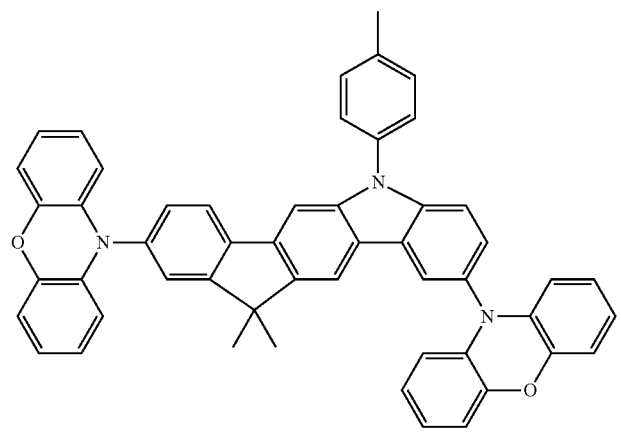

-continued
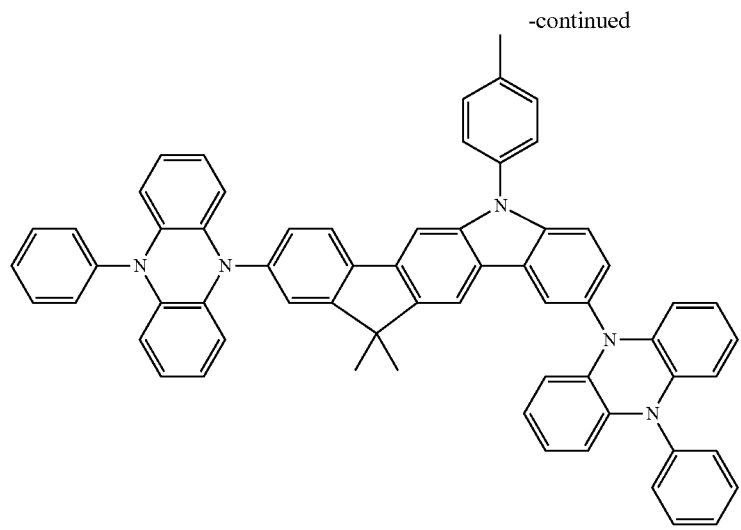
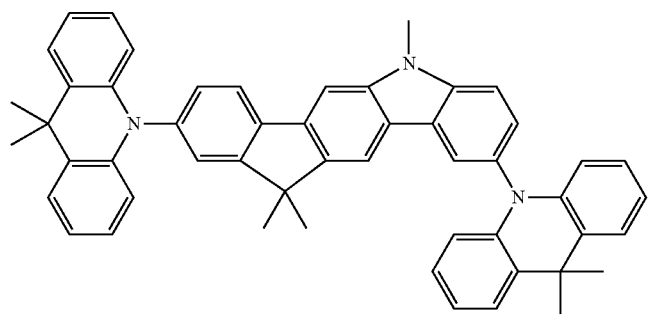
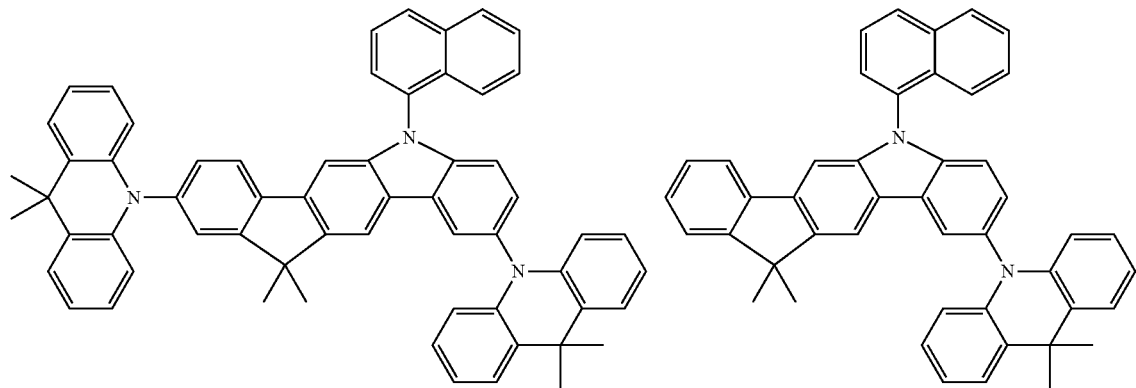
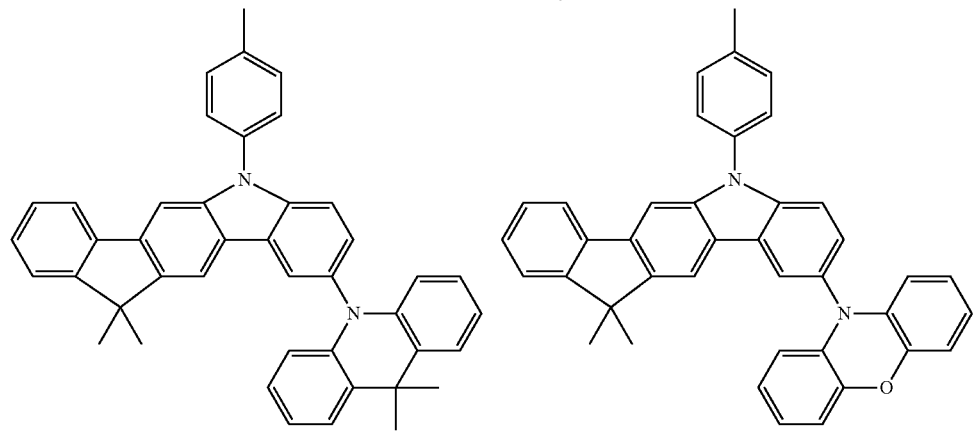

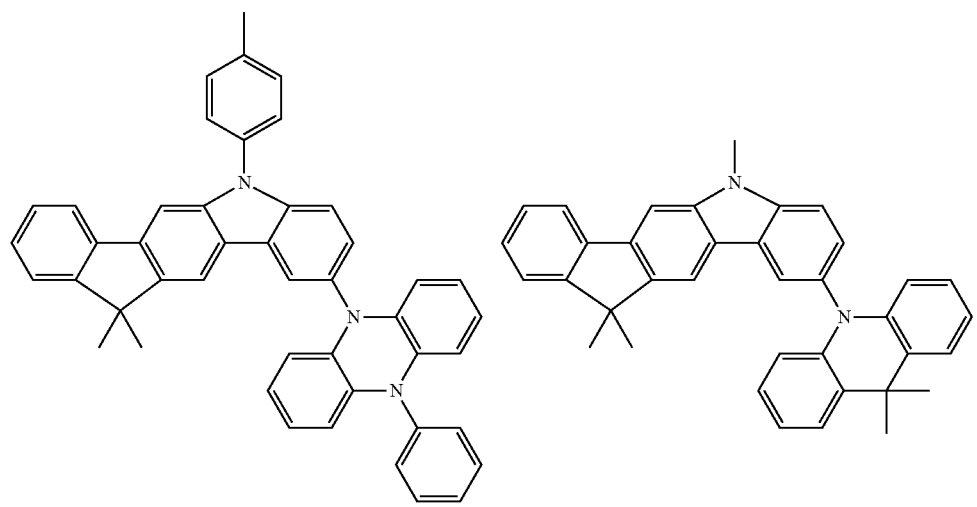
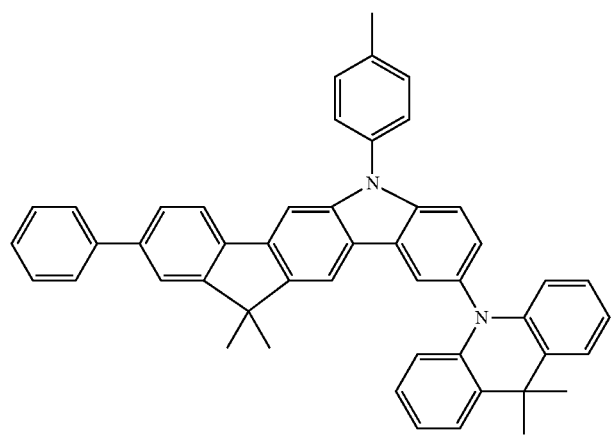
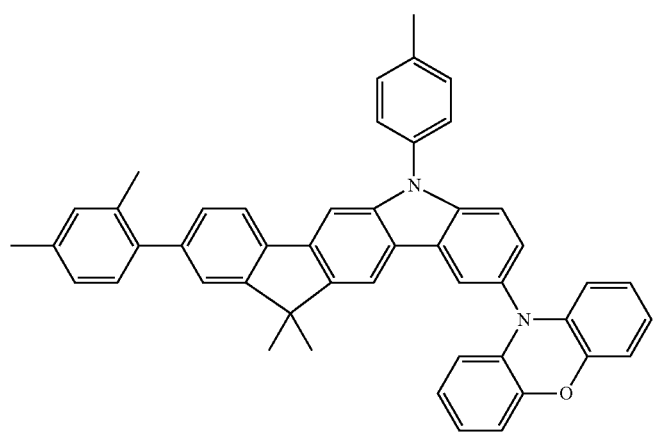

-continued
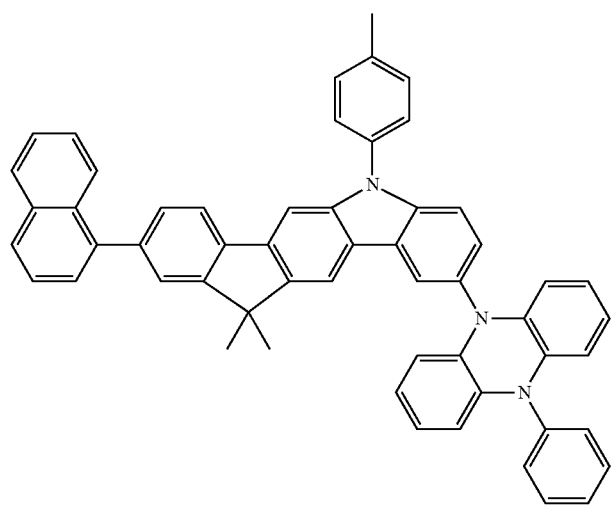
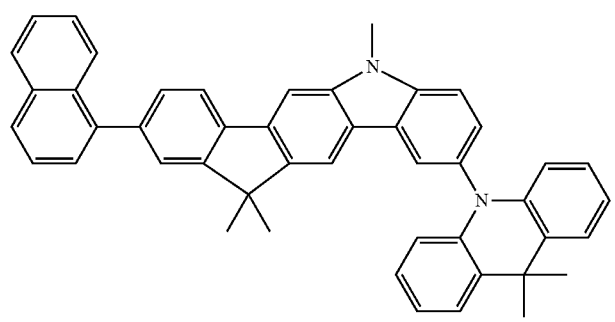
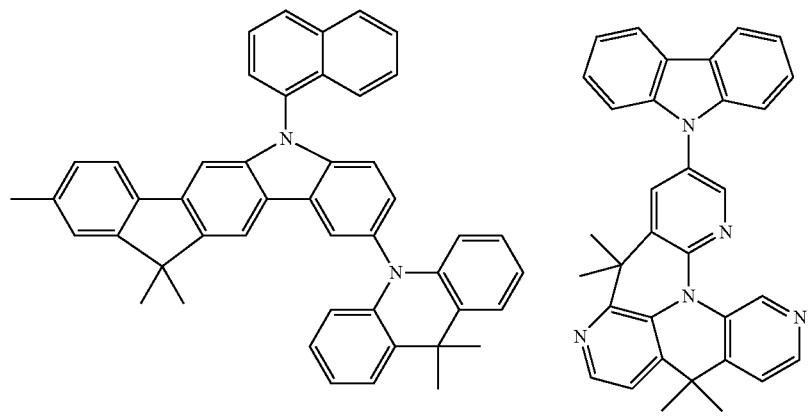
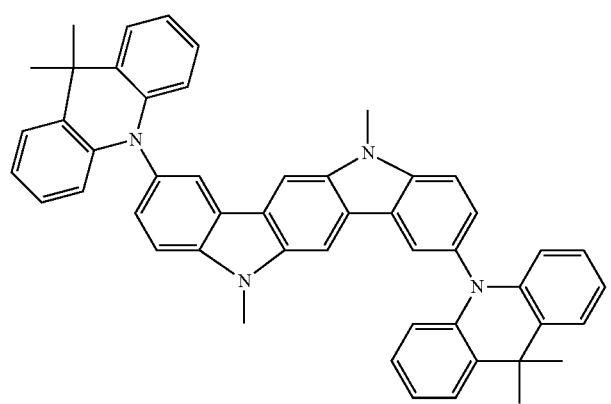

-continued
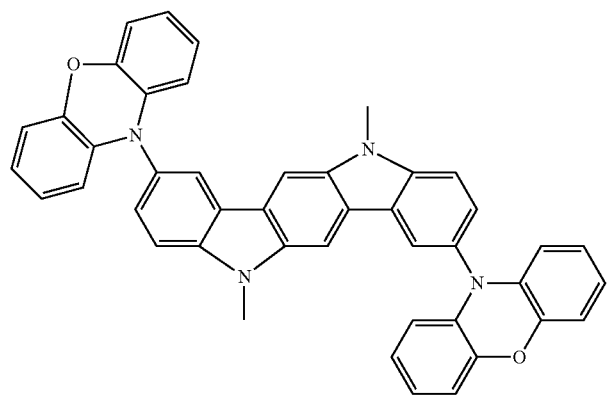
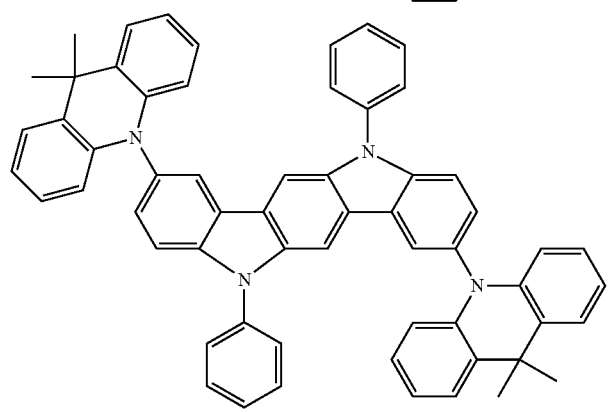
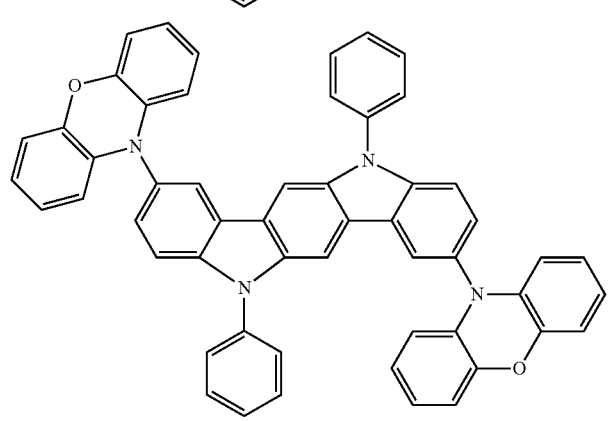
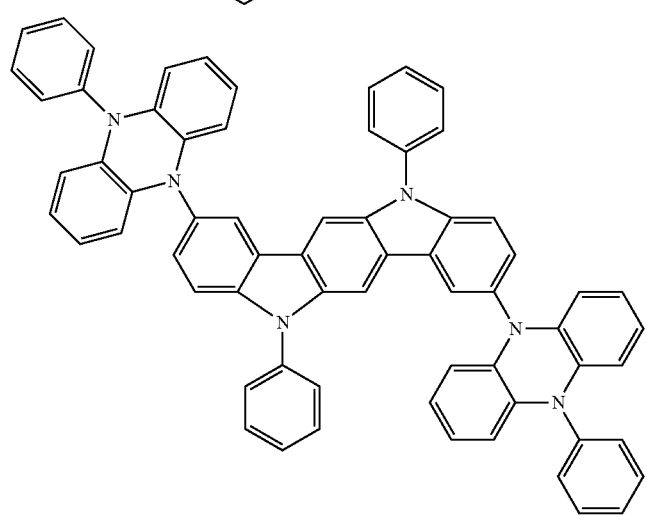
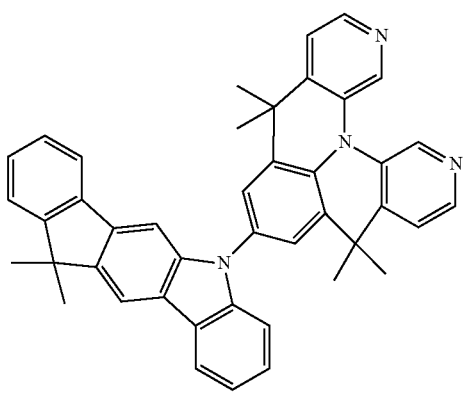

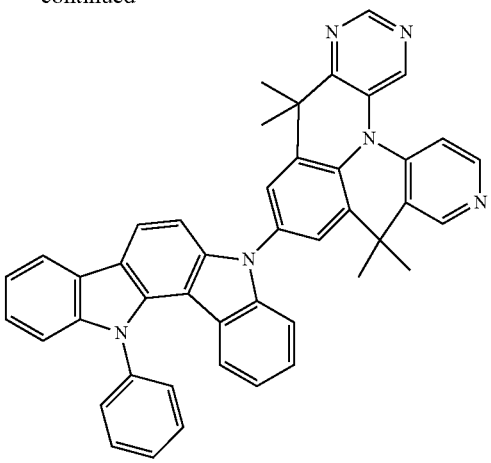

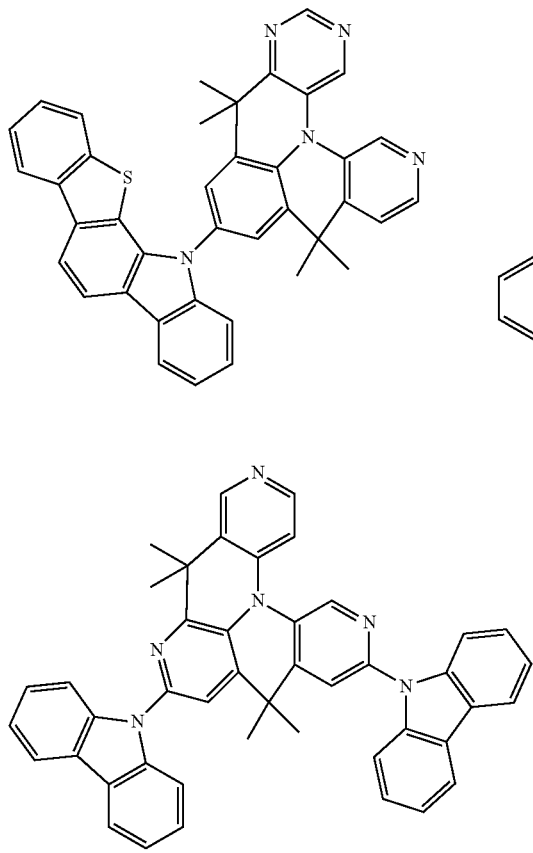

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl or heteroaryl group, which may in each case be substituted by the above-mentioned radicals R or $R^1$ and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via one or more single bonds are also taken to be aromatic or heteroaromatic ring systems in the sense of this invention.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals R and $R^1$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

For the purposes of the present description, the formulation that two or more radicals R (or $R^1$ or $R^2$) may form a ring with one another is intended to be taken to mean, inter alia, that the two radicals are linked to one another by a chemical bond. This is intended to be illustrated by the following scheme:

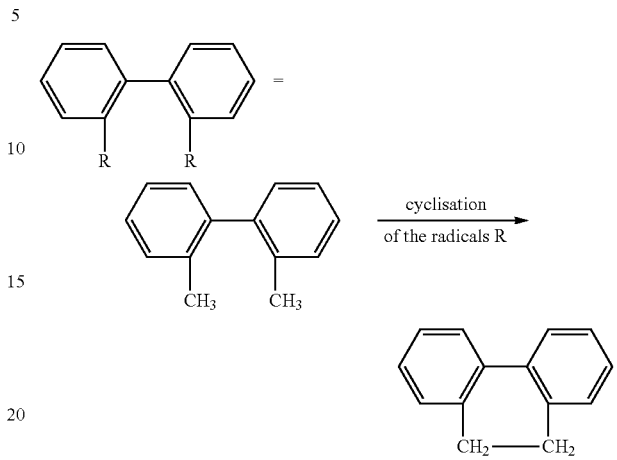

Furthermore, however, the above-mentioned formulation is also intended to be taken to mean that, in the case where one of the two radicals represents hydrogen, the second radical is bonded at the position at which the hydrogen atom was bonded, with formation of a ring. This is intended to be illustrated by the following scheme:

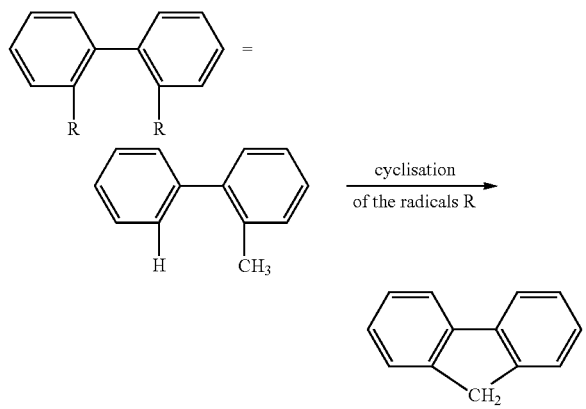

It should furthermore be emphasised for clarity that, for the purposes of the present description, an aromatic or heteroaromatic ring may also be represented by a central circle in the ring as an alternative to the classical Lewis notation.

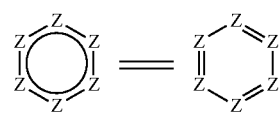

Furthermore, the numbering used for the purposes of the present description in the carbazole skeleton will be presented at this point:

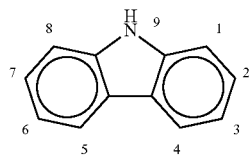

For the purposes of the present description, the formulation that a unit comprising two adjacent groups W (unit W-W) has been replaced by a group of the formula (3) is taken to mean that a group of the formula (3)

formula (3)

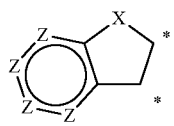

is present instead of the two adjacent groups W.

The C atoms labelled with * here adopt the positions in the six-membered ring which were previously occupied by the unit W-W. Consequently, the group of the formula (3) is condensed onto the six-membered ring which had previously contained the unit W-W.

It is preferred for a maximum of one unit W-W per six-membered ring in the compound according to the invention to have been replaced by a group of the formula (3). All other groups W in this six-membered ring are in this case equal to Z.

An example of a compound according to the invention in which a unit W-W has been replaced by a group of the formula (3) is the following compound of the formula (8).

formula (8)

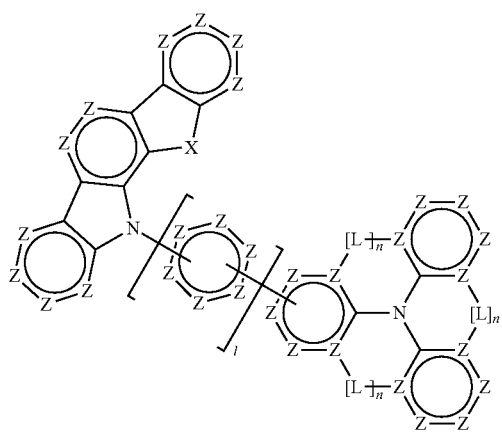

In a further preferred embodiment of the invention, only one unit W-W in the compounds of the formula (1) or (2) according to the invention has been replaced by a group of the formula (3).

In a further preferred embodiment of the invention, all groups W in formula (1) or (2) are equal to Z, and no unit W-W has been replaced by a group of the formula (3).

In a further preferred embodiment of the invention, the compounds according to the invention are represented by the formulae (4) to (14).

formula (4)

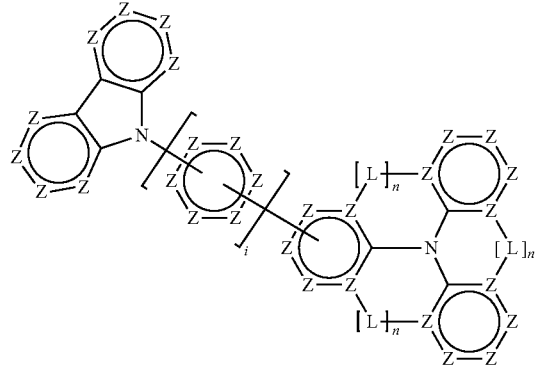

formula (5)

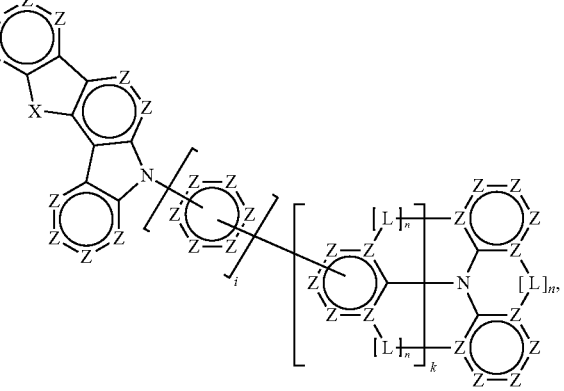

formula (6)

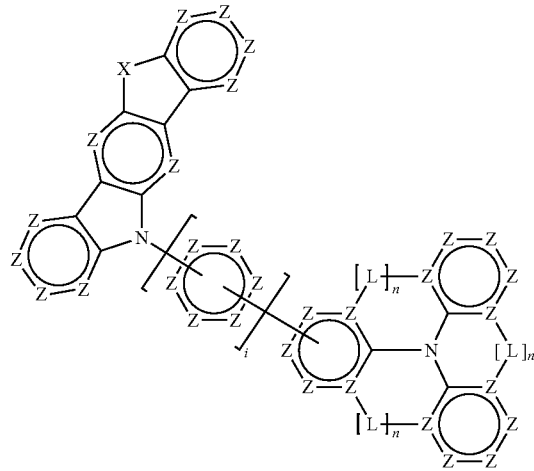

formula (7)
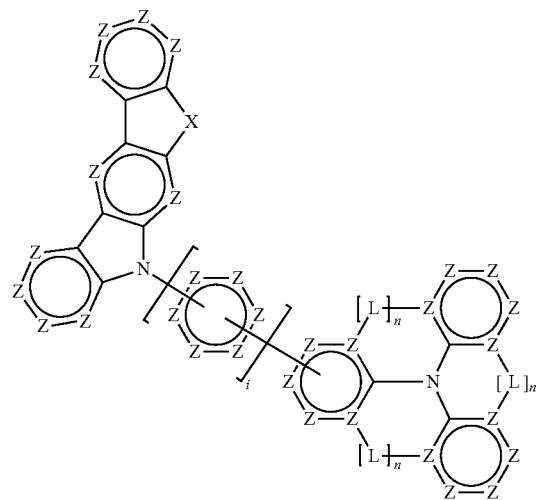
formula (8)
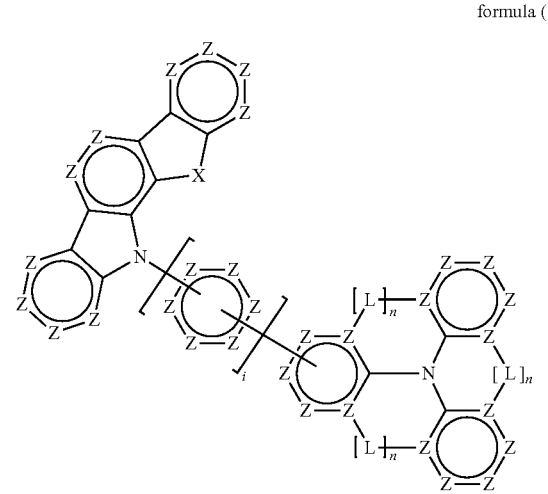
formula (9)
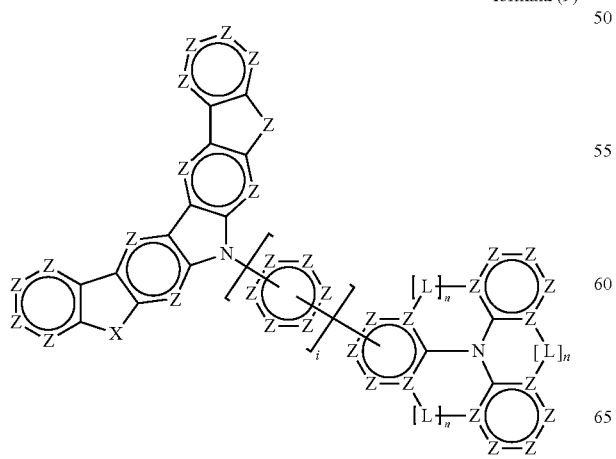
formula (10)
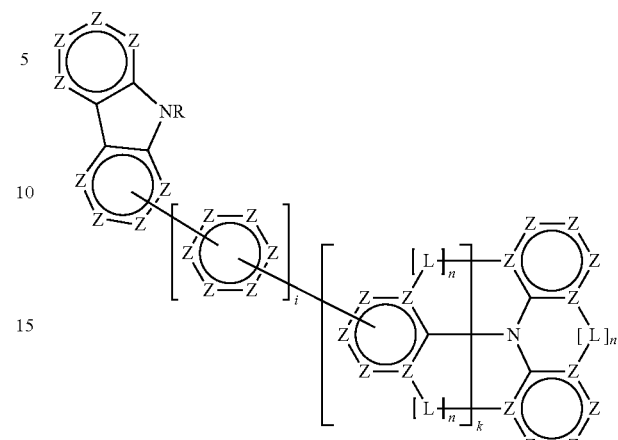
formula (11)
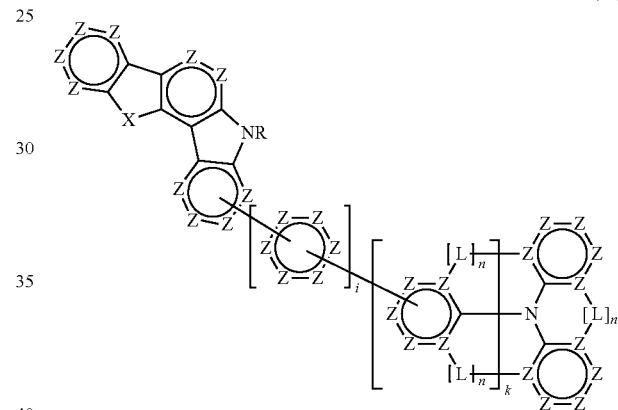
formula (12)
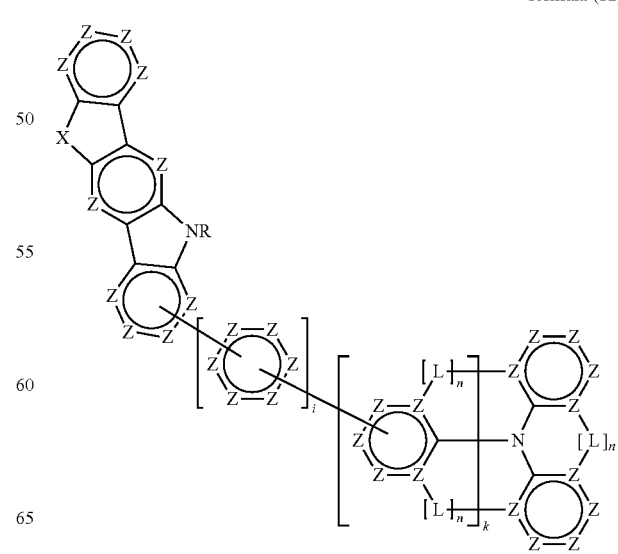

formula (13)

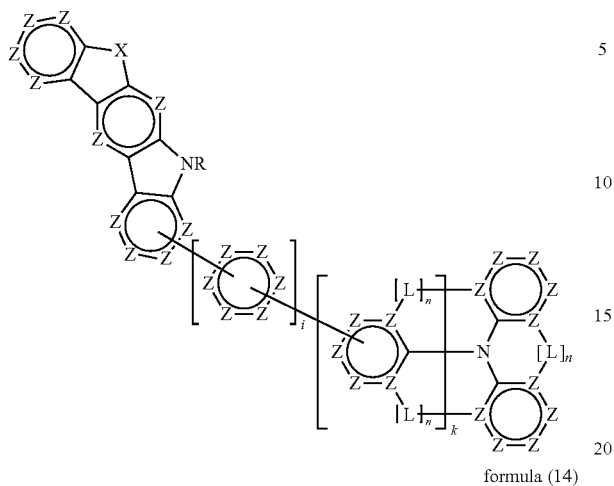

formula (14)

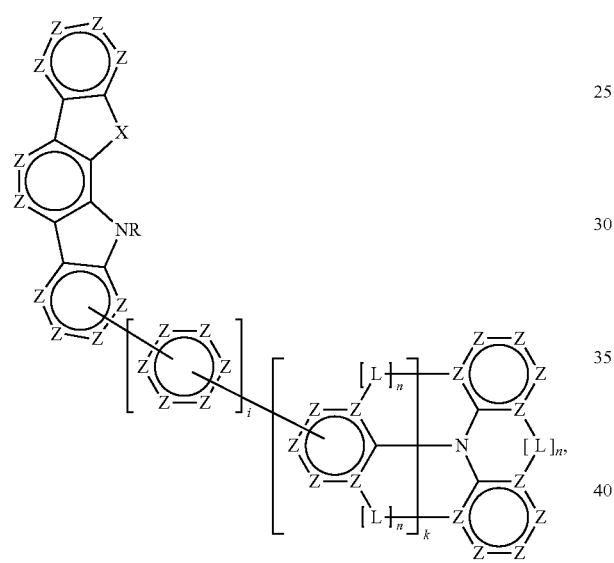

where the symbols and indices occurring are as defined above.

It is preferred in accordance with the invention for the bond from the carbazole group in the compounds of the formula (2) to emanate from the 2- or 3-position.

Particularly preferred embodiments of the compounds of the formula (1) or (2) conform to the following formulae (15) to (74):

formula (15)

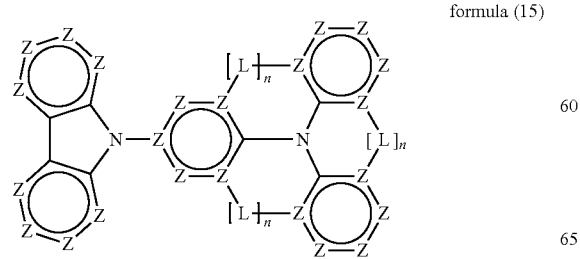

formula (16)

formula (17)

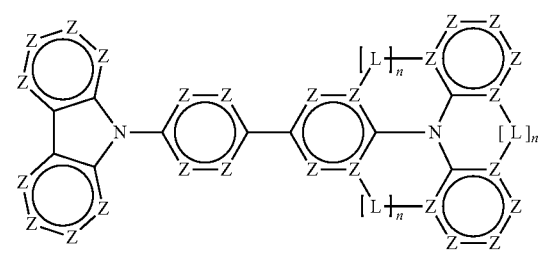

formula (18)

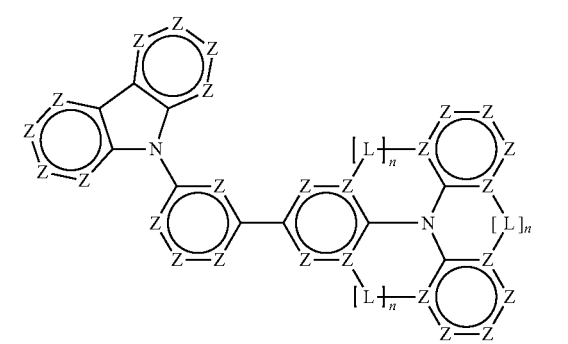

formula (19)

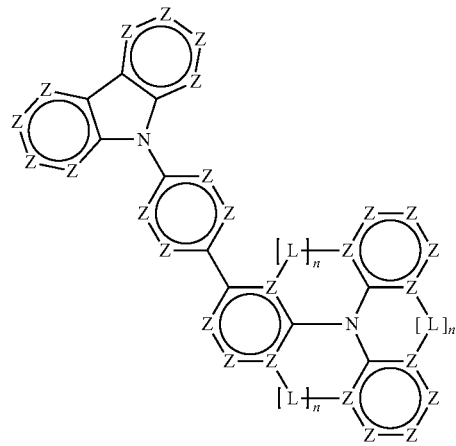

formula (20)
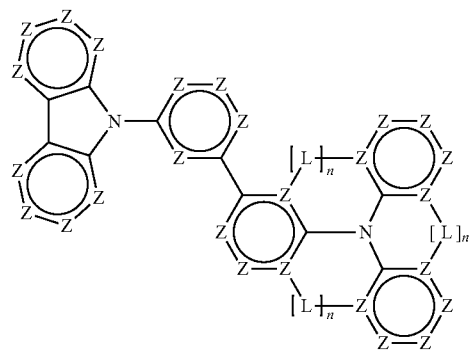
formula (21)
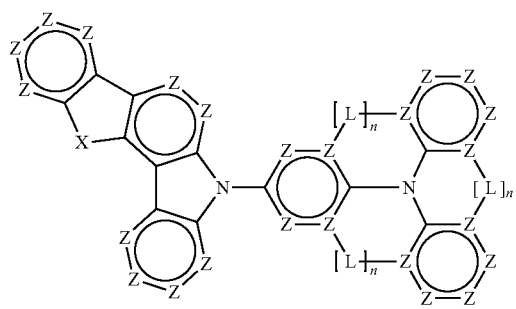
formula (22)
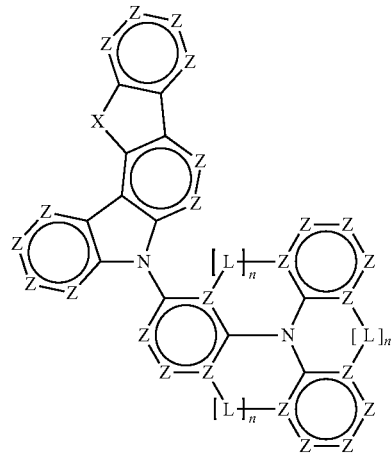
formula (23)
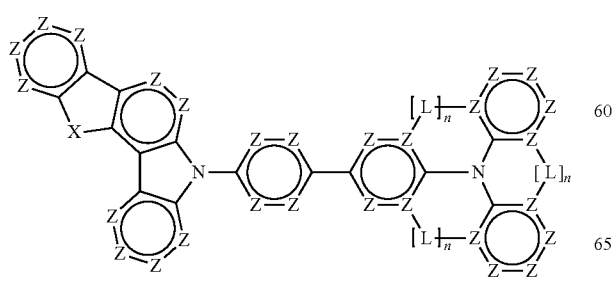
formula (24)
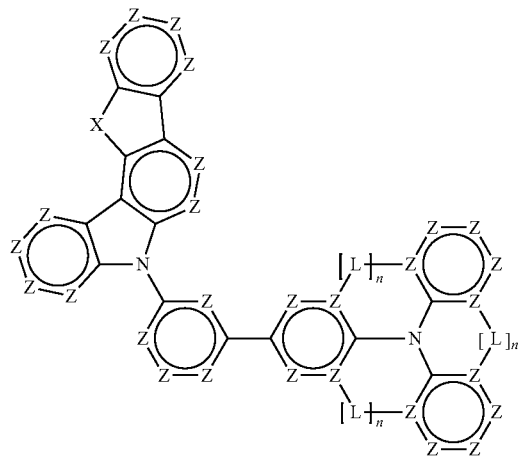
formula (25)
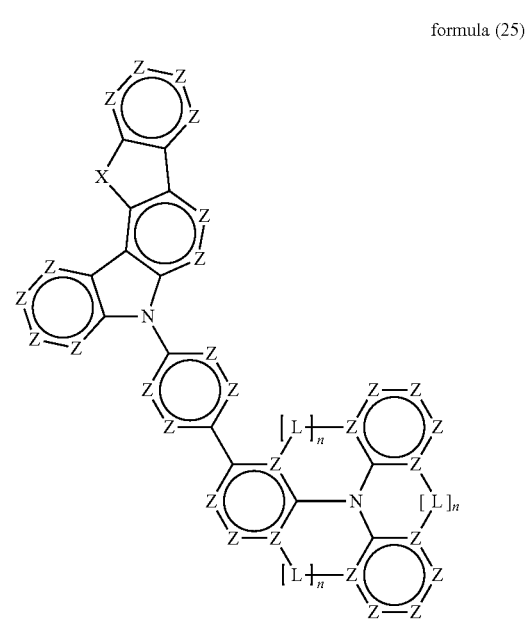
formula (26)
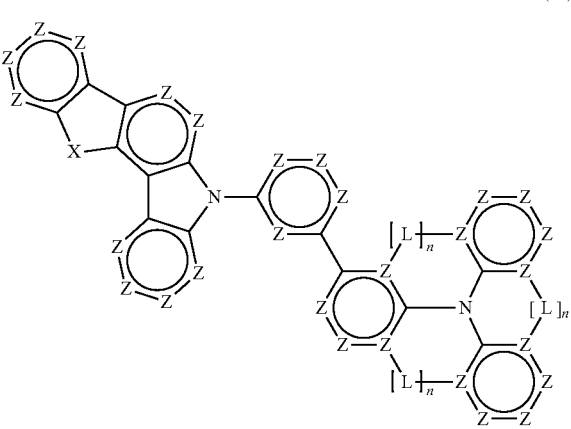

formula (27)
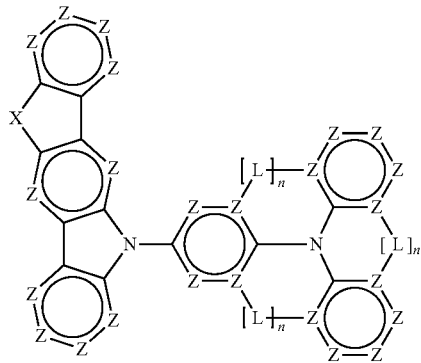
formula (28)
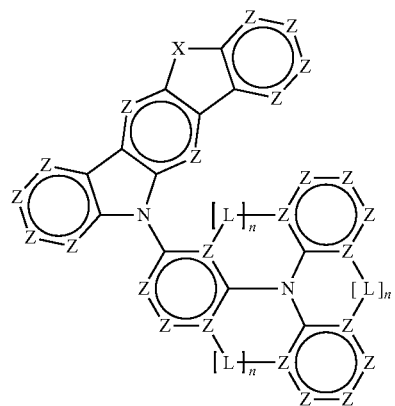
formula (29)
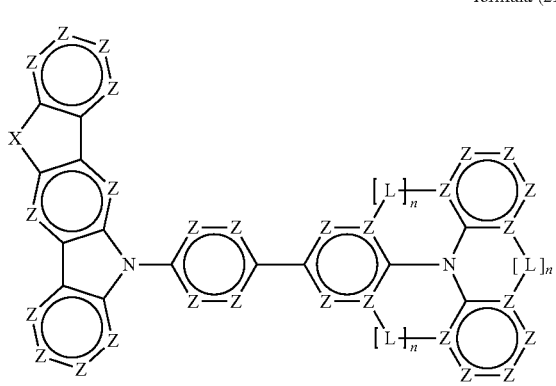
formula (30)
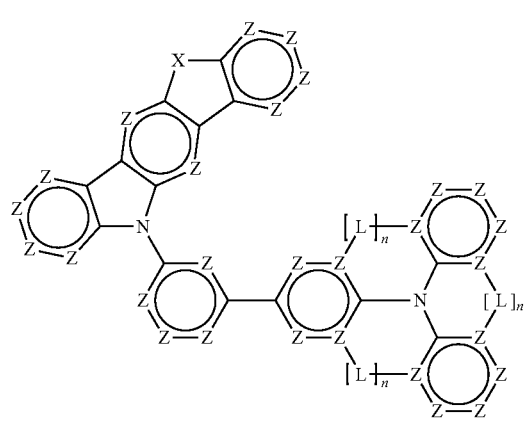
formula (31)
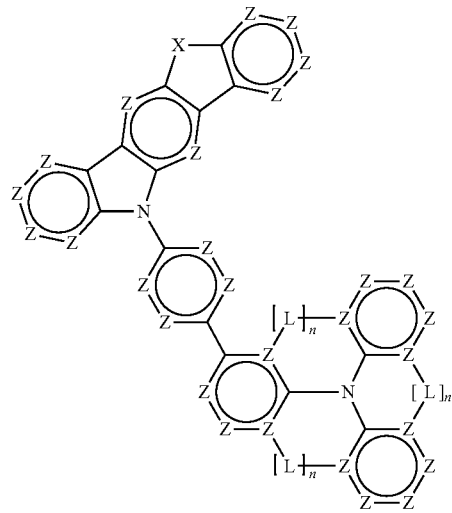
formula (32)
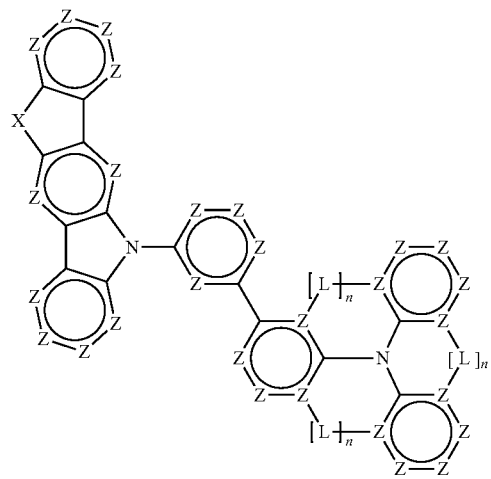
formula (33)
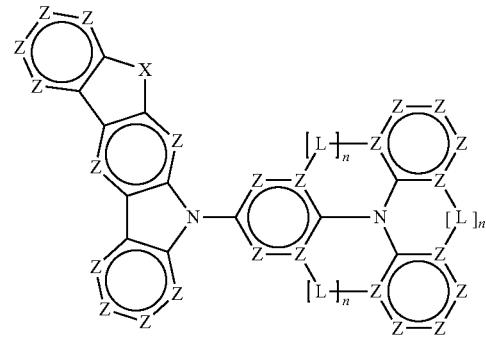

formula (34)
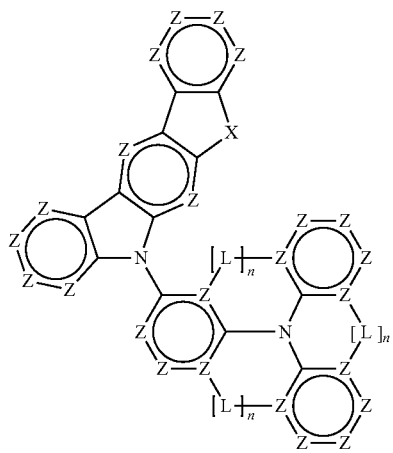
formula (35)
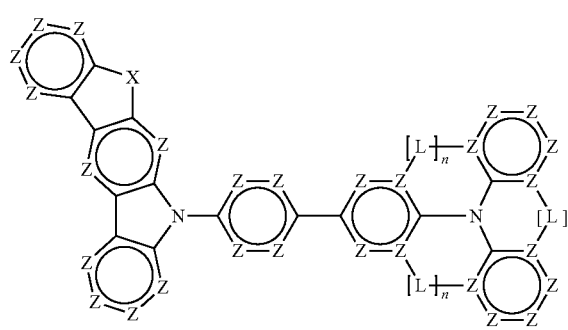
formula (36)
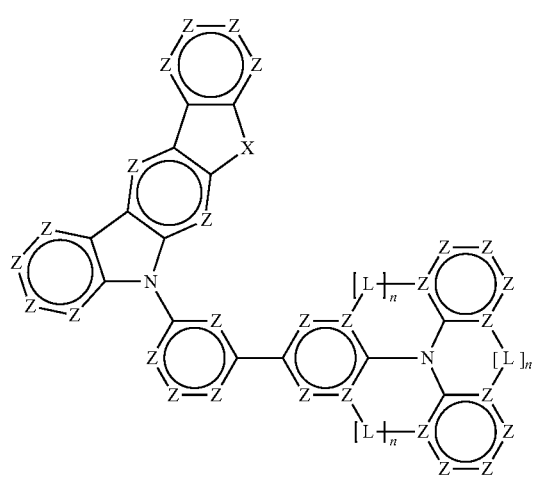
formula (37)
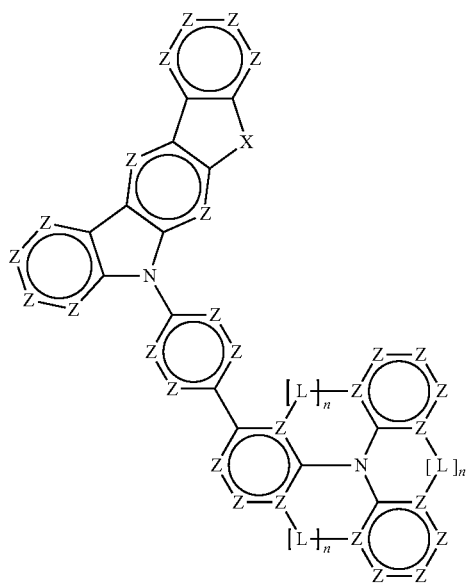
formula (38)
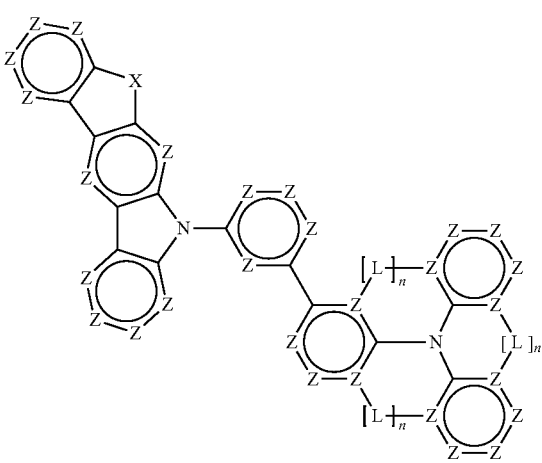
formula (39)
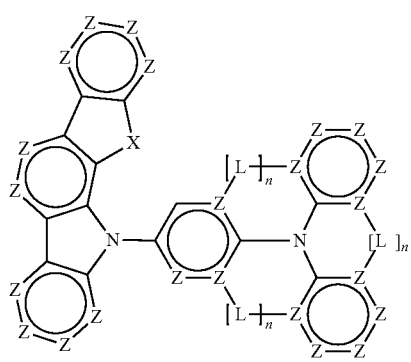

-continued
formula (40)
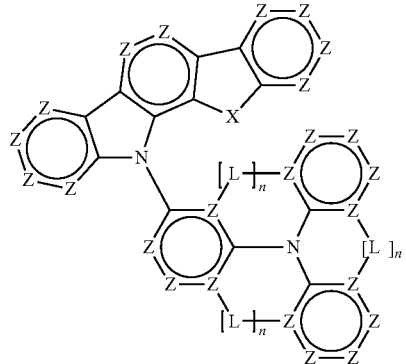
formula (41)
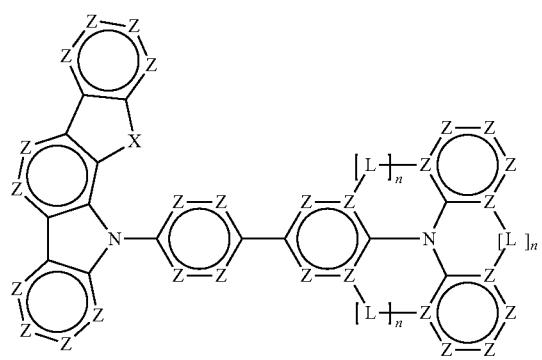
formula (42)
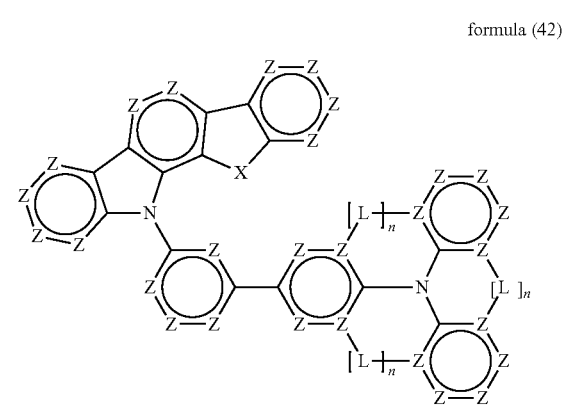
formula (43)
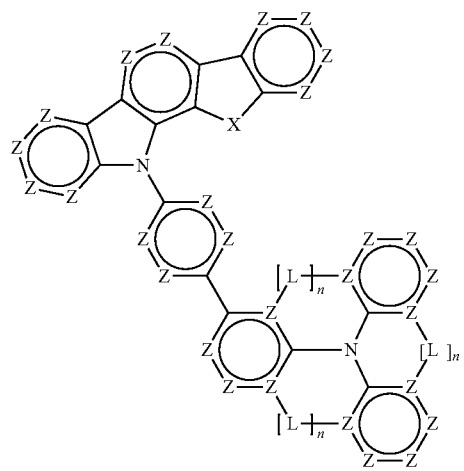
formula (44)
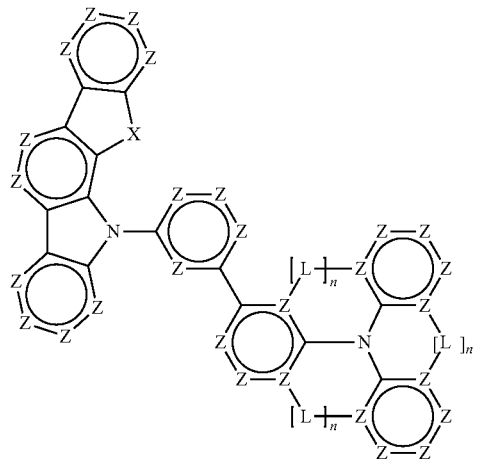
formula (45)
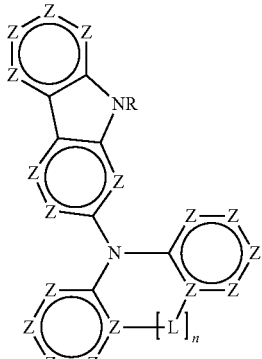
formula (46)
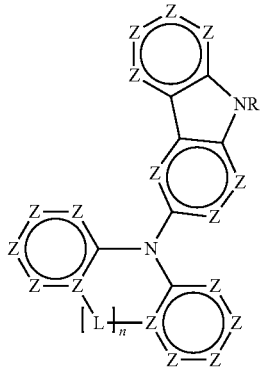

formula (47)
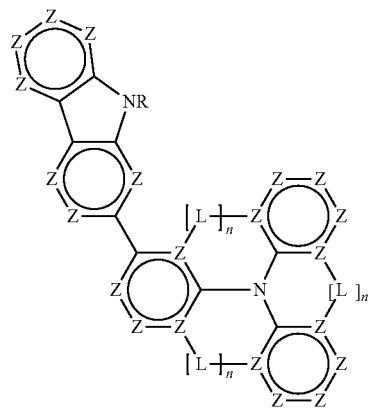
formula (48)
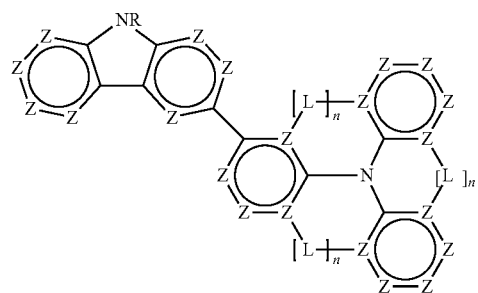
formula (49)
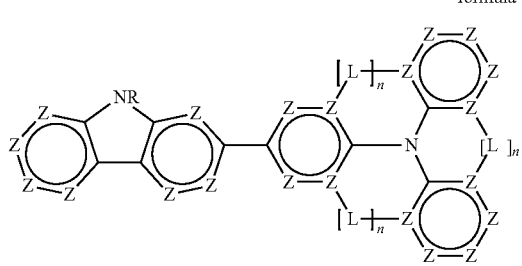
formula (50)
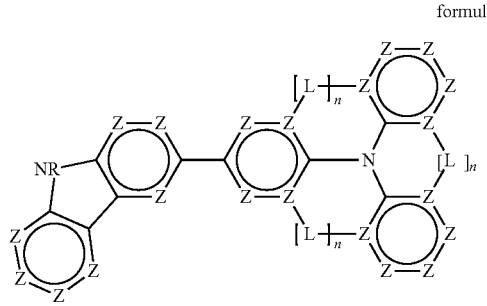
formula (51)
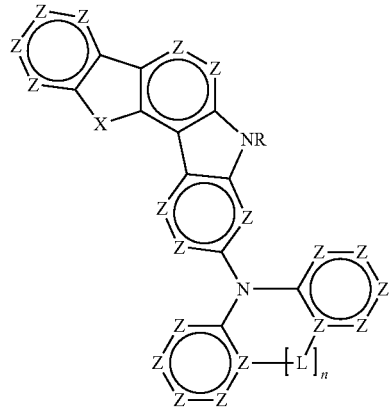
formula (52)
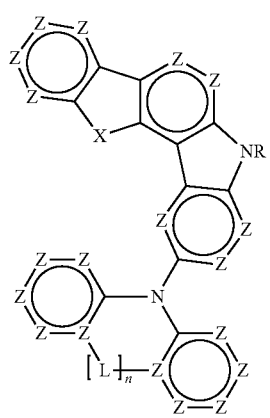
formula (53)
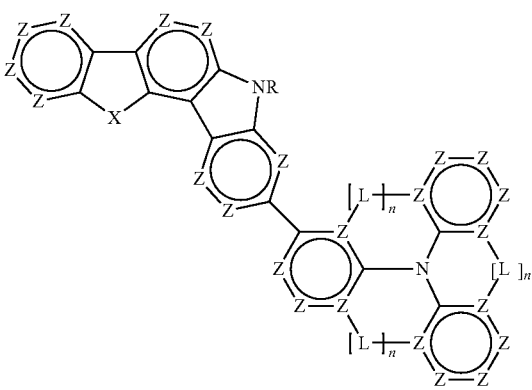
formula (54)
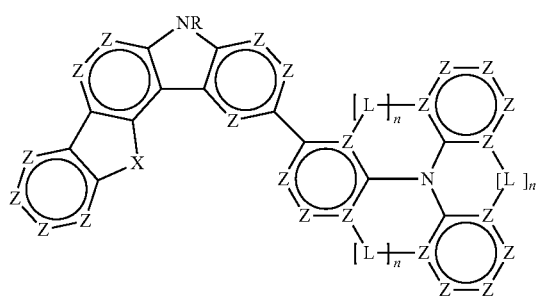

formula (55)
formula (56)
formula (57)
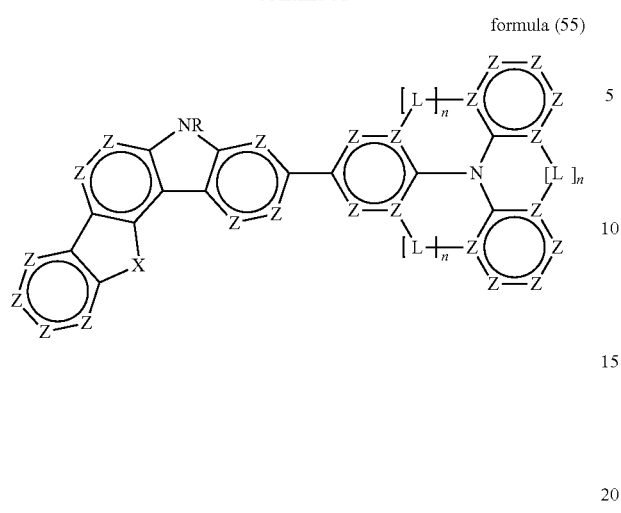
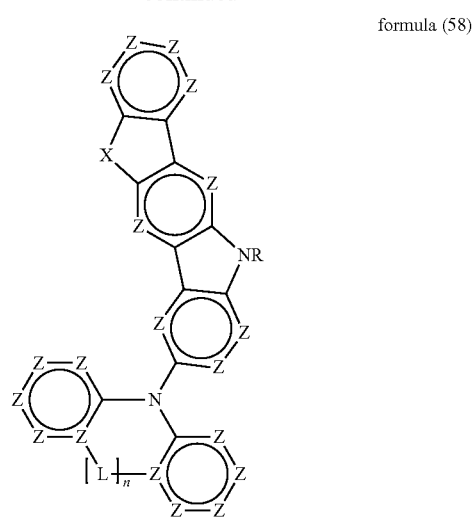
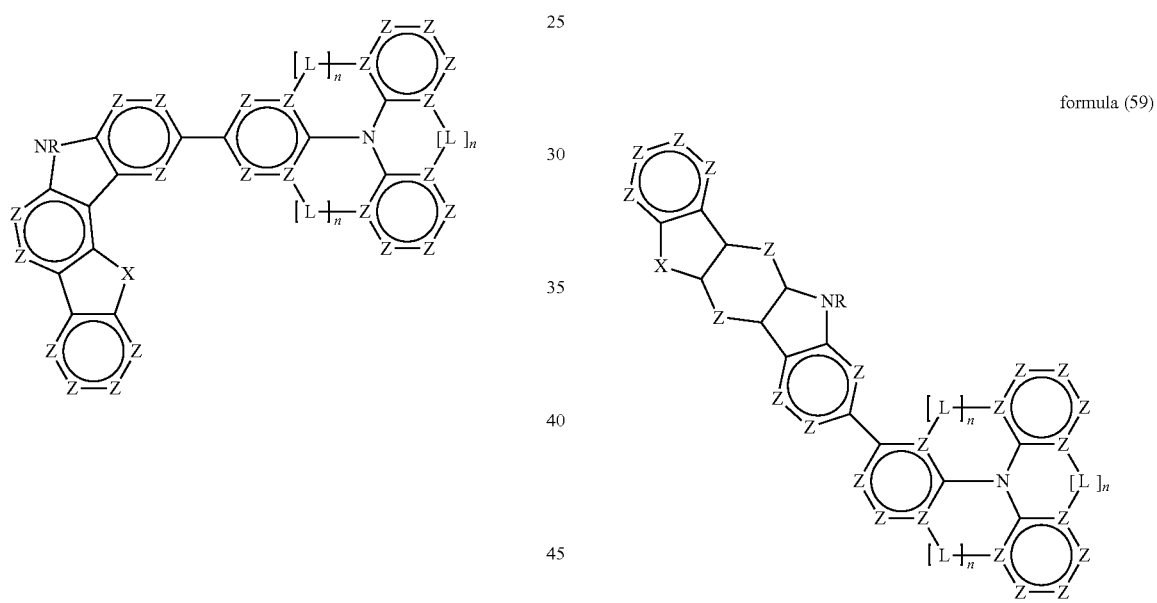
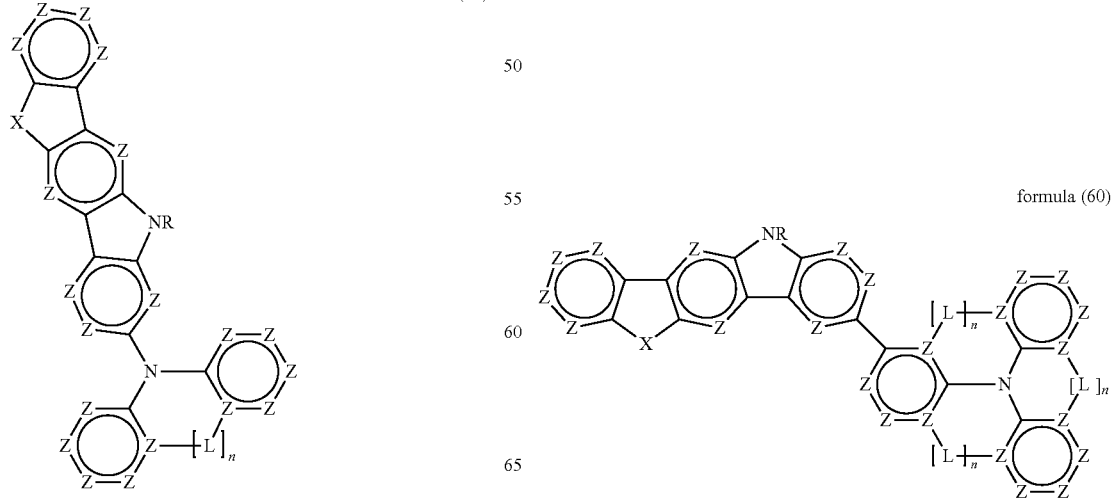
formula (58)
formula (59)
formula (60)

formula (61)
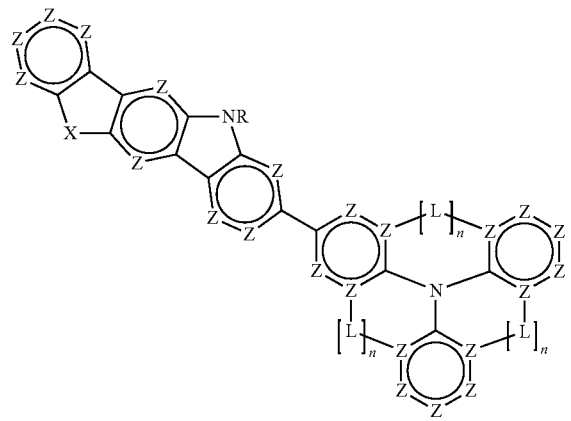
formula (62)
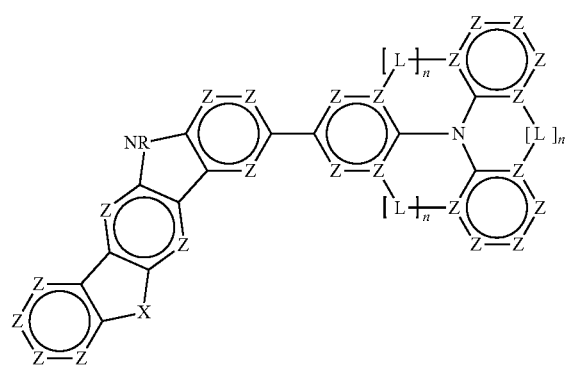
formula (63)
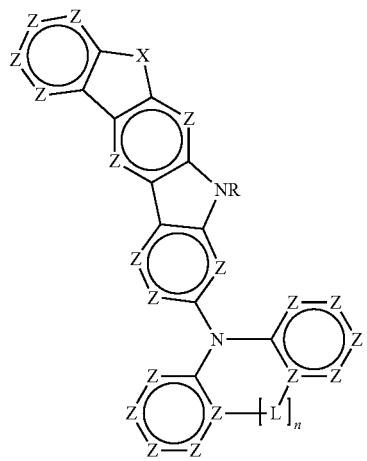
Formula (64)
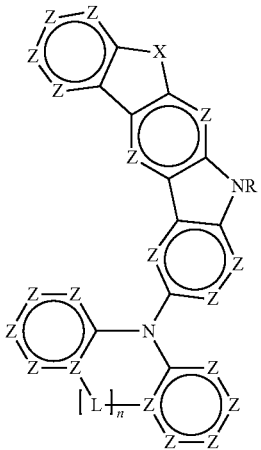
formula (65)
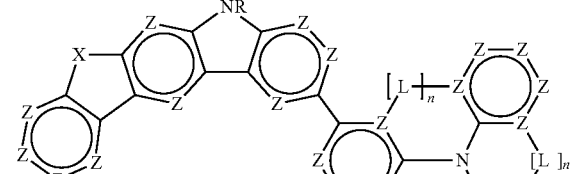
formula (66)
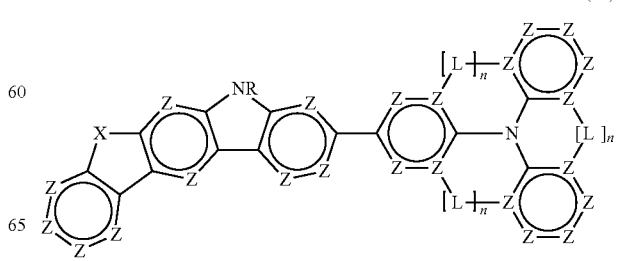
formula (67)

formula (68)

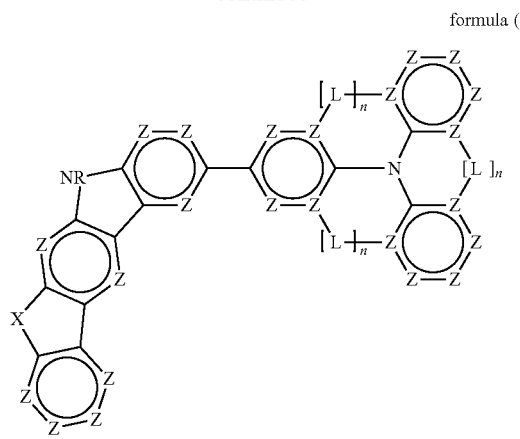

formula (69)

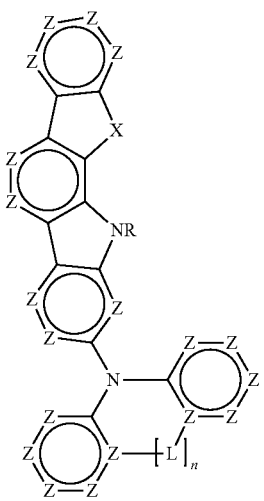

formula (70)

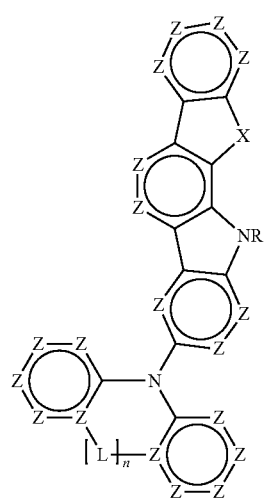

formula (71)

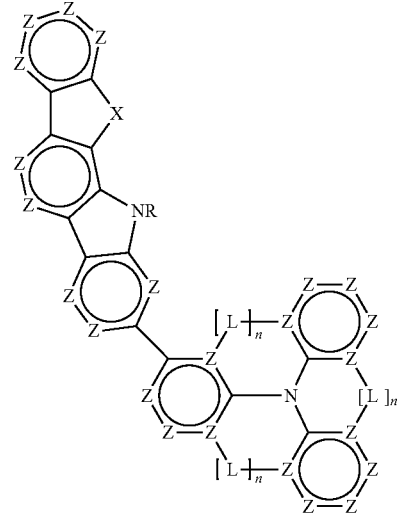

formula (72)

formula (73)

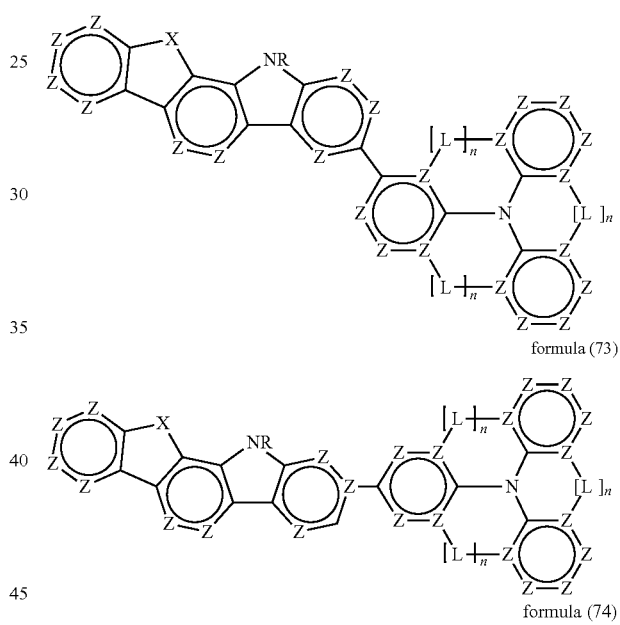

formula (74)

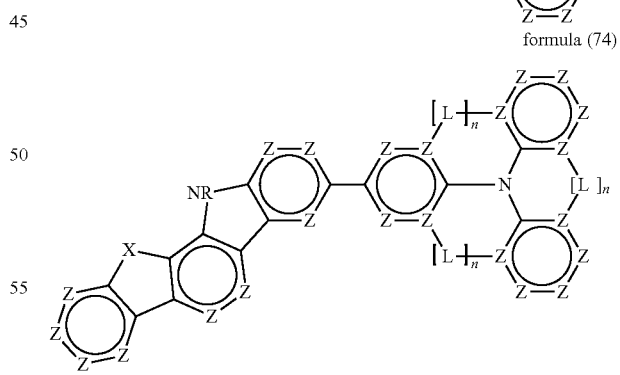

where the symbols and indices occurring are as defined above.

In a preferred embodiment of the invention, Z is equal to CR or, if a substituent is bonded to group Z, is equal to C. This preference applies to all embodiments of the compounds according to the invention.

It is furthermore preferred for L to be selected on each occurrence, identically or differently, from $C(R)_2$, NR, O, S, C=O, C=NR, S=O, S(=O)$_2$ and CR=CR. L is particularly preferably selected from C(R)$_2$, NR, O, S, S=O and S(=O)$_2$. L is very particularly preferably selected from CR$_2$ and NR.

In a further preferred embodiment of the invention, in the case where the sum of the values of the indices n is equal to 2 or 3, at least one group L is selected from NR, O, S, C=O, C=NR, S=O, S(=O)$_2$ and CR=CR, particularly preferably from NR, O, S, S=O and S(=O)$_2$.

In a preferred embodiment of the invention, X is selected from C(R)$_2$, NR, O, S, C=O, C=NR, S=O and S(=O)$_2$. X is particularly preferably selected from C(R)$_2$, NR, O, S, S=O and S(=O)$_2$. X is very particularly preferably selected from CR$_2$ and NR.

In a preferred embodiment of the invention, k is equal to 1.

In a further preferred embodiment of the invention, i is equal to 0 or 1.

In a further preferred embodiment of the invention, j is equal to 0 or 1.

In a further preferred embodiment of the invention, the sum of the values of the indices n is equal to 1 or 2.

In a preferred embodiment of the invention, a radical R which is part of a group Z in the embodiment CR represents carbazole or a carbazole derivative.

In a preferred embodiment of the invention, the compounds of the formula (1) and (2) only contain a single carbazole group. In this connection, a condensed heteroaromatic ring system, such as, for example, indenocarbazole or indolocarbazole, will by definition only count as a single carbazole group.

For the compounds according to the invention, it is preferred for a maximum of one substituent R to represent carbazole or a carbazole derivative. In a preferred embodiment of the invention, no radical R in the compounds according to the invention represents a carbazole derivative. A carbazole derivative here is taken to mean a carbazole which is substituted as desired.

The radical R is preferably selected on each occurrence, identically or differently, from H, D, F, CN, Si(R$^1$)$_3$, N(R$^1$)$_2$ or a straight-chain alkyl or alkoxy group having 1 to 20 C atoms or a branched or cyclic alkyl or alkoxy group having 3 to 20 C atoms, each of which may be substituted by one or more radicals R$^1$, where one or more adjacent or non-adjacent CH$_2$ groups may be replaced by —C≡C—, —R$^1$C=CR$^1$—, Si(R$^1$)$_2$, C=O, C=NR$^1$, —NR$^1$—, —O—, —S—, —COO— or —CONR$^1$—, or an aryl or heteroaryl group having 5 to 30 aromatic ring atoms, which may in each case be substituted by one or more radicals R$^1$, where two or more radicals R may be linked to one another and may form a ring.

The radical R$^1$ is preferably selected on each occurrence, identically or differently, from H, D, F, CN, Si(R$^2$)$_3$, N(R$^2$)$_2$ or a straight-chain alkyl or alkoxy group having 1 to 20 C atoms or a branched or cyclic alkyl or alkoxy group having 3 to 20 C atoms, each of which may be substituted by one or more radicals R$^2$, where one or more adjacent or non-adjacent CH$_2$ groups may be replaced by —C≡C—, —R$^2$C=CR$^2$—, Si(R$^2$)$_2$, C=O, C=NR$^2$, —NR$^2$—, —O—, —S—, —COO— or —CONR$^2$—, or an aryl or heteroaryl group having 5 to 30 aromatic ring atoms, which may in each case be substituted by one or more radicals R$^2$, where two or more radicals R$^1$ may be linked to one another and may form a ring.

In a further preferred embodiment of the invention, the radicals R are not linked to one another and do not form a ring.

In a further preferred embodiment of the invention, the radicals R$^1$ are not linked to one another and do not form a ring.

The general and preferred embodiments mentioned above can in accordance with the invention be combined with one another as desired.

For the purposes of the present invention, it is preferred for the respective preferred embodiments of the groups and indices L, X, R, R$^1$, n, k, i and j to occur in combination with the preferred embodiments in accordance with the formulae (4) to (14) and the particularly preferred embodiments in accordance with the formulae (15) to (74).

Examples of compounds according to the invention are given in the following table:

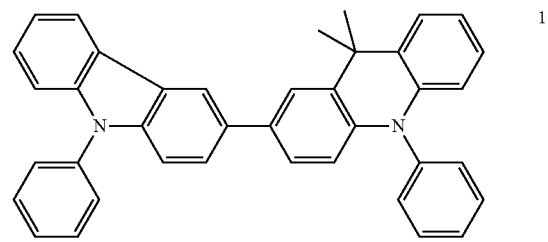

1

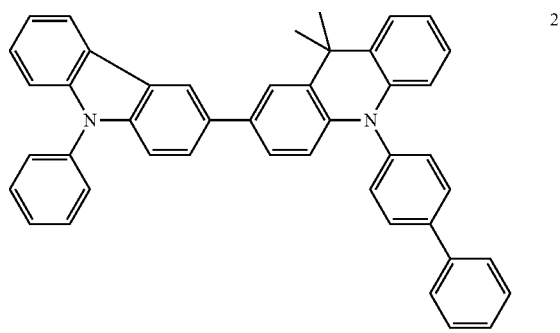

2

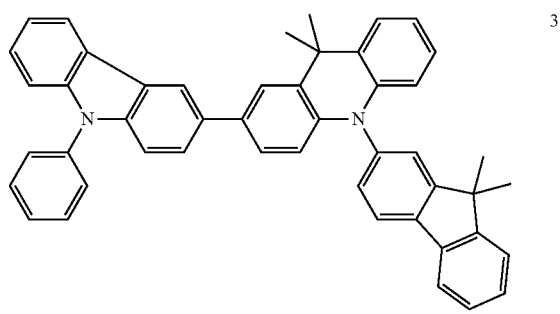

3

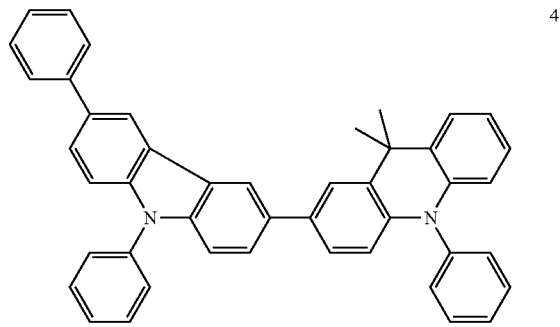

4

5
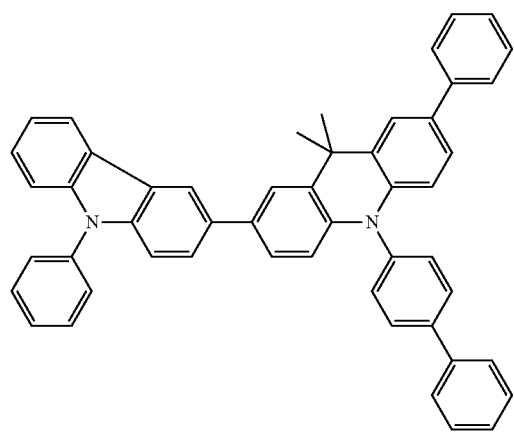 [SMILES: CC1(C)c2cc(-c3ccccc3)ccc2N(c2ccc(-c3ccccc3)cc2)c2ccc(-c3ccc4c(c3)c3ccccc3n4-c3ccccc3)cc21]
6
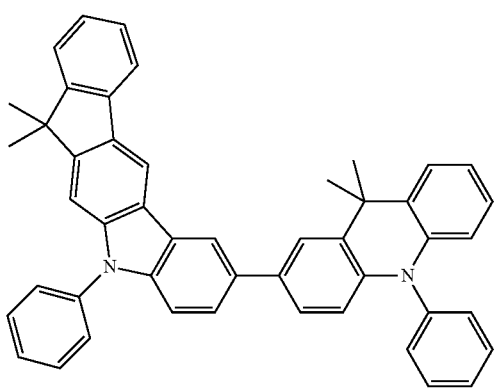 [SMILES: CC1(C)c2ccccc2-c2cc3c4cc(-c5ccc6c(c5)C(C)(C)c5ccccc5N6c5ccccc5)ccc4n(-c4ccccc4)c3cc21]
7
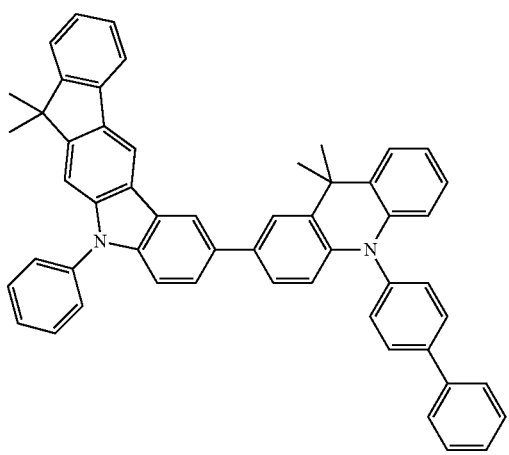 [SMILES: CC1(C)c2ccccc2-c2cc3c4cc(-c5ccc6c(c5)C(C)(C)c5ccccc5N6c5ccc(-c6ccccc6)cc5)ccc4n(-c4ccccc4)c3cc21]
8
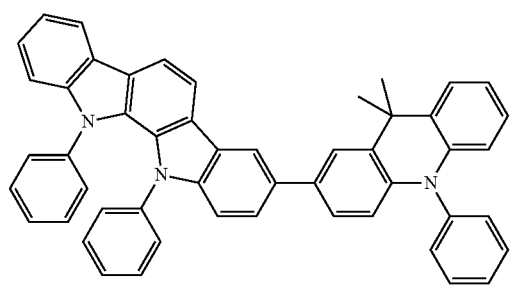 [SMILES: CC1(C)c2ccccc2N(c2ccccc2)c2ccc(-c3ccc4c(c3)c3ccc5c6ccccc6n(-c6ccccc6)c5c3n4-c3ccccc3)cc21]
9
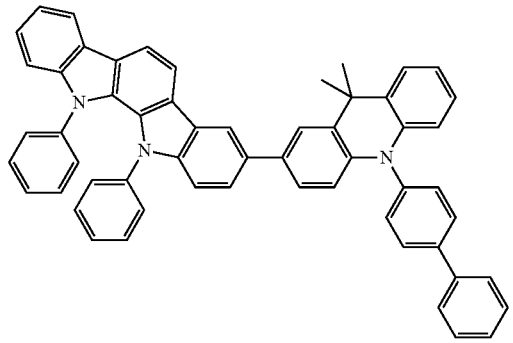 [SMILES: CC1(C)c2ccccc2N(c2ccc(-c3ccccc3)cc2)c2ccc(-c3ccc4c(c3)c3ccc5c6ccccc6n(-c6ccccc6)c5c3n4-c3ccccc3)cc21]
10
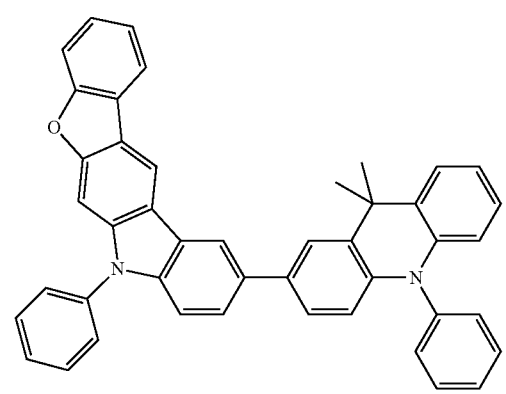 [SMILES: CC1(C)c2ccccc2N(c2ccccc2)c2ccc(-c3ccc4c(c3)c3cc5c(cc3n4-c3ccccc3)oc3ccccc35)cc21]
11
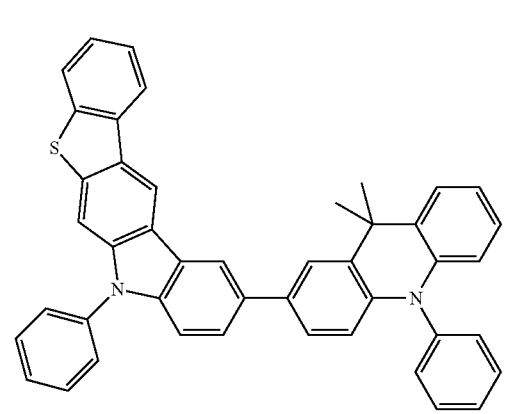 [SMILES: CC1(C)c2ccccc2N(c2ccccc2)c2ccc(-c3ccc4c(c3)c3cc5c(cc3n4-c3ccccc3)sc3ccccc35)cc21]
12
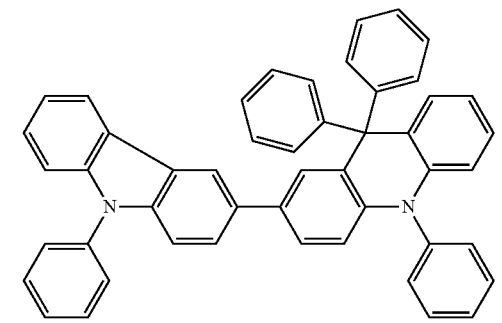 [SMILES: c1ccc(N2c3ccccc3C(c3ccccc3)(c3ccccc3)c3cc(-c4ccc5c(c4)c4ccccc4n5-c4ccccc4)ccc32)cc1]

| 53 -continued | 54 -continued |
|---|---|
| 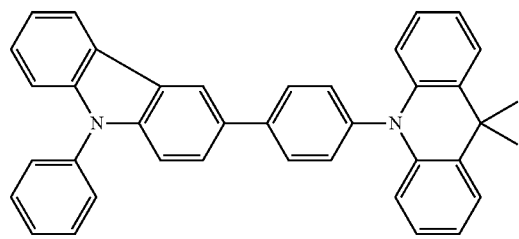 [SMILES: CC1(C)c2ccccc2N(c2ccc(-c3ccc4c(c3)c3ccccc3n4-c3ccccc3)cc2)c2ccccc21] 13 | 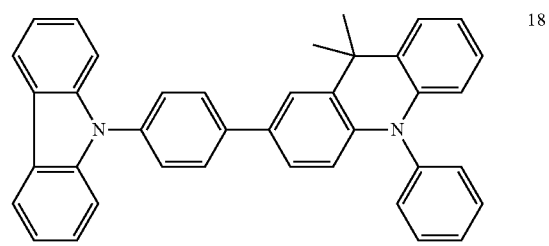 18 |
| 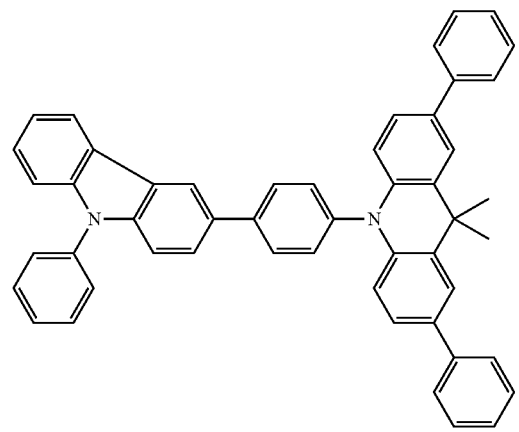 [SMILES: CC1(C)c2cc(-c3ccccc3)ccc2N(c2ccc(-c3ccc4c(c3)c3ccccc3n4-c3ccccc3)cc2)c2ccc(-c3ccccc3)cc21] 14 | 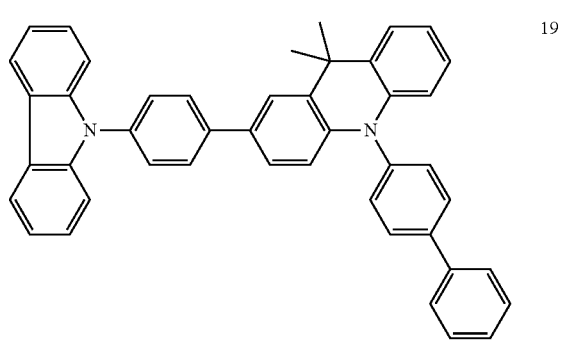 19 |
| 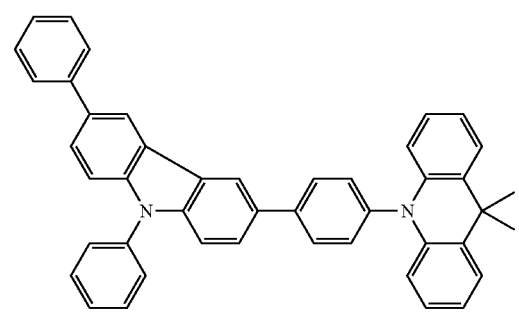 [SMILES: CC1(C)c2ccccc2N(c2ccc(-c3ccc4c(c3)c3cc(-c5ccccc5)ccc3n4-c3ccccc3)cc2)c2ccccc21] 15 | 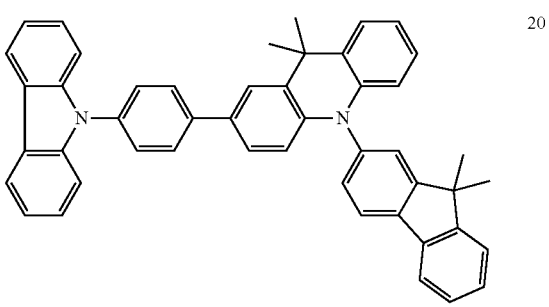 20 |
| 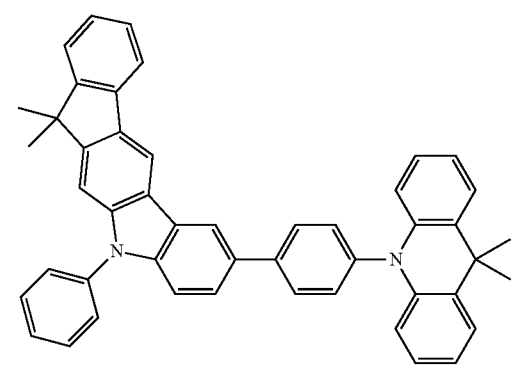 16 |  21 |
| 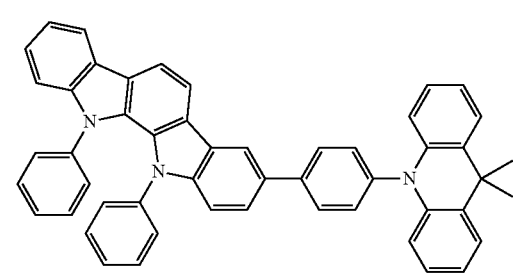 [SMILES: CC1(C)c2ccccc2N(c2ccc(-c3ccc4c(c3)c3ccc5c6ccccc6n(-c6ccccc6)c5c3n4-c3ccccc3)cc2)c2ccccc21] 17 | 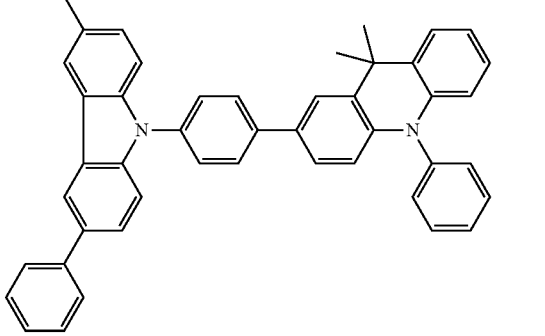 22 |

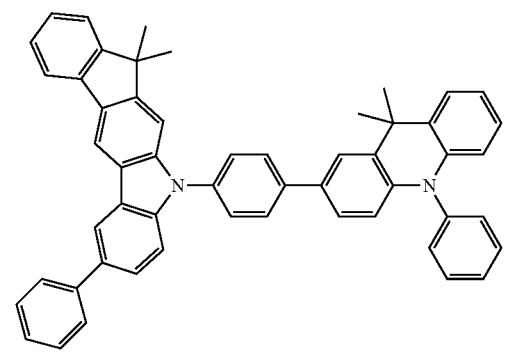 [SMILES: CC1(C)c2ccccc2-c2cc3c4cc(-c5ccccc5)ccc4n(-c4ccc(-c5ccc6c(c5)C(C)(C)c5ccccc5N6c5ccccc5)cc4)c3cc21]
23
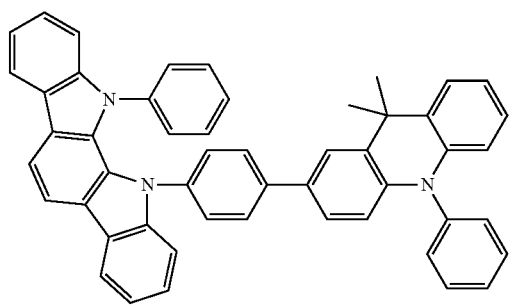 [SMILES: CC1(C)c2ccccc2N(c2ccccc2)c2ccc(-c3ccc(-n4c5ccccc5c5ccc6c7ccccc7n(-c7ccccc7)c6c54)cc3)cc21]
24
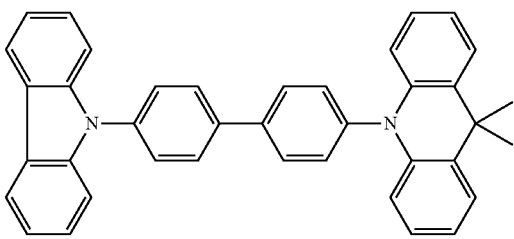 [SMILES: CC1(C)c2ccccc2N(c2ccc(-c3ccc(-n4c5ccccc5c5ccccc54)cc3)cc2)c2ccccc21]
25
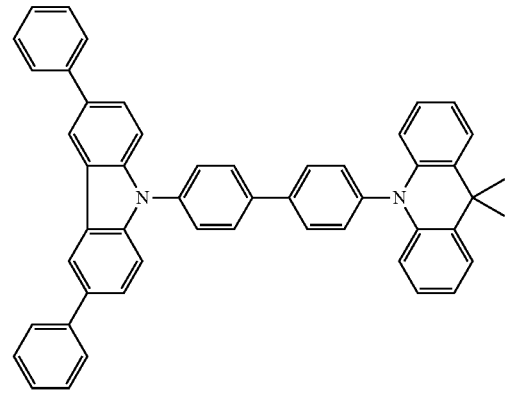 [SMILES: CC1(C)c2ccccc2N(c2ccc(-c3ccc(-n4c5ccc(-c6ccccc6)cc5c5cc(-c6ccccc6)ccc54)cc3)cc2)c2ccccc21]
26
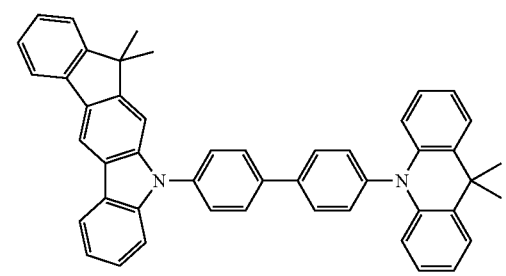 [SMILES: CC1(C)c2ccccc2-c2cc3c4ccccc4n(-c4ccc(-c5ccc(N6c7ccccc7C(C)(C)c7ccccc76)cc5)cc4)c3cc21]
27
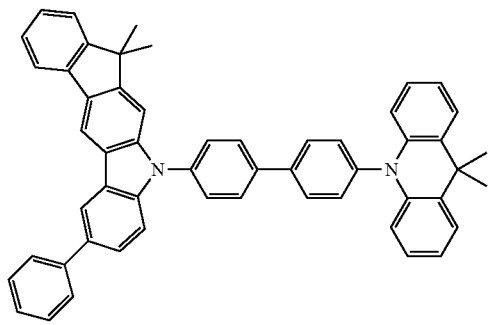 [SMILES: CC1(C)c2ccccc2-c2cc3c4cc(-c5ccccc5)ccc4n(-c4ccc(-c5ccc(N6c7ccccc7C(C)(C)c7ccccc76)cc5)cc4)c3cc21]
28
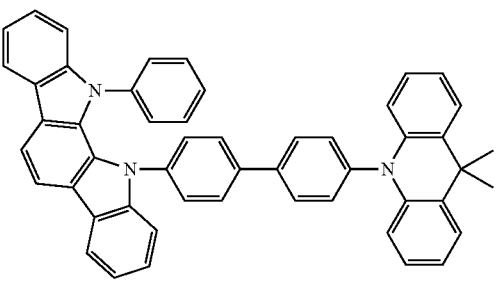 [SMILES: CC1(C)c2ccccc2N(c2ccc(-c3ccc(-n4c5ccccc5c5ccc6c7ccccc7n(-c7ccccc7)c6c54)cc3)cc2)c2ccccc21]
29
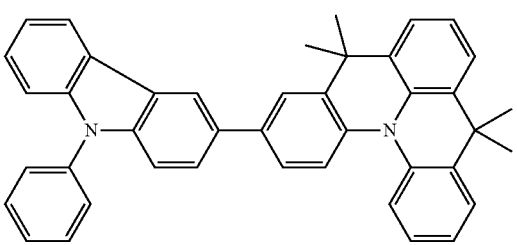 [SMILES: CC1(C)c2ccccc2N2c3ccc(-c4ccc5c(c4)c4ccccc4n5-c4ccccc4)cc3C(C)(C)c3cccc1c32]
30
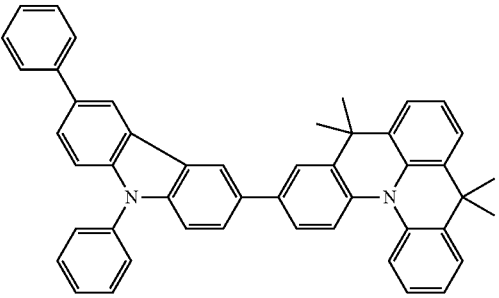 [SMILES: CC1(C)c2ccccc2N2c3ccc(-c4ccc5c(c4)c4cc(-c6ccccc6)ccc4n5-c4ccccc4)cc3C(C)(C)c3cccc1c32]
31
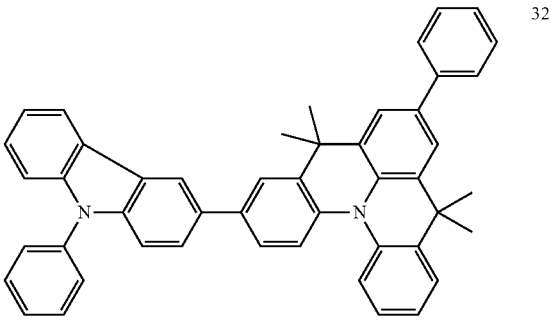
32

33
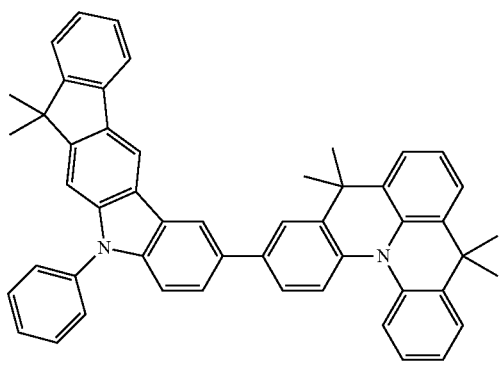 [SMILES: CC1(C)c2ccccc2-c2cc3c4cc(-c5ccc6c(c5)C(C)(C)c5cccc7c5N6c5ccccc5C7(C)C)ccc4n(-c4ccccc4)c3cc21]
34
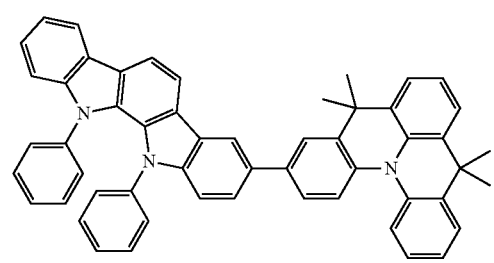 [SMILES: CC1(C)c2ccccc2N2c3ccc(-c4ccc5c(c4)c4ccc6c7ccccc7n(-c7ccccc7)c6c4n5-c4ccccc4)cc3C(C)(C)c3cccc1c32]
35
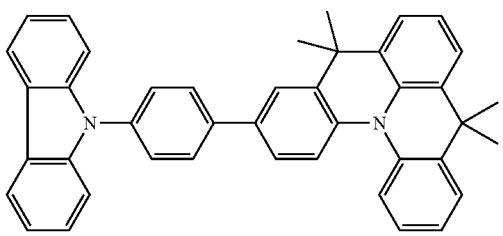 [SMILES: CC1(C)c2ccccc2N2c3ccc(-c4ccc(-n5c6ccccc6c6ccccc65)cc4)cc3C(C)(C)c3cccc1c32]
36
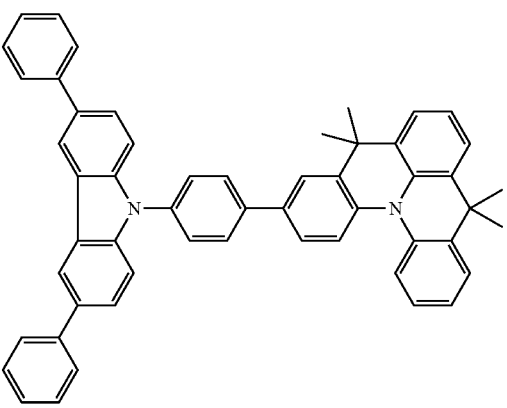 [SMILES: CC1(C)c2ccccc2N2c3ccc(-c4ccc(-n5c6ccc(-c7ccccc7)cc6c6cc(-c7ccccc7)ccc65)cc4)cc3C(C)(C)c3cccc1c32]
37
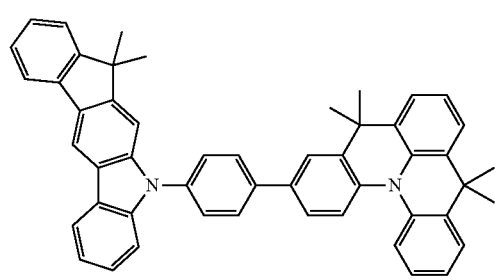 [SMILES: CC1(C)c2ccccc2-c2cc3c4ccccc4n(-c4ccc(-c5ccc6c(c5)C(C)(C)c5cccc7c5N6c5ccccc5C7(C)C)cc4)c3cc21]
38
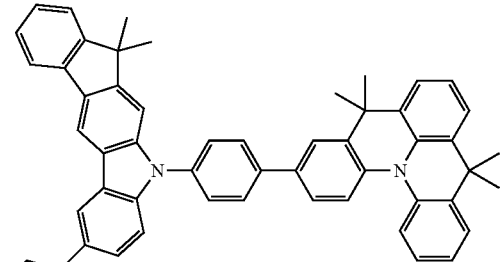
39
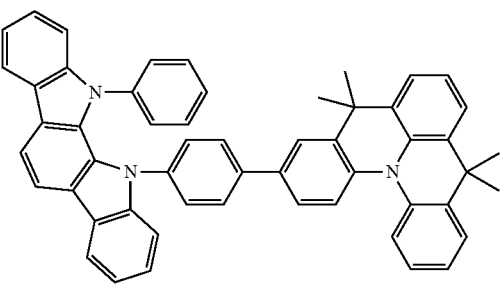 [SMILES: CC1(C)c2ccccc2N2c3ccc(-c4ccc(-n5c6ccccc6c6ccc7c8ccccc8n(-c8ccccc8)c7c65)cc4)cc3C(C)(C)c3cccc1c32]
40
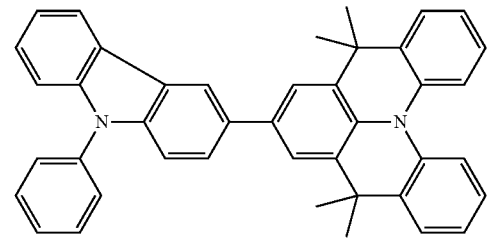 [SMILES: CC1(C)c2ccccc2N2c3ccccc3C(C)(C)c3cc(-c4ccc5c(c4)c4ccccc4n5-c4ccccc4)cc1c32]
41
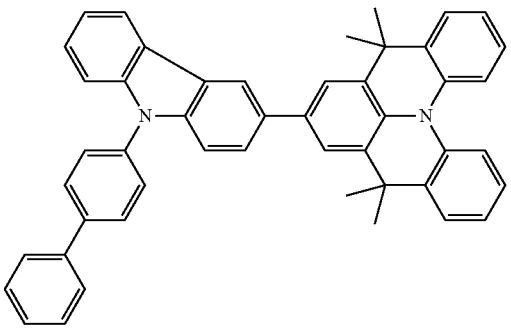 [SMILES: CC1(C)c2ccccc2N2c3ccccc3C(C)(C)c3cc(-c4ccc5c(c4)c4ccccc4n5-c4ccc(-c5ccccc5)cc4)cc1c32]
42
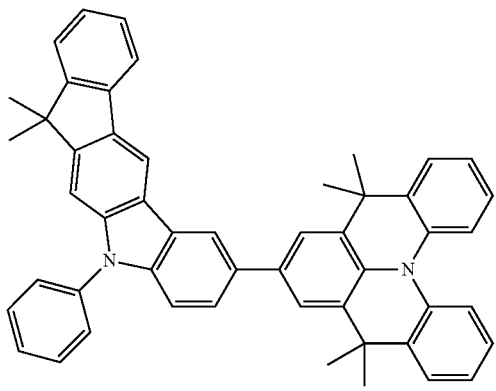 [SMILES: CC1(C)c2ccccc2-c2cc3c4cc(-c5cc6c7c(c5)C(C)(C)c5ccccc5N7c5ccccc5C6(C)C)ccc4n(-c4ccccc4)c3cc21]

| 59 -continued | 60 -continued |
|---|---|
| 43<br>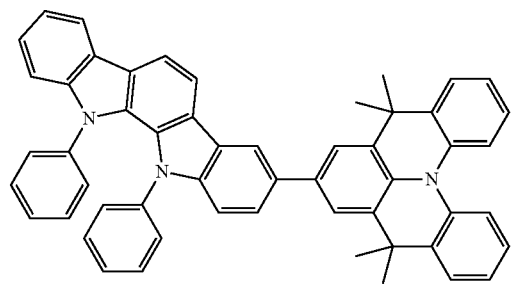 [SMILES: CC1(C)c2ccccc2N2c3ccccc3C(C)(C)c3cc(-c4ccc5c(c4)c4ccc6c7ccccc7n(-c7ccccc7)c6c4n5-c4ccccc4)cc1c32] | 47<br>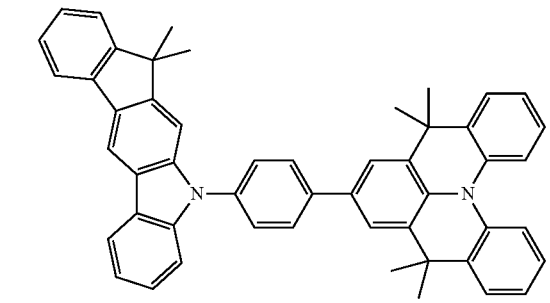 |
| 44<br>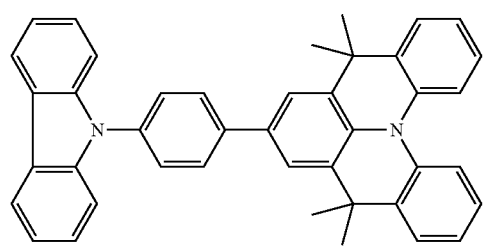 [SMILES: CC1(C)c2ccccc2N2c3ccccc3C(C)(C)c3cc(-c4ccc(-n5c6ccccc6c6ccccc65)cc4)cc1c32] | 48<br>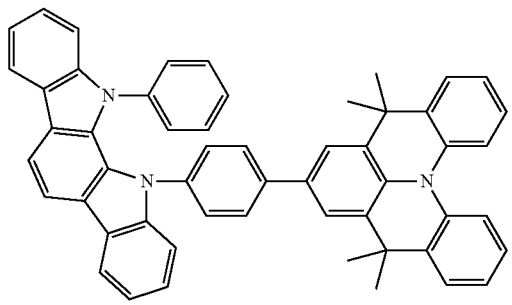 |
| 45<br>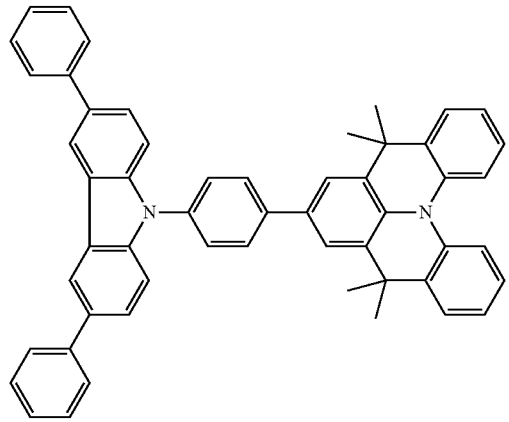 [SMILES: CC1(C)c2ccccc2N2c3ccccc3C(C)(C)c3cc(-c4ccc(-n5c6ccc(-c7ccccc7)cc6c6cc(-c7ccccc7)ccc65)cc4)cc1c32] | 49<br>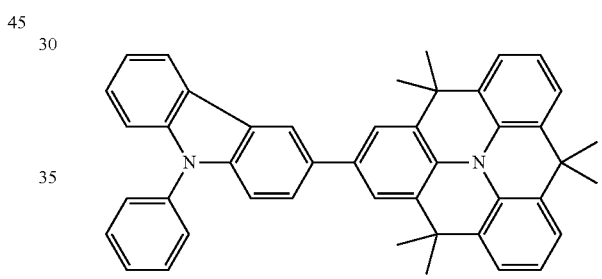 |
| 46<br>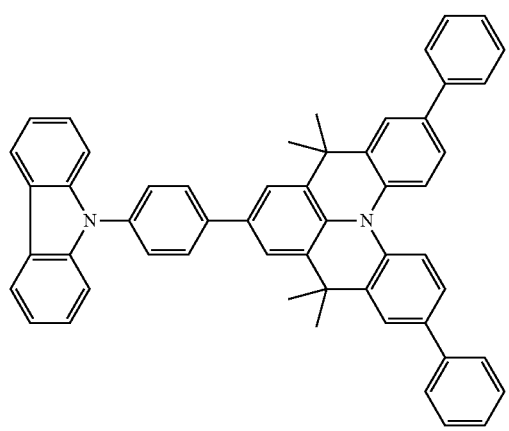 [SMILES: CC1(C)c2cc(-c3ccccc3)ccc2N2c3ccc(-c4ccccc4)cc3C(C)(C)c3cc(-c4ccc(-n5c6ccccc6c6ccccc65)cc4)cc1c32] | 50<br>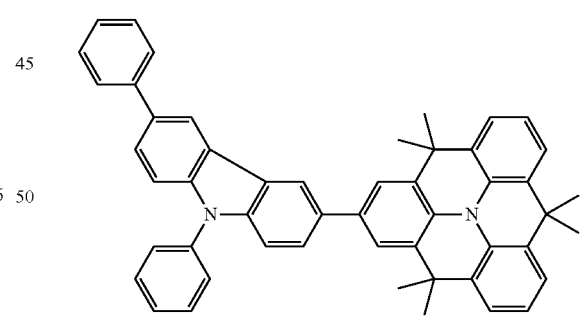<br>51<br>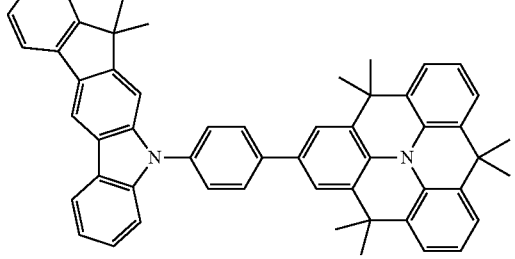 |

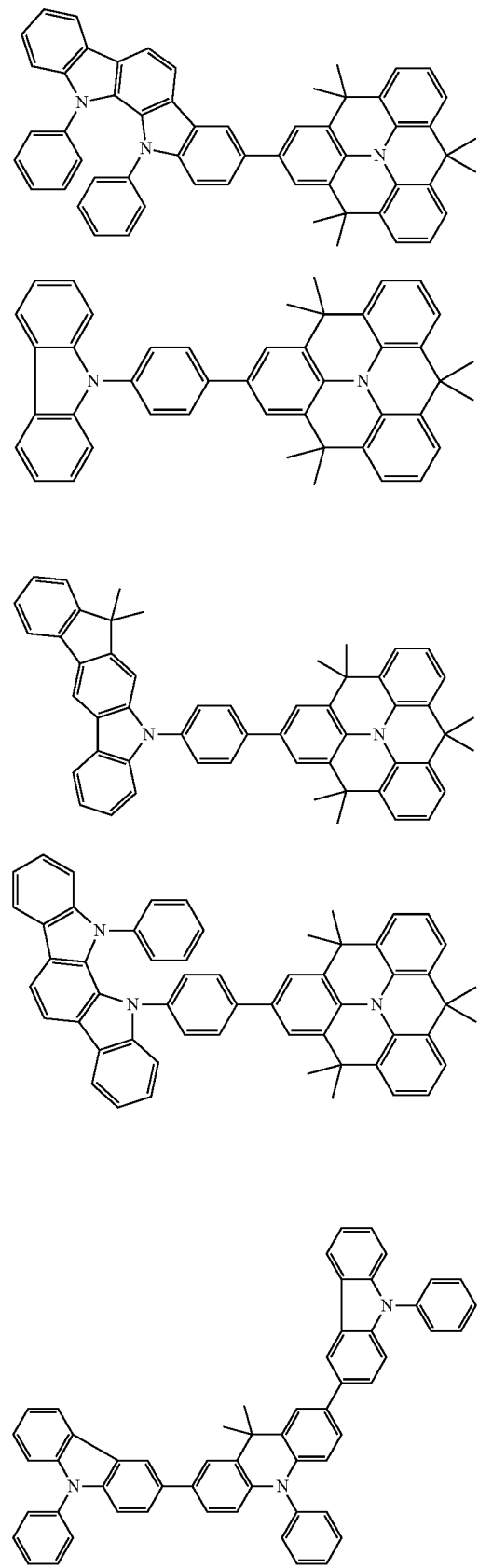
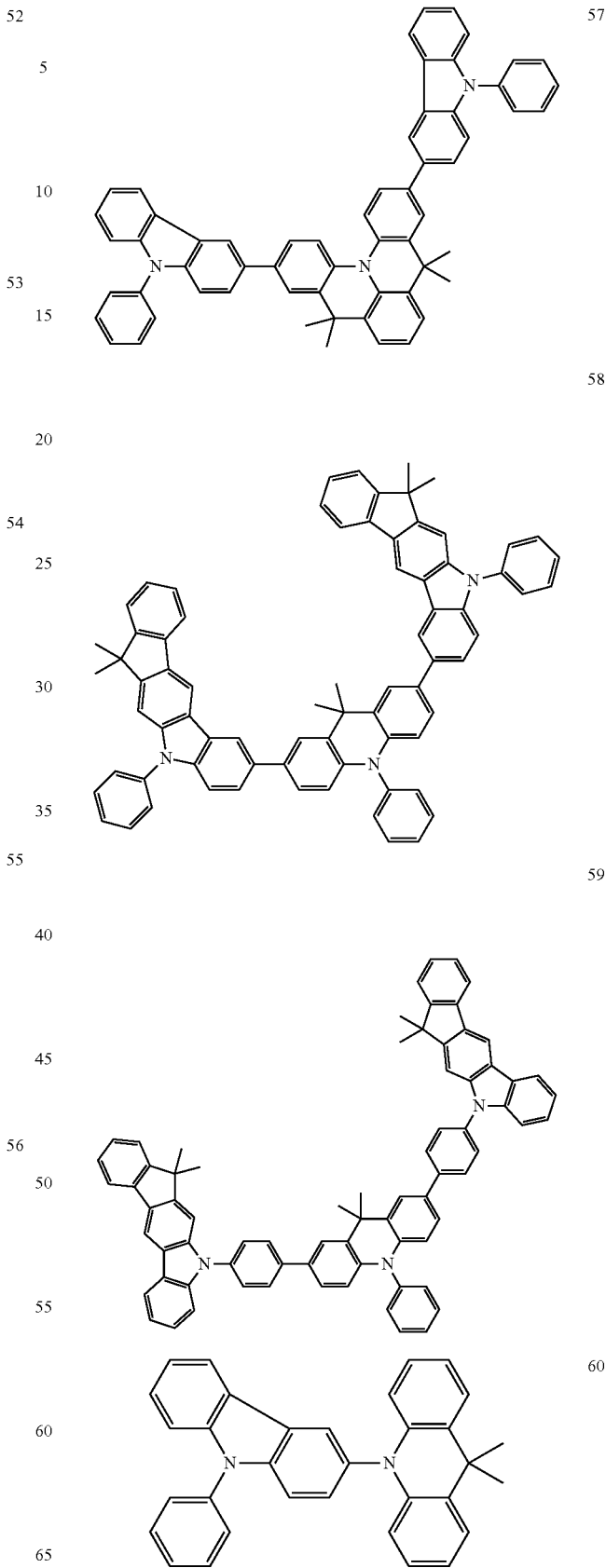

-continued
61
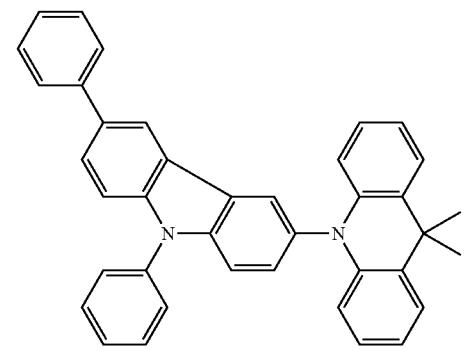 [SMILES: CC1(C)c2ccccc2N(c2ccc3c(c2)c2cc(-c4ccccc4)ccc2n3-c2ccccc2)c2ccccc21]
62
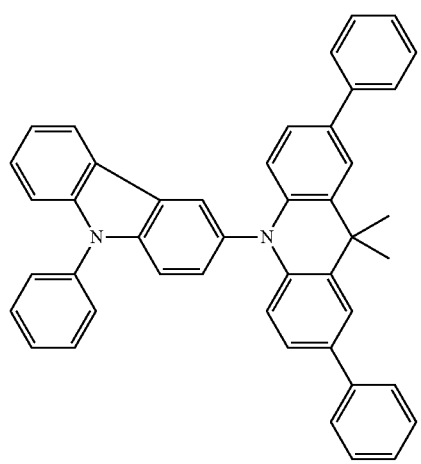 [SMILES: CC1(C)c2cc(-c3ccccc3)ccc2N(c2ccc3c(c2)c2ccccc2n3-c2ccccc2)c2ccc(-c3ccccc3)cc21]
63
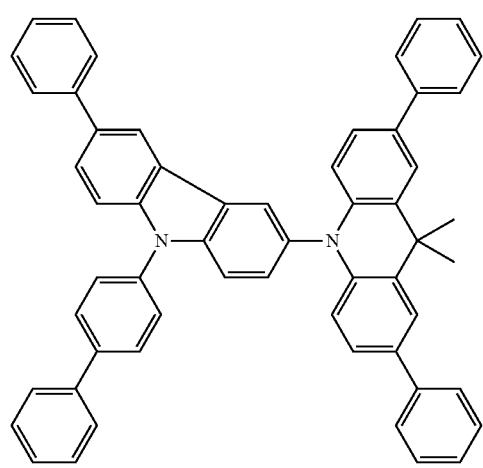 [SMILES: CC1(C)c2cc(-c3ccccc3)ccc2N(c2ccc3c(c2)c2cc(-c4ccccc4)ccc2n3-c2ccc(-c3ccccc3)cc2)c2ccc(-c3ccccc3)cc21]
64
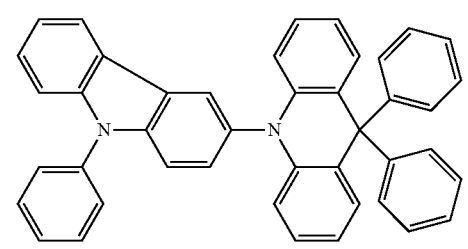 [SMILES: c1ccc(-n2c3ccccc3c3cc(N4c5ccccc5C(c5ccccc5)(c5ccccc5)c5ccccc54)ccc32)cc1]
-continued
65
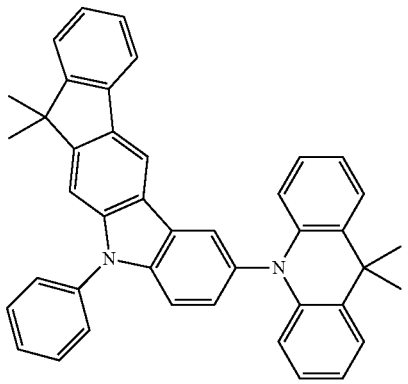 [SMILES: CC1(C)c2ccccc2-c2cc3c4cc(N5c6ccccc6C(C)(C)c6ccccc65)ccc4n(-c4ccccc4)c3cc21]
66
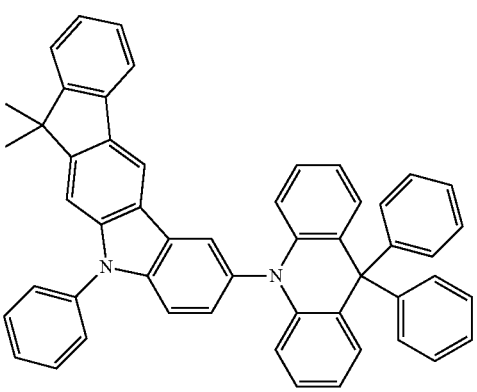 [SMILES: CC1(C)c2ccccc2-c2cc3c4cc(N5c6ccccc6C(c6ccccc6)(c6ccccc6)c6ccccc65)ccc4n(-c4ccccc4)c3cc21]
67
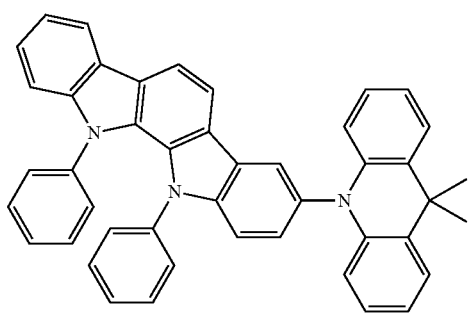 [SMILES: CC1(C)c2ccccc2N(c2ccc3c(c2)c2ccc4c5ccccc5n(-c5ccccc5)c4c2n3-c2ccccc2)c2ccccc21]
68
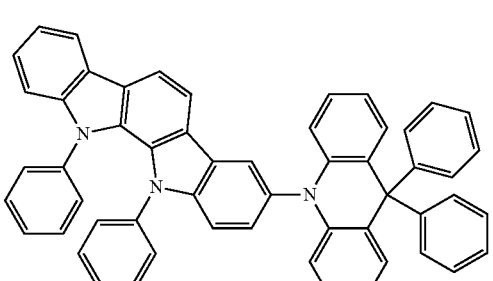
69
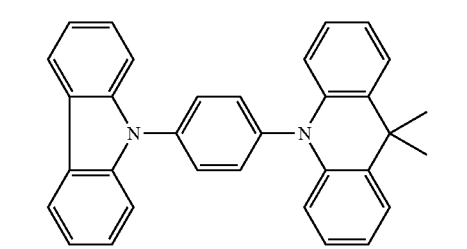 [SMILES: CC1(C)c2ccccc2N(c2ccc(-n3c4ccccc4c4ccccc43)cc2)c2ccccc21]

| 65 -continued | 66 -continued |
|---|---|
| 70<br>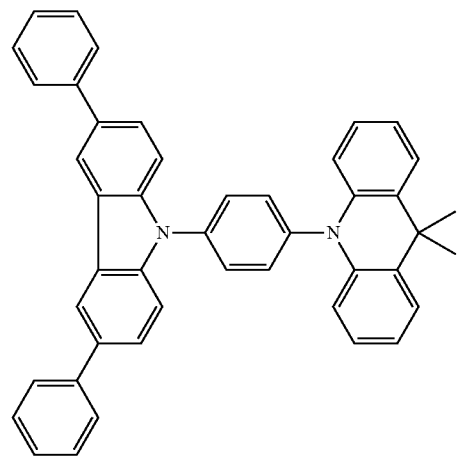 [SMILES: CC1(C)c2ccccc2N(c2ccc(-n3c4ccc(-c5ccccc5)cc4c4cc(-c5ccccc5)ccc43)cc2)c2ccccc21] | 74<br>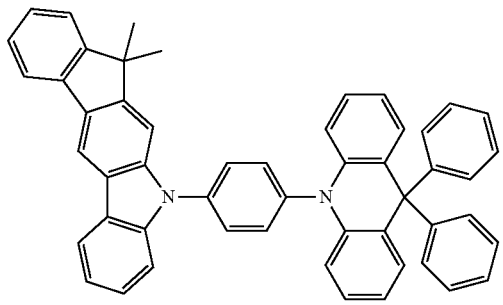 |
| 71<br>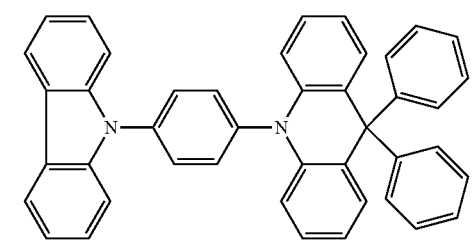 [SMILES: c1ccc(C2(c3ccccc3)c3ccccc3N(c3ccc(-n4c5ccccc5c5ccccc54)cc3)c3ccccc32)cc1] | 75<br>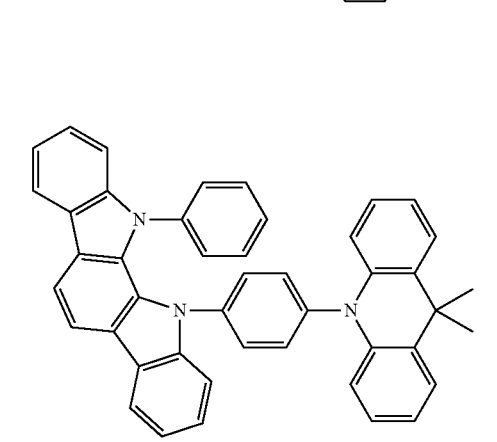 |
| 72<br>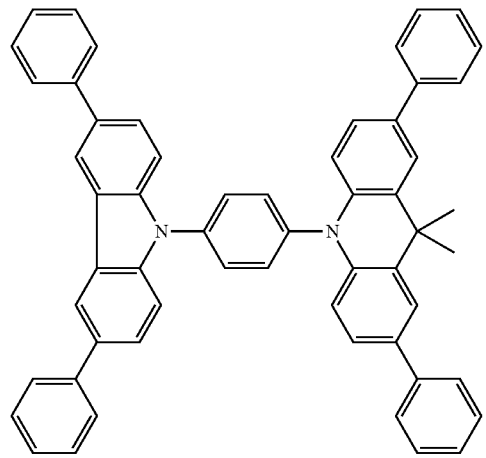 [SMILES: CC1(C)c2cc(-c3ccccc3)ccc2N(c2ccc(-n3c4ccc(-c5ccccc5)cc4c4cc(-c5ccccc5)ccc43)cc2)c2ccc(-c3ccccc3)cc21] | 76<br>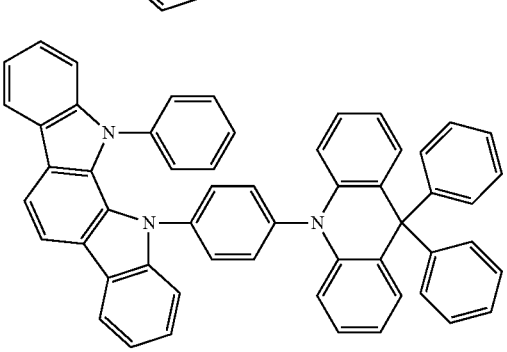 |
| 73<br>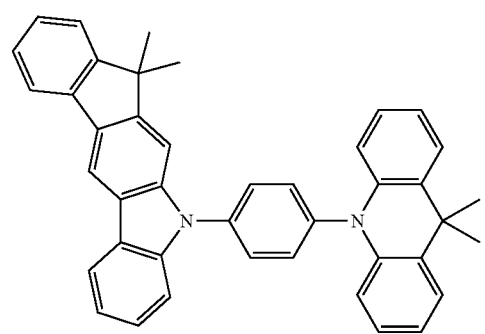 [SMILES: CC1(C)c2ccccc2-c2cc3c4ccccc4n(-c4ccc(N5c6ccccc6C(C)(C)c6ccccc65)cc4)c3cc21] | 77<br>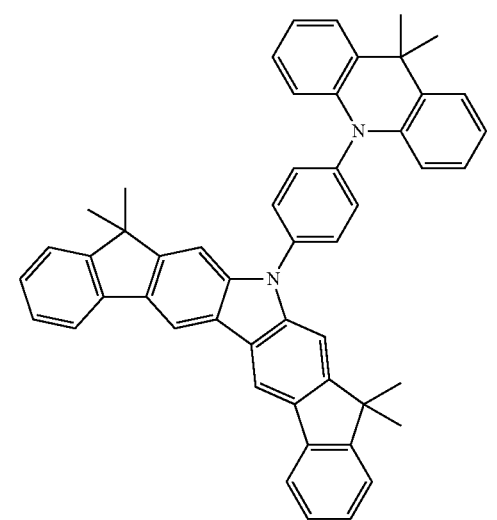 [SMILES: CC1(C)c2ccccc2-c2cc3c4cc5c(cc4n(-c4ccc(N6c7ccccc7C(C)(C)c7ccccc76)cc4)c3cc21)C(C)(C)c1ccccc1-5] |

78
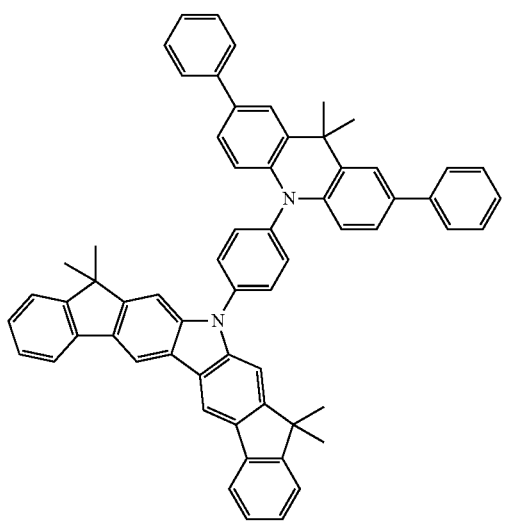 [SMILES: CC1(C)c2ccccc2-c2cc3c4cc5c(cc4n(-c4ccc(N6c7ccc(-c8ccccc8)cc7C(C)(C)c7cc(-c8ccccc8)ccc76)cc4)c3cc21)C(C)(C)c1ccccc1-5]
79
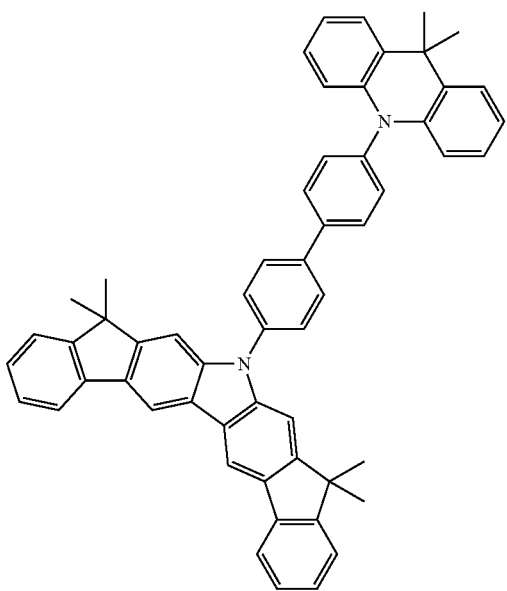 [SMILES: CC1(C)c2ccccc2-c2cc3c4cc5c(cc4n(-c4ccc(-c6ccc(N7c8ccccc8C(C)(C)c8ccccc87)cc6)cc4)c3cc21)C(C)(C)c1ccccc1-5]
80
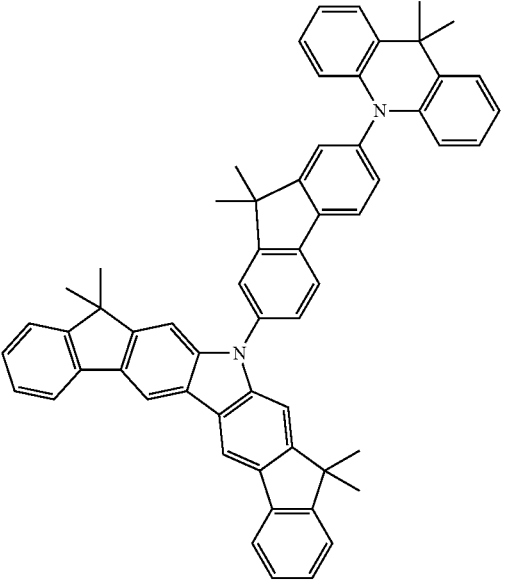 [SMILES: CC1(C)c2cc(N3c4ccccc4C(C)(C)c4ccccc43)ccc2-c2ccc(-n3c4cc5c(cc4c4cc6c(cc43)C(C)(C)c3ccccc3-6)-c3ccccc3C5(C)C)cc21]
81
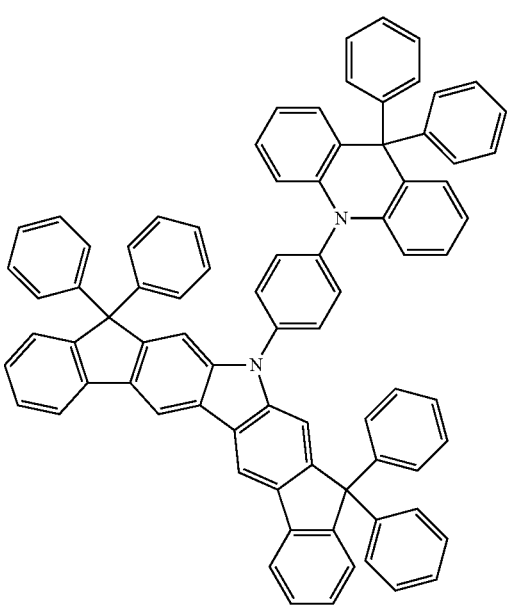 [SMILES: c1ccc(C2(c3ccccc3)c3ccccc3-c3cc4c5cc6c(cc5n(-c5ccc(N7c8ccccc8C(c8ccccc8)(c8ccccc8)c8ccccc87)cc5)c4cc32)C(c2ccccc2)(c2ccccc2)c2ccccc2-6)cc1]

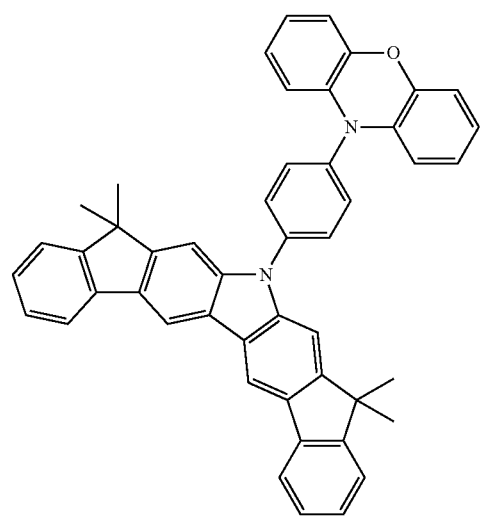 [SMILES: CC1(C)c2ccccc2-c2cc3c4cc5c(cc4n(-c4ccc(N6c7ccccc7Oc7ccccc76)cc4)c3cc21)C(C)(C)c1ccccc1-5]
82
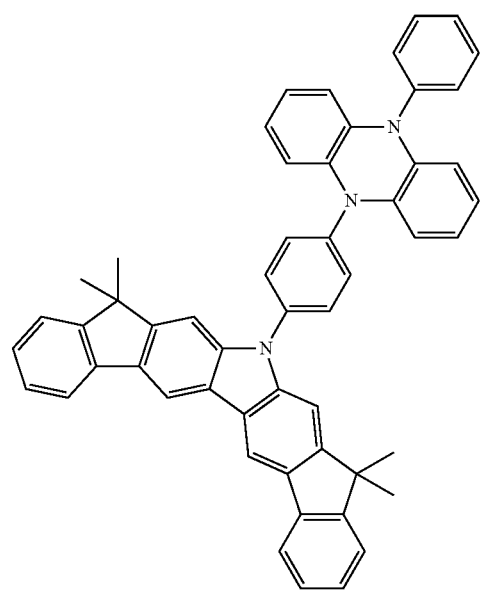 [SMILES: CC1(C)c2ccccc2-c2cc3c4cc5c(cc4n(-c4ccc(N6c7ccccc7N(c7ccccc7)c7ccccc76)cc4)c3cc21)C(C)(C)c1ccccc1-5]
83
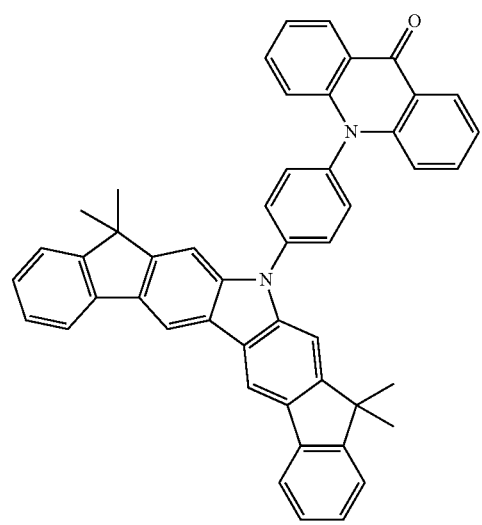 [SMILES: CC1(C)c2ccccc2-c2cc3c4cc5c(cc4n(-c4ccc(-n6c7ccccc7c(=O)c7ccccc76)cc4)c3cc21)C(C)(C)c1ccccc1-5]
84
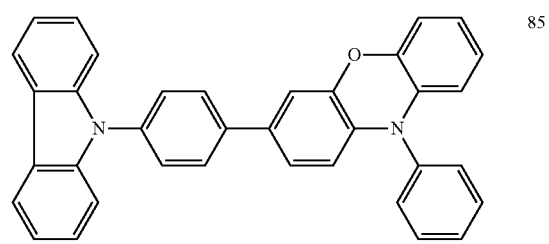
85
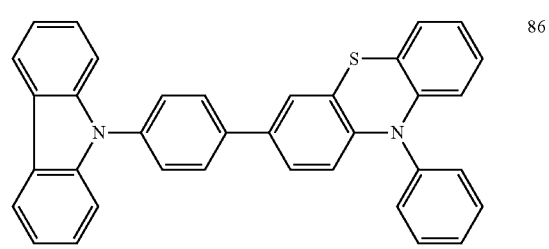
86
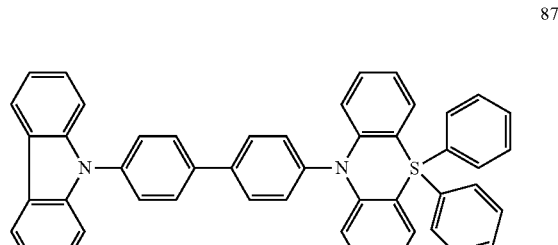
87
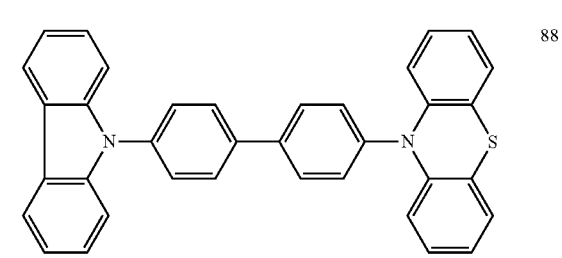
88
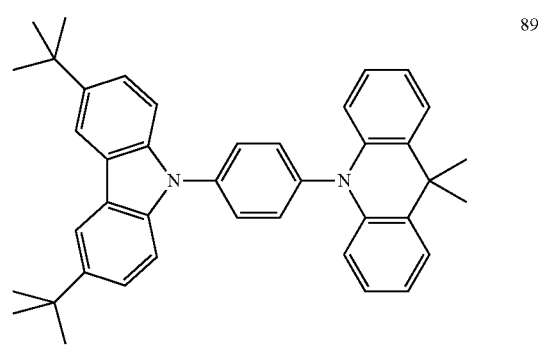
89
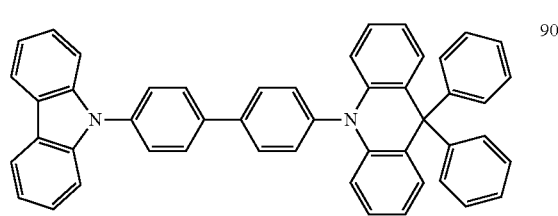
90

-continued
91
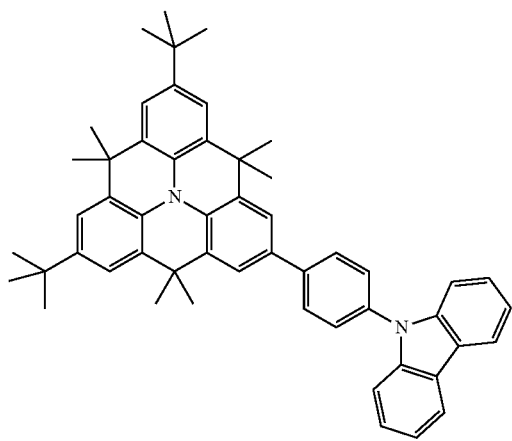 [SMILES: CC(C)(C)c1cc2c3c(c1)C(C)(C)c1cc(C(C)(C)C)cc4c1N3c1c(cc(-c3ccc(-n5c6ccccc6c6ccccc65)cc3)cc1C4(C)C)C2(C)C]
92
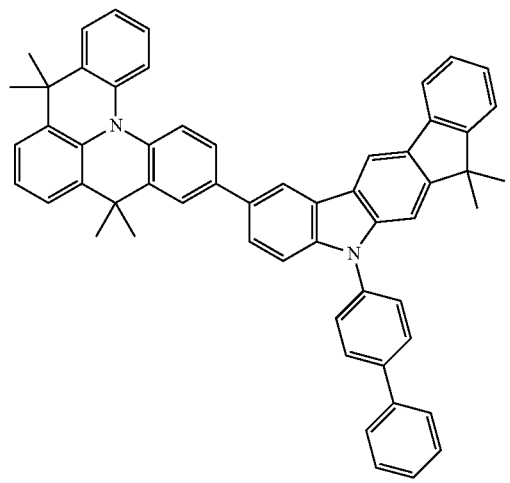
93
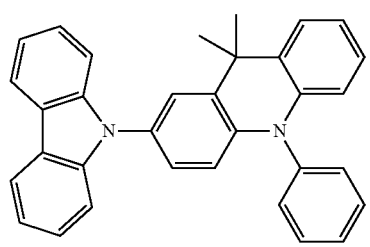 [SMILES: CC1(C)c2ccccc2N(c2ccccc2)c2ccc(-n3c4ccccc4c4ccccc43)cc21]
94
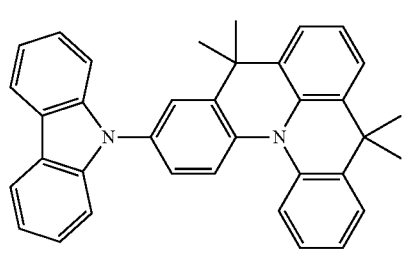 [SMILES: CC1(C)c2ccccc2N2c3ccc(-n4c5ccccc5c5ccccc54)cc3C(C)(C)c3cccc1c32]
-continued
95
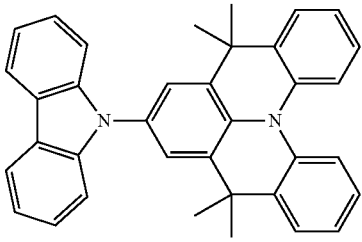 [SMILES: CC1(C)c2ccccc2N2c3ccccc3C(C)(C)c3cc(-n4c5ccccc5c5ccccc54)cc1c32]
96
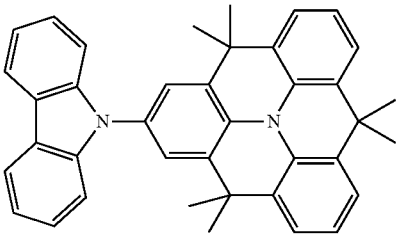 [SMILES: CC1(C)c2cccc3c2N2c4c1cccc4C(C)(C)c1cc(-n4c5ccccc5c5ccccc54)cc(c12)C3(C)C]
97
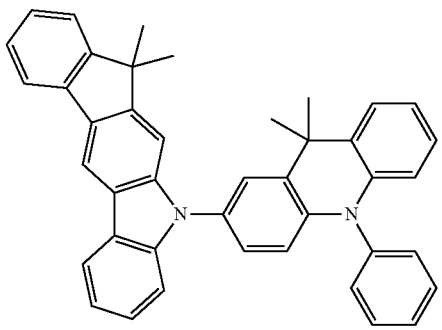 [SMILES: CC1(C)c2ccccc2-c2cc3c4ccccc4n(-c4ccc5c(c4)C(C)(C)c4ccccc4N5c4ccccc4)c3cc21]
98
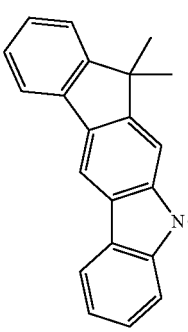
99
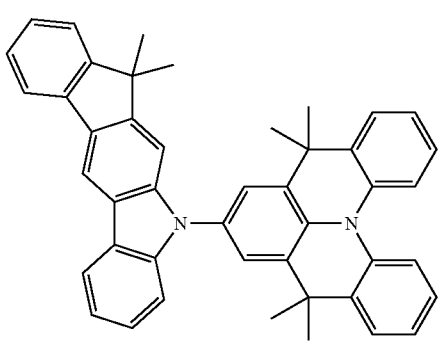 [SMILES: CC1(C)c2ccccc2-c2cc3c4ccccc4n(-c4cc5c6c(c4)C(C)(C)c4ccccc4N6c4ccccc4C5(C)C)c3cc21]

73
-continued
100
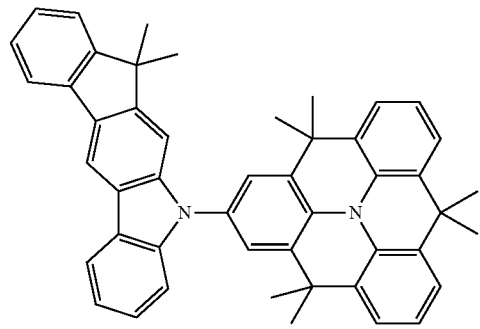 [SMILES: CC1(C)c2ccccc2-c2cc3c4ccccc4n(-c4cc5c6c(c4)C(C)(C)c4cccc7c4N6c4c(cccc4C5(C)C)C7(C)C)c3cc21]
101
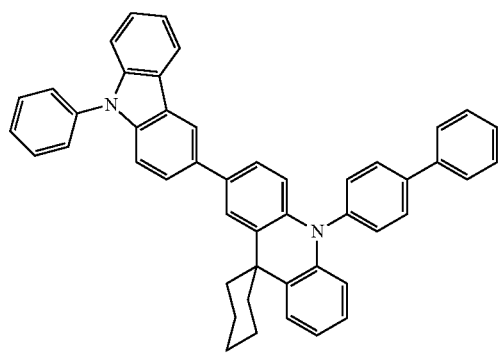 [SMILES: c1ccc(-c2ccc(N3c4ccccc4C4(CCCCC4)c4cc(-c5ccc6c(c5)c5ccccc5n6-c5ccccc5)ccc43)cc2)cc1]
102
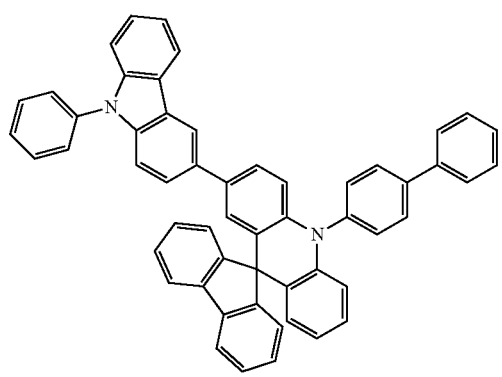 [SMILES: c1ccc(-c2ccc(N3c4ccccc4C4(c5ccccc5-c5ccccc54)c4cc(-c5ccc6c(c5)c5ccccc5n6-c5ccccc5)ccc43)cc2)cc1]
103
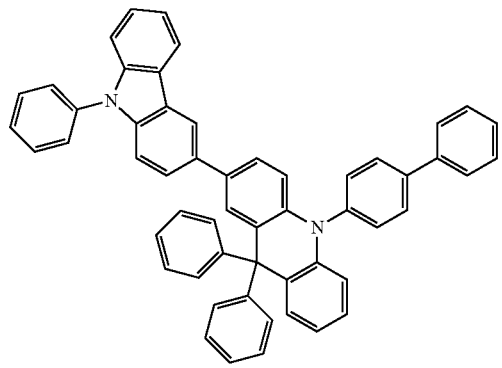 [SMILES: c1ccc(-c2ccc(N3c4ccccc4C(c4ccccc4)(c4ccccc4)c4cc(-c5ccc6c(c5)c5ccccc5n6-c5ccccc5)ccc43)cc2)cc1]
74
-continued
104
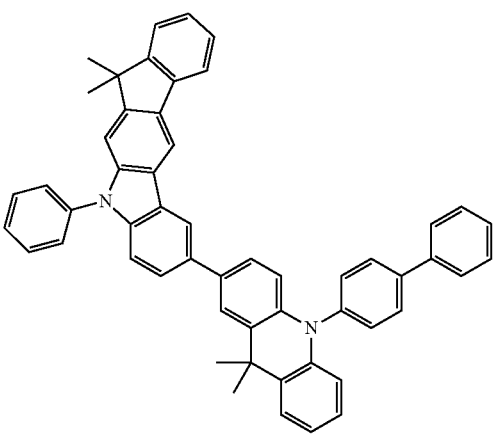 [SMILES: CC1(C)c2ccccc2-c2cc3c4cc(-c5ccc6c(c5)C(C)(C)c5ccccc5N6c5ccc(-c6ccccc6)cc5)ccc4n(-c4ccccc4)c3cc21]
105
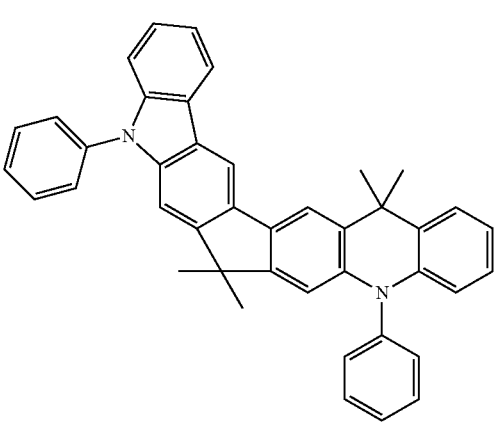 [SMILES: CC1(C)c2cc3c(cc2-c2cc4c5ccccc5n(-c5ccccc5)c4cc21)C(C)(C)c1ccccc1N3c1ccccc1]
106
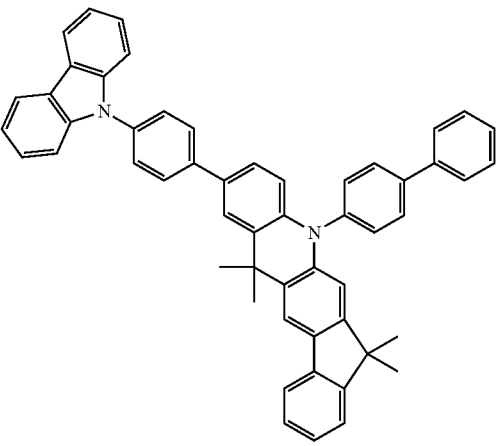 [SMILES: CC1(C)c2ccccc2-c2cc3c(cc21)N(c1ccc(-c2ccccc2)cc1)c1ccc(-c2ccc(-n4c5ccccc5c5ccccc54)cc2)cc1C3(C)C]
107
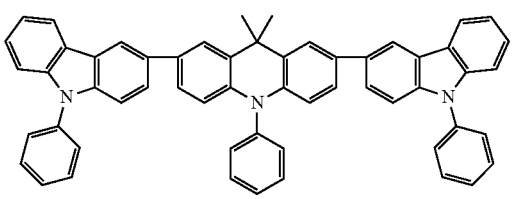 [SMILES: CC1(C)c2cc(-c3ccc4c(c3)c3ccccc3n4-c3ccccc3)ccc2N(c2ccccc2)c2ccc(-c3ccc4c(c3)c3ccccc3n4-c3ccccc3)cc21]

-continued
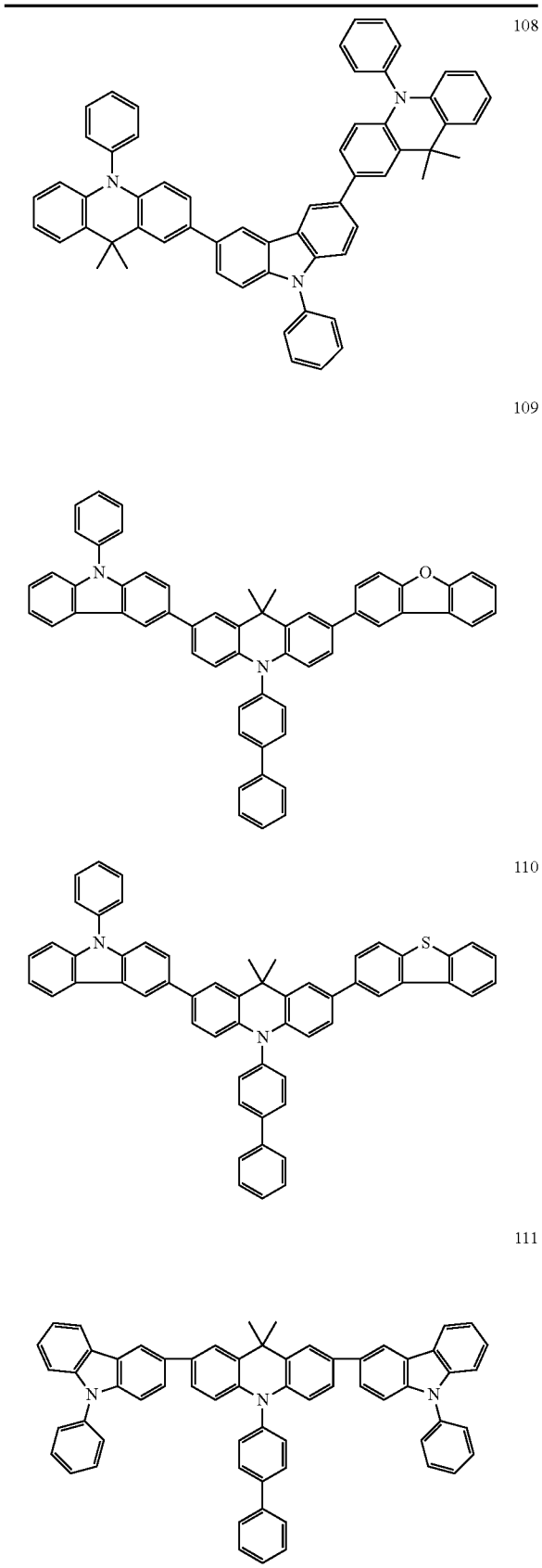
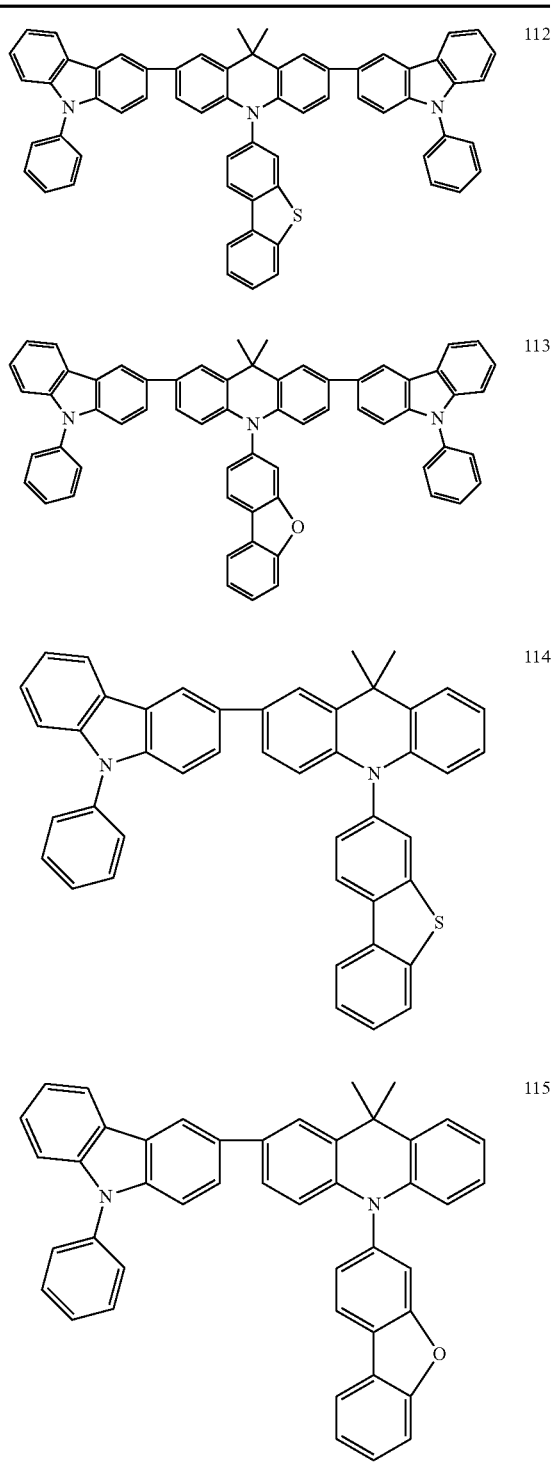
The compounds according to the invention can be prepared by synthetic steps which are known to the person skilled in the art, such as, for example, bromination, Suzuki coupling, Hartwig-Buchwald coupling, etc.
Examples of synthetic routes which lead to the compounds according to the invention will be shown below. The radical R here is as defined above.

Scheme 1

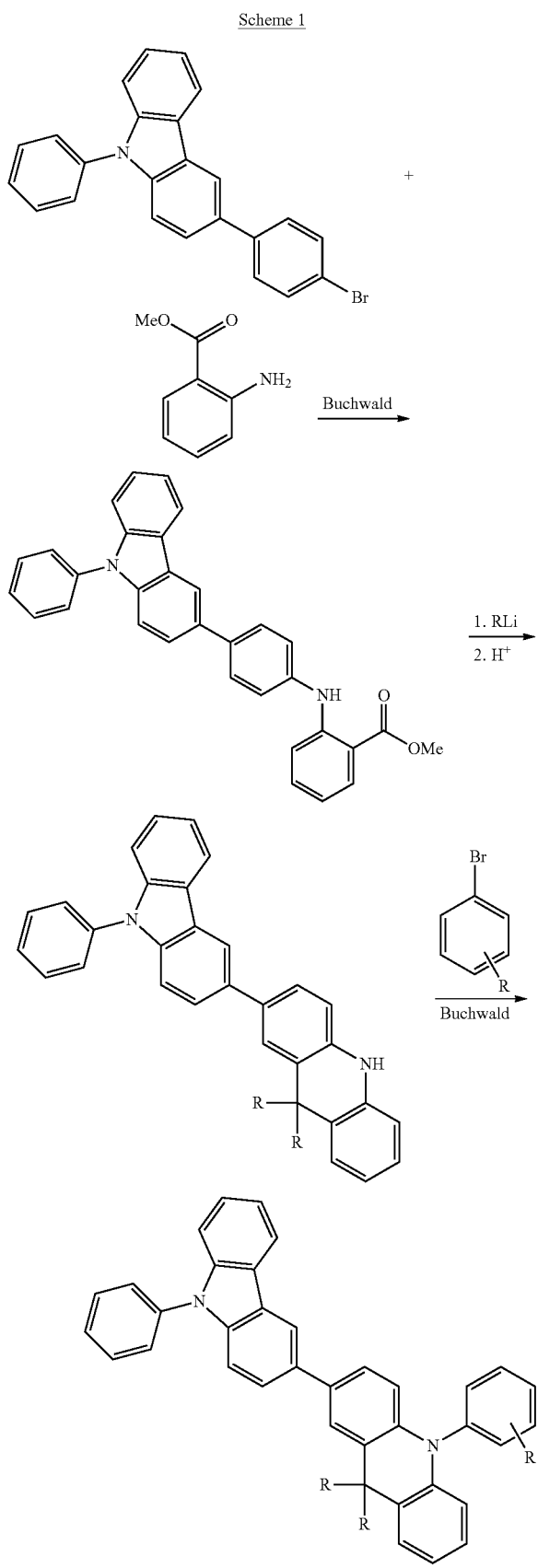

In Scheme 1, the carbazole derivative shown (CAS 1028647-93-9) is firstly reacted with a carboxylate-substituted arylamine in a Buchwald coupling. A cyclisation reaction is subsequently carried out after the addition reaction of two groups R by means of an organolithium reagent. The bridge is thus introduced via a divalent group —C(R)$_2$—. A substituent can subsequently be introduced on the free amino function of the resultant piperidine derivative via a Buchwald coupling.

The synthesis of N-aryl-substituted carbazole derivatives, which is shown in Scheme 2, proceeds substantially analogously. The starting compound is the N-arylcarbazole derivative shown below (CAS 212385-73-4).

Scheme 2

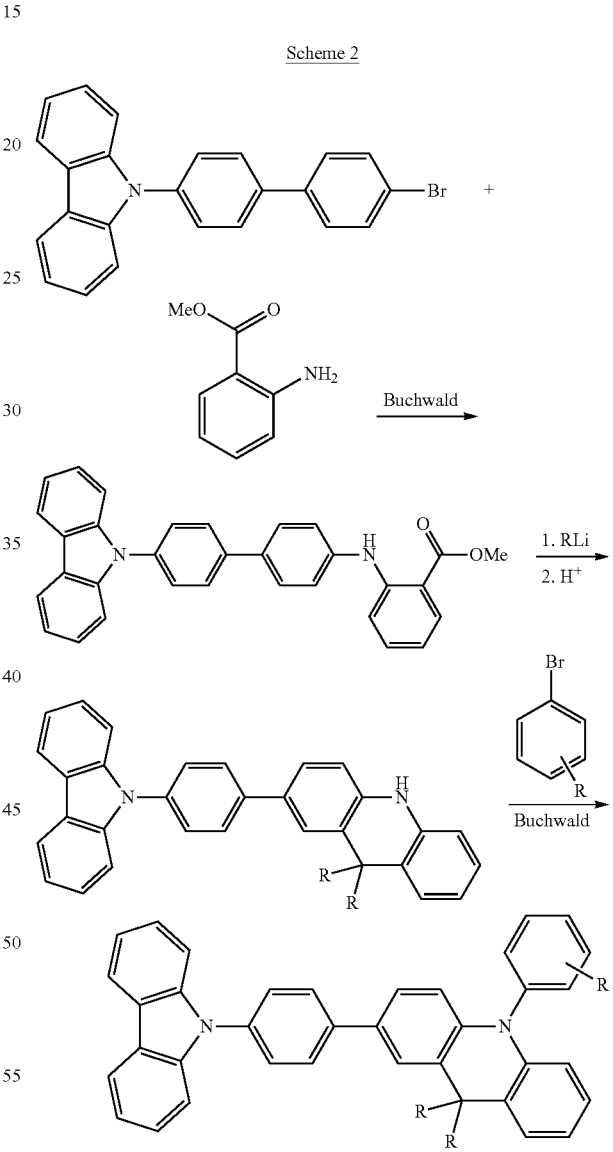

The divalent bridging group C(R)$_2$ may also be localised at another position in the compounds according to the invention. An example thereof is provided by Scheme 3a. To this end, the synthesis starts directly from a 9,10-dihydroacridine derivative, which can be reacted with a 3-bromine-substituted carbazole in a Buchwald coupling.

Alternatively, the reaction can also be carried out with an N-aryl-substituted carbazole, as shown by Scheme 3b.

Scheme 3
a)
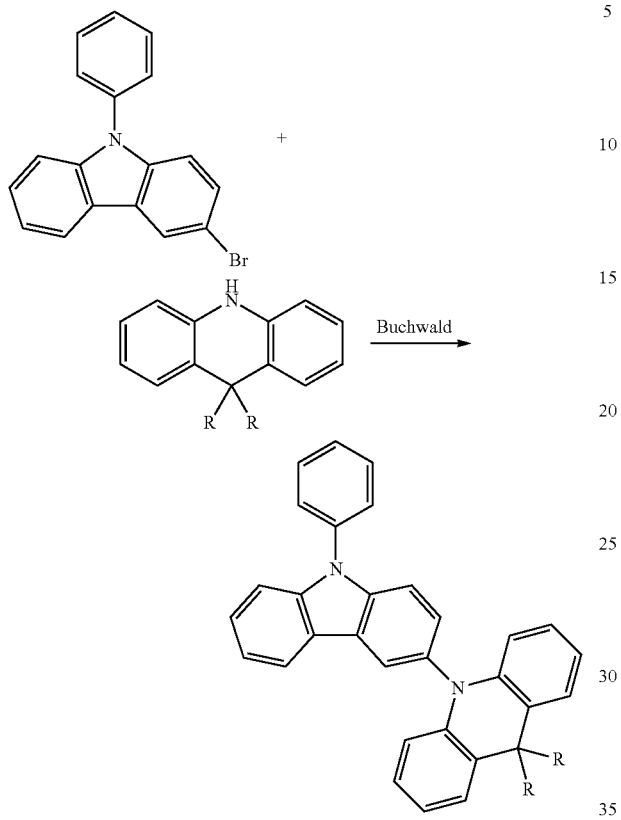
b)
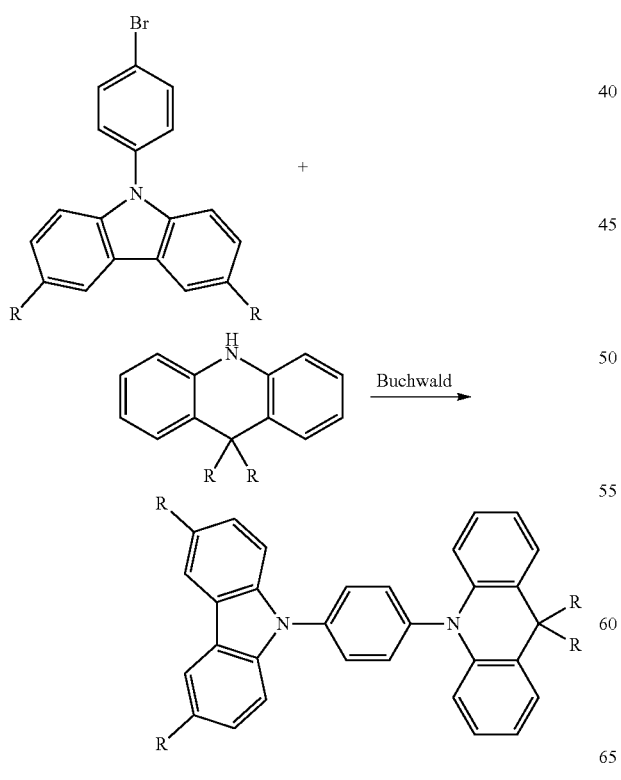
Arylamine derivatives which are multiply bridged by divalent groups can also be reacted with the carbazole derivatives shown. This gives compounds according to the invention in which two or three groups L are present.
The synthesis of two precursors of this type which contain two groups L is shown in Scheme 4a and b.
Scheme 4
a)
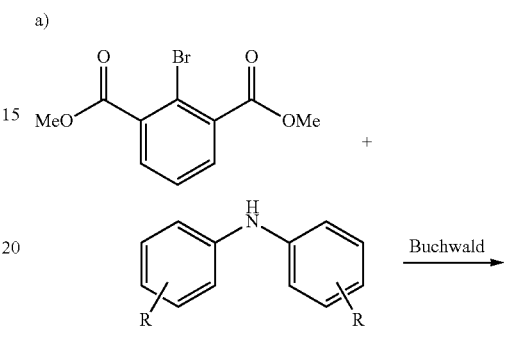
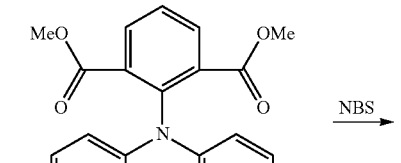
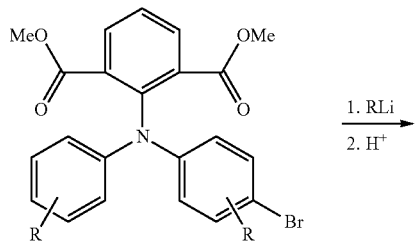
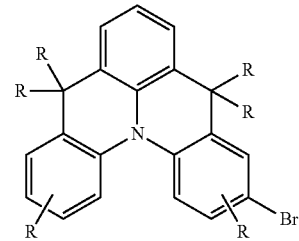
b)
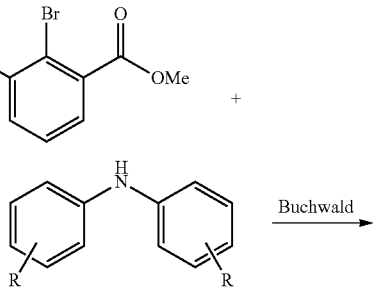

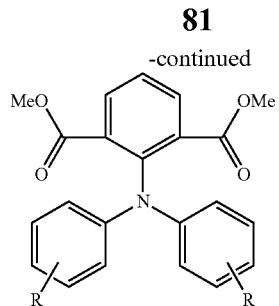

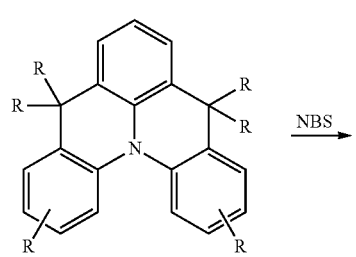

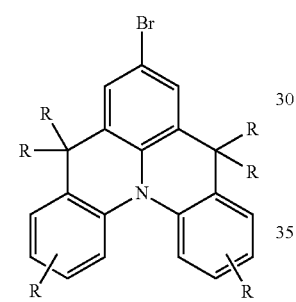

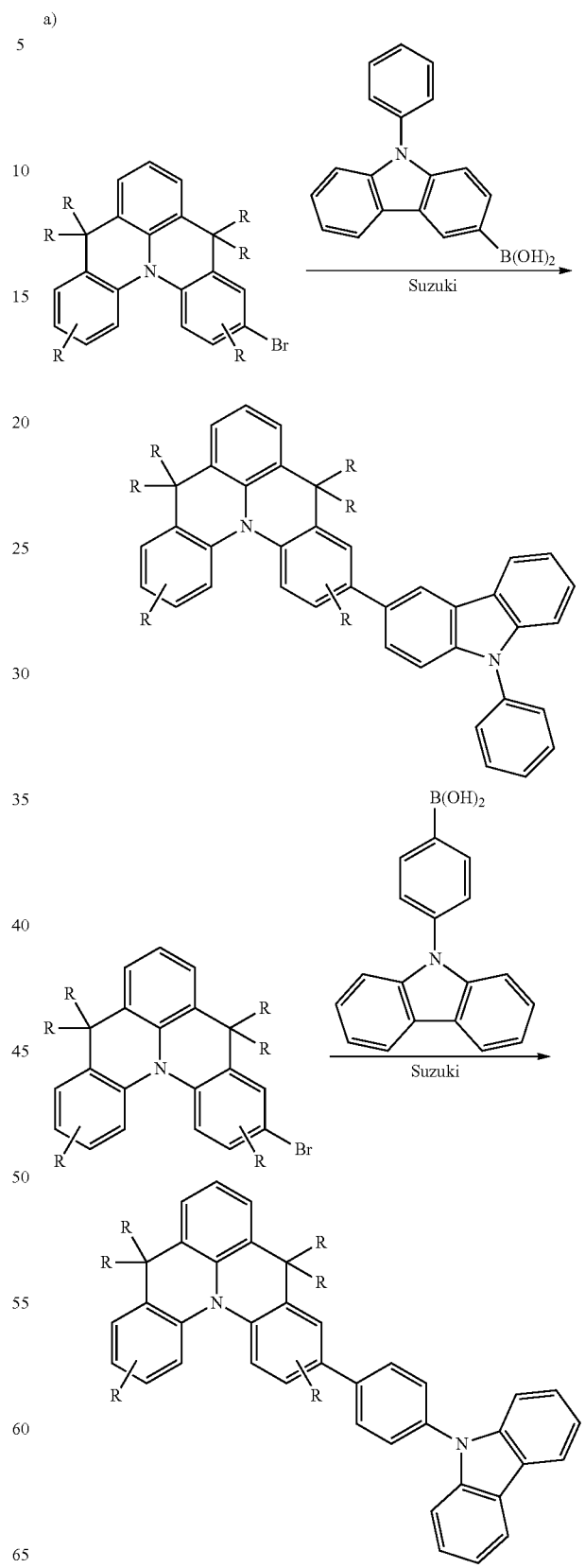

Scheme 5

The divalent groups —C(R)$_2$— are in this case obtained again by the addition of organolithium compounds onto the aromatic carboxylate group with subsequent acid-catalysed cyclisation.

It is furthermore possible to prepare compounds which are analogous to the compounds shown in Scheme 4, but which contain one or more bridging groups such as, for example, O, S or SO$_2$ instead of one or more bridging groups —CR$_2$—. As shown in the synthesis examples, the unbrominated starting compounds are in many cases commercially available.

The synthesis of triarylamine compounds which contain three bridging groups L (for example —CR$_2$— and —O—) is disclosed in the application WO 2007/031165.

Scheme 5a shows the synthesis of compounds according to the invention starting from the doubly bridged triarylamine precursor shown in Scheme 4a. Schemes 5b and 5c show analogously the synthesis of compounds according to the invention starting from the doubly bridged triarylamine precursor shown in Scheme 4 or starting from triarylamine compounds which contain three bridging groups L. Suzuki coupling reactions starting from boronic acid-substituted carbazole derivatives are employed here. Processes for the synthesis of boronic acid derivatives from the corresponding bromine-substituted derivatives are known to the person skilled in the art.

b)

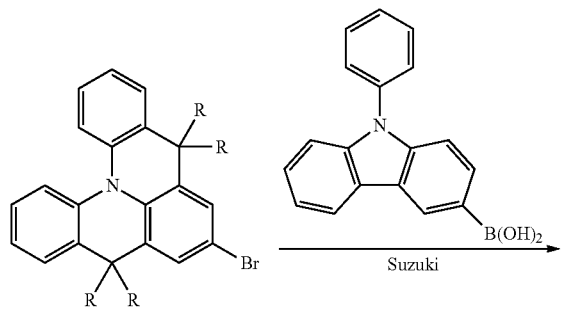

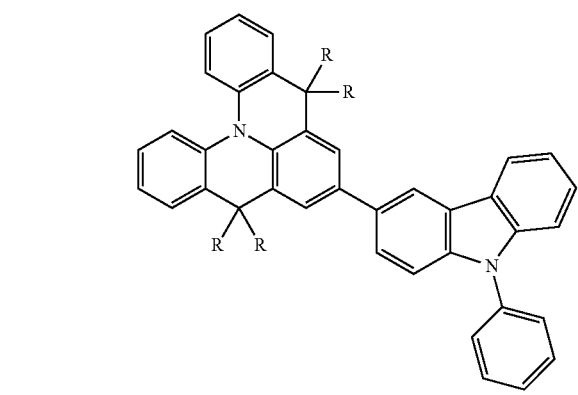

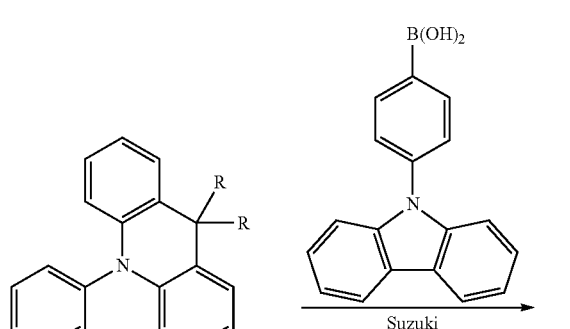

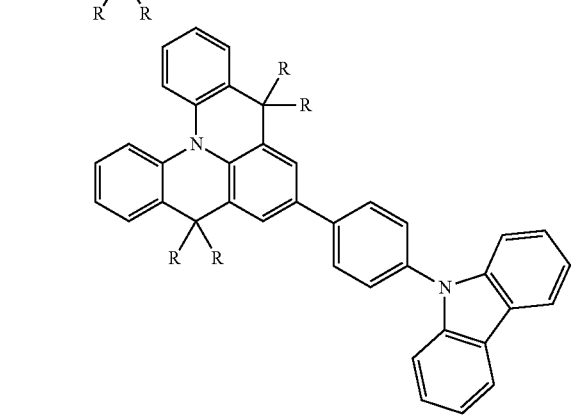

c)

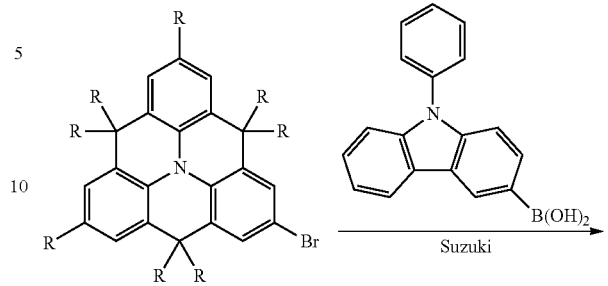

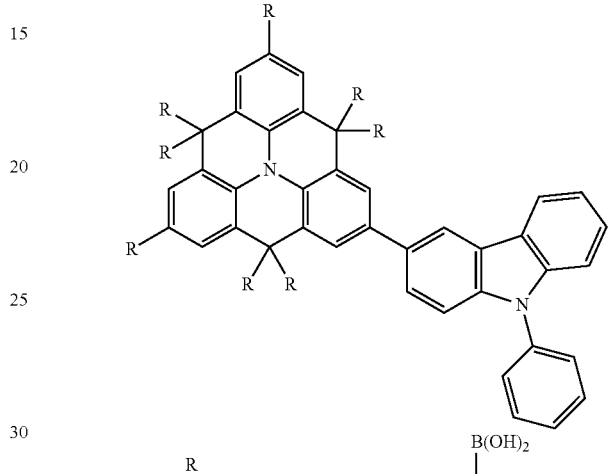

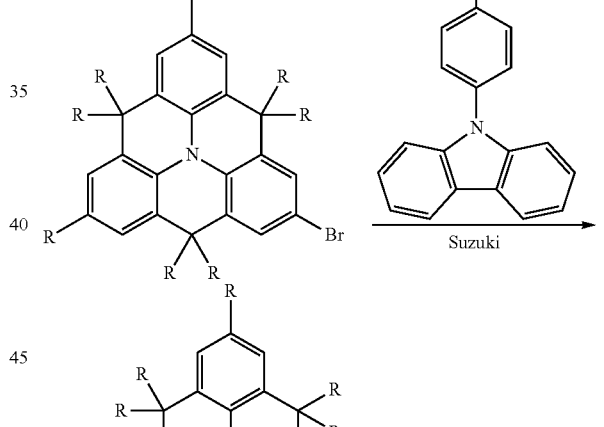

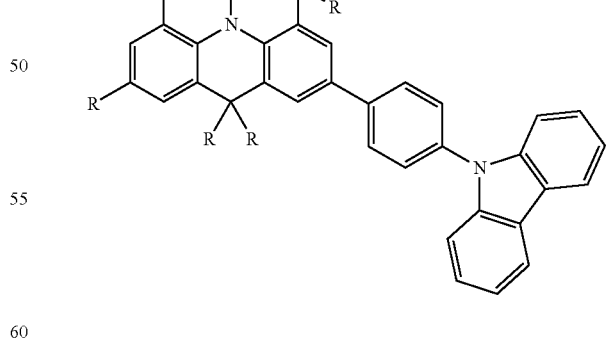

Instead of the starting compounds shown above, it is also possible analogously to employ compounds which contain one or more bridging groups such as, for example, O, S or SO$_2$ instead of the groups CR$_2$ shown above.

It is also possible to use the corresponding indeno- or indolocarbazole derivatives instead of the carbazole derivatives employed in the above schemes.

Examples of corresponding indeno- and indolocarbazole derivatives are shown in Scheme 6 below.

Scheme 6

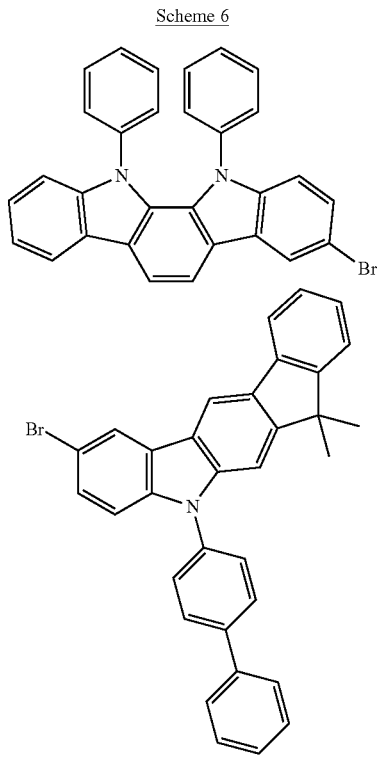

The synthesis of indenocarbazole derivatives, which can be employed as intermediates in the synthesis of the compounds according to the invention, is described, inter alia, in the application WO 2010/083873 and in the as yet unpublished applications DE 102009023155.2 and DE 102009031021.5. Furthermore, the synthesis of the indeno- or indolocarbazole derivatives may be known from the literature, such as, for example, in the case of the indolocarbazole depicted on the left in Scheme 6 (CAS 222044-88-4 for the unbrominated derivative).

The indeno- and indolocarbazole-based compounds according to the invention can in principle be prepared by the same synthetic routes as the corresponding carbazole-based compounds according to the invention by replacing the carbazole derivatives serving as Intermediates by corresponding indeno- or Indolocarbazole derivatives (cf. Schemes 1-5).

The present invention thus relates to a process for the preparation of compounds of the formula (1) or (2), comprising at least one coupling reaction for the linking of the moiety containing the carbazole group to the moiety containing the arylamino group. In a preferred embodiment of this process, a Suzuki, Hartwig-Buchwald, Stille or Yamamoto coupling is employed for the linking of the two moieties. Particularly preferred embodiments of processes for the preparation of the compounds according to the invention are the processes depicted in the schemes above.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (1) or (2), where the bond(s) to the polymer, oligomer or dendrimer may be localised at any desired positions substituted by R in formula (1) or (2). Depending on the linking of the compound of the formula (1) or (2), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (1) or (2) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (1) or (2) may, for example, be linked via a trivalent or polyvalent group, for example via a trivalent or polyvalent aromatic or heteroaromatic group, to give a branched or dendritic oligomer or polymer. For the recurring units of the formula (1) or (2) in oligomers, dendrimers and polymers, the same preferences apply as described above for compounds of the formula (1) or (2).

For the preparation of the oligomers or polymers, the monomers according to the invention are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689 or WO 07/006383), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (1) or (2) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 02/067343 A1 and WO 2005/026144 A1.

The invention also relates to formulations comprising at least one compound of the formula (1) or (2) or at least one polymer, oligomer or dendrimer containing at least one unit of the formula (1) or (2) and at least one solvent, preferably an organic solvent.

The formulations according to the invention are used, for example, in the production of organic electroluminescent devices, which is described in greater detail in a following section.

The compounds of the formula (1) or (2) according to the invention are suitable for use in electronic devices, in particular in organic electroluminescent devices (OLEDs). Depending on the substitution, the compounds are employed in various functions and in various layers of the organic electroluminescent device.

The invention therefore furthermore relates to the use of the compounds of the formula (1) or (2) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

Particular preference is given to organic electroluminescent devices comprising an anode, a cathode and at least one emitting layer, characterised in that at least one organic layer, which may be an emitting layer, a hole-transport layer or another layer, comprises at least one compound of the formula (1) or (2).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue and yellow, orange or red light are used in the emitting layers. Particular preference is given to three-layer systems, i.e. systems having three emitting layers, where at least one of these layers comprises at least one compound of the formula (1) or (2) and where the three layers exhibit blue, green and orange or red emission (for the basic structure see, for example, WO 2005/011013). Alternatively and/or additionally, the compounds according to the invention may also be present in the hole-transport layer. Emitters which have broad-band emission bands and thus exhibit white emission are likewise suitable for white emission.

It is preferred in accordance with the invention for the compound of the formula (1) or (2) to be employed in an electronic device comprising one or more phosphorescent dopants. The compound here can be used in various layers, preferably in a hole-transport layer, a hole-injection layer or in the emitting layer. However, the compound of the formula (1) or (2) can also be employed in accordance with the invention in an electronic device comprising one or more fluorescent dopants.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or Cu.

For the purposes of the present invention, all luminescent iridium, platinum or copper complexes are regarded as phosphorescent compounds.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (1) or (2) according to the invention in organic electroluminescent devices.

Examples of suitable phosphorescent emitter compounds are furthermore revealed by the following table:

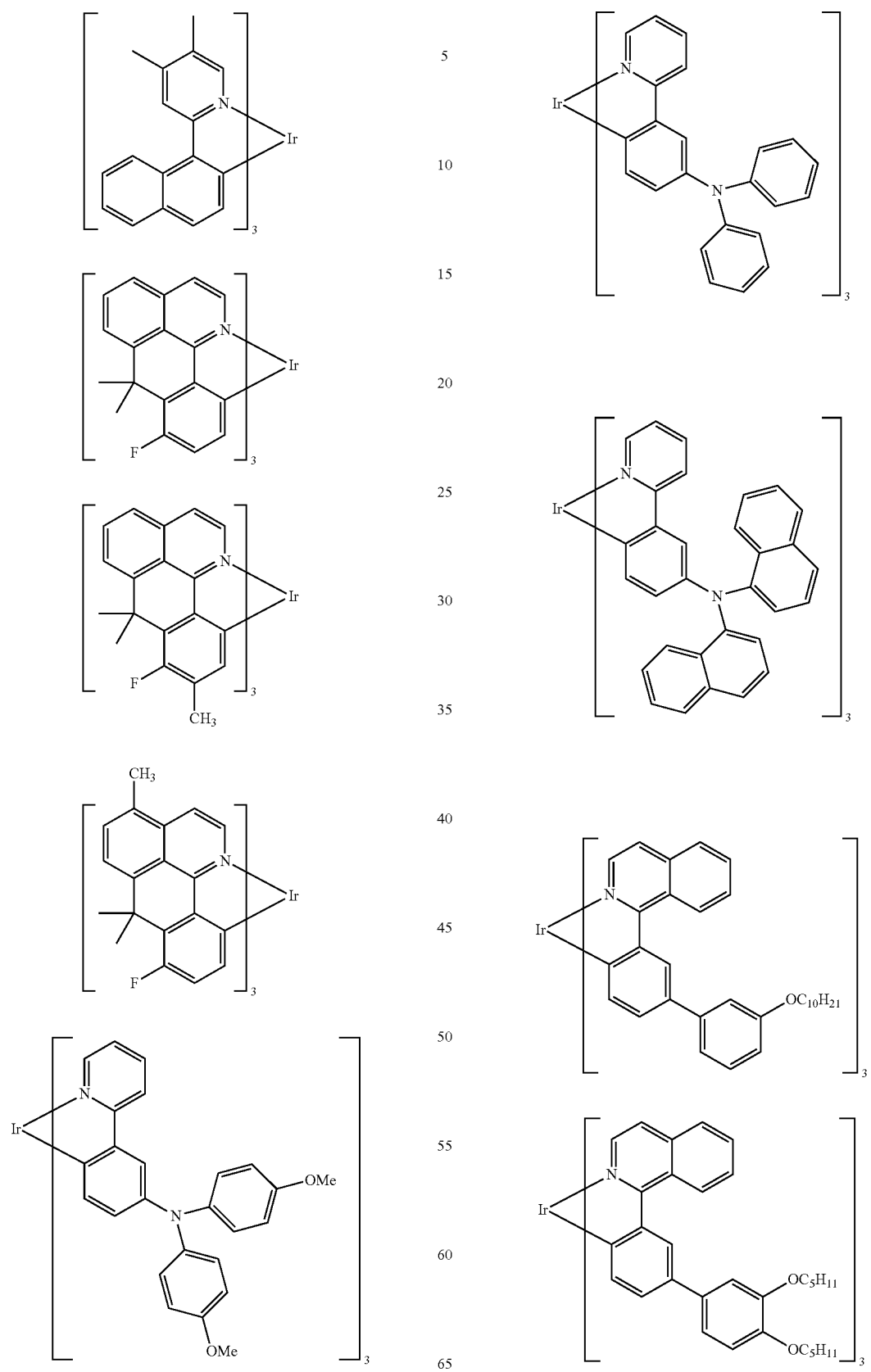

-continued
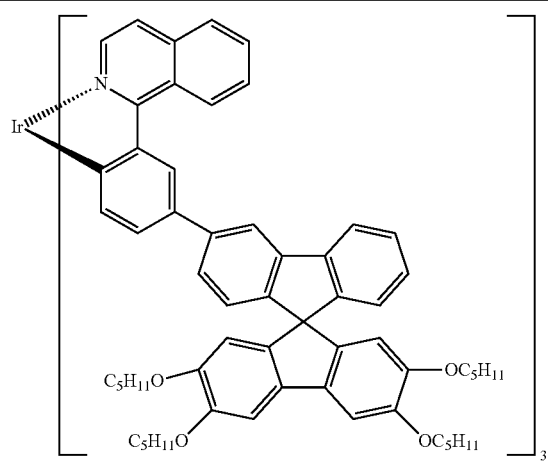
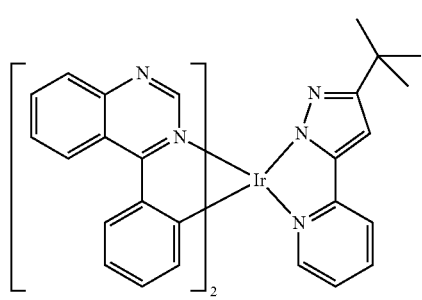
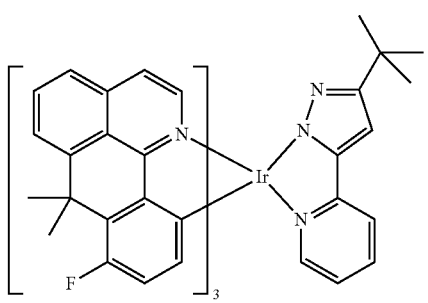
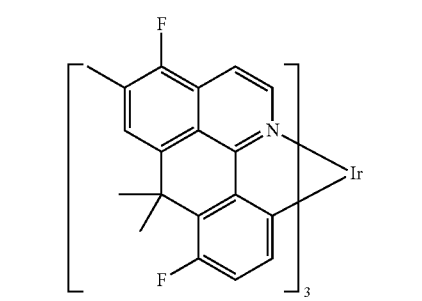
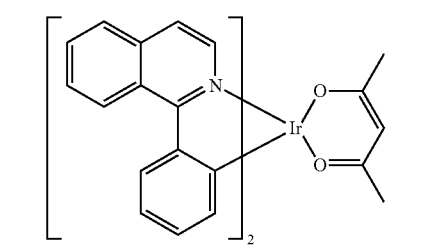
-continued
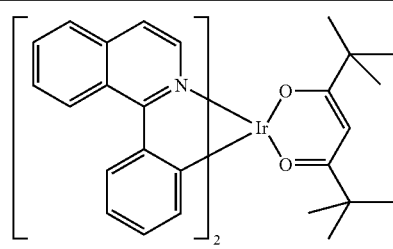
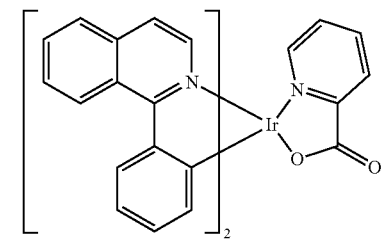
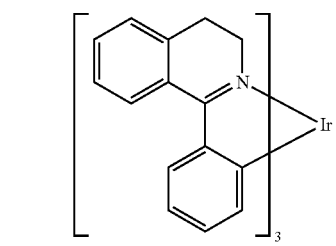
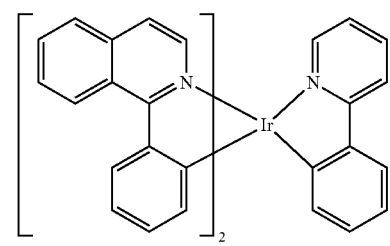
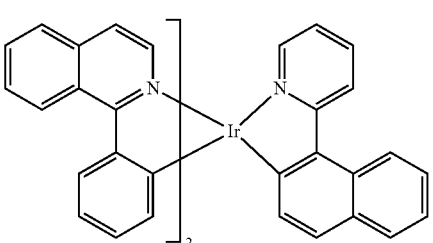
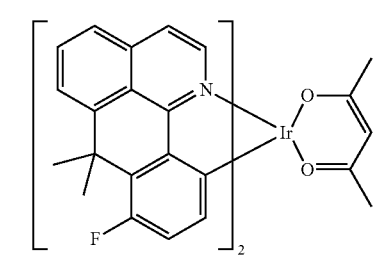

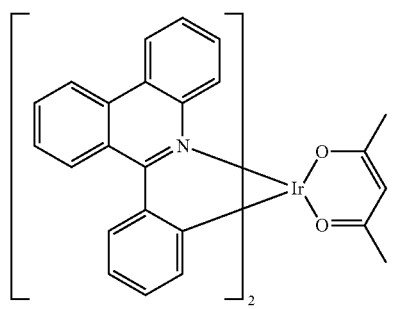
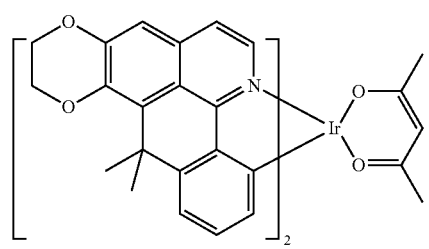
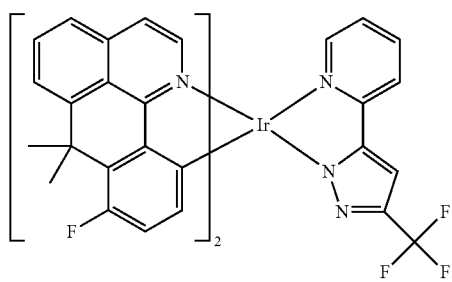
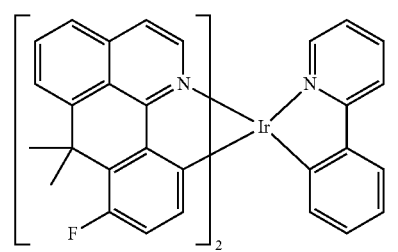
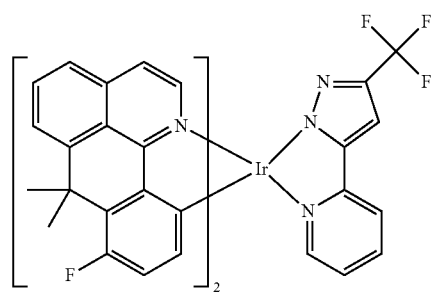
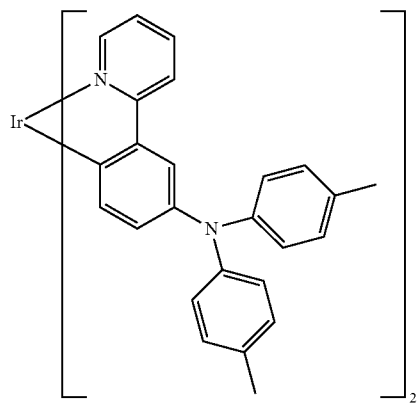
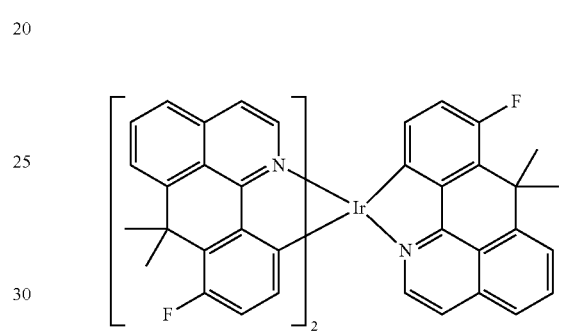
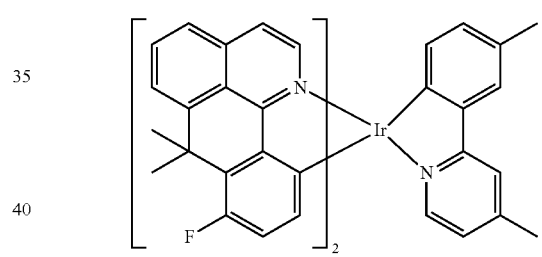
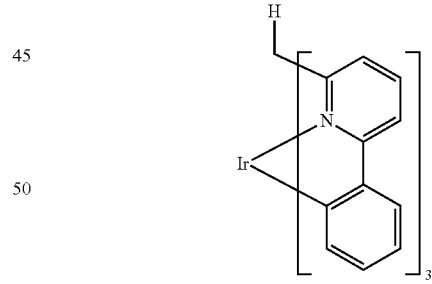
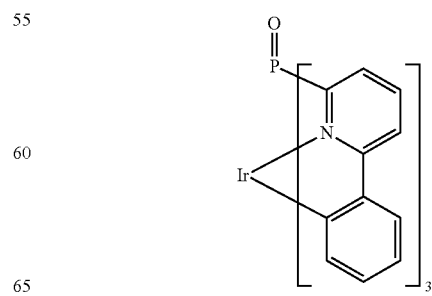

-continued
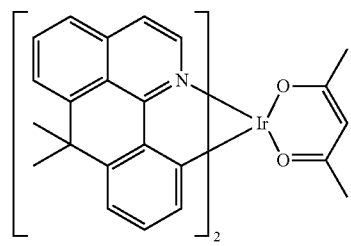
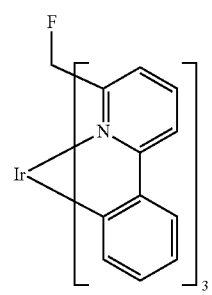
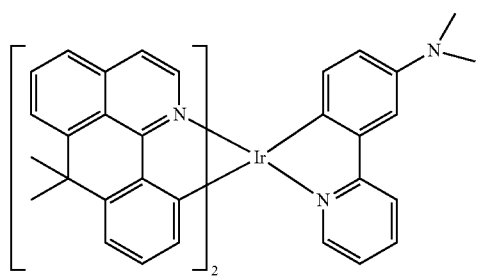
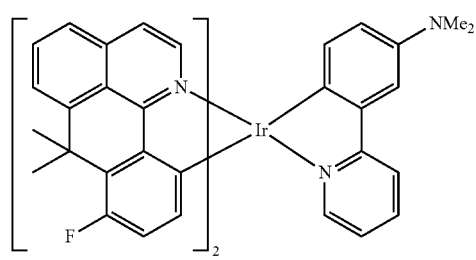
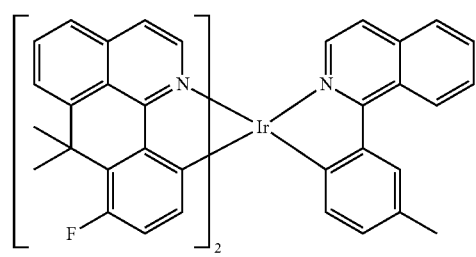
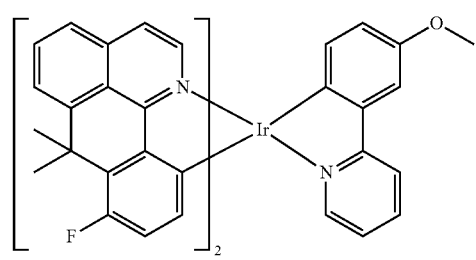
-continued
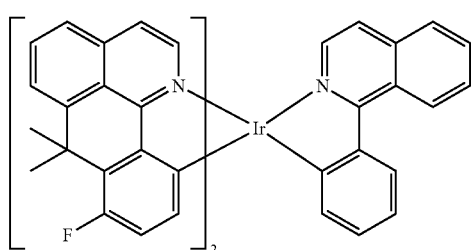
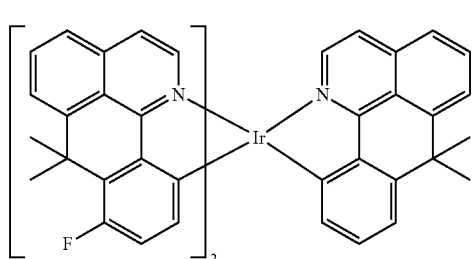
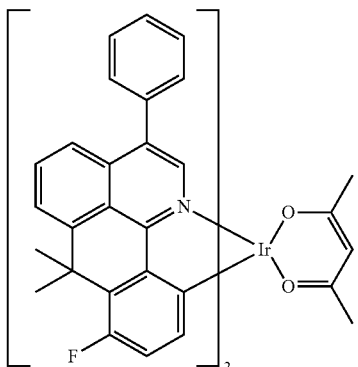
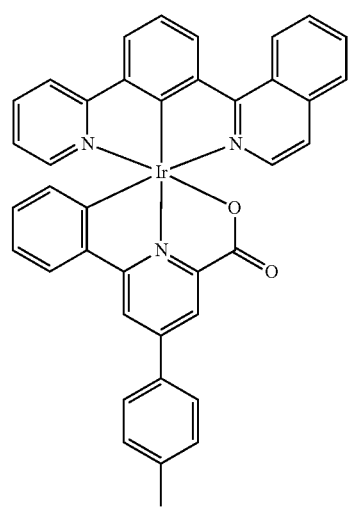

99
-continued
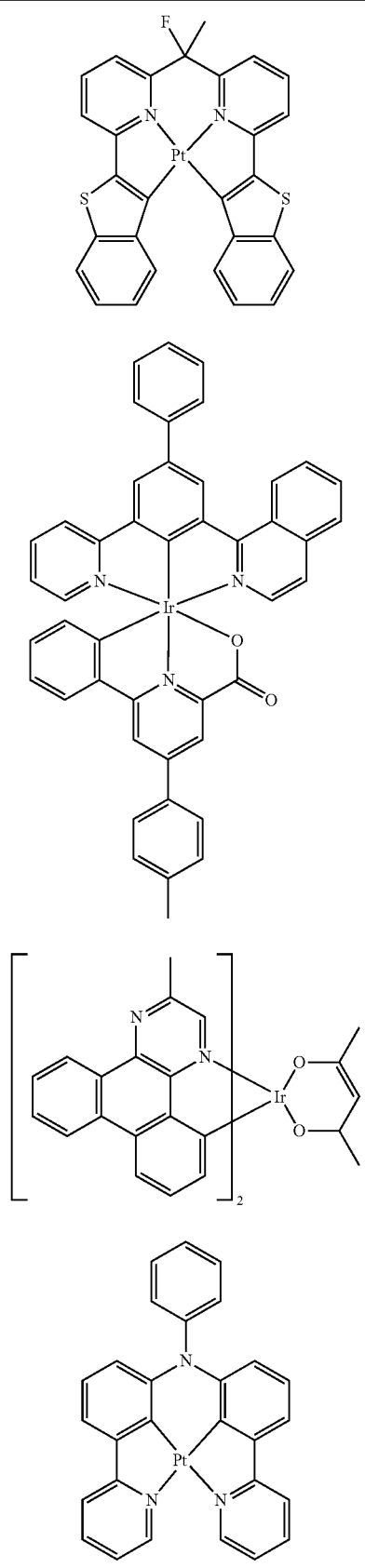
100
-continued
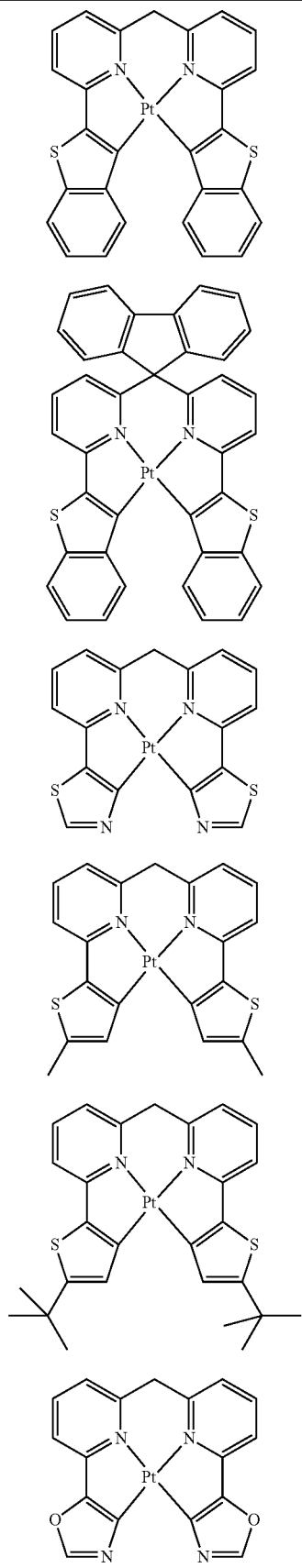

| 101 -continued | 102 -continued |
|---|---|
| 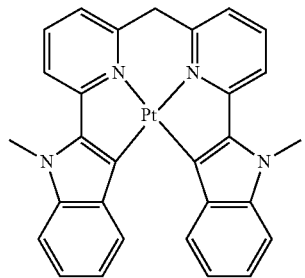 | 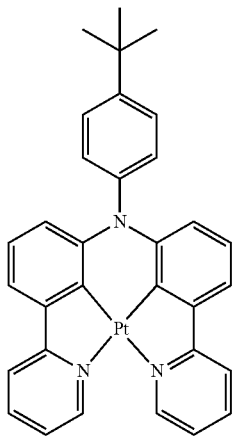 |
| 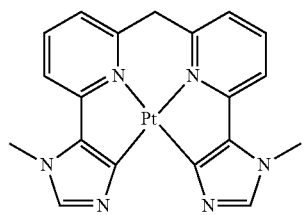 | 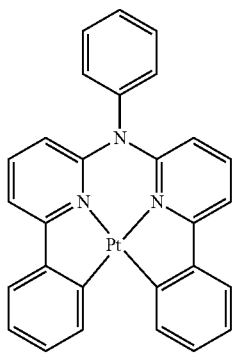 |
| 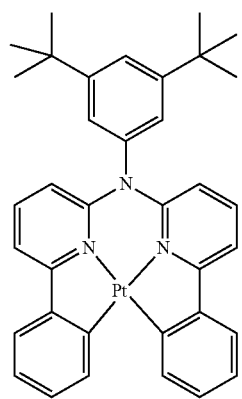 | 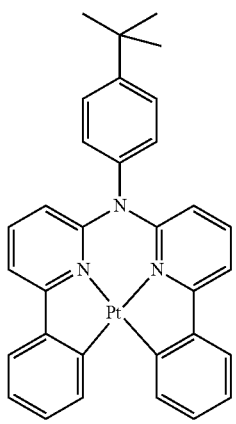 |
| 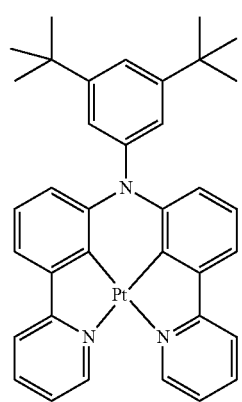 | 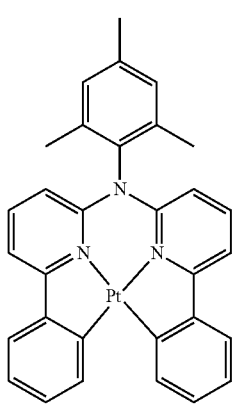 |

| 103 -continued | 104 -continued |
|---|---|
| 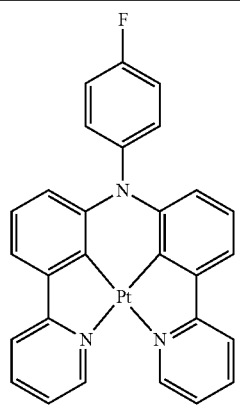 | 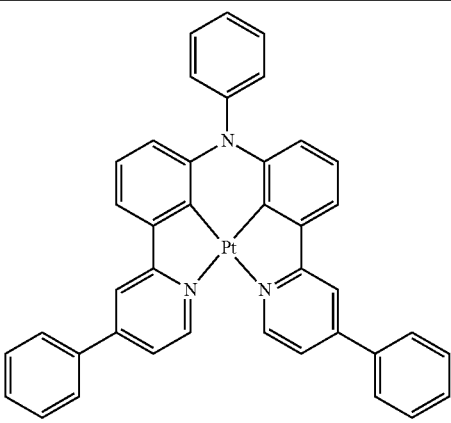 |
| 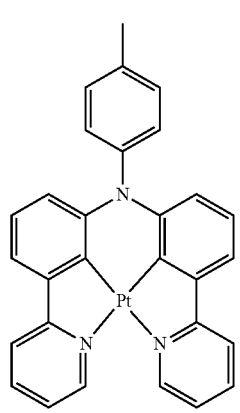 | 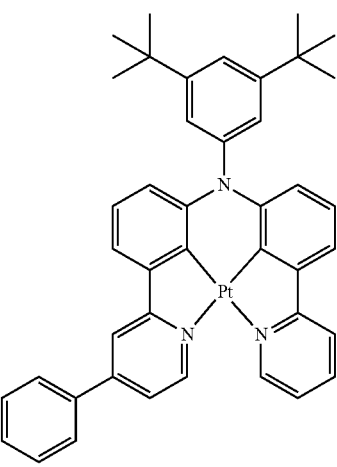 |
| 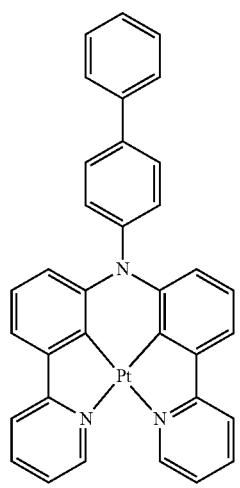 | 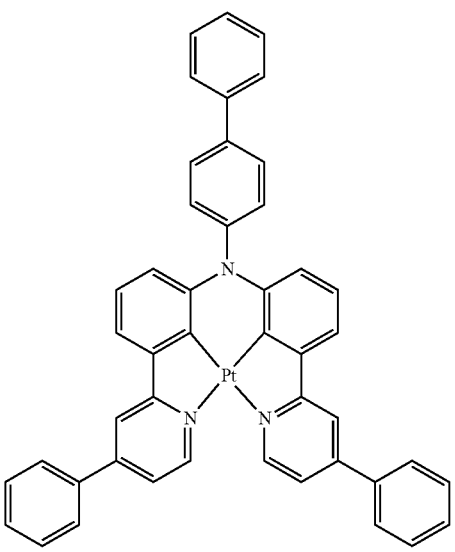 |

| 105 -continued | 106 -continued |
|---|---|
| 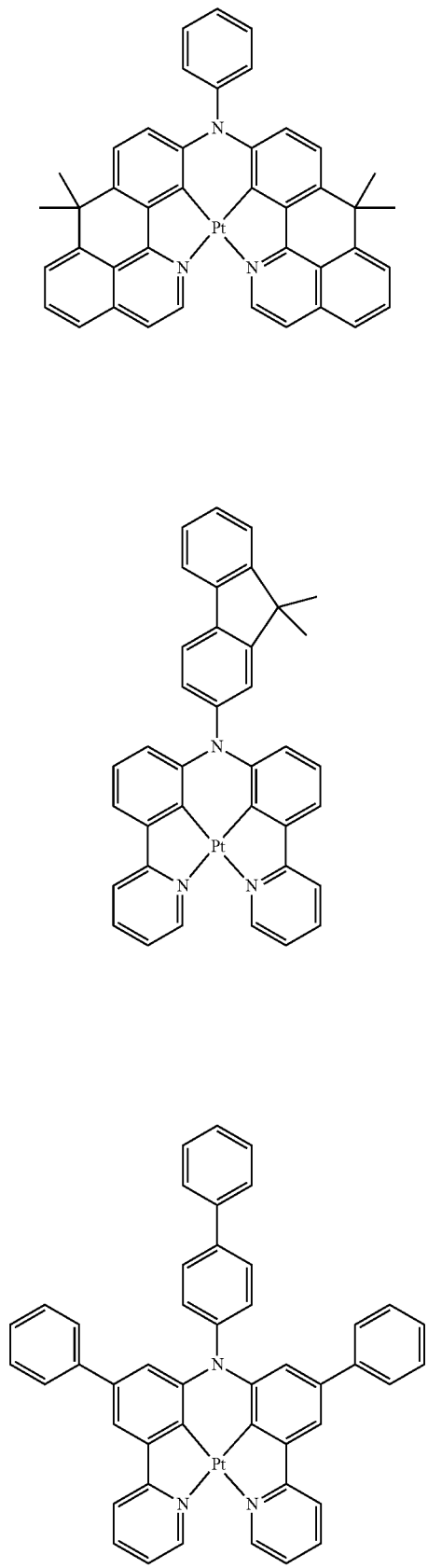 | 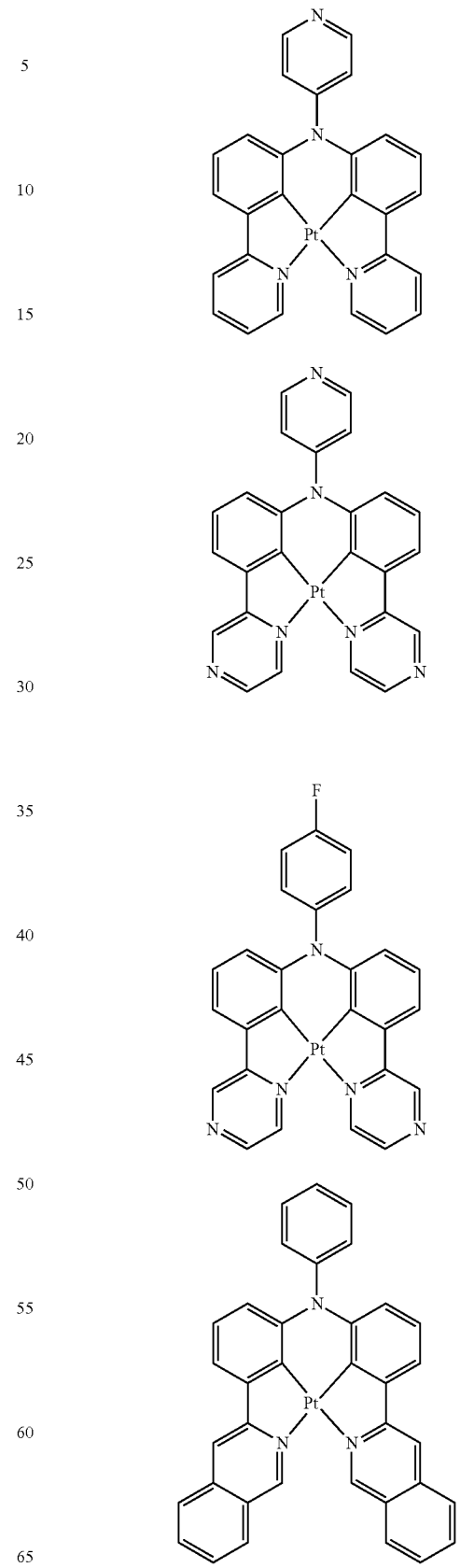 |

107
-continued
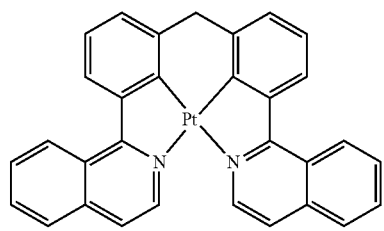
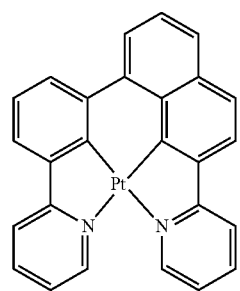
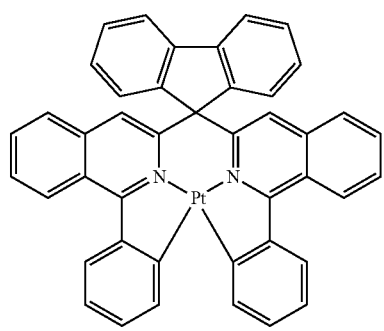
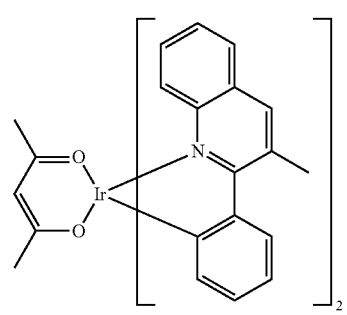
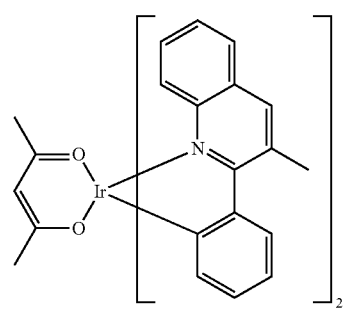
108
-continued
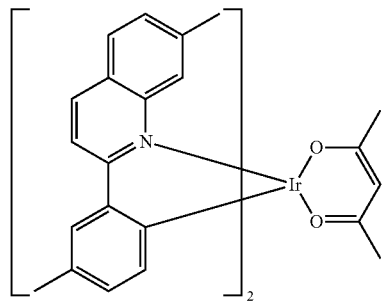
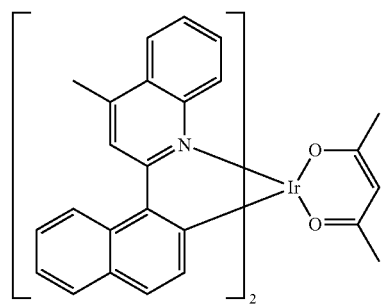
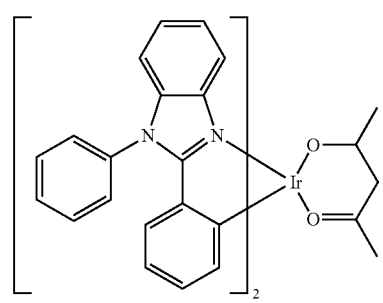
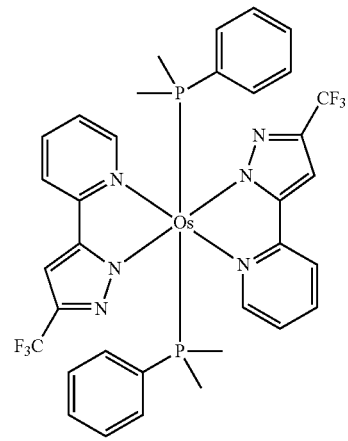
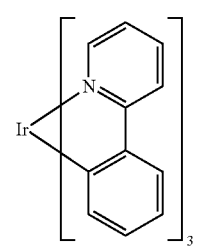

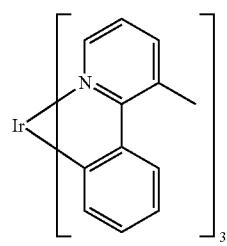
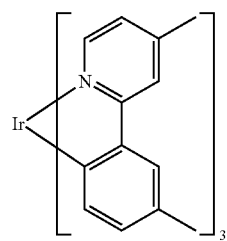
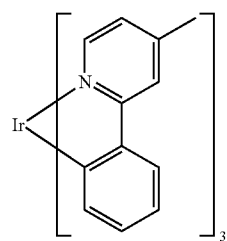
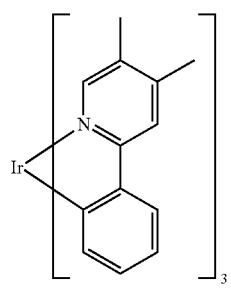
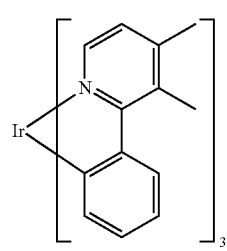
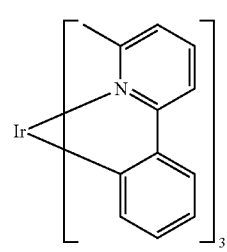
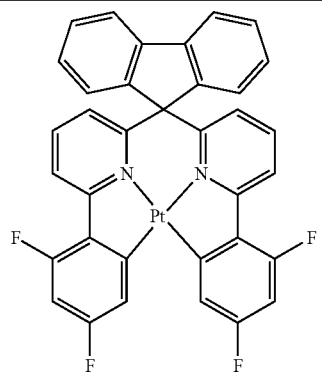
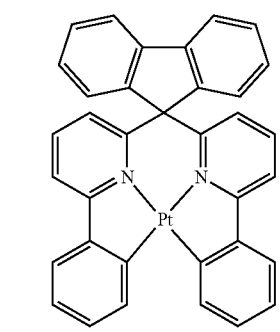
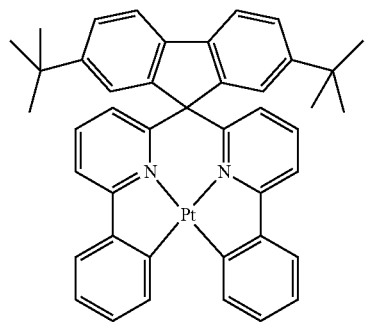
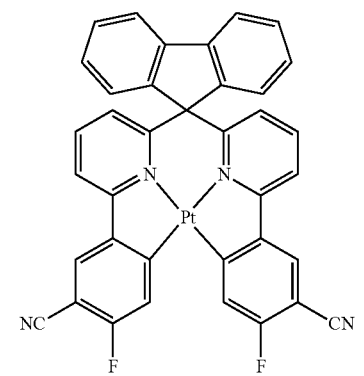

111
-continued
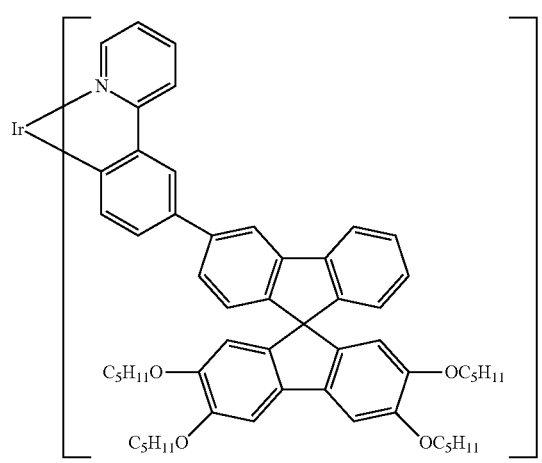
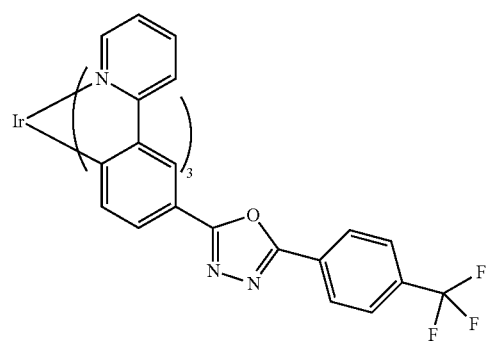
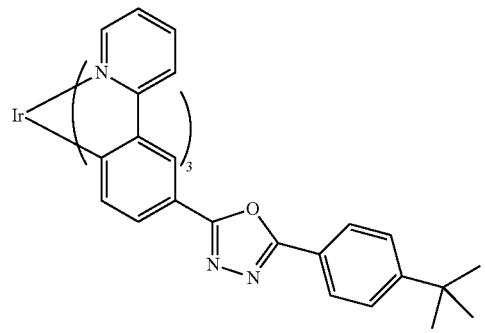
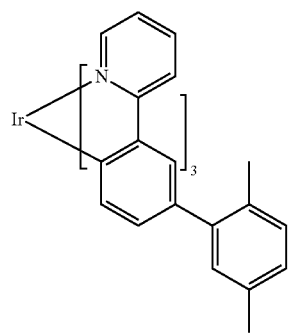
112
-continued
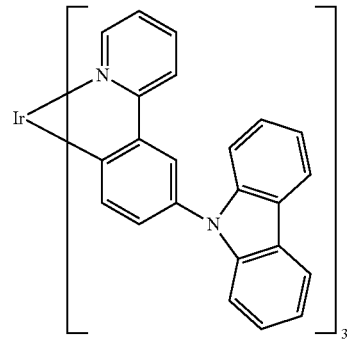
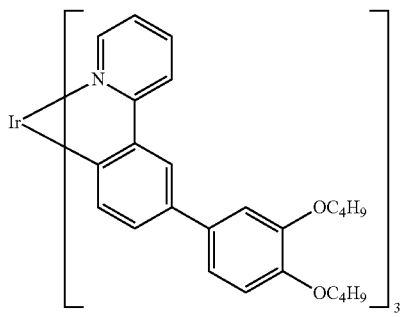
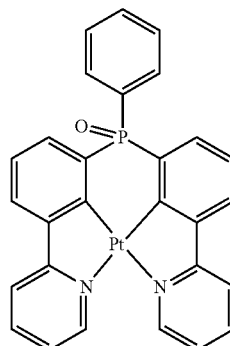
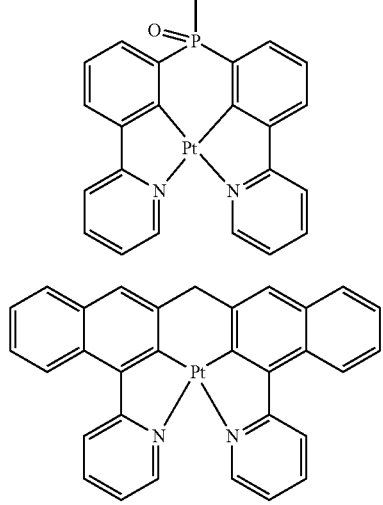
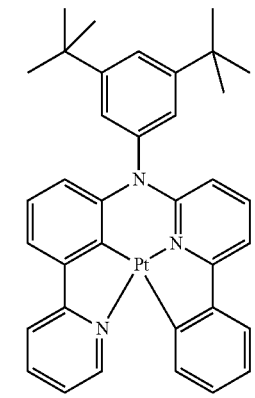

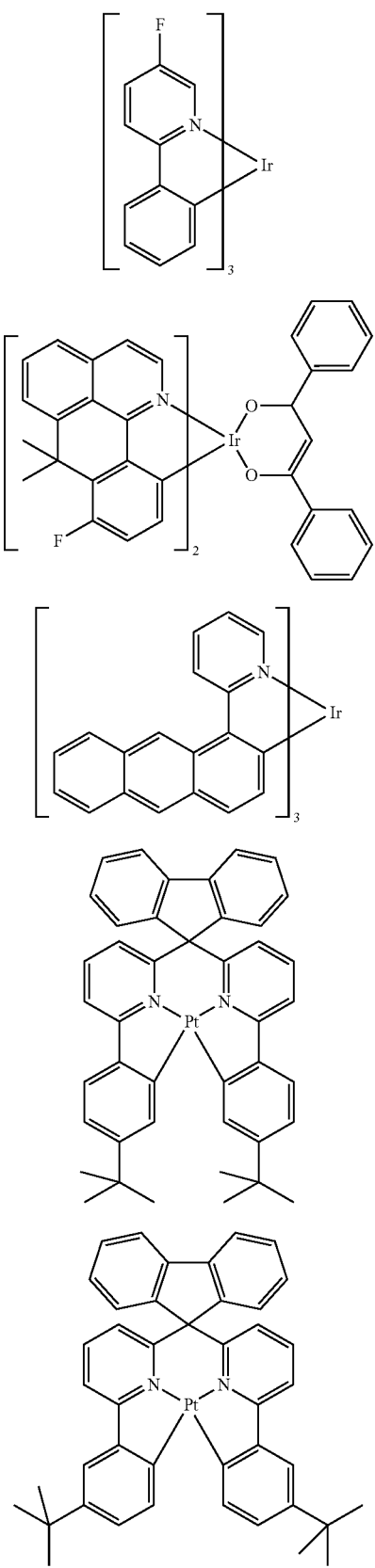
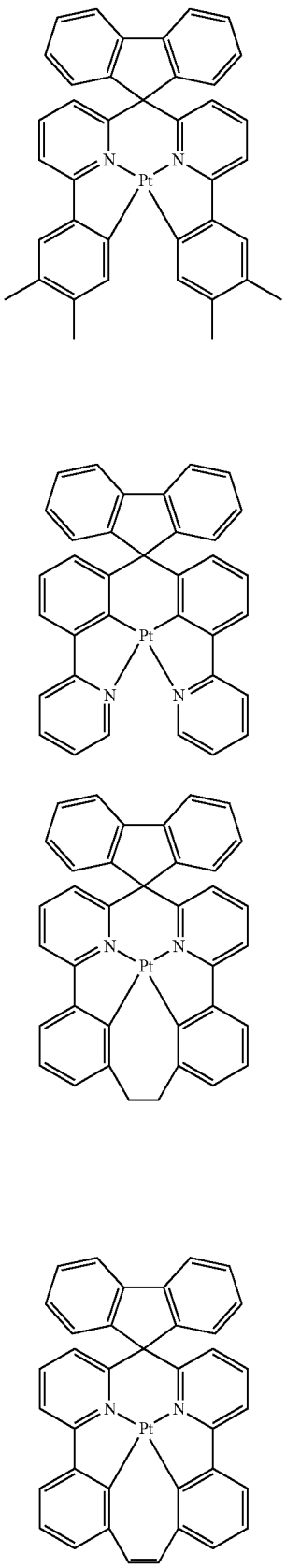

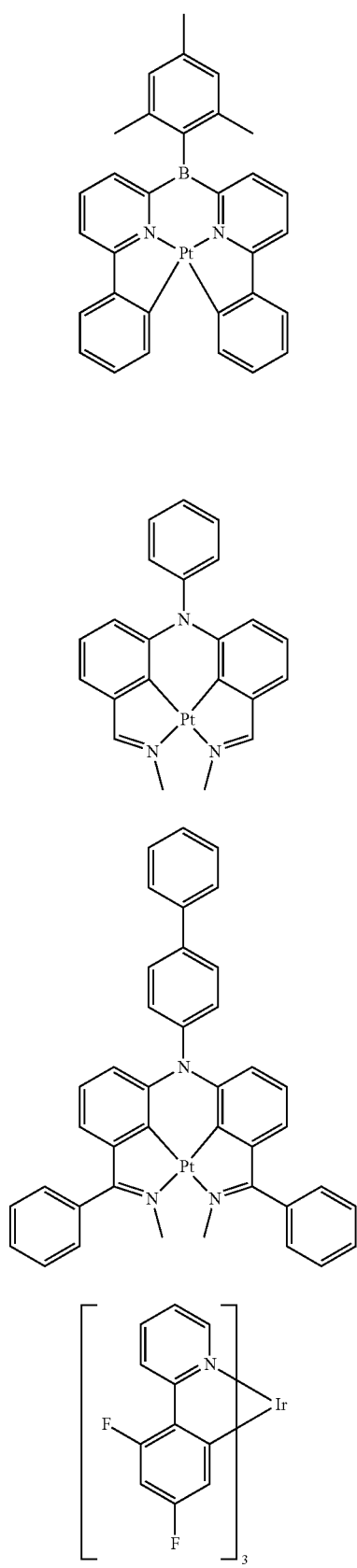

117
-continued
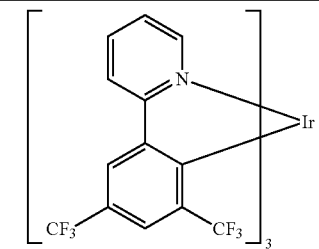
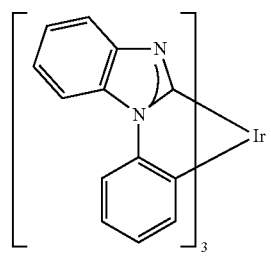
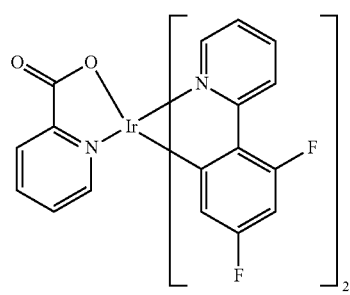
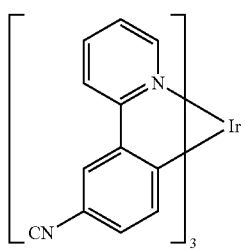
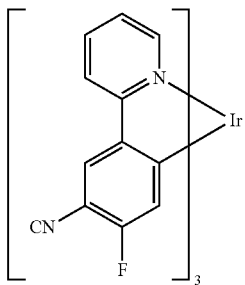
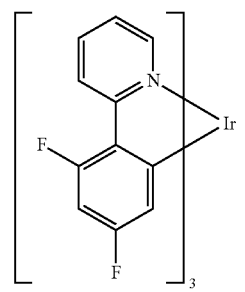
118
-continued
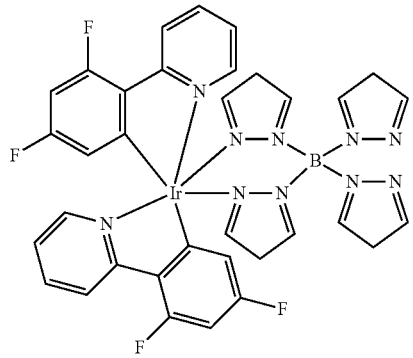
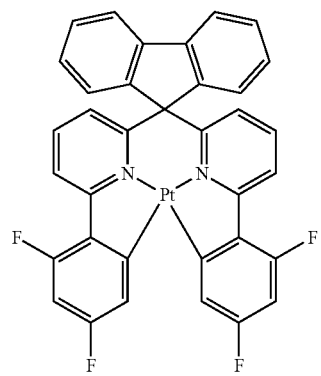
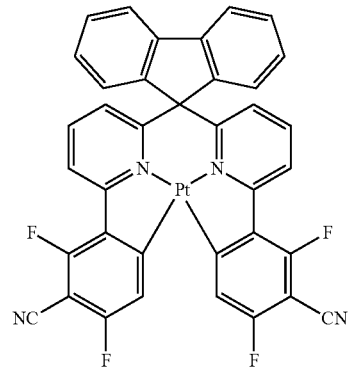
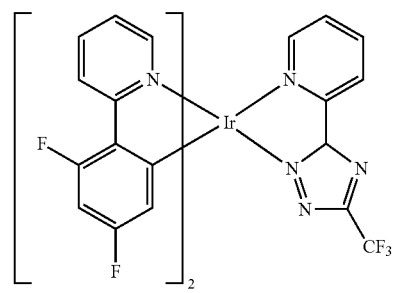

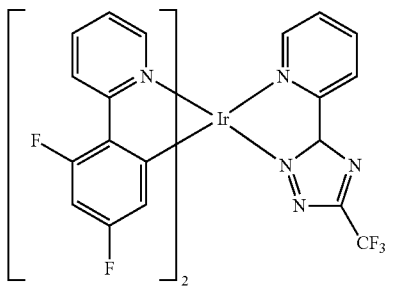

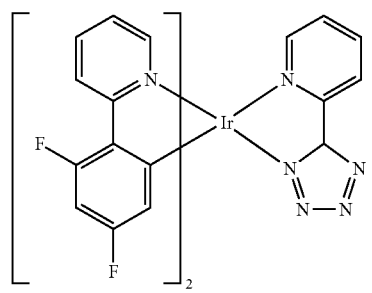

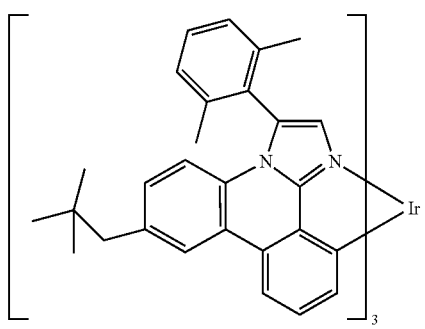

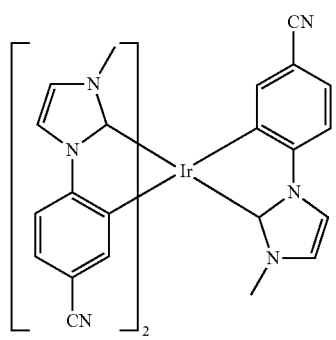

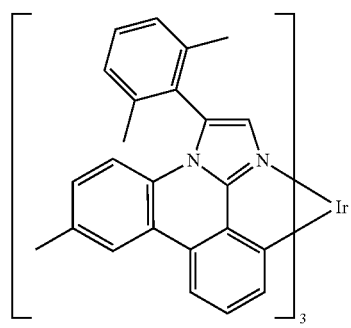

In a preferred embodiment of the invention, the compounds of the formula (1) or (2) are employed as hole-transport material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. The hole-transport layer may be directly adjacent to the emission layer. If the compounds of the formula (1) or (2) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (1) or (2) is used as hole-transport material in combination with a hexaazatriphenylene derivative as described in US 2007/0092755. The hexaazatriphenylene derivative is particularly preferably employed in its own layer here.

If the compound of the formula (1) or (2) is employed as hole-transport material in a hole-transport layer, the compound can be employed as pure material, i.e. in a proportion of 100% in the hole-transport layer, or it can be employed in combination with one or more further compounds in the hole-transport layer.

In a further embodiment of the present invention, the compounds of the formula (1) or (2) are employed as matrix material in combination with one or more dopants, preferably phosphorescent dopants.

A dopant is taken to mean the component whose proportion in the mixture is the smaller in a system comprising a matrix material and a dopant. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (1) or (2) are used as a component of mixed matrix systems. The mixed-matrix systems preferably comprise two or three different matrix materials, particularly preferably two different matrix materials. The two different matrix materials here may be present in a ratio of 1:10 to 1:1, preferably in a ratio of 1:4 to 1:1. The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed-matrix systems are preferably employed in phosphorescent organic electroluminescent devices.

Particularly suitable matrix materials, which can be employed in combination with the compounds according to the invention as matrix components of a mixed-matrix system, are aromatic ketones, aromatic phosphine oxides or aromatic sulfoxides or sulfones, for example in accordance with WO 04/013080, WO 04/093207, WO 06/005627 or the unpublished application DE 102008033943.1, triarylamines, carbazole derivatives, for example CBP (N,N-biscarbazolyl-biphenyl) or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with the application WO 2010/015306, WO 2007/063754 or WO 2008/056746, zinc complexes, for example in accordance with EP 652273 or WO 09/062578, diazasilole or tetraazasilole derivatives, for example in accordance with the application WO 2010/054729, diazaphosphole derivatives, for example in accordance with the application WO 2010/054730, or indenocarbazole derivatives, for example in accordance with the unpublished application DE 102009023155.2.

Preferred phosphorescent dopants for use in mixed-matrix systems comprising the compounds according to the invention are the phosphorescent dopants mentioned in the above table.

In a further embodiment of the invention, the compounds of the formula (1) or (2) are employed as emitting materials in an emitting layer. The compounds are suitable, in particular, as emitting compounds if they contain a plurality of diarylamino groups. In this case, the compounds according to the invention are particularly preferably used as green or blue emitters.

Preferred matrix materials for use in combination with the compounds according to the invention as fluorescent emitters are mentioned in one of the following sections.

The materials preferably employed for the respective functions in the electronic devices according to the invention are mentioned below.

Preferred fluorescent emitter materials are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms.

Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of emitter materials from the class of the styrylamines are substituted or unsubstituted tristilbenamines or the emitter materials described in WO 06/000388, WO 06/058737, WO 06/000389, WO 07/065549 and WO 07/115610. Preference is furthermore given to the condensed hydro carbons disclosed in the application WO 2010/012328.

Preferred emitter materials are furthermore the compounds of the formula (1) or (2) according to the invention.

Suitable emitter materials are furthermore the structures depicted in the following table, and the derivatives of these structures disclosed in JP 06/001973, WO 04/047499, WO 06/098080, WO 07/065678, US 2005/0260442 and WO 04/092111.

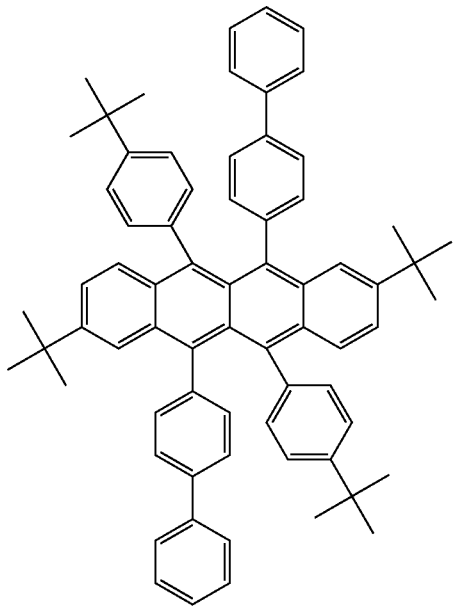 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

123
-continued
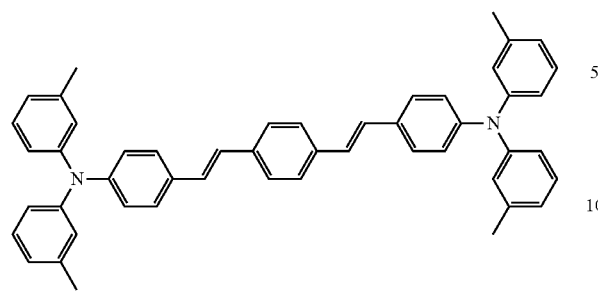
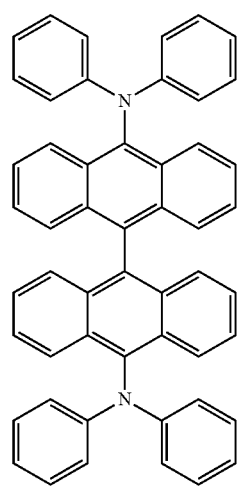 [SMILES: c1ccc(N(c2ccccc2)c2c3ccccc3c(-c3c4ccccc4c(N(c4ccccc4)c4ccccc4)c4ccccc34)c3ccccc23)cc1]
124
-continued
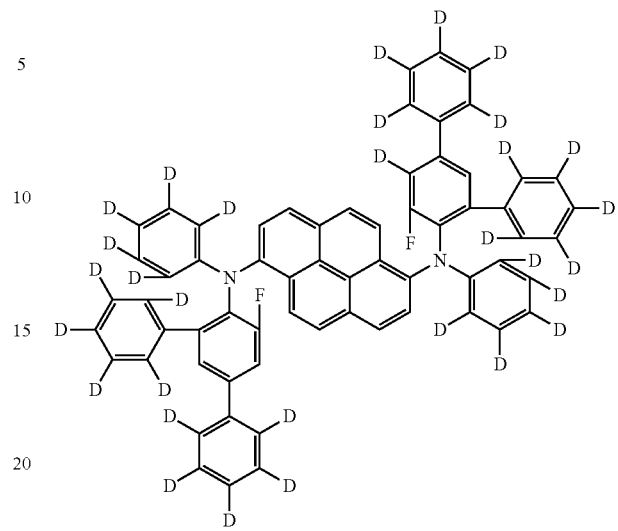
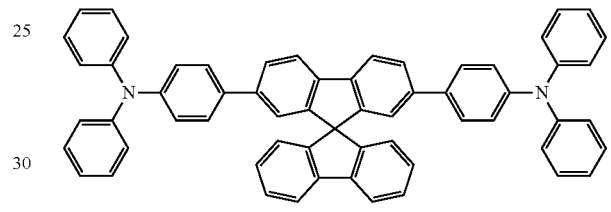
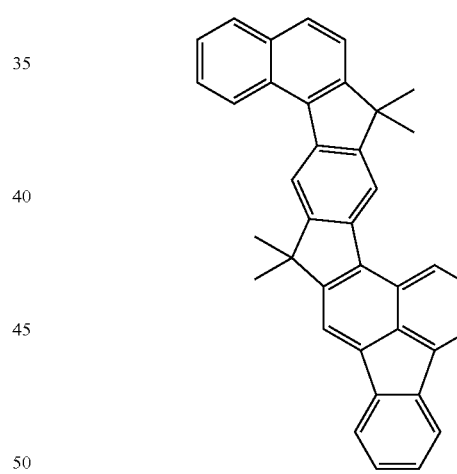
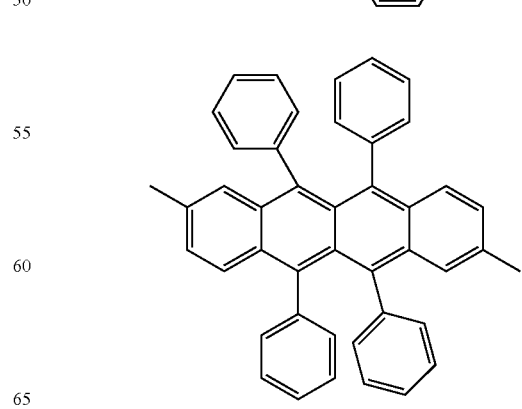

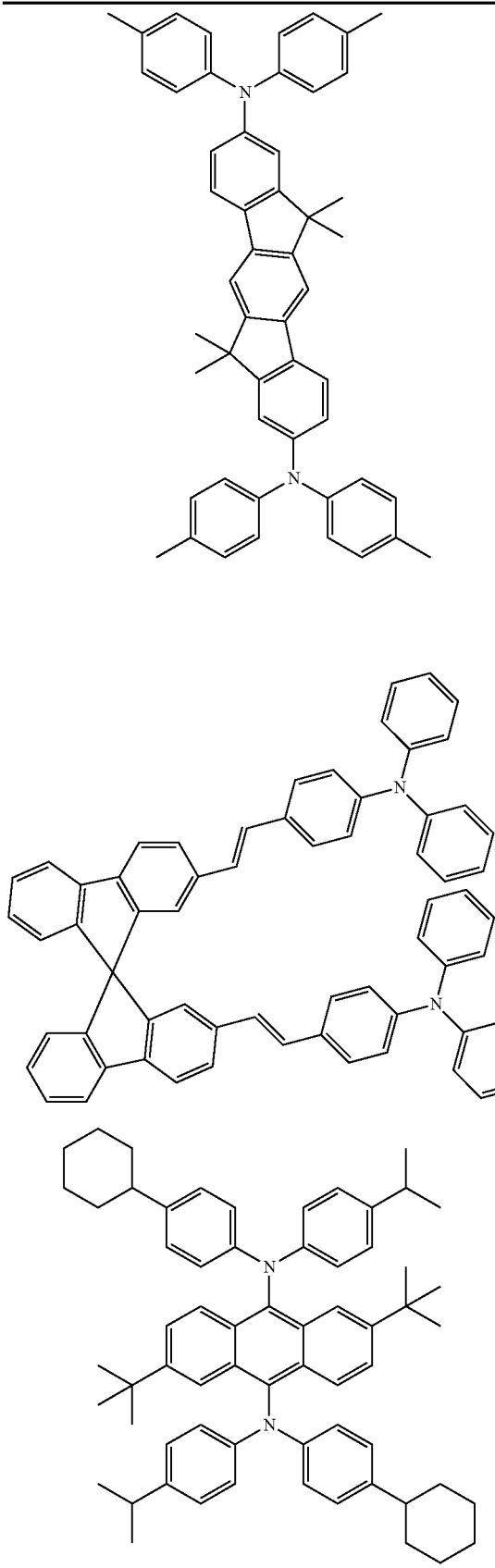
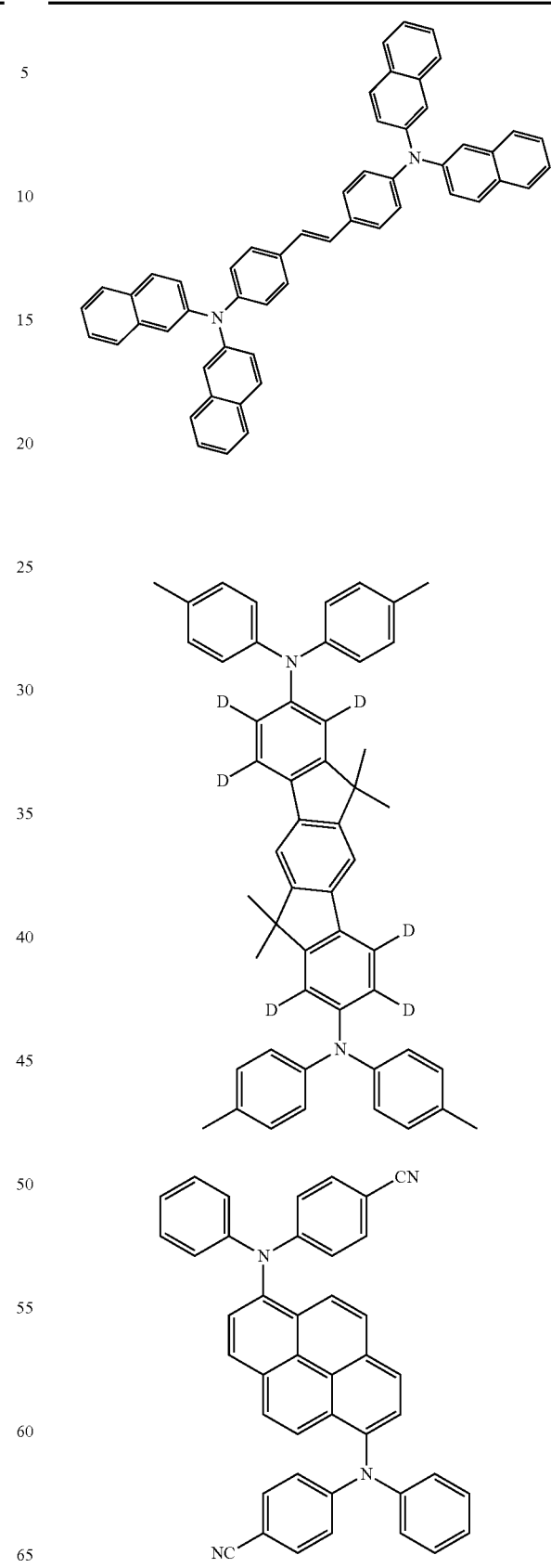

| 127 -continued | 128 -continued |
|---|---|
| 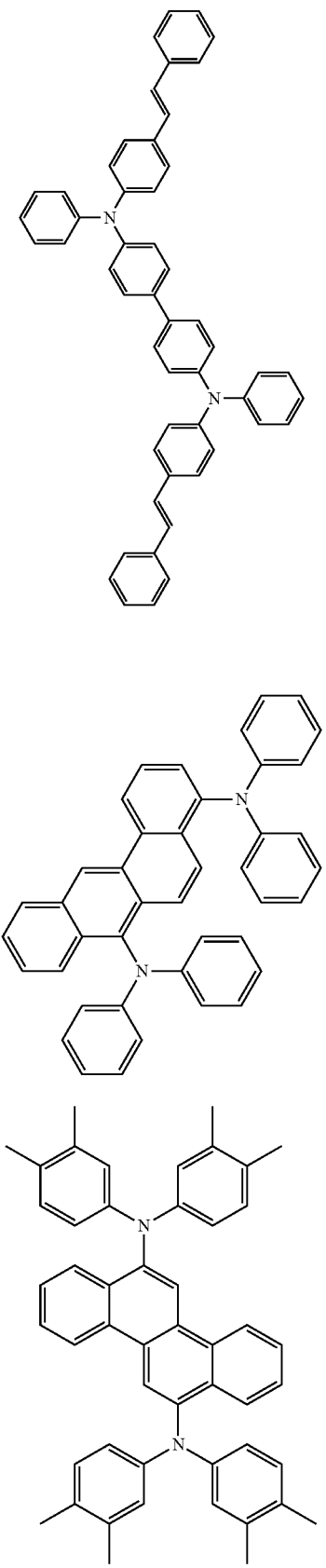 | 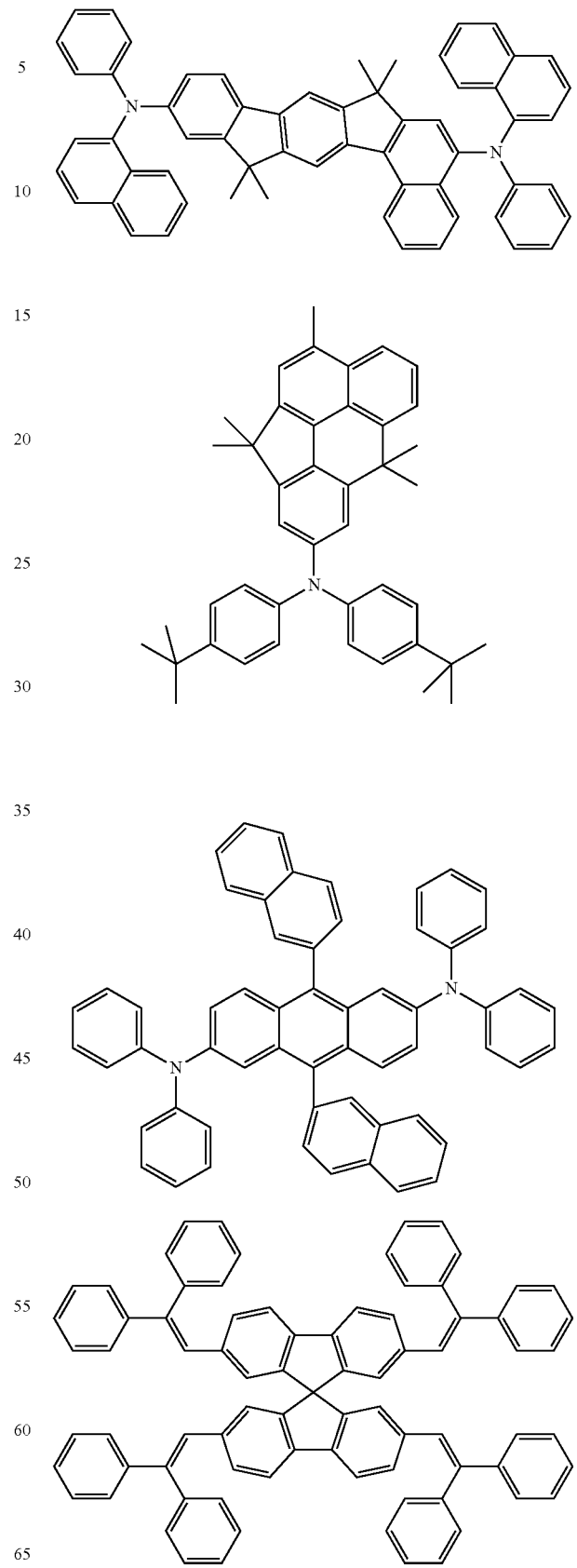 |

| 129 -continued | 130 -continued |
|---|---|
| 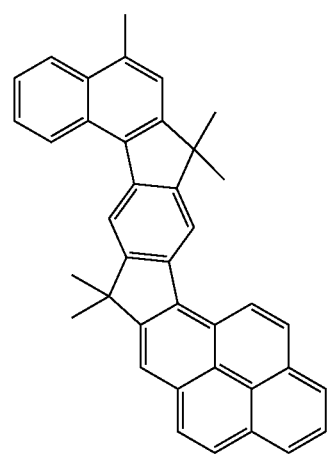 [SMILES: Cc1cc2c(c3ccccc13)-c1cc3c(cc1C2(C)C)-c1c(cc2ccc4cccc5ccc1c2c45)C3(C)C]<br>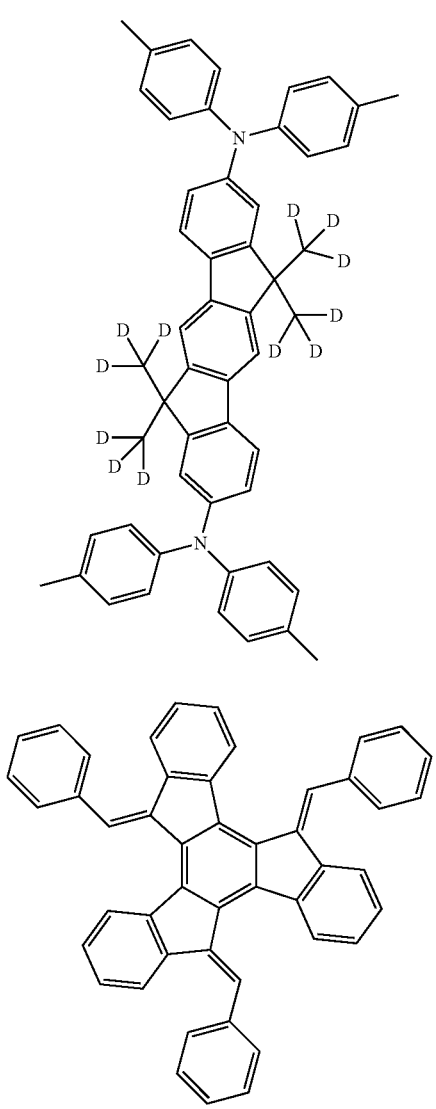 | 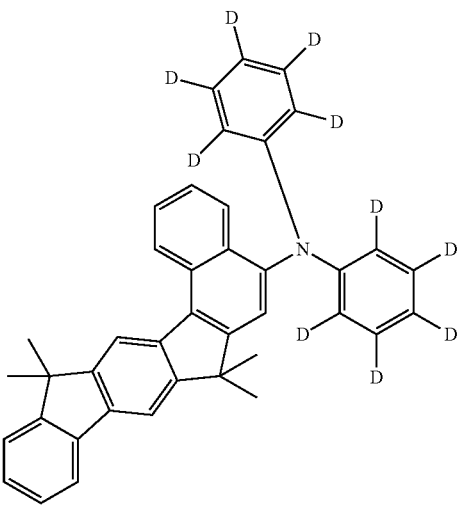 [SMILES: [2H]c1c([2H])c([2H])c(N(c2c([2H])c([2H])c([2H])c([2H])c2[2H])c2cc3c(c4ccccc24)-c2cc4c(cc2C3(C)C)-c2ccccc2C4(C)C)c([2H])c1[2H]]<br>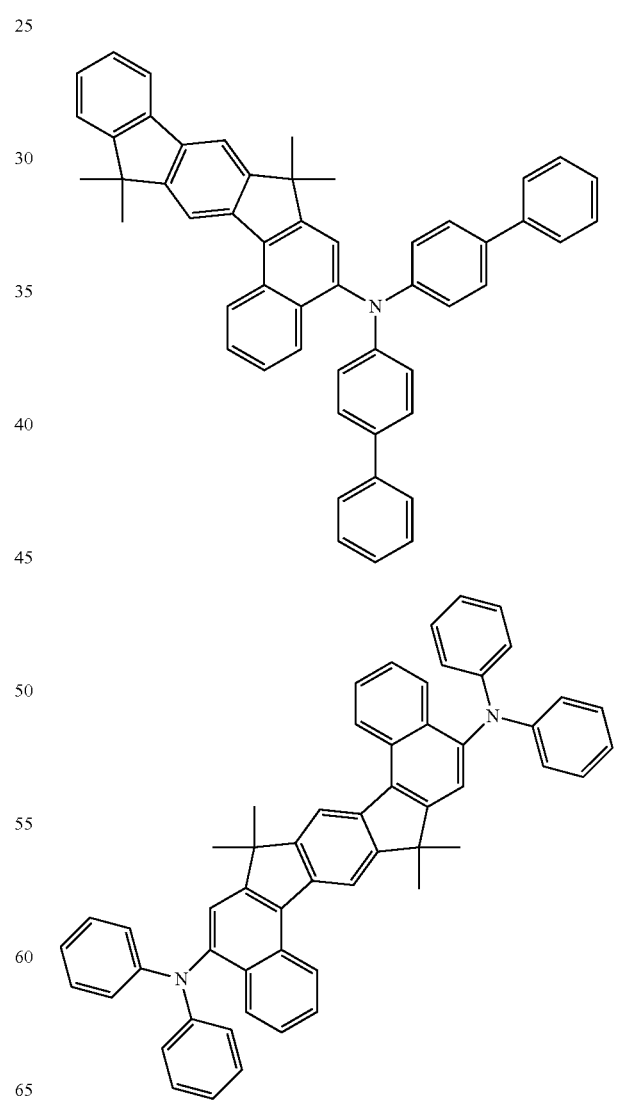 |

131
-continued
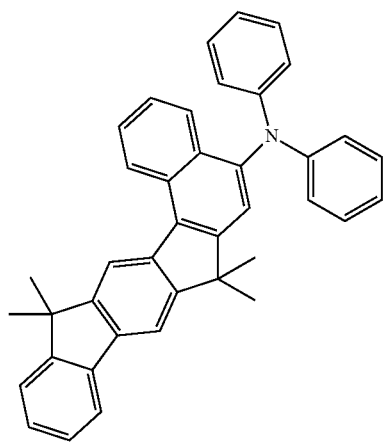 [SMILES: CC1(C)c2ccccc2-c2cc3c(cc21)-c1c(cc(N(c2ccccc2)c2ccccc2)c2ccccc12)C3(C)C]
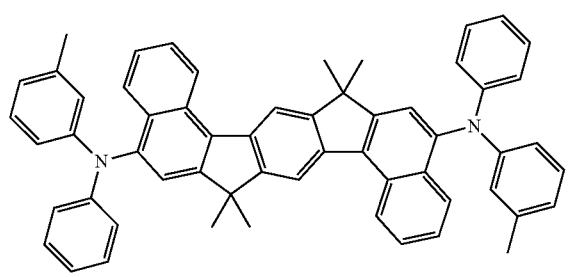 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
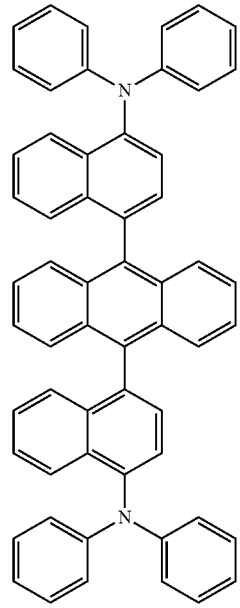 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]
132
-continued
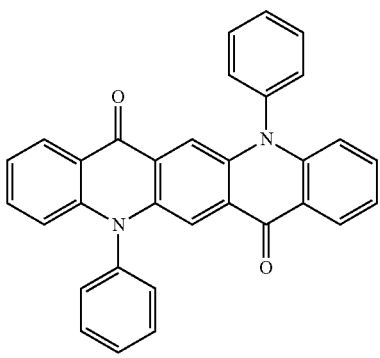 [SMILES: O=c1c2ccccc2n(-c2ccccc2)c2cc3c(=O)c4ccccc4n(-c4ccccc4)c3cc12]
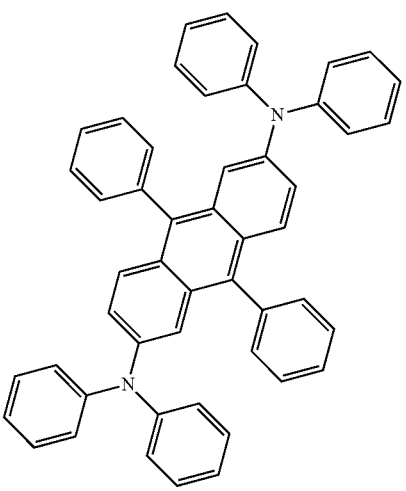 [SMILES: c1ccc(-c2c3ccc(N(c4ccccc4)c4ccccc4)cc3c(-c3ccccc3)c3ccc(N(c4ccccc4)c4ccccc4)cc23)cc1]
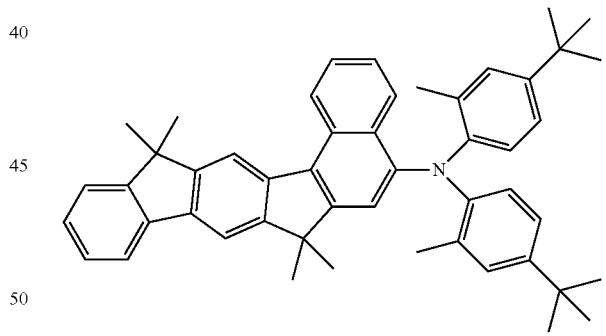
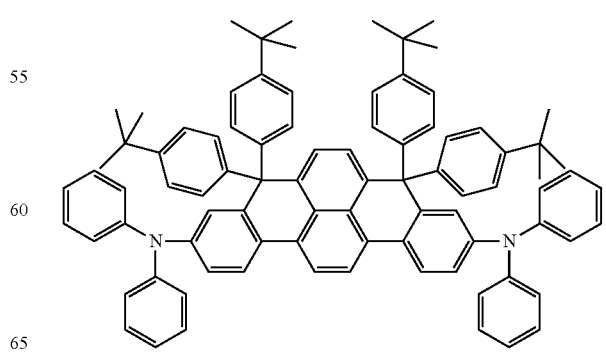

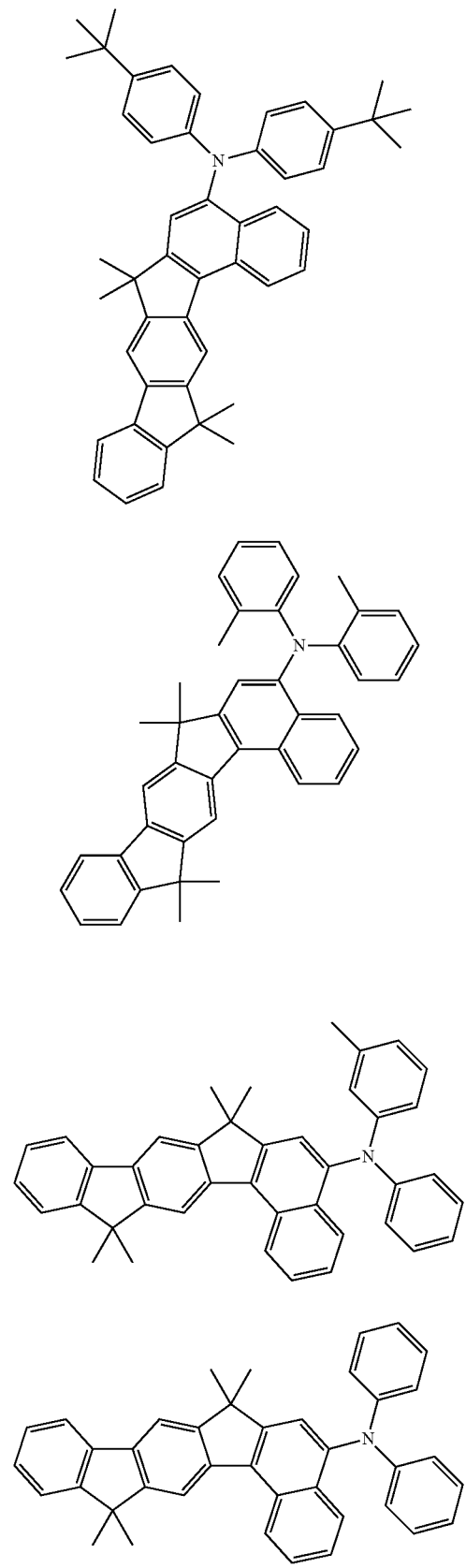
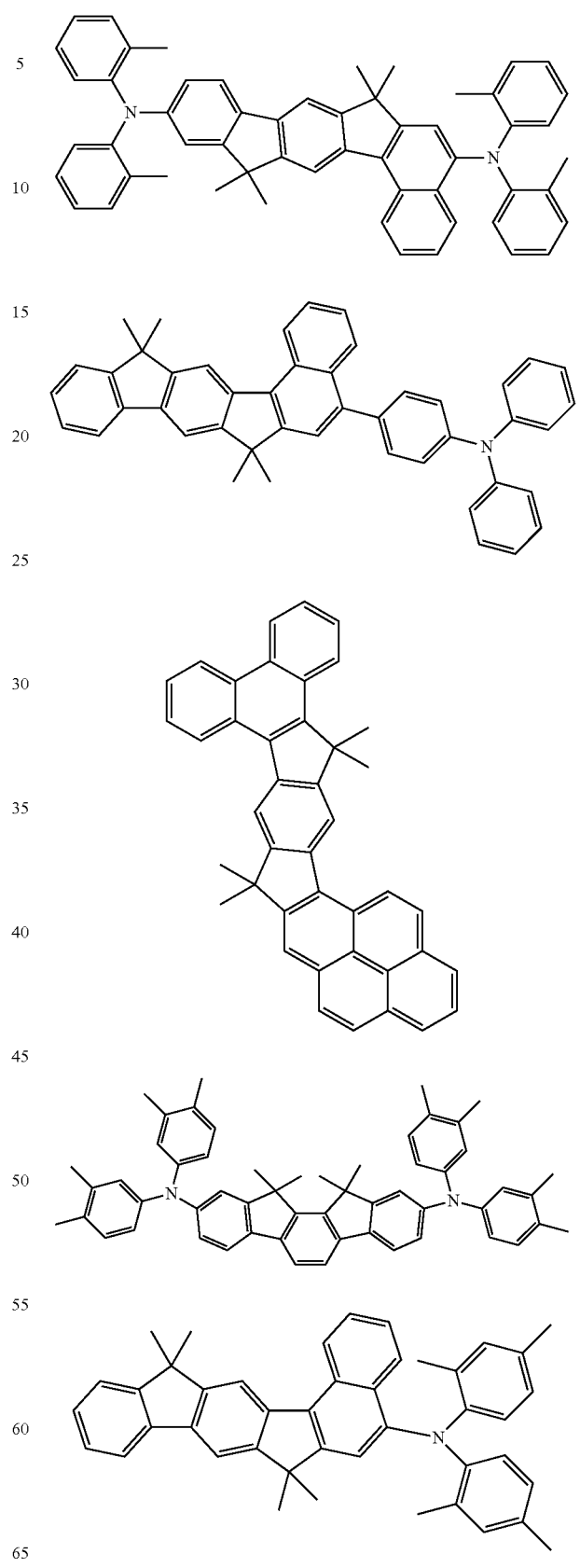

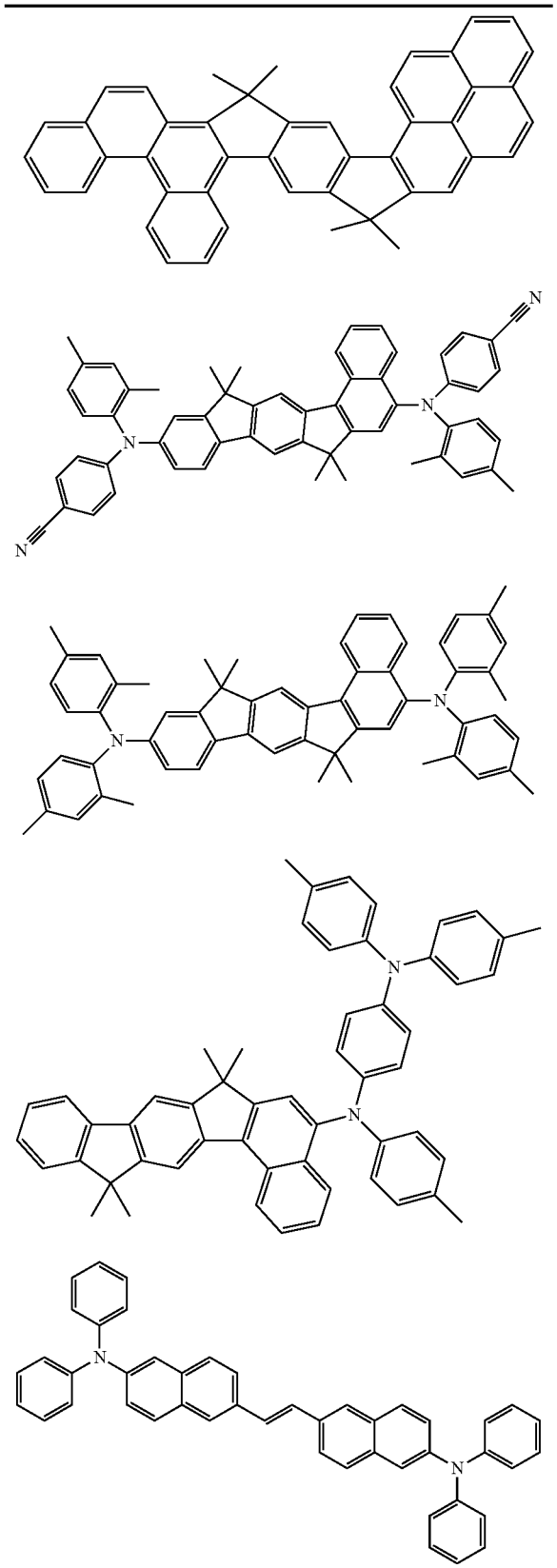

ferred matrix materials are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145239). Suitable matrix materials are furthermore preferably the compounds according to the invention. Apart from the compounds according to the invention, particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Apart from the compounds according to the invention, very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials, preferably for fluorescent dopants, are, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.

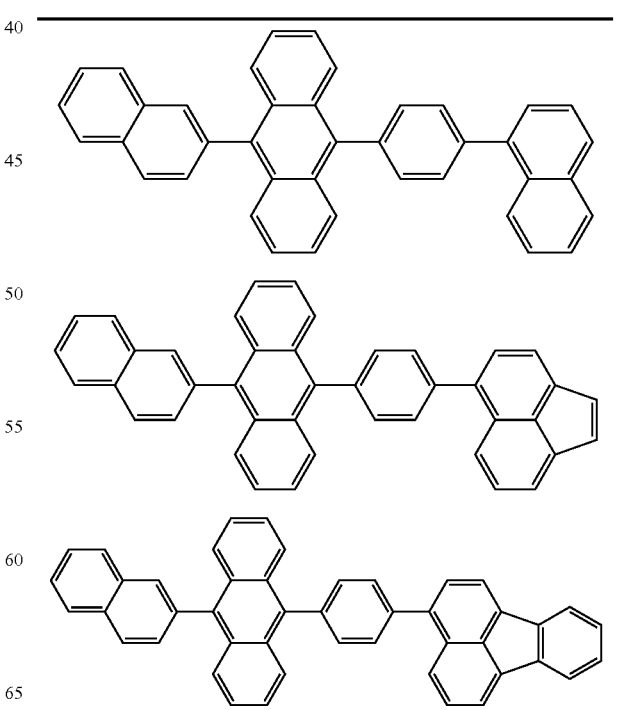

Suitable matrix materials, preferably for fluorescent dopants, are materials from various classes of substance. Pre- 137
-continued
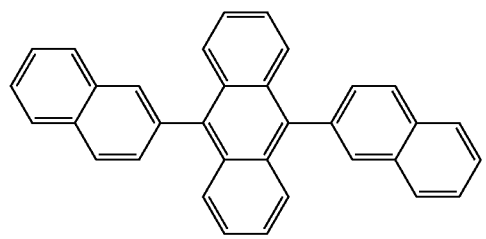 [SMILES: c1ccc2cc(-c3c4ccccc4c(-c4ccc5ccccc5c4)c4ccccc34)ccc2c1]
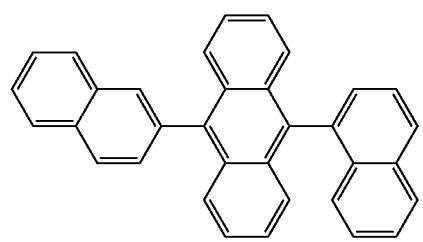 [SMILES: c1ccc2cc(-c3c4ccccc4c(-c4cccc5ccccc45)c4ccccc34)ccc2c1]
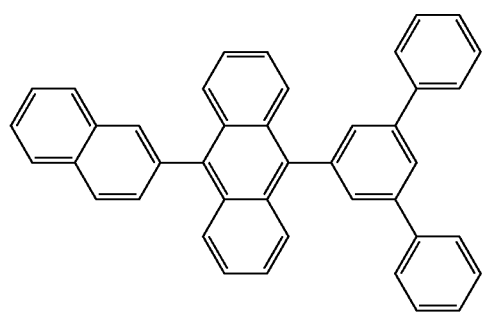 [SMILES: c1ccc(-c2cc(-c3ccccc3)cc(-c3c4ccccc4c(-c4ccc5ccccc5c4)c4ccccc34)c2)cc1]
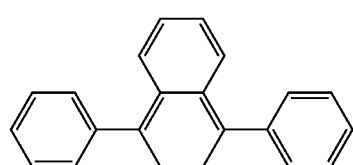
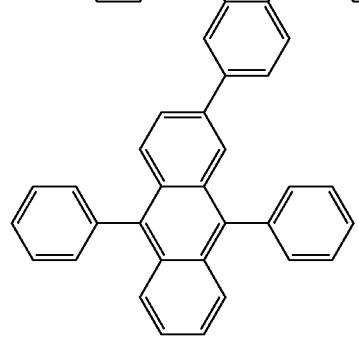
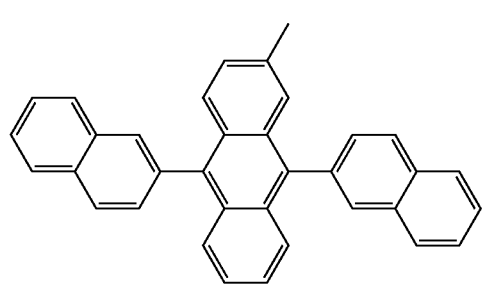 [SMILES: Cc1ccc2c(-c3ccc4ccccc4c3)c3ccccc3c(-c3ccc4ccccc4c3)c2c1]
138
-continued
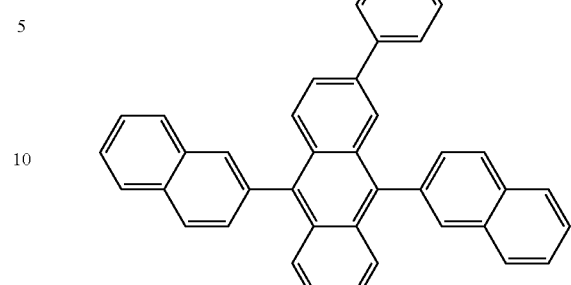
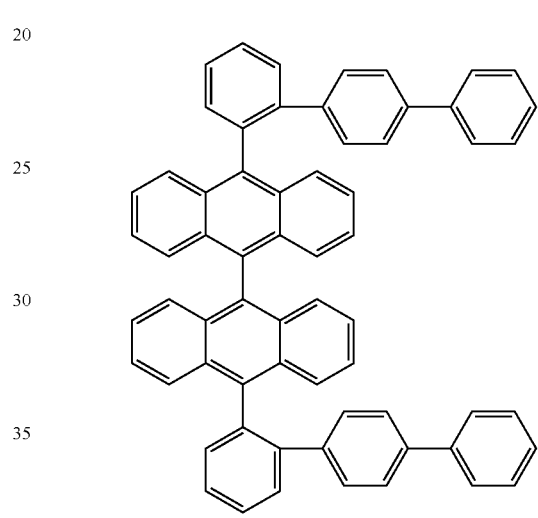
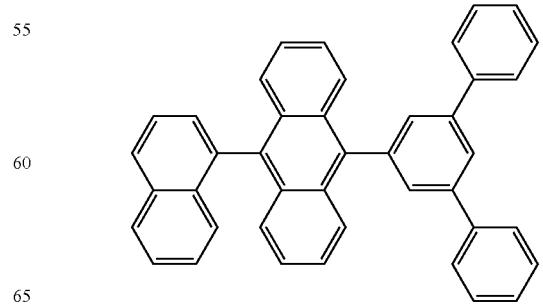

139
-continued
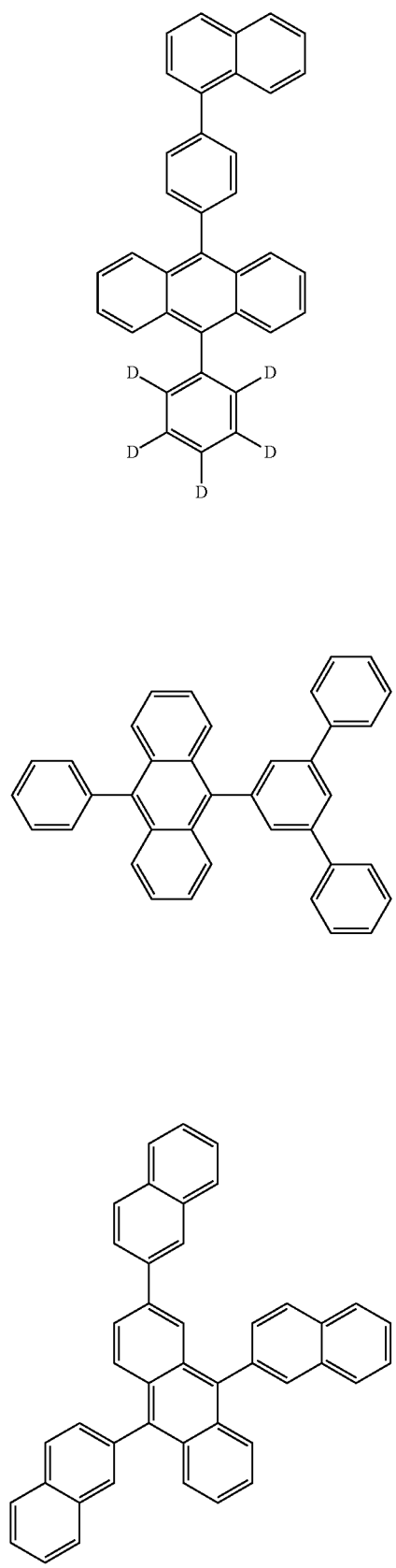
140
-continued
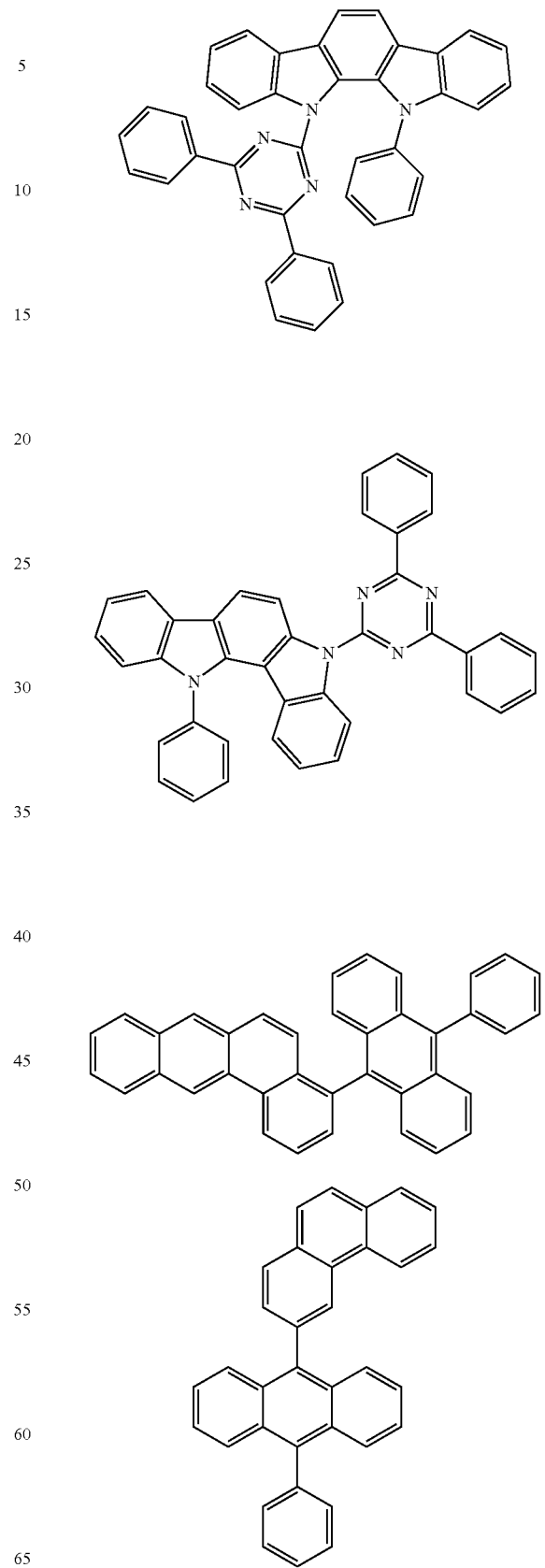

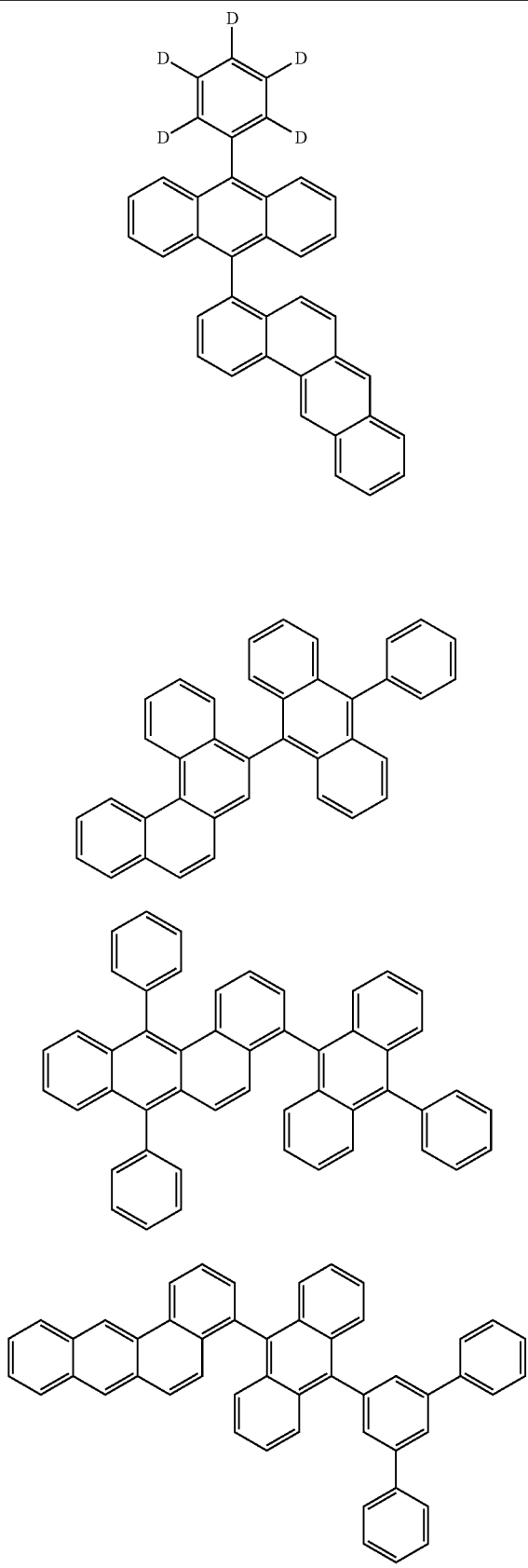
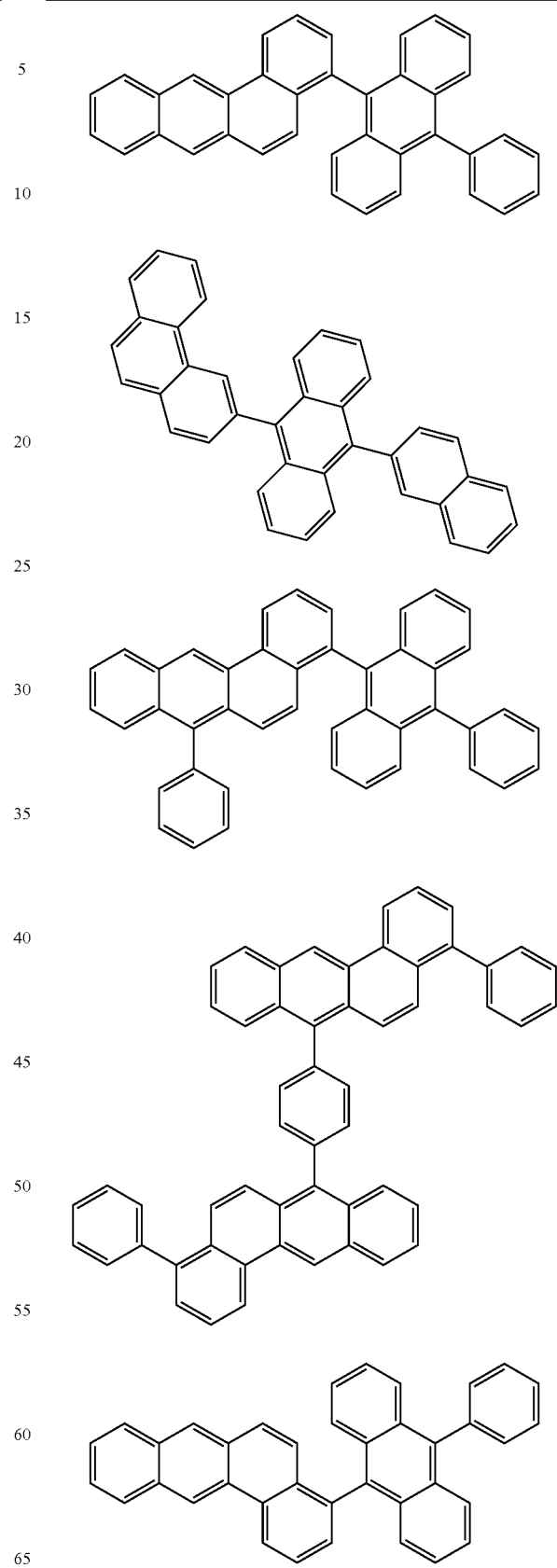

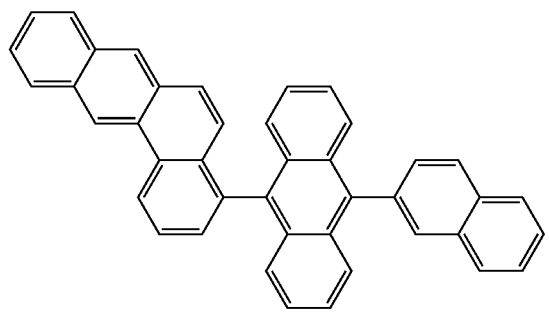 [SMILES: c1ccc2cc(-c3c4ccccc4c(-c4cccc5c4ccc4cc6ccccc6cc45)c4ccccc34)ccc2c1]
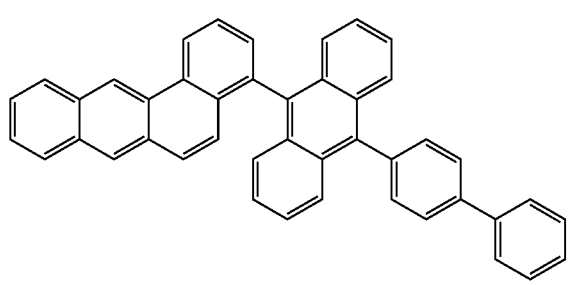 [SMILES: c1ccc(-c2ccc(-c3c4ccccc4c(-c4cccc5c4ccc4cc6ccccc6cc45)c4ccccc34)cc2)cc1]
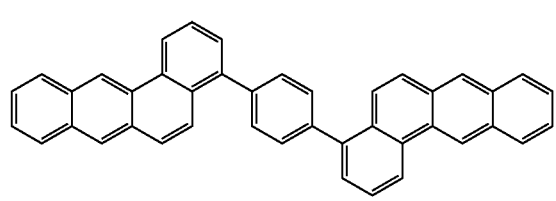 [SMILES: c1ccc2cc3c(ccc4c(-c5ccc(-c6cccc7c6ccc6cc8ccccc8cc67)cc5)cccc43)cc2c1]
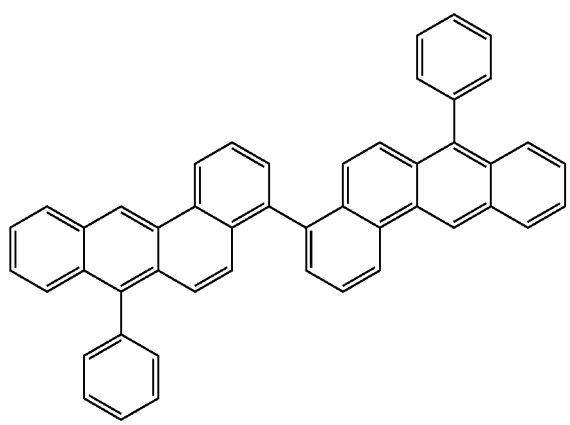 [SMILES: c1ccc(-c2c3ccccc3cc3c2ccc2c(-c4cccc5c4ccc4c(-c6ccccc6)c6ccccc6cc45)cccc23)cc1]
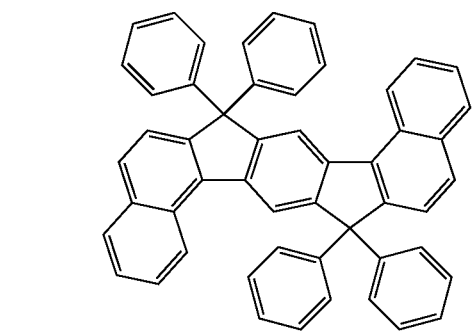 [SMILES: c1ccc(C2(c3ccccc3)c3cc4c(cc3-c3c2ccc2ccccc32)C(c2ccccc2)(c2ccccc2)c2ccc3ccccc3c2-4)cc1]
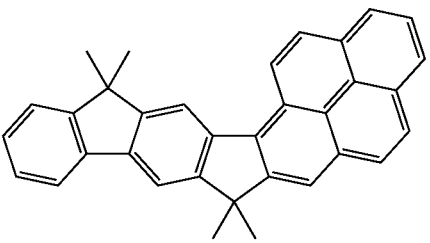 [SMILES: CC1(C)c2ccccc2-c2cc3c(cc21)-c1c(cc2ccc4cccc5ccc1c2c45)C3(C)C]
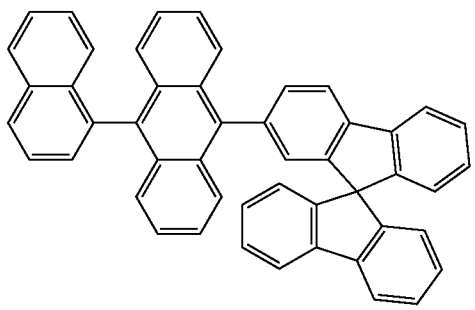 [SMILES: c1ccc2c(c1)-c1ccccc1C21c2ccccc2-c2ccc(-c3c4ccccc4c(-c4cccc5ccccc45)c4ccccc34)cc21]
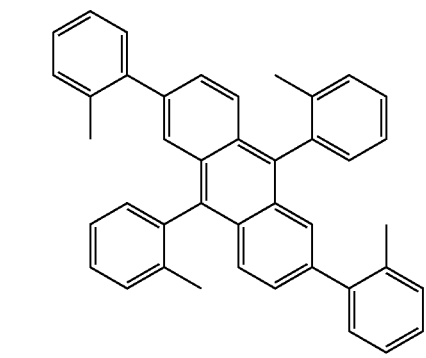 [SMILES: Cc1ccccc1-c1ccc2c(-c3ccccc3C)c3cc(-c4ccccc4C)ccc3c(-c3ccccc3C)c2c1]
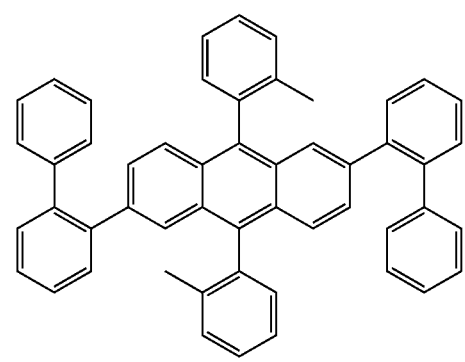 [SMILES: Cc1ccccc1-c1c2ccc(-c3ccccc3-c3ccccc3)cc2c(-c2ccccc2C)c2ccc(-c3ccccc3-c3ccccc3)cc12]
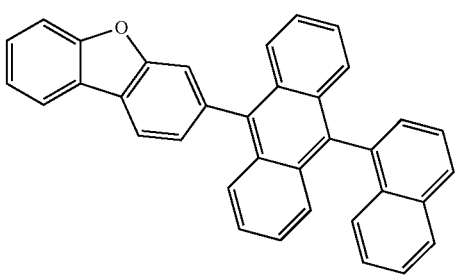 [SMILES: c1ccc2c(-c3c4ccccc4c(-c4ccc5c(c4)oc4ccccc45)c4ccccc34)cccc2c1]

-continued

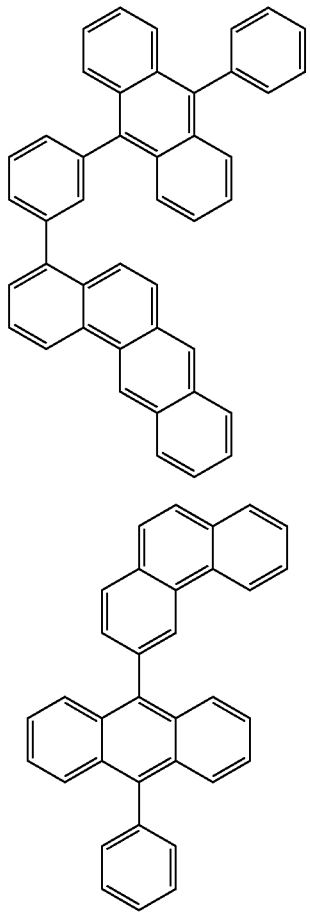

Besides the compounds according to the invention, suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to facilitate either irradiation of the organic material (organic solar cells) or the coupling-out of light (OLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials; in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (1) or (2) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (1) or (2) can be employed in displays, as light sources in lighting applications and as light sources in medical and/or cosmetic applications (for example light therapy).

The compounds according to the invention are distinguished by good hole mobility. On use in a hole-transport layer, the compounds therefore exhibit a low dependence of the operating voltage on the thickness of the hole-transport layer.

Furthermore, the compounds according to the invention are distinguished by high oxidation and temperature stability, which has a positive effect on the processability and lifetime of the electronic devices comprising the materials.

The compounds are furthermore very highly suitable for use as matrix materials in mixed-matrix systems, where they preferably result in a reduction in the operating voltage and an increase in the lifetime of the electronic devices.

In summary, the compounds according to the invention effect one or more of the above-mentioned advantages on use in electronic devices, namely an increase in the efficiency of the device, an increase in the lifetime and/or a reduction in the operating voltage.

The invention is explained in greater detail by the following working examples, without wishing it to be restricted thereby.

USE EXAMPLES

A) Synthesis Examples

The following syntheses were carried out, unless indicated otherwise, under a protective-gas atmosphere. The starting materials were purchased from ALDRICH or ABCR.

Example 1: Synthesis of 10-biphenyl-4-yl-9,9-dimethyl-2-(9-phenyl-9H-carbazol-3-yl)-9,10-dihydroacridine (HTM2)

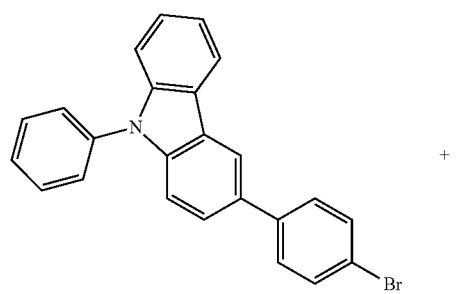

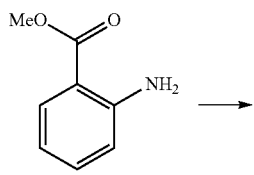

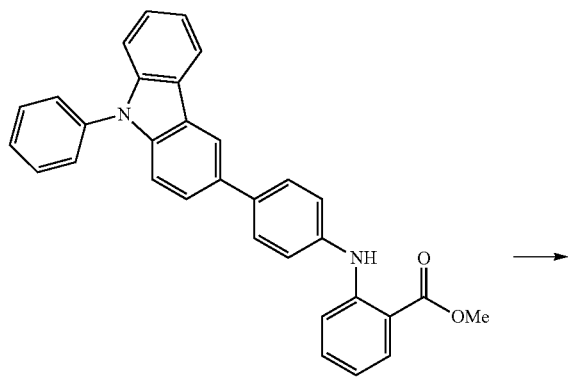

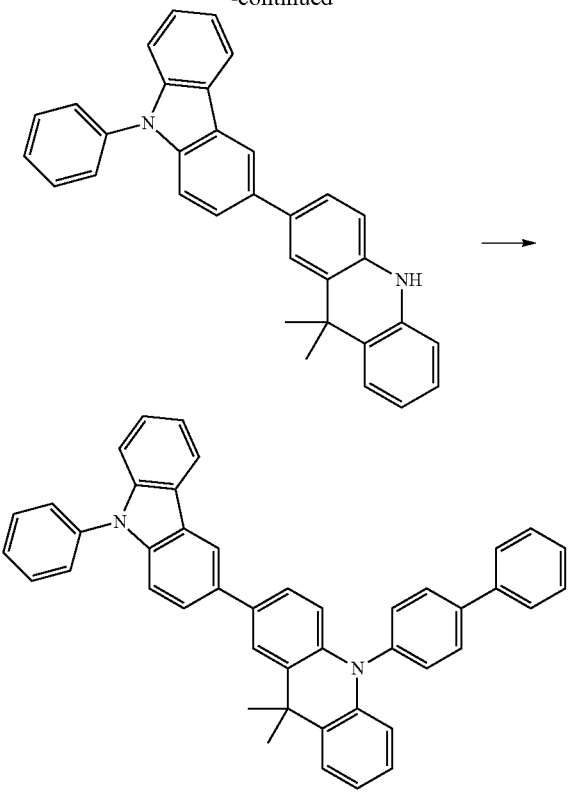

a) Methyl 2-[4-(9-phenyl-9H-carbazol-3-yl)phenylamino]benzoate

Caesium carbonate (25.4 g, 78 mmol), palladium acetate (0.9 g, 4 mmol) and xantphos (1.5 g, 8 mmol) are added to a solution of 3-(4-bromo phenyl)-9-phenyl-9H-carbazole (CAS 1028647-93-9, 31.0 g, 78 mmol) and methyl anthranilate (10.1 ml, 78 mmol) in degassed toluene (300 ml), and the mixture is heated under reflux for 8 h. The precipitated salts are filtered off, and the mother liquor is evaporated in vacuo. The residue is extracted with chloroform in a Soxhlet extractor and subsequently recrystallised from toluene.

Yield: 26.0 g (55 mmol), 71% of theory, colourless solid.

b) 9,9-Dimethyl-2-(9-phenyl-9H-carbazol-3-yl)-9,10-dihydroacridine

Methyl 2-[4-(9-phenyl-9H-carbazol-3-yl)phenylamino]benzoate (26.0 g, 55 mmol) is added in portions to a suspension of anhydrous cerium(III) chloride (15.0 g, 61 mmol) in dried tetrahydrofuran (400 ml). A 3 M solution of methylmagnesium chloride in tetrahydrofuran (56.2 ml, 169 mmol) is subsequently added dropwise at 0° C., and the mixture is stirred at room temperature for 20 h. The reaction mixture is neutralised using 25% acetic acid (about 55 ml) with ice-cooling and diluted with dist. water and ethyl acetate. The aqueous phase is extracted with ethyl acetate, dried over sodium sulfate and evaporated in vacuo.

The residue is dissolved in dichloromethane (100 ml) and added dropwise over the course of 20 min to a solution of polyphosphoric acid (43.4 g, 376 mmol) and methanesulfonic acid (24.9 ml, 379 mmol) in dichloro methane (100 ml). The reaction mixture is stirred at room temperature for 1 h and subsequently evaporated in vacuo. The residue is taken up in ethyl acetate, washed with dist. water, dried over sodium sulfate and evaporated in vacuo. The crude product is dissolved in ethyl acetate/dichloromethane (15/1), filtered through basic aluminium oxide and purified by recrystallisation from ethyl acetate.

Yield: 18.7 g (42 mmol), 75% of theory, colourless solid.

c) 10-Biphenyl-4-yl-9,9-dimethyl-2-(9-phenyl-9H-carbazol-3-yl)-9,10-dihydroacridine Caesium carbonate (26.0 g, 80 mmol), palladium acetate (0.4 g, 2 mmol) and xantphos (0.8 g, 4 mmol) are added to a solution of 9,9-dimethyl-2-(9-phenyl-9H-carbazol-3-yl)-9,10-dihydroacridine (18.0 g, 40 mmol) and 4-bromobiphenyl (9.3 g, 40 mmol) in degassed toluene (250 ml), and the mixture is heated under reflux for 8 h. The precipitated salts are filtered off, and the mother liquor is evaporated in vacuo. The residue is extracted with toluene in a Soxhlet extractor. The crude product is subsequently recrystallised four times from toluene and purified by sublimation twice in vacuo ($p=5\times10^{-5}$ mbar, T=290° C.).

Yield: 8.6 g (14 mmol), 36% of theory, purity >99.9% according to HPLC, colourless solid.

Example 2: Synthesis of 10-biphenyl-4-yl-2-(4-carbazol-9-ylphenyl)-9,9-dimethyl-9,10-dihydroacridine (HTM3)

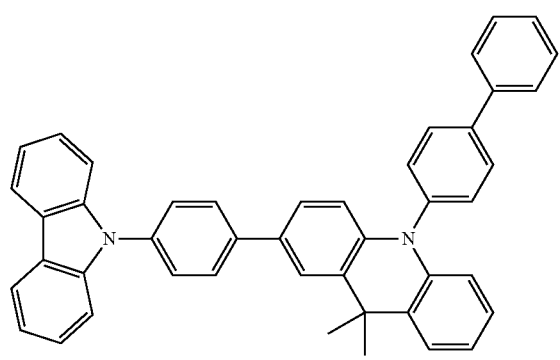 [SMILES: CC1(C)c2ccccc2N(c2ccc(-c3ccccc3)cc2)c2ccc(-c3ccc(-n4c5ccccc5c5ccccc54)cc3)cc21]

10-Biphenyl-4-yl-2-(4-carbazol-9-ylphenyl)-9,9-dimethyl-9,10-dihydroacridine is prepared analogously to Example 1 starting from 9-(4'-bromo-[1,1'-biphenyl]-4-yl)-9H-carbazole (CAS 212385-73-4) and methyl anthranilate in three steps.

Yield after sublimation: 7.2 g (12 mmol), 37% of theory, purity >99.9% according to HPLC, colourless solid.

Example 3: Synthesis of 9,9-diphenyl-10-(9-phenyl-9H-carbazol-3-yl)-9,10-dihydroacridine (H3)

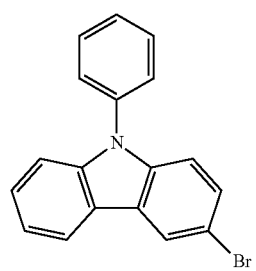

+

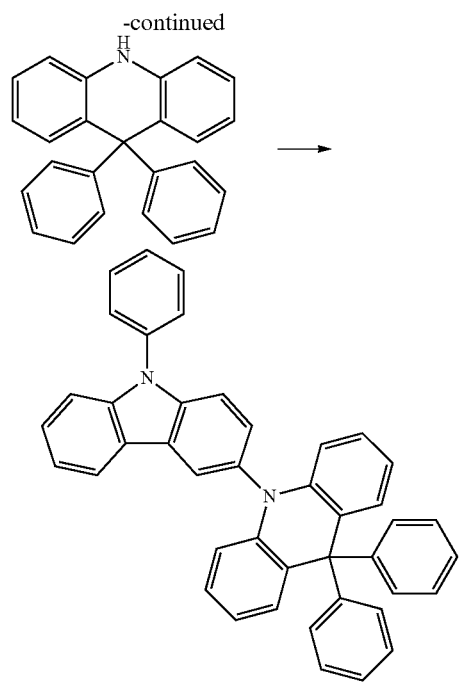

Caesium carbonate (30.6 g, 94 mmol), palladium acetate (0.5 g, 2 mmol) and xantphos (0.9 g, 5 mmol) are added to a solution of 9,10-dihydro-9,9-diphenylacridine (CAS 20474-15-1, 15.7 g, 47 mmol) and 3-bromo-9-phenyl-9H-carbazole (CAS 1153-85-1, 15.1 g, 47 mmol) in degassed toluene (300 ml), and the mixture is heated under reflux for 8 h. The precipitated salts are filtered off, and the mother liquor is evaporated in vacuo. The residue is extracted with toluene in a Soxhlet extractor. The crude product is subsequently recrystallised three times from toluene and purified by sublimation twice in vacuo ($p=5\times10^{-5}$ mbar, T=280° C.).

Yield: 10.5 g (18 mmol), 38% of theory, purity >99.9% according to HPLC, colourless solid.

Example 4: Synthesis of 9,9-dimethyl-10-[4-(9-phenyl-9H-carbazol-3-yl)phenyl]-9,10-dihydroacridine (HTM4)

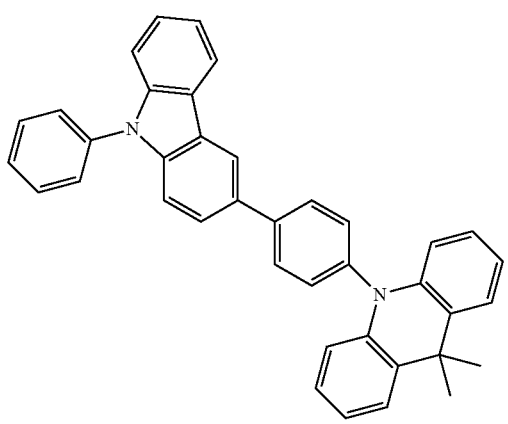 [SMILES: CC1(C)c2ccccc2N(c2ccc(-c3ccc4c(c3)c3ccccc3n4-c3ccccc3)cc2)c2ccccc21]

9,9-Dimethyl-10-[4-(9-phenyl-9H-carbazol-3-yl)phenyl]-9,10-dihydroacridine is prepared analogously to Example 3 starting from 3-(4-bromophenyl)-9-phenyl-9H- carbazole (CAS 1028647-93-9) and 9,10-dihydro-9,9-dimethylacridine (CAS 6267-02-3).

Yield after sublimation: 9.6 g (18 mmol), 36% of theory, purity >99.9% according to HPLC, colourless solid.

Example 5: Synthesis of 10-[4-(3,6-di-tert-butylcarbazol-9-yl)phenyl]-9,9-dimethyl-9,10-dihydroacridine (H4)

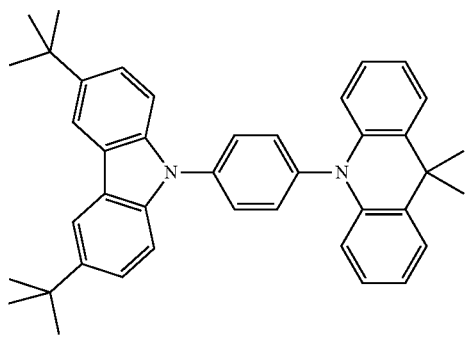 [SMILES: CC(C)(C)c1ccc2c(c1)c1cc(C(C)(C)C)ccc1n2-c1ccc(N2c3ccccc3C(C)(C)c3ccccc32)cc1]

10-[4-(3,6-Di-tert-butylcarbazol-9-yl)phenyl]-9,9-dimethyl-9,10-dihydroacridine is prepared analogously to Example 3 starting from 9-(4-bromophenyl)-3,6-bis-tert-butyl-9H-carbazole (CAS 601454-33-5) and 9,10-dihydro-9,9-dimethylacridine (CAS 6267-02-3).

Yield after sublimation: 11.2 g (20 mmol), 39% of theory, purity >99.9% according to HPLC, colourless solid.

Example 6: Synthesis of 10-(4'-carbazol-9-ylbiphenyl-4-yl)-9,9-diphenyl-9,10-dihydroacridine (H5)

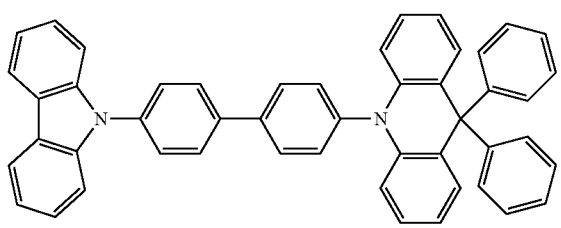 [SMILES: c1ccc(C2(c3ccccc3)c3ccccc3N(c3ccc(-c4ccc(-n5c6ccccc6c6ccccc65)cc4)cc3)c3ccccc32)cc1]

10-(4'-Carbazol-9-ylbiphenyl-4-yl)-9,9-diphenyl-9,10-dihydroacridine is prepared analogously to Example 3 starting from 9-(4'-bromo-[1,1'-biphenyl]-4-yl)-9H-carbazole (CAS 212385-73-4) and 9,10-dihydro-9,9-diphenyl acridine (CAS 20474-15-1).

Yield after sublimation: 8.7 g (13 mmol), 34% of theory, purity >99.9% according to HPLC, colourless solid.

Example 7: Synthesis of 5,5,9,9-tetramethyl-3-(9-phenyl-9H-carbazol-3-yl)-5H,9H-13b-azanaphtho[3,2,1-de]anthracene (HTM5)

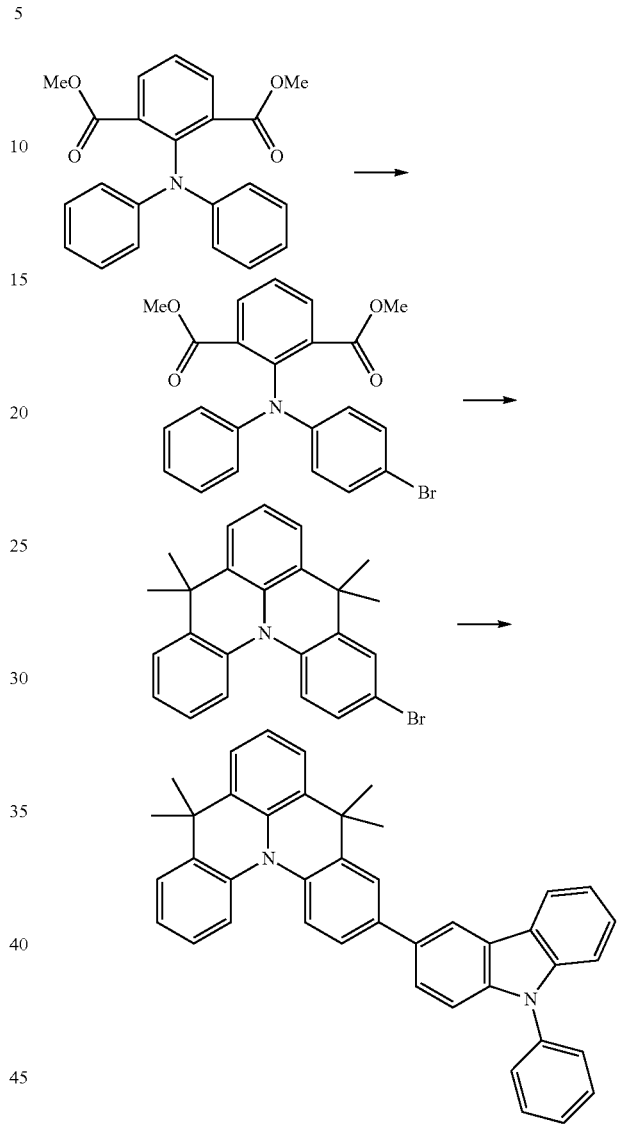

a) Dimethyl 2-[(4-bromophenyl)phenylamino]isophthalate

N-Bromosuccinimide (35.4 g, 199 mmol) is added in portions to a solution of dimethyl 2-diphenylaminoisophthalate (CAS 66131-47-3, 80 g, 221 mmol) in chloroform (2000 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.

Yield: 57.2 g (129 mmol), 65% of theory, colourless solid.

b) 3-Bromo-5,5,9,9-tetramethyl-5H,9H-13b-azanaphtho[3,2,1-de]anthracene

Dimethyl 2-[(4-bromophenyl)phenylamino]isophthalate (57.0 g, 129 mmol) is added in portions to a suspension of anhydrous cerium(III) chloride (35.0 g, 142 mmol) in dried tetrahydrofuran (800 ml). A 3 M solution of methylmagnesium chloride in tetrahydrofuran (129.0 ml, 387 mmol) is subsequently added dropwise at 0° C., and the mixture is stirred at room temperature for 20 h. The reaction mixture is neutralised using 25% acetic acid (about 120 ml) with ice-cooling and diluted with dist. water and ethyl acetate. The aqueous phase is extracted with ethyl acetate, dried over sodium sulfate and evaporated in vacuo.

The residue is dissolved in dichloromethane (200 ml) and added dropwise over the course of 20 min to a solution of polyphosphoric acid (101.1 g, 877 mmol) and methanesulfonic acid (57.5 ml, 877 mmol) in dichloromethane (200 ml). The reaction mixture is stirred at room temperature for 1 h and subsequently evaporated in vacuo. The residue is taken up in ethyl acetate, washed with dist. water, dried over sodium sulfate and evaporated in vacuo. The residue is dissolved in ethyl acetate and filtered through basic aluminium oxide. The crude product is subsequently recrystallised from ethyl acetate.

Yield: 39.6 g (98 mmol), 76% of theory, colourless solid.

c) 5,5,9,9-Tetramethyl-3-(9-phenyl-9H-carbazol-3-yl)-5H,9H-13b-azanaphtho[3,2,1-de]anthracene (9-Phenyl-9H-carbazol-3-yl)boronic acid (CAS 854952-58-2, 33.0 g, 115 mmol), 3-bromo-5,5,9,9-tetramethyl-5H,9H-13b-azanaphtho[3,2,1-de]anthracene (39.0 g, 96 mmol) and potassium phosphate monohydrate (66.3 g, 288 mmol) are initially introduced in a mixture of 300 ml of dist. water, 200 ml of toluene and 100 ml of dioxane and saturated with $N_2$ for 30 min. Tetrakis(triphenylphosphine)palladium (3.3 g, 3 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised four times from toluene and purified by sublimation twice in vacuo (p=5×10⁻⁵ mbar, T=290° C.).

Yield: 17.6 g (31 mmol), 32% of theory, purity >99.9% according to HPLC, colourless solid.

Example 8: Synthesis of 3-(4-carbazol-9-ylphenyl)-5,5,9,9-tetramethyl-5H,9H-13b-azanaphtho[3,2,1-de]anthracene (H6)

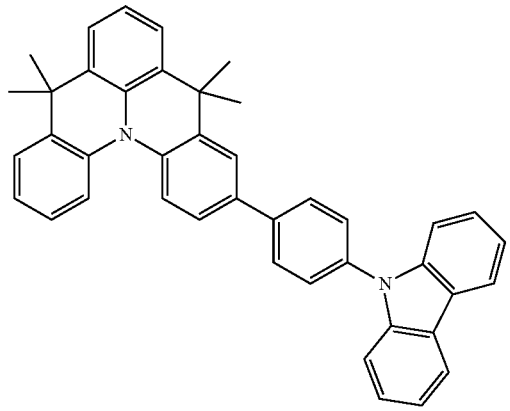 [SMILES: CC1(C)c2ccccc2N2c3ccc(-c4ccc(-n5c6ccccc6c6ccccc65)cc4)cc3C(C)(C)c3cccc1c32]

3-(4-Carbazol-9-ylphenyl)-5,5,9,9-tetramethyl-5H,9H-13b-azanaphtho[3,2,1-de]anthracene is prepared analogously to Example 7c) starting from 3-bromo-5,5,9,9-tetramethyl-5H,9H-13b-azanaphtho[3,2,1-de]anthracene and [4-(carbazol-9-yl)phenyl]boronic acid (CAS 419536-33-7).

Yield after sublimation: 9.4 g (17 mmol), 37% of theory, purity >99.9% according to HPLC, colourless solid.

Example 9: Synthesis of 5,5,9,9-tetramethyl-7-(9-phenyl-9H-carbazol-3-yl)-5H,9H-13b-azanaphtho[3,2,1-de]anthracene (HTM6)

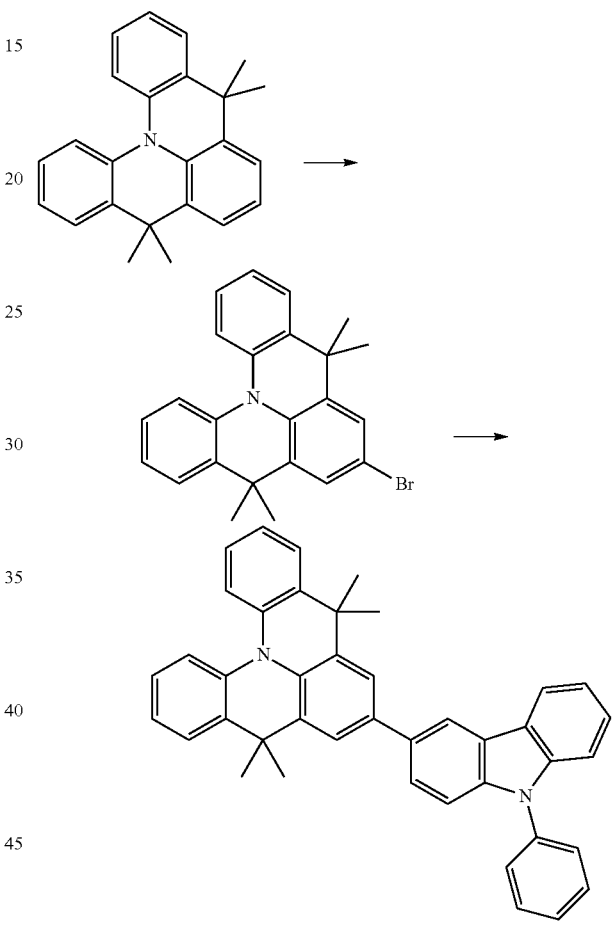

a) 7-Bromo-5,5,9,9-tetramethyl-5H,9H-13b-azanaphtho[3,2,1-de]anthracene

N-Bromosuccinimide (24.7 g, 139 mmol) is added in portions to a solution of 5,5,9,9-tetramethyl-5H,9H-13b-azanaphtho[3,2,1-de]anthracene (CAS 52066-62-3, 50 g, 154 mmol) in chloroform (1000 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.

Yield: 35.6 g (88 mmol), 63% of theory, colourless solid.

b) 5,5,9,9-Tetramethyl-7-(9-phenyl-9H-carbazol-3-yl)-5H,9H-13b-azanaphtho[3,2,1-de]anthracene (9-Phenyl-9H-carbazol-3-yl)boronic acid (CAS 854952-58-2, 29.9 g, 104 mmol), 7-bromo-5,5,9,9-tetramethyl-5H,9H-13b-azanaphtho[3,2,1-de]anthracene (35.0 g, 87 mmol) and potassium phosphate monohydrate (60.1 g, 261 mmol) are initially introduced in a mixture of 300 ml of dist. water, 200 ml of toluene and 100 ml of dioxane and saturated with $N_2$ for 30 min. Tetrakis(triphenylphosphine)palladium (3.0 g, 3 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised four times from toluene and purified by sublimation twice in vacuo (p=5×10⁻⁵ mbar, T=290° C.).

Yield: 17.0 g (30 mmol), 34% of theory, purity >99.9% according to HPLC, colourless solid.

Example 10: Synthesis of 7-(4-carbazol-9-ylphenyl)-5,5,9,9-tetramethyl-5H,9H-13b-azanaphtho[3,2,1-de]anthracene (H7)

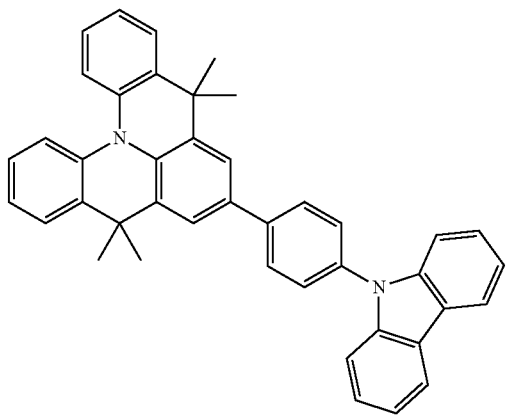 [SMILES: CC1(C)c2ccccc2N2c3ccccc3C(C)(C)c3cc(-c4ccc(-n5c6ccccc6c6ccccc65)cc4)cc1c32]

7-(4-Carbazol-9-ylphenyl)-5,5,9,9-tetramethyl-5H,9H-13b-azanaphtho[3,2,1-de]anthracene is prepared analogously to Example 9b) starting from 7-bromo-5,5,9,9-tetramethyl-5H,9H-13b-azanaphtho[3,2,1-de]anthracene and [4-(carbazol-9-yl)phenyl]boronic acid (CAS 419536-33-7).

Yield after sublimation: 10.3 g (18 mmol), 34% of theory, purity >99.9% according to HPLC, colourless solid.

Example 11: Synthesis of 4,4,8,8,12,12-hexamethyl-2-(9-phenyl-9H-carbazol-3-yl)-4H,8H,12H-12c-azadibenzo[cd,mn]pyrene (HTM7)

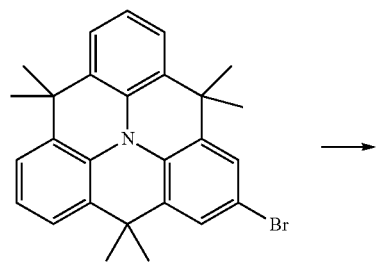 →

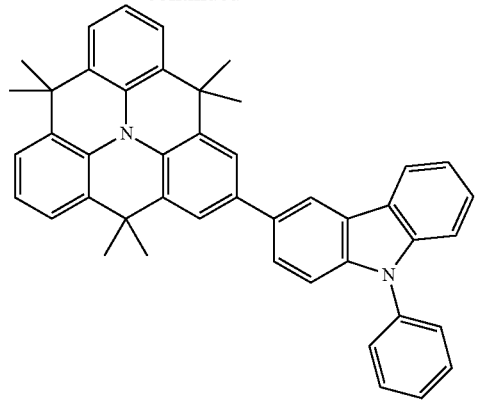

(9-Phenyl-9H-carbazol-3-yl)boronic acid (CAS 854952-58-2, 31.0 g, 108 mmol), 2-bromo-4,4,8,8,12,12-hexamethyl-4H,8H,12H-12c-azadibenzo[cd,mn]pyrene (40.0 g, 90 mmol) and potassium phosphate monohydrate (62.2 g, 270 mmol) are initially introduced in a mixture of 300 ml of dist. water, 200 ml of toluene and 100 ml of dioxane and saturated with $N_2$ for 30 min. Tetrakis(triphenylphosphine)palladium (3.1 g, 3 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised three times from toluene and purified by sublimation twice in vacuo (p=5×10⁻⁵ mbar, T=295° C.).

Yield: 15.8 g (26 mmol), 29% of theory, purity >99.9% according to HPLC, colourless solid.

Example 12: Synthesis of 2,6-di-tert-butyl-10-(4-carbazol-9-ylphenyl)-4,4,8,8,12,12-hexamethyl-4H,8H,12H-12c-azadibenzo[cd,mn]pyrene (HTM8)

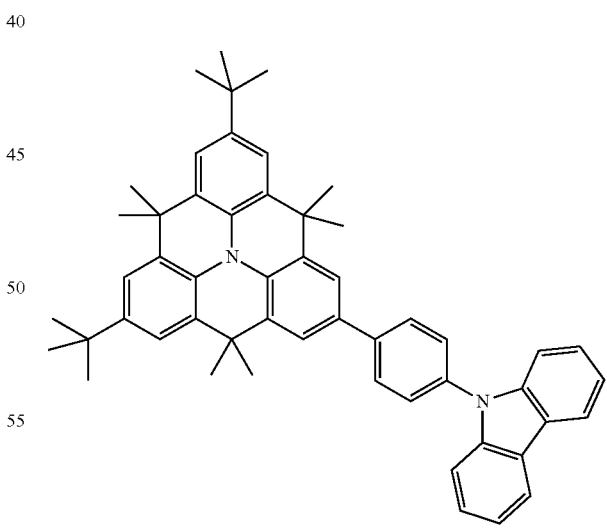

2,6-Di-tert-butyl-10-(4-carbazol-9-ylphenyl)-4,4,8,8,12,12-hexamethyl-4H,8H,12H-12c-azadibenzo[cd,mn]pyrene is prepared analogously to Example 11 starting from 2-bromo-6,10-di-tert-butyl-4,4,8,8,12,12-hexamethyl-4H,8H,12H-12c-azadibenzo[cd,mn]pyrene (CAS 1097721-82-8) and [4-(carbazol-9-yl)phenyl]boronic acid (CAS 419536-33-7).

Yield after sublimation: 7.8 g (11 mmol), 27% of theory, purity >99.9% according to HPLC, colourless solid.

Example 13: Synthesis of 3-(10-biphenyl-4-yl-12,12-dimethyl-10,12-dihydro-10-azaindeno[2,1-b]fluoren-7-yl)-5,5,9,9-tetramethyl-5H,9H-13b-azanaphtho[3,2,1-de]anthracene (HTM9)

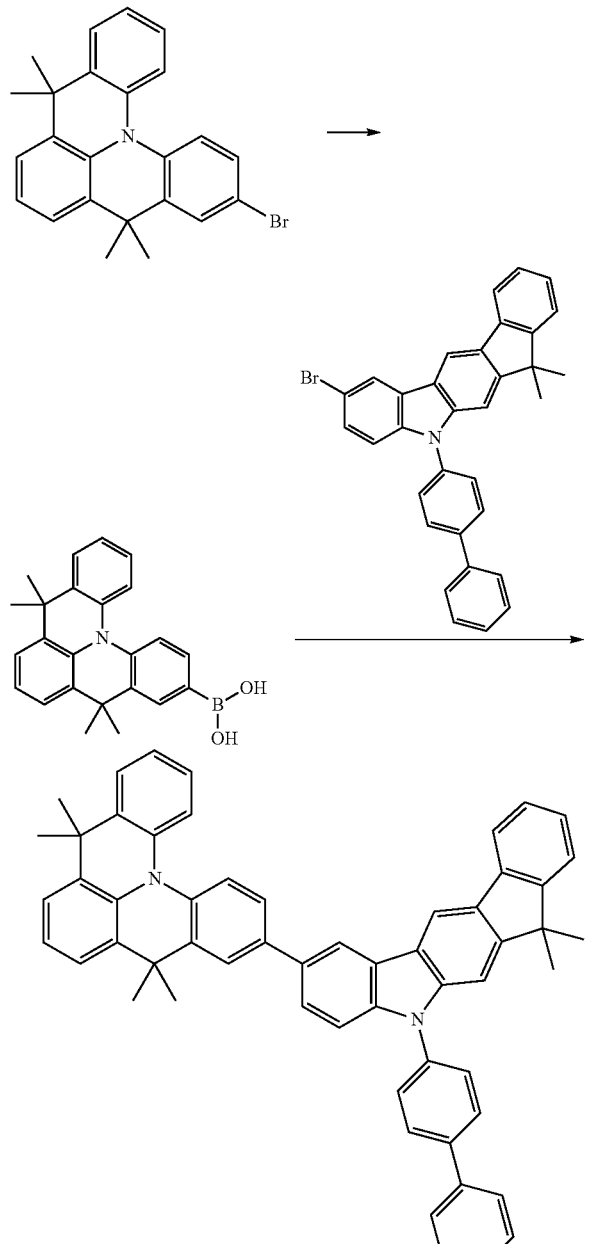

a) 5,5,9,9-Tetramethyl-5H,9H-13b-azanaphtho[3,2,1-de]anthracene-3-boronic acid 74.5 ml (149 mmol) of a 2 M solution of n-butyllithium in cyclohexane are slowly added to a solution of 3-bromo-5,5,9,9-tetramethyl-5H,9H-13b-azanaphtho[3,2,1-de]anthracene (Example 7b, 50.0 g, 124 mmol) in dry tetrahydrofuran (600 ml) at −75° C. The reaction mixture is stirred at −75° C. for 1 h, 27.6 ml (248 mmol) of trimethyl borate are added, and the mixture is warmed overnight at room temperature. For work-up, the mixture is diluted with ethyl acetate/dist. water/glacial acetic acid (6/2/1). The organic phase is separated off, washed with dist. water and dried over sodium sulfate. The crude product obtained after removal of the solvent in vacuo is employed in the next step without further purification.

Yield: 39.9 g (108 mmol), 87% of theory, colourless solid.

b) 3-(10-Biphenyl-4-yl-12,12-dimethyl-10,12-dihydro-10-azaindeno[2,1-b]fluoren-7-yl)-5,5,9,9-tetramethyl-5H,9H-13b-azanaphtho[3,2,1-de]anthracene 5,5,9,9-Tetramethyl-5H,9H-13b-azanaphtho[3,2,1-de]anthracene-3-boronic acid (20.0 g, 54 mmol), 10-biphenyl-4-yl-7-bromo-12,12-dimethyl-10,12-dihydro-10-azaindeno[2,1-b]fluorene (see as yet unpublished DE 102009023155.2, 23.2 g, 45 mmol) and potassium phosphate monohydrate (31.1 g, 135 mmol) are initially introduced in a mixture of 150 ml of dist. water, 100 ml of toluene and 50 ml of dioxane and saturated with $N_2$ for 30 min. Tetrakis(triphenylphosphine)palladium (1.6 g, 1 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised five times from toluene and purified by sublimation twice in vacuo (p=5×× $10^{-5}$ mbar, T=320° C.).

Yield: 10.9 g (14 mmol), 32% of theory, purity >99.9% according to HPLC, colourless solid.

Example 14: Synthesis of 3-(11,12-diphenyl-11,12-dihydro-11,12-diazaindeno[2,1-a]fluoren-3-yl)-5,5,9,9-tetramethyl-5H,9H-13b-azanaphtho[3,2,1-de]anthracene (HTM10)

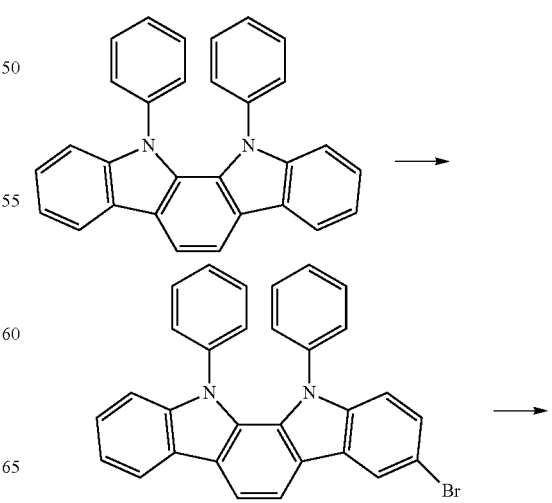

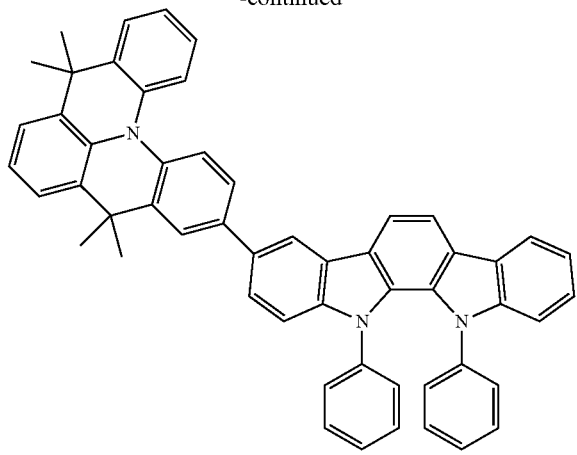

a) 3-Bromo-(11,12-diphenyl-11,12-dihydro-11,12-diazaindeno[2,1-a]fluorene

N-Bromosuccinimide (15.7 g, 88 mmol) is added in portions to a solution of 11,12-diphenyl-11,12-dihydro-11,12-diazaindeno[2,1-a]fluorene (CAS 222044-88-4, 40 g, 98 mmol) in chloroform (800 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.

Yield: 28.3 g (58 mmol), 66% of theory, colourless solid.

b) 3-(11,12-Diphenyl-11,12-dihydro-11,12-diazaindeno[2,1-a]fluoren-3-yl)-5,5,9,9-tetramethyl-5H,9H-13b-azanaphtho[3,2,1-de]anthracene 5,5,9,9-Tetramethyl-5H,9H-13b-azanaphtho[3,2,1-de]anthracene-3-boronic acid (Example 13a, 19.0 g, 51 mmol), 3-bromo-(11,12-diphenyl-11,12-dihydro-11,12-diazaindeno[2,1-a]fluorene (21.0 g, 43 mmol) and potassium phosphate monohydrate (29.7 g, 129 mmol) are initially introduced in a mixture of 150 ml of dist. water, 100 ml of toluene and 50 ml of dioxane and saturated with $N_2$ for 30 min. Tetrakis(triphenylphosphine)palladium (1.5 g, 1 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised five times from toluene and purified by sublimation twice in vacuo ($p=5\times10^{-5}$ mbar, T=315° C.).

Yield: 9.5 g (13 mmol), 30% of theory, purity >99.9% according to HPLC, colourless solid.

Examples 15-26: Syntheses of Compounds Containing Bridging Groups —O— and —S— a) Synthesis of the Precursor 7-bromo-9,9-dimethyl-9H-quino[3,2,1-kl]phenothiazine

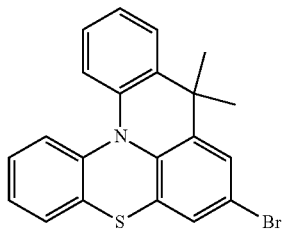

N-Bromosuccinimide (24.7 g, 139 mmol) is added in portions to a solution of 9,9-dimethyl-9H-quino[3,2,1-kl]phenothiazine (CAS 73183-70-7, 48.5 g, 154 mmol) in chloroform (1000 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.

Yield: 41.9 g (104 mmol), 69% of theory, colourless solid.

b) Synthesis of the Precursor 7-bromo-9,9-dimethyl-9H-quino[3,2,1-kl]phenoxazine

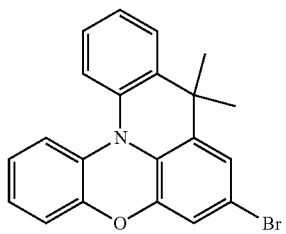

N-Bromosuccinimide (24.7 g, 139 mmol) is added in portions to a solution of 9,9-dimethyl-9H-quino[3,2,1-kl]phenoxazine (CAS 73183-73-0, 46 g, 154 mmol) in chloroform (1000 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.

Yield: 37 g (100 mmol), 64% of theory, colourless solid.

c) Synthesis of the Precursor 7-bromo-1,4-benzothiazino[2,3,4-kl]phenothiazine

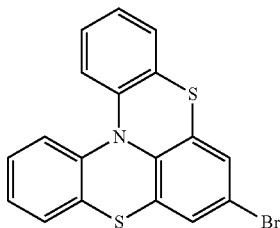

N-Bromosuccinimide (24.7 g, 139 mmol) is added in portions to a solution of 1,4-benzothiazino[2,3,4-kl]phenothiazine (CAS 1050521-47, 48.5 g, 154 mmol) in chloroform (1000 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.
Yield: 42 g (110 mmol), 64% of theory, colourless solid.

d) Synthesis of the Precursor 7-bromo 1,4-benzoxazino[2,3,4-kl]phenoxazine

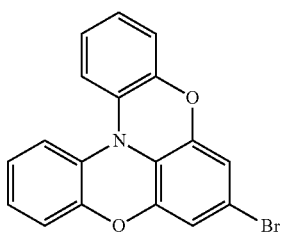

N-Bromosuccinimide (24.7 g, 139 mmol) is added in portions to a solution of 1,4-benzoxazino[2,3,4-kl]phenoxazine (CAS 784189-24-8, 42 g, 154 mmol) in chloroform (1000 ml) at 0° C. with exclusion of light, and the mixture is stirred at this temperature for 2 h. The reaction is terminated by addition of sodium sulfite solution, and the mixture is stirred at room temperature for a further 30 min. After phase separation, the organic phase is washed with water, and the aqueous phase is extracted with dichloromethane. The combined organic phases are dried over sodium sulfate and evaporated in vacuo. The residue is dissolved in ethyl acetate and filtered through silica gel. The crude product is subsequently recrystallised from heptane.
Yield: 31 g (89 mmol), 58% of theory, colourless solid.

e) Synthesis of Compound Examples 15-26

General Procedure for Compound Example 15: 9,9-Dimethyl-7-(9-phenyl-9H-carbazol-3-yl)-9H-5-thia-13b-azanaphtho[3,2,1-de]anthracene (HTM12)

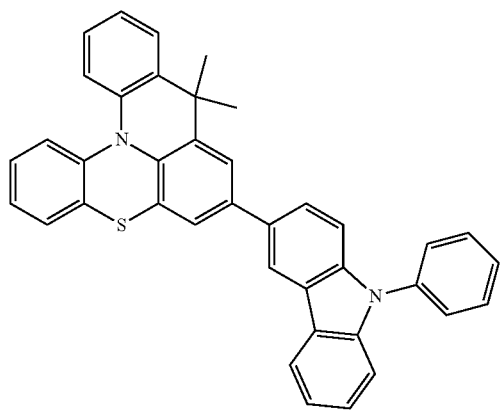 [SMILES: CC1(C)c2ccccc2N2c3ccccc3Oc3cc(-c4ccc5c(c4)c4ccccc4n5-c4ccccc4)cc1c32]

(9-Phenyl-9H-carbazol-3-yl)boronic acid (CAS 854952-58-2, 33.0 g, 115 mmol), 7-bromo-9,9-dimethyl-9H-quino[3,2,1-kl]-phenothiazine (27 g, 96 mmol) and potassium phosphate monohydrate (66.3 g, 288 mmol) are initially introduced in a mixture of 300 ml of dist. water, 200 ml of toluene and 100 ml of dioxane and saturated with $N_2$ for 30 min. Tetrakis(triphenylphosphine)palladium (3.3 g, 3 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised four times from toluene and purified by sublimation twice in vacuo ($p=5\times10^{-5}$ mbar, T=290° C.).
Yield: 28 g (50 mmol), 75% of theory, purity >99.9% according to HPLC, colourless solid.

The following compounds are obtained analogously (Examples 16-26):

| Ex. | Starting material 1 | Starting material 2 | Product | Yield |
|---|---|---|---|---|
| 16 (HTM15) | | | | 63% |

419536-33-7

-continued

| Ex. | Starting material 1 | Starting material 2 | Product | Yield |
|---|---|---|---|---|
| 17 (HTM17) | | 1001911-63-2 | | 73% |
| 18 (HTM11) | | 854952-58-2 | | 79% |
| 19 (HTM16) | | 1001911-63-2 | | 70% |
| 20 (H8) | | 419536-33-7 | | 74% |

-continued
| Ex. | Starting material 1 | Starting material 2 | Product | Yield |
|---|---|---|---|---|
| 21 (HTM14) | 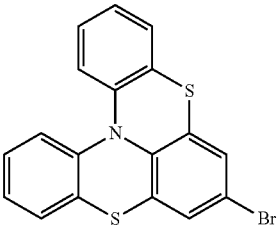 [SMILES: Brc1cc2c3c(c1)Sc1ccccc1N3c1ccccc1S2] | 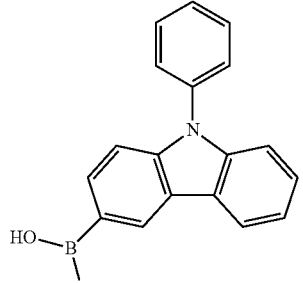 854952-58-2 | 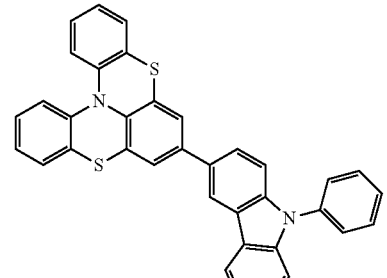 | 77% |
| 22 (HTM18) | 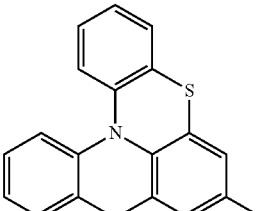 | 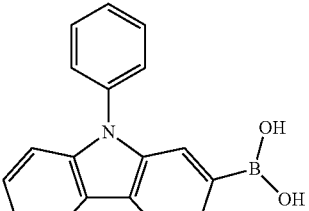 1001911-63-2 | 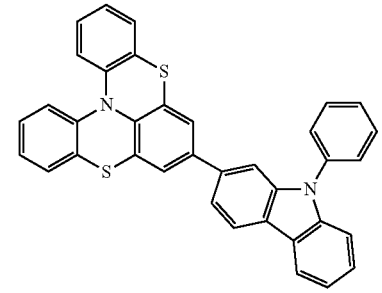 [SMILES: c1ccc(-n2c3ccccc3c3ccc(-c4cc5c6c(c4)Sc4ccccc4N6c4ccccc4S5)cc32)cc1] | 63% |
| 23 (H9) | 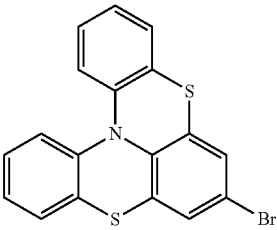 [SMILES: Brc1cc2c3c(c1)Sc1ccccc1N3c1ccccc1S2] | 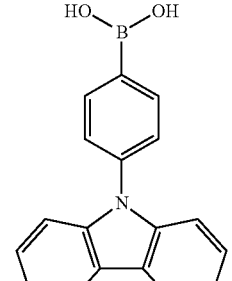 419536-33-7 | 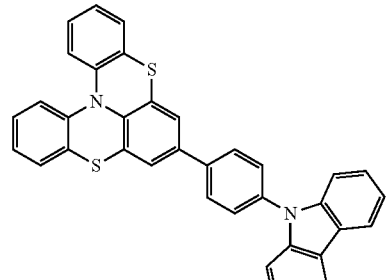 | 56% |
| 24 (HTM13) | 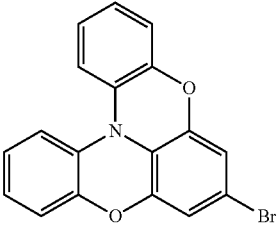 [SMILES: Brc1cc2c3c(c1)Oc1ccccc1N3c1ccccc1O2] | 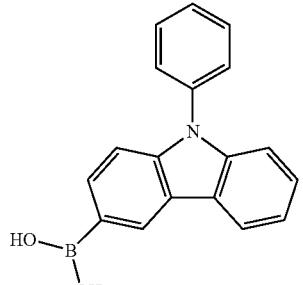 854952-58-2 | 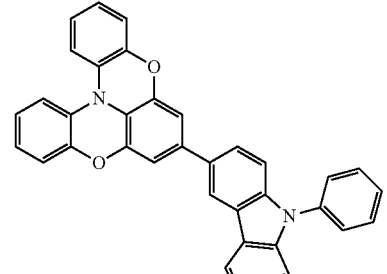 | 70% |

-continued

| Ex. | Starting material 1 | Starting material 2 | Product | Yield |
|---|---|---|---|---|
| 25 (HTM19) | 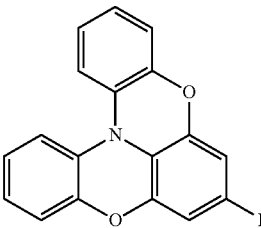 | 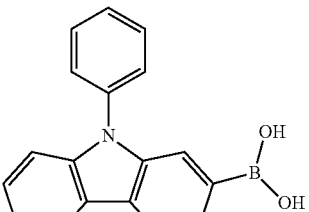 1001911-63-2 | 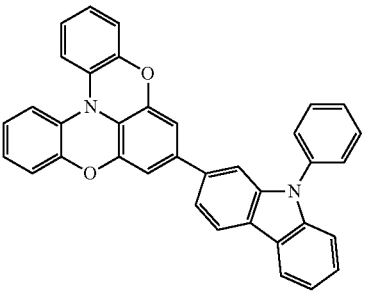 [SMILES: c1ccc(-n2c3ccccc3c3ccc(-c4cc5c6c(c4)Oc4ccccc4N6c4ccccc4O5)cc32)cc1] | 78% |
| 26 (H10) | 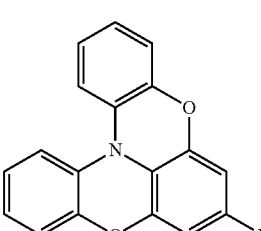 | 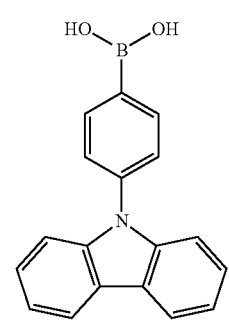 419536-33-7 | 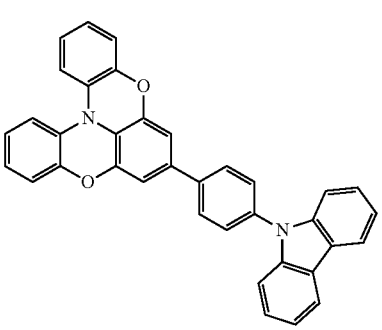 [SMILES: c1ccc2c(c1)Oc1cc(-c3ccc(-n4c5ccccc5c5ccccc54)cc3)cc3c1N2c1ccccc1O3] | 77% |

Example 27: Synthesis of 9,9-dimethyl-10-phenyl-2,7-bis-(9-phenyl-9H-carbazol-3-yl)-9,10-dihydroacridine a) 2,7-Dibromo-9,9-dimethyl-9,10-dihydroacridine b) 2,7-Dibromo-9,9-dimethyl-10-phenyl-9,10-dihydroacridine

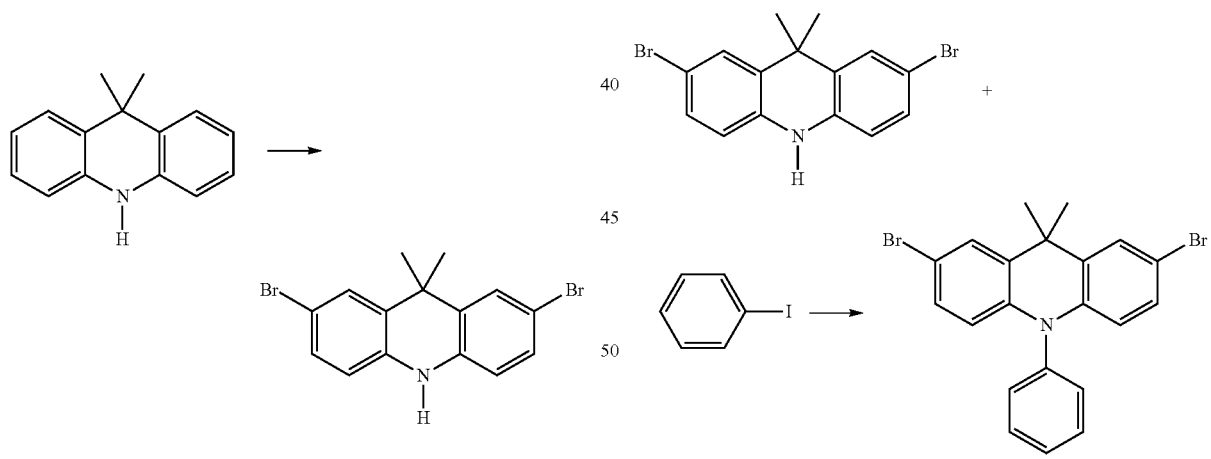

N-Bromosuccinimide (94.5 g, 531 mmol) is added in portions to a solution of 9,9-dimethyl-9,10-dihydroacridine (CAS 6267-02-3, 45 g, 252 mmol) in chloroform (1000 ml) at 0° C. with exclusion of light, and the mixture is stirred at this temperature for 2 h. 500 ml of water are subsequently added to the mixture. After phase separation, the organic phase is washed with water, and the aqueous phase is extracted with chloroform. The combined organic phases are dried over sodium sulfate and evaporated in vacuo. The residue is dissolved in ethyl acetate and filtered through silica gel. The crude product is subsequently recrystallised from heptane.

Yield: 64.7 g (176 mmol), 70% of theory, colourless solid.

A degassed solution of 16.6 ml (147 mmol) of 4-iodobenzene and 45.1 g (123 mmol) of 2,7-dibromo-9,9-dimethyl-9,10-dihydroacridine in 600 ml of toluene is saturated with $N_2$ for 1 h. Then, firstly 2.09 ml (8.6 mmol) of $P(tBu)_3$, then 1.38 g (6.1 mmol) of palladium(II) acetate are added to the solution, and 17.7 g (185 mmol) of NaOtBu in the solid state are subsequently added. The reaction mixture is heated under reflux for 1 h. After cooling to room temperature, 500 ml of water are carefully added. The aqueous phase is washed with 3×50 ml of toluene, dried over $MgSO_4$, and the solvent is removed in vacuo. Filtration of the crude product through silica gel with heptane/ethyl acetate (20:1) gives 44.1 g (99.6 mmol, 81%) of 2,7-dibromo-9,9-dimethyl-10-phenyl-9,10-dihydroacridine as pale-yellow crystals.

c) 9,9-Dimethyl-10-phenyl-2,7-bis-(9-phenyl-9H-carbazol-3-yl)-9,10-dihydroacridine

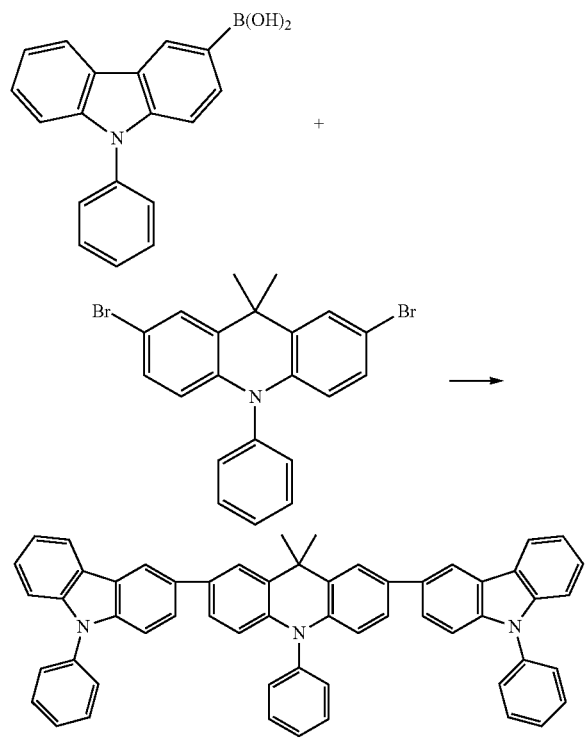

(9-Phenyl-9H-carbazol-3-yl)boronic acid (CAS 854952-58-2, 60.6 g, 211 mmol), 2,7-dibromo-9,9-dimethyl-10-phenyl-9,10-dihydroacridine (42.5 g, 96 mmol) and potassium phosphate monohydrate (66.3 g, 288 mmol) are initially introduced in a mixture of 300 ml of dist. water, 200 ml of toluene and 100 ml of dioxane and saturated with $N_2$ for 30 min. Tetrakis(triphenylphosphine)palladium (3.3 g, 3 mmol) is subsequently added, and the mixture is heated under reflux for 3 h. After dilution with toluene, the organic phase is separated off, washed twice with water, dried over $Na_2SO_4$ and evaporated in vacuo. The residue is extracted with toluene in a Soxhlet extractor. The crude product is subsequently recrystallised four times from toluene and purified by sublimation twice in vacuo.

Yield: 21.5 g (50 mmol), 75% of theory, purity >99.9% according to HPLC, colourless solid.

B) Device Examples

OLEDs according to the invention and OLEDs in accordance with the prior art are produced by a general process in accordance with WO 04/058911, which is adapted to the circumstances described here (layer-thickness variation, materials).

The data for various OLEDs are presented in Examples C1 to I44 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing.

These coated glass plates form the substrates to which the OLEDs are applied. The OLEDs have basically the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials employed for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation. A specification such as ST1:CBP:TER1 (55%:35%:10%) here means that material ST1 is present in the layer in a proportion by volume of 55%, CBP is present in the layer in a proportion of 35% and TER1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectrum are determined at a luminous density of 1000 cd/m², and the CIE 1931 x and y colour coordinates are calculated therefrom. The term U1000 in Table 2 denotes the voltage required for a luminous density of 1000 cd/m². CE1000 and PE1000 denote the current and power efficiencies achieved at 1000 cd/m=. Finally, EQE1000 is the external quantum efficiency at an operating luminous density of 1000 cd/m². The lifetime LT is defined as the time after which the luminous density drops from the initial luminous density L0 to a certain proportion L1 on operation at constant current. A specification of L0=4000 cd/m² and L1=80% in Table 2 means that the lifetime indicated in column LT corresponds to the time after which the initial luminous density of the corresponding OLED drops from 4000 cd/m² to 3200 cd/m². The values for the lifetime can be converted into a specification for other initial luminous densities with the aid of conversion formulae known to the person skilled in the art. The lifetime for an initial luminous density of 1000 cd/m² is a usual specification here.

The data for the various OLEDs are summarised in Table 2. Example C1-C16 are comparative examples in accordance with the prior art, Examples I1-I44 show data of OLEDs in which materials according to the invention are employed.

Some of the examples are explained in greater detail below in order to illustrate the advantages of the compounds according to the invention. However, it should be pointed out that this only represents a selection of the data shown in Table 2. As revealed by the table, significant improvements over the prior art are also achieved on use of the compounds according to the invention which are not discussed in detail below.

In some cases, an improvement in all parameters is achieved, but in some cases only an improvement in either the efficiency or the voltage or the lifetime is observed. However, even the improvement of one of the said parameters represents a significant advance, since different applications require optimisation with respect to different parameters.

Use of Compounds According to the Invention as Hole-Transport or Hole-Injection Materials OLEDs C1-C4 are comparative examples in accordance with the prior art in which fluorescent dopants D1-D3 are employed in combination with matrix materials H1 and H2, hole-transport materials HTM1, SpNPB, NPB, the carbazole-substituted planar amine PACbz and electron-transport materials $Alq_3$, ETM1, ST1 and ST2.

If material HTM1 in accordance with the prior art is replaced by compound HTM7 according to the invention (Examples I1, I2 and C2, C3), the current efficiency of the OLEDs remains approximately the same, while the operating voltage drops slightly and the lifetime increases significantly by up to about 30% (Examples I1, C3). A similar improvement in the performance data is obtained if HTM7 is employed directly as hole-injection layer (Examples I24, C5). In this case, the improvement in the lifetime is about 40%, and the power efficiency also increases significantly by about 10% due to the significantly reduced operating voltage.

Significant improvements are likewise obtained on use of compounds according to the Invention if these are directly adjacent to the emission layer of a fluorescent OLED (Examples I3-I12, I25, C1-4). The use of compounds HTM2 and HTM3 according to the invention is mentioned here merely by way of example compared with NPB and PACbz (Examples I3, I6-8, C1-4, C15). On replacement of NPB by HTM3 in combination with the amine-free dopant D3, a significant increase in the power efficiency by about 15% is obtained (Examples I3, C4), and a very significant increase in the lifetime by somewhat more than 50%.

Compared with PACbz, compound HTM3 in combination with dopant D1 exhibits an approximately 30% increased lifetime; compared with NPB, the increase is somewhat greater than 40% (Examples I7, C2, C15).

The compounds according to the invention also exhibit advantages in OLEDs which comprise a phosphorescent emission layer if they are employed as hole-transport material. This is demonstrated with reference to OLEDs which comprise compound ST1 as matrix material and the red-phosphorescent compound TER2 or the green-emitting dopant TEG1 as dopant (Examples I13-16, C5, C8, C16).

With compound HTM2 according to the invention, an approximately 20% increased power efficiency is obtained compared with EBM1, for example (Examples I13, C8); with HTM7, the lifetime can be increased very significantly by almost 40% (Examples I15, C8).

The use of compounds according to the invention on the hole-transport side of OLEDs thus produces significant improvements with respect to operating voltage, efficiency and lifetime.

Use of Compounds According to the Invention as Component in Mixed-Matrix Systems The use of compounds according to the invention as component in mixed-matrix systems is described below. Systems are shown here which consist of two matrix materials and one dopant. The compounds in accordance with the prior art used are the materials CBP, TCTA and FTPh (Examples C6, C7, C9-C14). The materials according to the invention used are compounds H3-H10 (Examples I17-I27, I29, I30). The compounds ST1, Ket1 and DAP1 are used as the second matrix component.

If, for example, compound H3 according to the invention is used in combination with ketone matrix Ket1, an increase in the lifetime by more than 50% compared with the prior art is obtained (Examples C9 and I18). Together with ST1 as second matrix component, a very significant improvement in the power efficiency by more than 25% compared with the prior art can furthermore be achieved (Examples C7, I17). This is attributable, in particular, to the operating voltage, which is significantly improved by 0.7 V compared with the prior art. As revealed by Table 2, similar improvements can be achieved with other materials according to the invention, including in red-phosphorescent OLEDs.

Significant improvements thus arise compared with mixed-matrix components in accordance with the prior art, especially with respect to voltage and lifetime. Since the materials according to the invention can be employed together with very different classes of matrix materials (ST1, Ket1, DAP1), it can be expected that significant improvements can also be achieved in combination with other classes of matrix materials, such as, for example, indolocarbazoles, dibenzothiophene derivatives, dibenzofuran derivatives or the like.

TABLE 1

Structure of the OLEDs

| Ex. | HIL Thickness | HTL Thickness | IL Thickness | EBL Thickness | EMU Thickness | HBL Thickness | ETL Thickness | EIL Thickness |
|---|---|---|---|---|---|---|---|---|
| C1 | HIL1 5 nm | HTM1 140 nm | — | NPB 20 nm | H1:D1 (95%:5%) 30 nm | — | $Alq_3$ 20 nm | LiF 1 nm |
| C2 | HIL1 5 nm | HTM1 140 nm | — | NPB 20 nm | H1:D1 (95%:5%) 30 nm | — | ETM1:LiQ (50%:50%) 20 nm | — |
| C3 | HIL1 5 nm | HTM1 110 nm | — | NPB 20 nm | H2:D2 (90%:10%) 30 nm | — | $Alq_3$ 20 nm | LiF 1 nm |
| C4 | HIL1 5 nm | SpNPB 40 nm | — | NPB 20 nm | H2:D3 (98.5%:1.5%) 30 nm | — | ST2:LiQ (50%:50%) 20 nm | — |
| C5 | — | HTM1 20 nm | — | NPB 20 nm | ST1:TER2 (85%:15%) 30 nm | — | $Alq_3$ 20 nm | LiF 1 nm |
| C6 | — | HTM1 20 nm | — | NPB 20 nm | ST1:CBP:TER1 (45%:45%:10%) 30 nm | ST1 10 nm | $Alq_3$ 20 nm | LiF 1 nm |
| C7 | — | HTM1 70 nm | HIL1 5 nm | EBM1 90 nm | ST1:CBP:TEG1 (30%:60%:10%) 30 nm | ST1 10 nm | ST1:LiQ (50%:50%) 30 nm | — |

TABLE 1-continued

Structure of the OLEDs

| Ex. | HIL Thickness | HTL Thickness | IL Thickness | EBL Thickness | EMU Thickness | HBL Thickness | ETL Thickness | EIL Thickness |
|---|---|---|---|---|---|---|---|---|
| C8 | — | HTM1 70 nm | HIL1 5 nm | EBM1 20 nm | ST1:TEG1 (90%:10%) 30 nm | ST1 10 nm | ST1:LiQ (50%:50%) 30 nm | — |
| C9 | HIL1 20 nm | — | — | EBM1 20 nm | Ket1:FTPh:TEG1 (30%:60%:10%) 30 nm | Ket1 10 nm | ETM2 20 nm | LiF 1 nm |
| C10 | HIL1 20 nm | — | — | EBM1 20 nm | Ket1:FTPh:TEG1 (60%:30%:10%) 30 nm | Ket1 10 nm | ETM2 20 nm | LiF 1 nm |
| C11 | HIL1 20 nm | — | — | EBM1 20 nm | Ket1:TCTA:TEG1 (60%:30%:10%) 30 nm | Ket1 10 nm | ETM2 20 nm | LiF 1 nm |
| C12 | HIL1 20 nm | — | — | EBM1 20 nm | Ket1:CBP:TEG1 (60%:30%:10%) 30 nm | Ket1 10 nm | ETM2 20 nm | LiF 1 nm |
| C13 | — | HTM1 70 nm | HIL1 5 nm | EBM1 90 nm | DAP1:CBP:TEG1 (30%:60%:10%) 30 nm | — | ST1:LiQ (50%:50%) 30 nm | — |
| C14 | — | HTM1 70 nm | HIL1 5 nm | EBM1 90 nm | ST1:TCTA:TEG1 (30%:60%:10%) 30 nm | — | ST1:LiQ (50%:50%) 30 nm | — |
| C15 | HIL1 5 nm | HTM1 140 nm | — | PACbz 20 nm | H1:D1 (95%:5%) 30 nm | — | ETM1:LiQ (50%:50%) 20 nm | — |
| C16 | — | HTM1 70 nm | HIL1 5 nm | PACbz 20 nm | ST1:TEG1 (90%:10%) 30 nm | ST1 10 nm | ST1:LiQ (50%:50%) 30 nm | — |
| I1 | HIL1 5 nm | HTM7 110 nm | — | NPB 20 nm | H2:D2 (90%:10%) 30 nm | — | Alq3 20 nm | LiF 1 nm |
| I2 | HIL1 5 nm | HTM7 140 nm | — | NPB 20 nm | H1:D1 (95%:5%) 30 nm | — | ETM1:LiQ (50%:50%) 20 nm | — |
| I3 | HIL1 5 nm | SpNPB 40 nm | — | HTM3 20 nm | H2:D3 (98.5%:1.5%) 30 nm | — | ST2:LiQ (50%:50%) 20 nm | — |
| I4 | HIL1 5 nm | SpNPB 40 nm | — | HTM4 20 nm | H2:D3 (98.5%:1.5%) 30 nm | — | ST2:LiQ (50%:50%) 20 nm | — |
| I5 | HIL1 5 nm | SpNPB 40 nm | — | HTM8 20 nm | H2:D3 (98.5%:1.5%) 30 nm | — | ST2:LiQ (50%:50%) 20 nm | — |
| I6 | HIL1 6 nm | HTM1 140 nm | — | HTM2 20 nm | H1:D1 (95%:5%) 30 nm | — | Alq3 20 nm | LiF 1 nm |
| I7 | HIL1 6 nm | HTM1 140 nm | — | HTM2 20 nm | H1:D1 (95%:5%) 30 nm | — | ETM1:LiQ (50%:50%) 20 nm | — |
| I8 | HIL1 5 nm | HTM1 110 nm | — | HTM2 20 nm | H2:D2 (90%:10%) 30 nm | — | Alq3 20 nm | LiF 1 nm |
| I9 | HIL1 5 nm | HTM1 140 nm | — | HTM5 20 nm | H1:D1 (95%:5%) 30 nm | — | ETM1:LiQ (50%:50%) 20 nm | — |
| I10 | HIL1 5 nm | HTM1 140 nm | — | HTM6 20 nm | H1:D1 (95%:5%) 30 nm | — | ETM1:LiQ (50%:50%) 20 nm | — |
| I11 | HIL1 5 nm | HTM1 140 nm | — | HTM9 20 nm | H1:D1 (95%:5%) 30 nm | — | ETM1:LiQ (50%:50%) 20 nm | — |
| I12 | HIL1 5 nm | HTM1 140 nm | — | HTM7 20 nm | H1:D1 (95%:5%) 30 nm | — | ETM1:LiQ (50%:50%) 20 nm | — |
| I13 | — | HTM1 70 nm | HIL1 5 nm | HTM2 20 nm | ST1:TEG1 (90%:10%) 30 nm | ST1 10 nm | ST1:LiQ (50%:50%) 30 nm | — |
| I14 | — | HTM1 70 nm | HIL1 5 nm | HTM6 20 nm | ST1:TEG1 (90%:10%) 30 nm | ST1 10 nm | ST1:LiQ (50%:50%) 30 nm | — |
| I15 | — | HTM1 70 nm | HIL1 5 nm | HTM7 20 nm | ST1:TEG1 (90%:10%) 30 nm | ST1 10 nm | ST1:LiQ (60%:50%) 30 nm | — |
| I16 | — | HTM1 20 nm | — | HTM2 20 nm | ST1:TER2 (85%:15%) 30 nm | — | Alq3 20 nm | LiF 1 nm |
| I17 | — | HTM1 70 nm | HIL1 5 nm | EBM1 90 nm | ST1:H3:TEG1 (30%:60%:10%) 30 nm | ST1 10 nm | ST1:LiQ (50%:50%) 30 nm | — |
| I18 | HIL1 20 nm | — | — | EBM1 20 nm | Ket1:H3:TEG1 (30%:60%:10%) 30 nm | Ket1 10 nm | ETM2 20 nm | LiF 1 nm |
| I19 | — | HTM1 70 nm | HIL1 5 nm | EBM1 90 nm | DAP1:H3:TEG1 (30%:60%:10%) 30 nm | — | ST1:LiQ (50%:50%) 30 nm | — |
| I20 | — | HTM1 70 nm | HIL1 5 nm | EBM1 90 nm | ST1:H5:TEG1 (30%:60%:10%) 30 nm | ST1 10 nm | ST1:LiQ (50%:50%) 30 nm | — |
| I21 | HIL1 20 nm | — | — | EBM1 20 nm | Ket1:H7:TEG1 (30%:60%:10%) 30 nm | Ket1 10 nm | ETM2 20 nm | LiF 1 nm |
| I22 | — | HTM1 20 nm | — | NPB 20 nm | ST1:H4:TER1 (45%:45%:10%) 30 nm | ST1 10 nm | Alq3 20 nm | LiF 1 nm |

TABLE 1-continued

| | | | | Structure of the OLEDs | | | | |
|---|---|---|---|---|---|---|---|---|
| Ex. | HIL Thickness | HTL Thickness | IL Thickness | EBL Thickness | EMU Thickness | HBL Thickness | ETL Thickness | EIL Thickness |
| I23 | — | HTM1 20 nm | — | NPB 20 nm | ST1:H6:TER1 (45%:45%:10%) 30 nm | ST1 10 nm | Alq$_3$ 20 nm | LiF 1 nm |
| I24 | — | HTM7 20 nm | — | NPB 20 nm | ST1:TER2 (85%:15%) 30 nm | — | Alq$_3$ 20 nm | LiF 1 nm |
| I25 | HIL1 5 nm | HTM1 140 nm | — | HTM9 20 nm | H1:D1 (95%:5%) 30 nm | — | ETM1:LiQ (50%:50%) 20 nm | — |
| I26 | — | HTM1 20 nm | — | NPB 20 nm | ST1:H8:TER1 (45%:45%:10%) 30 nm | ST1 10 nm | Alq$_3$ 20 nm | LiF 1 nm |
| I27 | — | HTM1 70 nm | HIL1 5 nm | EBM1 90 nm | ST1:H8:TEG1 (30%:60%:10%) 30 nm | ST1 10 nm | ST1:LiQ (50%:50%) 30 nm | — |
| I28 | HIL1 5 nm | SpNPB 40 nm | — | H8 20 nm | H2:D3 (98.5%:1.5%) 30 nm | — | ST2:LiQ (50%:50%) 20 nm | — |
| I29 | — | HTM1 20 nm | — | NPB 20 nm | ST1:H9:TER1 (45%:45%:10%) 30 nm | ST1 10 nm | Alq$_3$ 20 nm | LiF 1 nm |
| I30 | — | HTM1 20 nm | — | NPB 20 nm | ST1:H10:TER1 (45%:45%:10%) 30 nm | ST1 10 nm | Alq$_3$ 20 nm | LiF 1 nm |
| I31 | HIL1 5 nm | HTM1 140 nm | — | HTM11 20 nm | H1:D1 (95%:5%) 30 nm | — | ETM1:LiQ (50%:50%) 20 nm | — |
| I32 | HIL1 5 nm | HTM1 110 nm | — | HTM11 20 nm | H2:D2 (90%:10%) 30 nm | — | Alq$_3$ 20 nm | LiF 1 nm |
| I33 | — | HTM1 70 nm | HIL1 5 nm | HTM11 20 nm | ST1:TEG1 (90%:10%) 30 nm | ST1 10 nm | ST1:LiQ (50%:50%) 30 nm | — |
| I34 | — | HTM1 70 nm | HIL1 5 nm | HTM12 20 nm | ST1:TEG1 (90%:10%) 30 nm | ST1 10 nm | ST1:LiQ (50%:50%) 30 nm | — |
| I35 | — | HTM1 70 nm | HIL1 5 nm | HTM13 20 nm | ST1:TEG1 (90%:10%) 30 nm | ST1 10 nm | ST1:LiQ (50%:50%) 30 nm | — |
| I36 | — | HTM1 70 nm | HIL1 5 nm | HTM14 20 nm | ST1:TEG1 (90%:10%) 30 nm | ST1 10 nm | ST1:LiQ (50%:50%) 30 nm | — |
| I37 | — | HTM1 70 nm | HIL1 5 nm | HTM15 20 nm | ST1:TEG1 (90%:10%) 30 nm | ST1 10 nm | ST1:LiQ (50%:50%) 30 nm | — |
| I38 | — | HTM1 70 nm | HIL1 5 nm | HTM16 20 nm | ST1:TEG1 (90%:10%) 30 nm | ST1 10 nm | ST1:LiQ (50%:50%) 30 nm | — |
| I39 | — | HTM1 70 nm | HIL1 5 nm | HTM17 20 nm | ST1:TEG1 (90%:10%) 30 nm | ST1 10 nm | ST1:LiQ (50%:50%) 30 nm | — |
| I40 | — | HTM1 70 nm | HIL1 5 nm | HTM18 20 nm | ST1:TEG1 (90%:10%) 30 nm | ST1 10 nm | ST1:LiQ (50%:50%) 30 nm | — |
| I41 | — | HTM1 70 nm | HIL1 5 nm | HTM19 20 nm | ST1:TEG1 (90%:10%) 30 nm | ST1 10 nm | ST1:LiQ (50%:50%) 30 nm | — |
| I42 | HIL1 5 nm | HTM1 140 nm | — | HTM16 20 nm | H1:D1 (95%:5%) 30 nm | — | ETM1:LiQ (50%:50%) 20 nm | — |
| I43 | HIL1 5 nm | HTM1 110 nm | — | HTM16 20 nm | H2:D2 (90%:10%) 30 nm | — | Alq$_3$ 20 nm | LiF 1 nm |
| I44 | HIL1 5 nm | SpNPB 40 nm | — | HTM16 20 nm | H2:D3 (98.5%:1.5%) 30 nm | — | ST2:LiQ (50%:50%) 20 nm | — |

TABLE 2

Data for the OLEDs

| Ex. | U1000 (V) | CE1000 (cd/A) | PE1000 (lm/W) | EQE 1000 | CIE x/y at 1000 cd/m$^2$ | L0 (cd/m$^2$) | L1 % | LT (h) |
|---|---|---|---|---|---|---|---|---|
| C1 | 6.4 | 5.1 | 2.5 | 4.2% | 0.14/0.15 | 6000 | 50 | 150 |
| C2 | 4.7 | 8.1 | 5.4 | 6.3% | 0.14/0.15 | 6000 | 50 | 145 |
| C3 | 5.0 | 17.1 | 10.7 | 5.0% | 0.28/0.61 | 25000 | 50 | 480 |
| C4 | 4.3 | 9.8 | 7.1 | 7.6% | 0.14/0.16 | 6000 | 50 | 210 |
| C5 | 6.5 | 9.0 | 4.3 | 8.3% | 0.66/0.33 | 1000 | 50 | 18000 |
| C6 | 5.2 | 8.1 | 4.9 | 11.4% | 0.68/0.32 | 1000 | 50 | 15000 |
| C7 | 4.4 | 48 | 34 | 13.3% | 0.37/0.60 | 4000 | 80 | 450 |
| C8 | 4.2 | 52 | 39 | 14.5% | 0.36/0.60 | 4000 | 80 | 330 |
| C9 | 4.3 | 45 | 33 | 12.6% | 0.36/0.61 | 1000 | 50 | 39000 |
| C10 | 4.0 | 46 | 36 | 12.8% | 0.36/0.61 | 1000 | 50 | 34000 |
| C11 | 3.9 | 42 | 34 | 11.6% | 0.35/0.60 | 1000 | 50 | 14000 |
| C12 | 4.1 | 44 | 34 | 12.3% | 0.36/0.61 | 1000 | 50 | 25000 |
| C13 | 4.6 | 47 | 32 | 13.2% | 0.36/0.60 | 1000 | 50 | 43000 |
| C14 | 4.2 | 43 | 32 | 12.0% | 0.35/0.60 | 1000 | 50 | 17000 |

TABLE 2-continued

Data for the OLEDs

| Ex. | U1000 (V) | CE1000 (cd/A) | PE1000 (lm/W) | EQE 1000 | CIE x/y at 1000 cd/m$^2$ | L0 (cd/m$^2$) | L1 % | LT (h) |
|---|---|---|---|---|---|---|---|---|
| C15 | 4.8 | 8.0 | 5.2 | 6.2% | 0.14/0.15 | 6000 | 50 | 160 |
| C16 | 4.3 | 51 | 37 | 14.2% | 0.36/0.60 | 4000 | 80 | 350 |
| I1 | 4.8 | 16.7 | 10.9 | 4.9% | 0.28/0.61 | 25000 | 50 | 615 |
| I2 | 4.5 | 8.3 | 6.8 | 6.5% | 0.14/0.15 | 6000 | 50 | 180 |
| I3 | 4.0 | 10.5 | 8.2 | 8.1% | 0.14/0.16 | 6000 | 50 | 320 |
| I4 | 4.1 | 10.2 | 7.8 | 7.8% | 0.14/0.16 | 6000 | 50 | 305 |
| I5 | 4.3 | 9.3 | 6.8 | 7.2% | 0.14/0.16 | 6000 | 50 | 270 |
| I6 | 6.1 | 5.1 | 2.6 | 4.2% | 0.14/0.15 | 6000 | 50 | 200 |
| I7 | 4.5 | 7.7 | 5.4 | 6.0% | 0.14/0.15 | 6000 | 50 | 210 |
| I8 | 4.8 | 17.5 | 11.5 | 5.1% | 0.28/0.61 | 25000 | 50 | 655 |
| I9 | 4.6 | 8.0 | 5.5 | 6.3% | 0.14/0.15 | 6000 | 50 | 185 |
| I10 | 4.6 | 7.6 | 5.2 | 5.9% | 0.14/0.15 | 6000 | 50 | 185 |
| I11 | 4.6 | 7.8 | 5.3 | 6.1% | 0.14/0.15 | 6000 | 50 | 190 |
| I12 | 4.5 | 8.5 | 5.9 | 6.6% | 0.14/0.15 | 6000 | 50 | 225 |
| I13 | 4.2 | 63 | 47 | 17.5% | 0.36/0.60 | 4000 | 80 | 400 |
| I14 | 4.0 | 56 | 44 | 15.5% | 0.36/0.60 | 4000 | 80 | 375 |
| I15 | 4.1 | 61 | 47 | 17.1% | 0.36/0.60 | 4000 | 80 | 455 |
| I16 | 5.8 | 10.3 | 5.6 | 9.5% | 0.66/0.33 | 1000 | 50 | 29000 |
| I17 | 3.7 | 51 | 43 | 14.3% | 0.37/0.61 | 4000 | 80 | 585 |
| I18 | 3.6 | 52 | 45 | 14.5% | 0.36/0.61 | 1000 | 50 | 60000 |
| I19 | 3.7 | 46 | 39 | 13.0% | 0.37/0.60 | 1000 | 50 | 56000 |
| I20 | 3.8 | 52 | 43 | 14.5% | 0.36/0.61 | 4000 | 80 | 610 |
| I21 | 3.5 | 49 | 44 | 13.7% | 0.36/0.61 | 1000 | 50 | 57000 |
| I22 | 4.9 | 8.8 | 5.6 | 12.3% | 0.68/0.32 | 1000 | 50 | 18000 |
| I23 | 4.7 | 9.1 | 6.1 | 12.7% | 0.68/0.32 | 1000 | 50 | 23000 |
| I24 | 6.1 | 9.3 | 4.8 | 8.6% | 0.66/0.33 | 1000 | 50 | 26000 |
| I25 | 4.5 | 7.5 | 5.2 | 6.0% | 0.14/0.15 | 6000 | 50 | 175 |
| I26 | 4.9 | 8.7 | 5.6 | 12.2% | 0.68/0.32 | 1000 | 50 | 17000 |
| I27 | 4.4 | 47 | 33 | 12.9% | 0.37/0.61 | 4000 | 80 | 490 |
| I28 | 4.2 | 10.7 | 8.0 | 8.3% | 0.14/0.16 | 6000 | 50 | 215 |
| I29 | 5.0 | 8.4 | 5.3 | 11.8% | 0.68/0.32 | 1000 | 50 | 17000 |
| I30 | 5.1 | 8.5 | 5.2 | 12.0% | 0.68/0.32 | 1000 | 50 | 21000 |
| I31 | 4.7 | 9.5 | 6.4 | 7.4% | 0.14/0.15 | 6000 | 50 | 190 |
| I32 | 4.9 | 18.5 | 11.8 | 5.4% | 0.28/0.61 | 25000 | 50 | 640 |
| I33 | 4.2 | 57 | 43 | 15.9% | 0.36/0.60 | 4000 | 80 | 390 |
| I34 | 4.1 | 55 | 43 | 15.4% | 0.36/0.60 | 4000 | 80 | 310 |
| I35 | 4.1 | 57 | 43 | 15.8% | 0.36/0.60 | 4000 | 80 | 350 |
| I36 | 4.2 | 55 | 41 | 15.2% | 0.36/0.60 | 4000 | 80 | 300 |
| I37 | 4.3 | 56 | 41 | 15.6% | 0.36/0.60 | 4000 | 80 | 290 |
| I38 | 4.1 | 52 | 40 | 14.4% | 0.36/0.60 | 4000 | 80 | 350 |
| I39 | 4.2 | 55 | 41 | 15.3% | 0.36/0.61 | 4000 | 80 | 300 |
| I40 | 4.1 | 56 | 42 | 15.5% | 0.36/0.59 | 4000 | 80 | 270 |
| I41 | 4.3 | 58 | 42 | 16.0% | 0.36/0.60 | 4000 | 80 | 280 |
| I42 | 4.6 | 8.8 | 6.0 | 6.9% | 0.14/0.15 | 6000 | 50 | 110 |
| I43 | 4.8 | 17.8 | 11.5 | 5.2% | 0.28/0.61 | 25000 | 50 | 410 |
| I44 | 4.2 | 10.1 | 7.7 | 7.9% | 0.14/0.16 | 6000 | 50 | 180 |

TABLE 3

Structural formulae of the materials

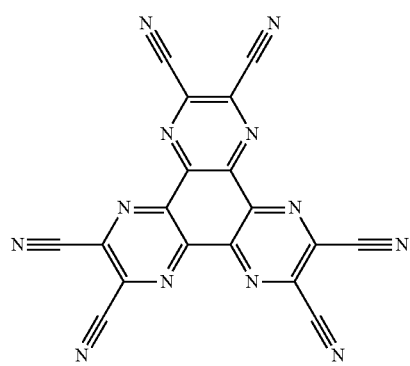 [SMILES: N#Cc1nc2c3nc(C#N)c(C#N)nc3c3nc(C#N)c(C#N)nc3c2nc1C#N]

HIL1

TABLE 3-continued

Structural formulae of the materials

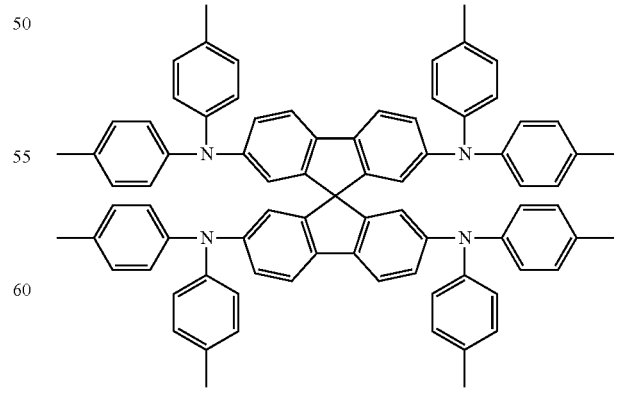

HTM1 (prior art)

TABLE 3-continued
Structural formulae of the materials
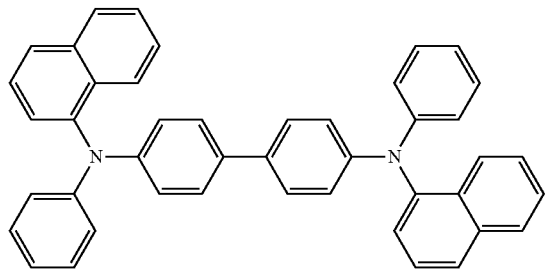 [SMILES: c1ccc(N(c2ccc(-c3ccc(N(c4ccccc4)c4cccc5ccccc45)cc3)cc2)c2cccc3ccccc23)cc1]
NPB (prior art)
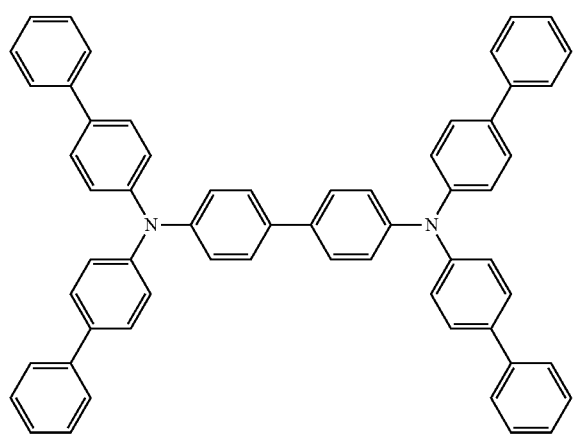 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
EBM1 (prior art)
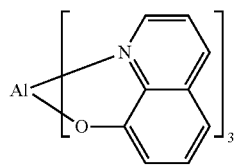
Alq₃
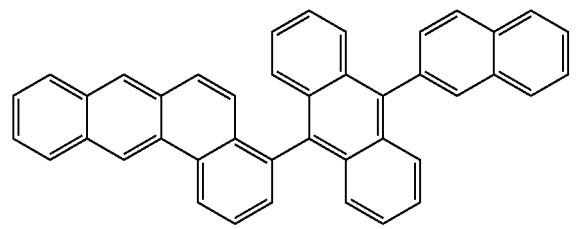 [SMILES: c1ccc2cc(-c3c4ccccc4c(-c4cccc5c4ccc4cc6ccccc6cc45)c4ccccc34)ccc2c1]
H1
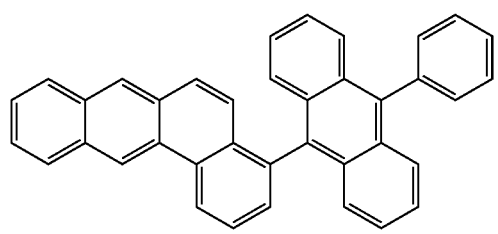 [SMILES: c1ccc(-c2c3ccccc3c(-c3cccc4c3ccc3cc5ccccc5cc34)c3ccccc23)cc1]
H2
TABLE 3-continued
Structural formulae of the materials
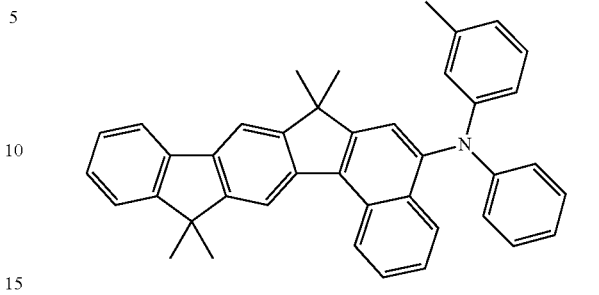
D1
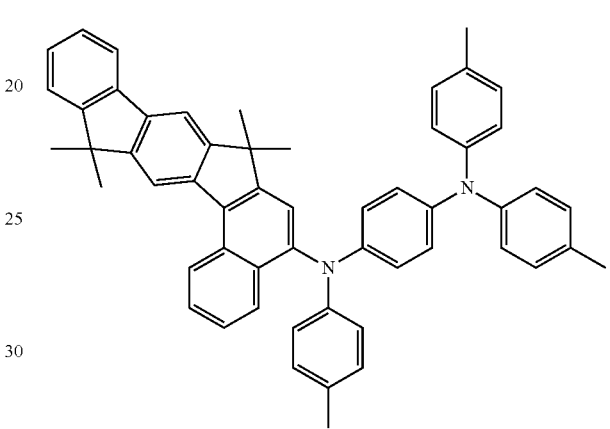
D2
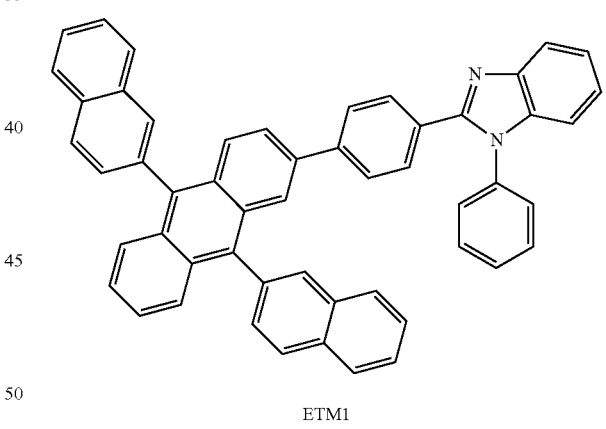
ETM1
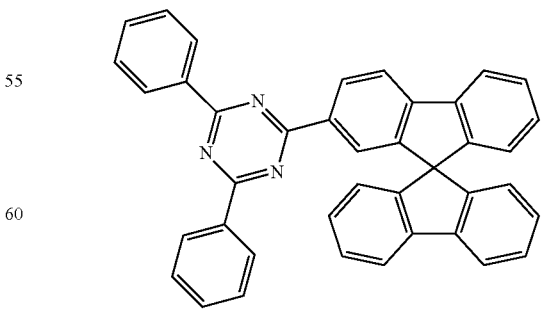
ST1

TABLE 3-continued
Structural formulae of the materials
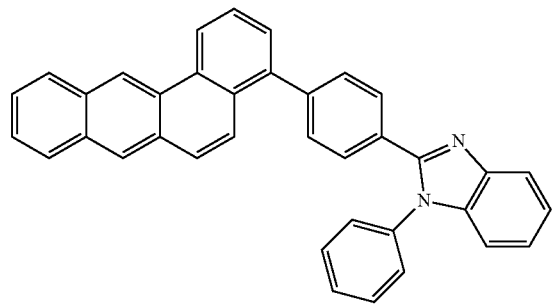 [SMILES: c1ccc(-n2c(-c3ccc(-c4cccc5c4ccc4cc6ccccc6cc45)cc3)nc3ccccc32)cc1]
ETM2
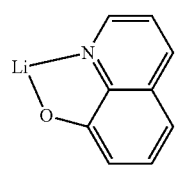
LiQ
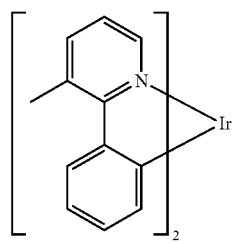
TEG1
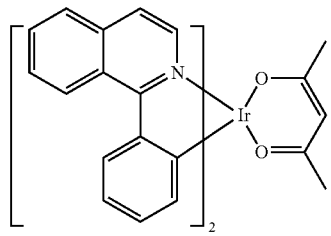
TER1
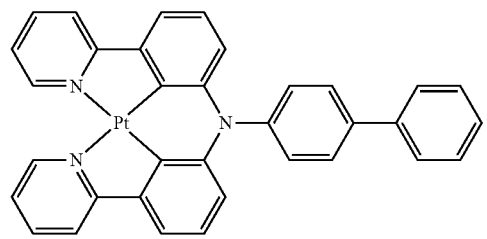
TER2
TABLE 3-continued
Structural formulae of the materials
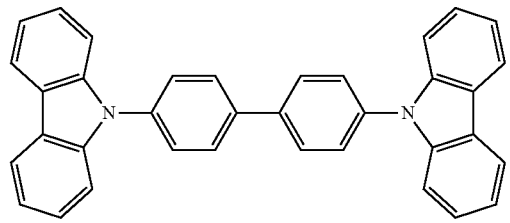 [SMILES: c1ccc2c(c1)c1ccccc1n2-c1ccc(-c2ccc(-n3c4ccccc4c4ccccc43)cc2)cc1]
CBP (prior art)
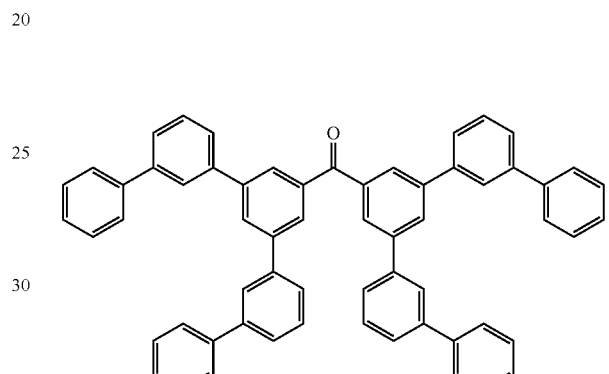
Ket1 (prior art)
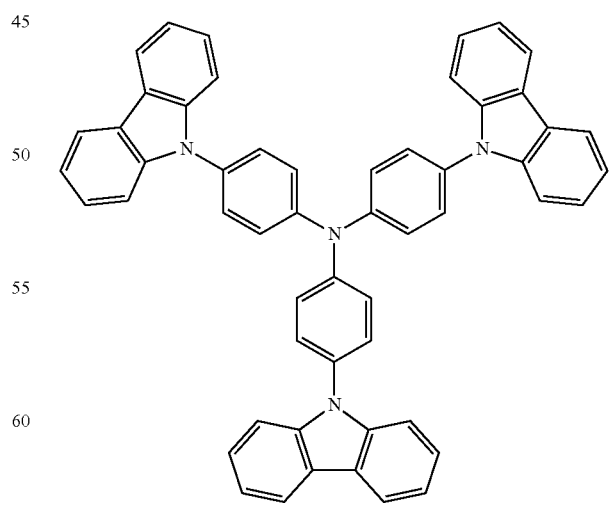
TCTA (prior art)

TABLE 3-continued
Structural formulae of the materials
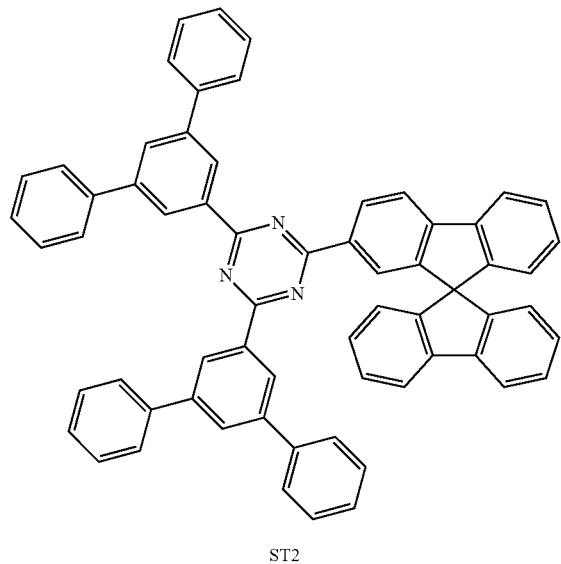
ST2
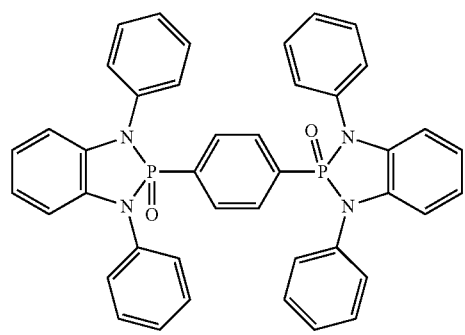 [SMILES: O=P1(c2ccc(P3(=O)N(c4ccccc4)c4ccccc4N3c3ccccc3)cc2)N(c2ccccc2)c2ccccc2N1c1ccccc1]
DAP1
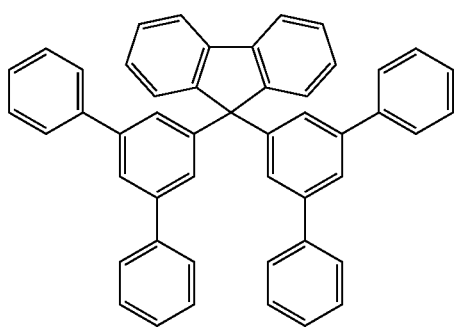 [SMILES: c1ccc(-c2cc(-c3ccccc3)cc(C3(c4cc(-c5ccccc5)cc(-c5ccccc5)c4)c4ccccc4-c4ccccc43)c2)cc1]
FTPh (prior art)
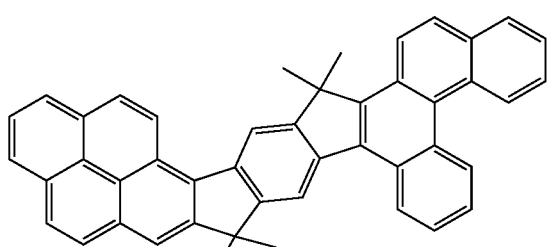
D3
TABLE 3-continued
Structural formulae of the materials
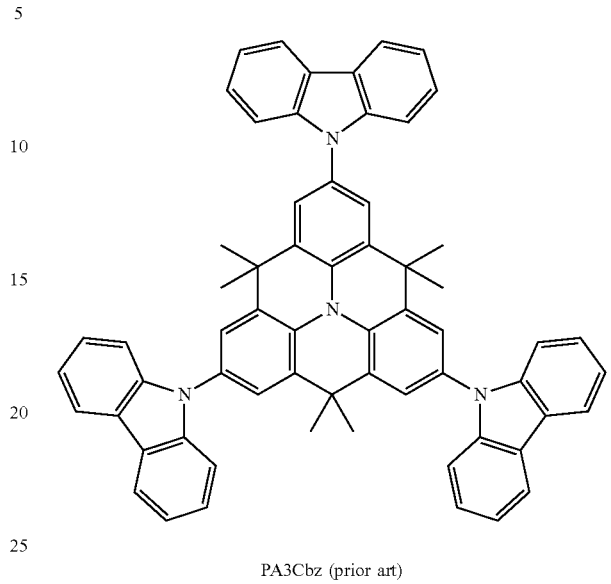
PA3Cbz (prior art)
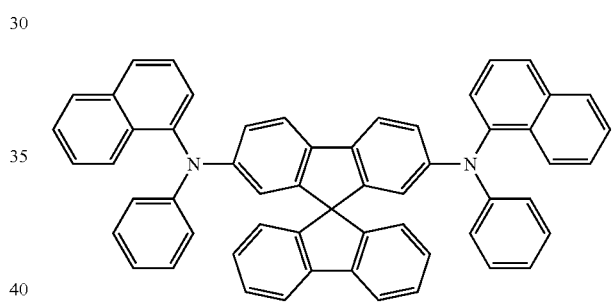
SpNPB
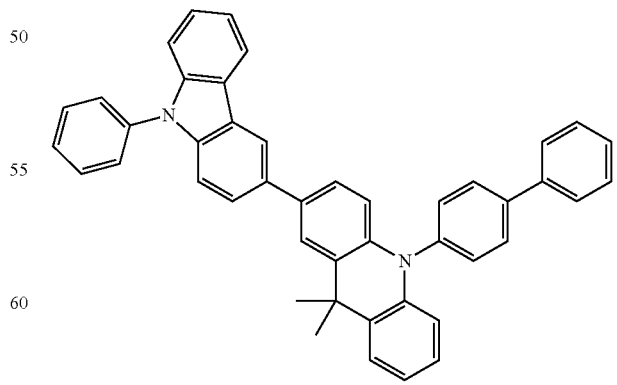
HTM2 (according to the invention)

TABLE 3-continued

Structural formulae of the materials

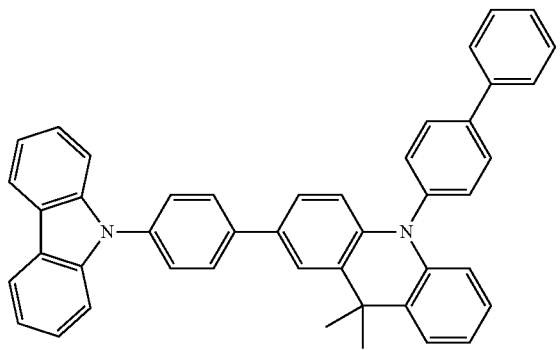 [SMILES: CC1(C)c2ccccc2N(c2ccc(-c3ccccc3)cc2)c2ccc(-c3ccc(-n4c5ccccc5c5ccccc54)cc3)cc21]

HTM3 (according to the invention)

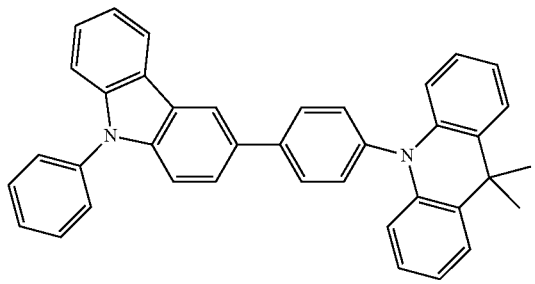 [SMILES: CC1(C)c2ccccc2N(c2ccc(-c3ccc4c(c3)c3ccccc3n4-c3ccccc3)cc2)c2ccccc21]

HTM4 (according to the invention)

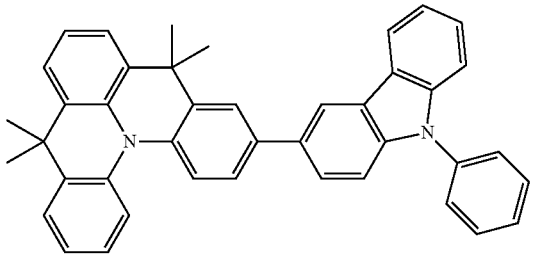 [SMILES: CC1(C)c2ccccc2N2c3ccc(-c4ccc5c(c4)c4ccccc4n5-c4ccccc4)cc3C(C)(C)c3cccc1c32]

HTM5 (according to the invention)

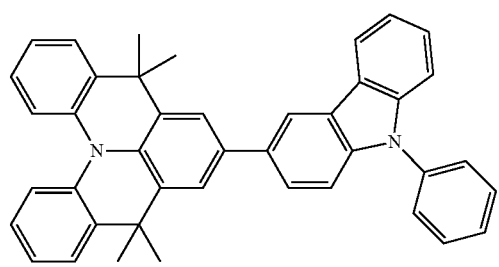 [SMILES: CC1(C)c2ccccc2N2c3ccccc3C(C)(C)c3cc(-c4ccc5c(c4)c4ccccc4n5-c4ccccc4)cc1c32]

HTM6 (according to the invention)

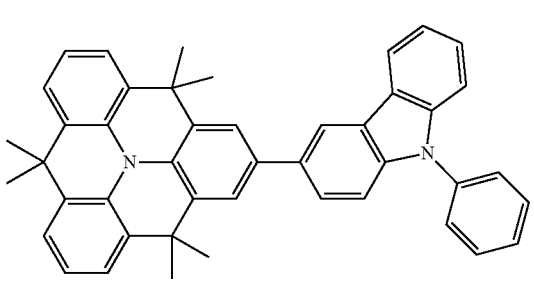 [SMILES: CC1(C)c2cccc3c2N2c4c1cccc4C(C)(C)c1cc(-c4ccc5c(c4)c4ccccc4n5-c4ccccc4)cc(c12)C3(C)C]

HTM7 (according to the invention)

TABLE 3-continued

Structural formulae of the materials

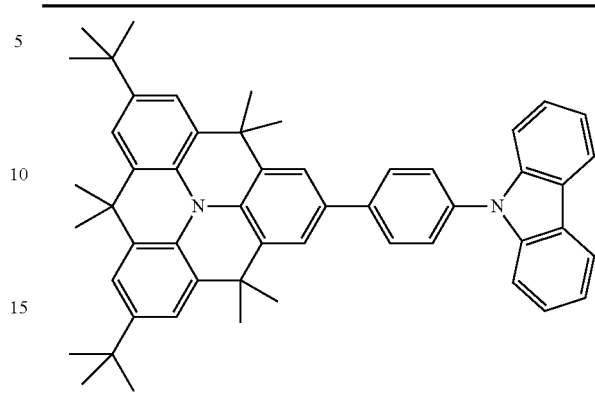

HTM8 (according to the invention)

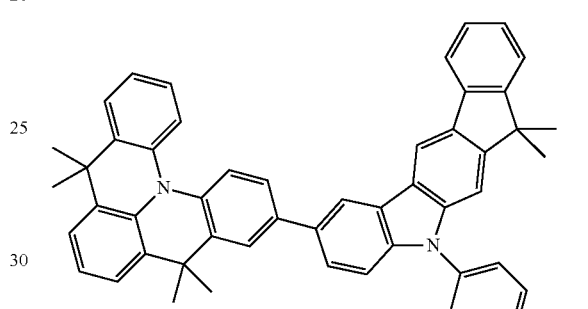

HTM9 (according to the invention)

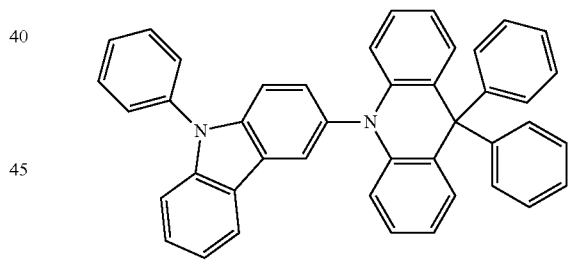

H3 (according to the invention)

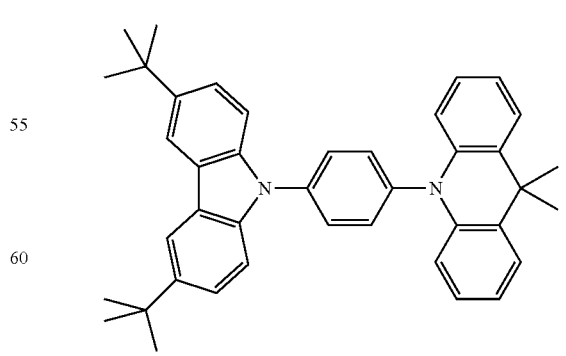

H4 (according to the invention)

TABLE 3-continued

Structural formulae of the materials

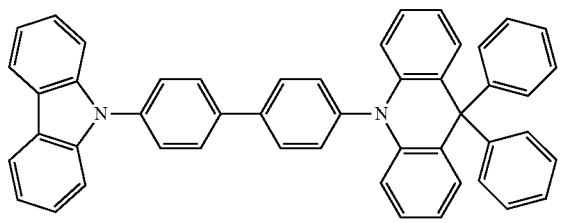 [SMILES: c1ccc(C2(c3ccccc3)c3ccccc3N(c3ccc(-c4ccc(-n5c6ccccc6c6ccccc65)cc4)cc3)c3ccccc32)cc1]

H5 (according to the invention)

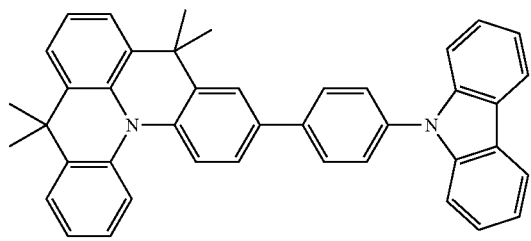 [SMILES: CC1(C)c2ccccc2N2c3ccc(-c4ccc(-n5c6ccccc6c6ccccc65)cc4)cc3C(C)(C)c3cccc1c32]

H6 (according to the invention)

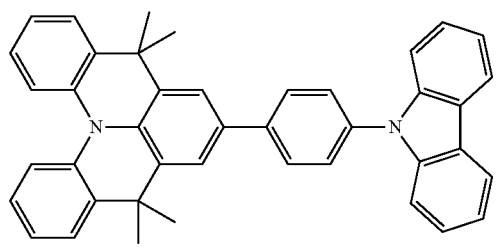 [SMILES: CC1(C)c2ccccc2N2c3ccccc3C(C)(C)c3cc(-c4ccc(-n5c6ccccc6c6ccccc65)cc4)cc1c32]

H7 (according to the invention)

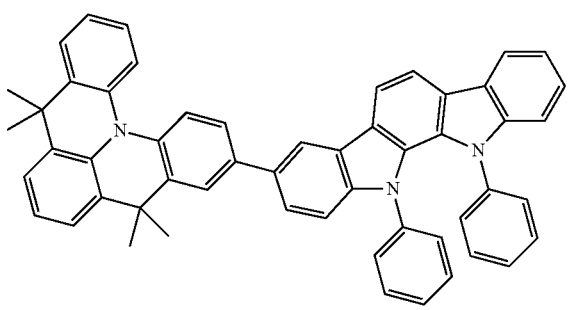 [SMILES: CC1(C)c2ccccc2N2c3ccc(-c4ccc5c(c4)c4ccc6c7ccccc7n(-c7ccccc7)c6c4n5-c4ccccc4)cc3C(C)(C)c3cccc1c32]

HTM10 (according to the invention)

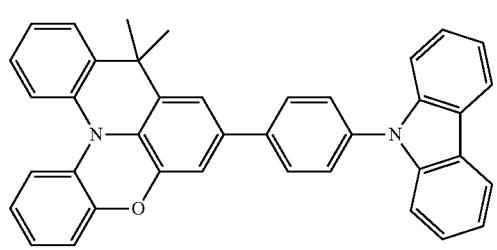 [SMILES: CC1(C)c2ccccc2N2c3ccccc3Oc3cc(-c4ccc(-n5c6ccccc6c6ccccc65)cc4)cc1c32]

H8 (according to the invention)

TABLE 3-continued

Structural formulae of the materials

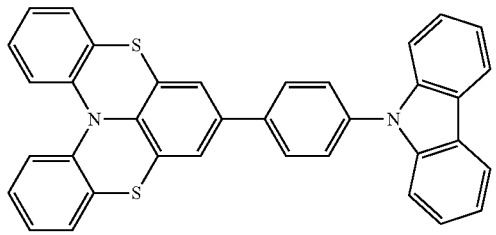 [SMILES: c1ccc2c(c1)Sc1cc(-c3ccc(-n4c5ccccc5c5ccccc54)cc3)cc3c1N2c1ccccc1S3]

H9 (according to the invention)

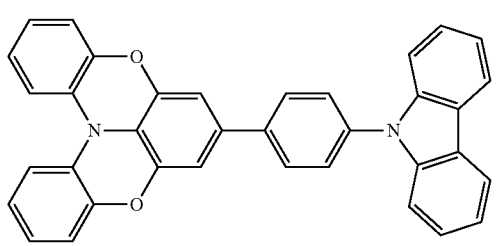

H10 (according to the invention)

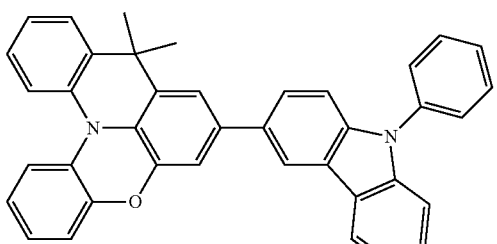

HTM11 (according to the invention)

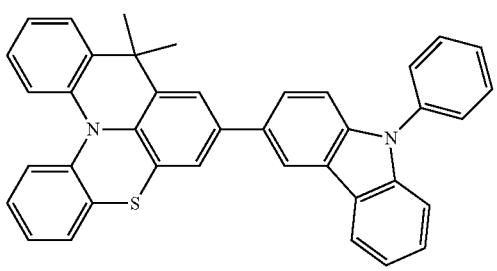 [SMILES: CC1(C)c2ccccc2N2c3ccccc3Sc3cc(-c4ccc5c(c4)c4ccccc4n5-c4ccccc4)cc1c32]

HTM12 (according to the invention)

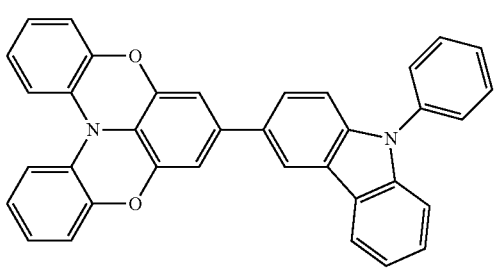 [SMILES: c1ccc(-n2c3ccccc3c3cc(-c4cc5c6c(c4)Oc4ccccc4N6c4ccccc4O5)ccc32)cc1]

HTM13 (according to the invention)

TABLE 3-continued

Structural formulae of the materials

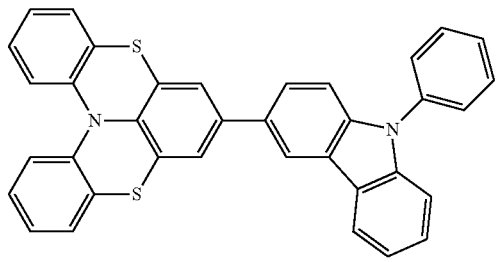

HTM14 (according to the invention)

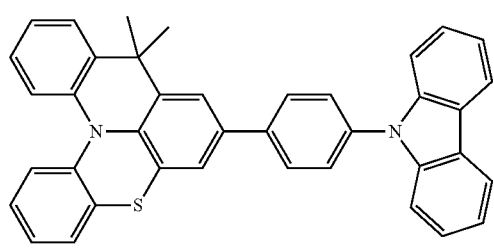

HTM15 (according to the invention)

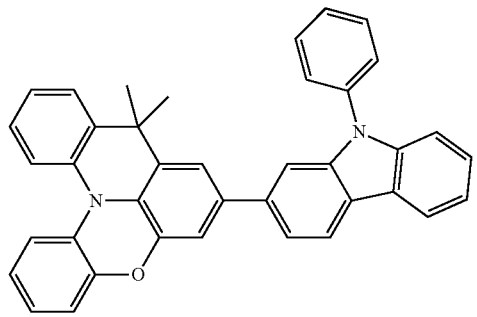 [SMILES: CC1(C)c2ccccc2N2c3ccccc3Oc3cc(-c4ccc5c6ccccc6n(-c6ccccc6)c5c4)cc1c32]

HTM16 (according to the invention)

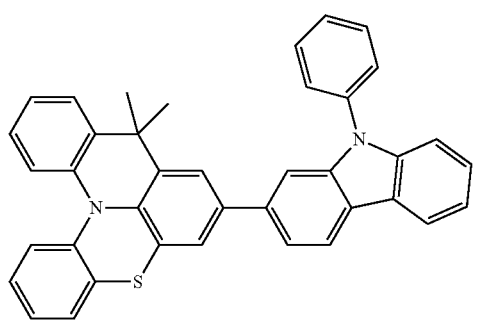

HTM17 (according to the invention)

TABLE 3-continued

Structural formulae of the materials

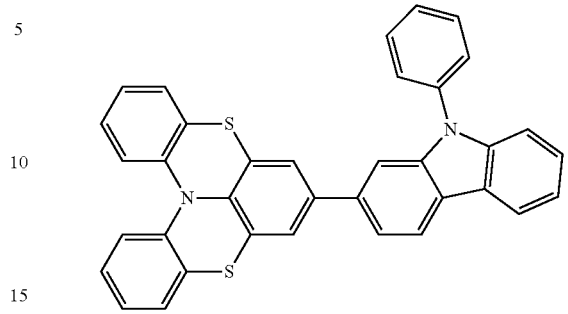

HTM18 (according to the invention)

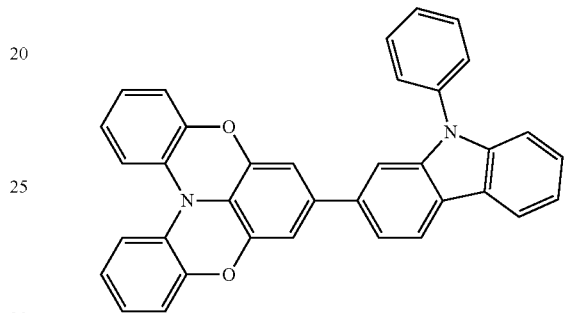

HTM19 (according to the invention)

The invention claimed is:

1. A compound of the formula (17)

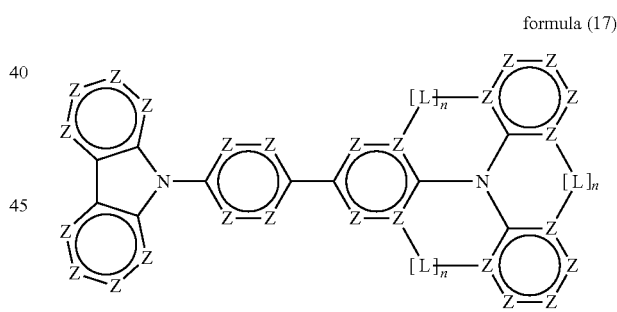

formula (17)

where the following applies to the symbols and indices occurring:

Z is on each occurrence, identically or differently, CR, or is equal to C if a substituent is bonded to the group Z;

L is on each occurrence, identically or differently, a divalent group selected from the group consisting of $C(R)_2$ and NR;

R is, identically or differently on each occurrence, H, D, F, Cl, Br, I, CHO, $N(R^1)_2$, $C(=O)R^1$, $P(=O)(R^1)_2$, $S(=O)_2R^1$, $S(=O)_2R^1$, $CR^1=C(R^1)_2$, CN, $NO_2$, $Si(R^1)_3$, $B(OR^1)_2$, $OSO_2R^1$, OH, $COOR^1$, $CON(R^1)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by —R¹C=CR¹—, —C≡C—, Si(R¹)₂, Ge(R¹)₂, Sn(R¹)₂, C=O, C=S, C=Se, C=NR¹, P(=O)(R¹), SO, SO₂, NR¹, —O—, —S—, —COO— or —CONR¹— and where one or more H atoms may be replaced by D, F, Cl, Br, I, CN or NO₂, or an aromatic ring system having 6 to 60 aromatic ring atoms or heteroaromatic ring system having 5 to 60 aromatic ring atoms, which may in each case be substituted by one or more radicals R¹, or an aryloxy group having 6 to 60 aromatic ring atoms or heteroaryloxy group having 5 to 60 aromatic ring atoms, which may be substituted by one or more radicals R¹, or a combination of these systems;

R¹ is, identically or differently on each occurrence, H, D, F, Cl, Br, I, CHO, N(R²)₂, C(=O)R², P(=O)(R²)₂, S(=O)R², S(=O)₂R², CR²=C(R²)₂, CN, NO₂, Si(R²)₃, B(OR²)₂, OSO₂R², OH, COOR², CON(R²)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R², where one or more non-adjacent CH₂ groups may be replaced by —R²C=CR²—, —C≡C—, Si(R²)₂, Ge(R²)₂, Sn(R²)₂, C=O, C=S, C=Se, C=NR², P(=O)(R²), SO, SO₂, NR², —O—, —S—, —COO— or —CONR²— and where one or more H atoms may be replaced by D, F, Cl, Br, I, CN or NO₂, or an aromatic ring system having 6 to 60 aromatic ring atoms or heteroaromatic ring system having 5 to 60 aromatic ring atoms, which may in each case be substituted by one or more radicals R², or an aryloxy group having 6 to 60 aromatic ring atoms or heteroaryloxy group having 5 to 60 aromatic ring atoms, which may be substituted by one or more radicals R², or a combination of these systems;

R² is, identically or differently on each occurrence, H, D, F or an aliphatic, aromatic and/or heteroaromatic organic radical having 1 to 20 C atoms, in which, in addition, one or more H atoms may be replaced by D or F;

n is on each occurrence, identically or differently, 0 or 1, where the sum of the values of the indices n is 1;

and where the compound contains only a single carbazole group.

2. The compound according to claim 1, wherein R is on each occurrence, identically or differently, H, D, F, CN, Si(R¹)₃, N(R¹)₂ or a straight-chain alkyl or alkoxy group having 1 to 20 C atoms or a branched or cyclic alkyl or alkoxy group having 3 to 20 C atoms, each of which may be substituted by one or more radicals R¹, where one or more adjacent or non-adjacent CH₂ groups may be replaced by —C≡C—, —R¹C=CR¹—, Si(R¹)₂, C=O, C=NR¹, —NR¹—, —O—, —S—, —COO— or —CONR¹—, or an aryl group having 6 to 30 aromatic ring atoms or heteroaryl group having 5 to 30 aromatic ring atoms, which may in each case be substituted by one or more radicals R¹.

3. An oligomer, polymer or dendrimer comprising one or more compounds according to claim 1, whereon the bond(s) to the polymer, oligomer or dendrimer may be localised at any desired positions substituted by a radical R in formula (17).

4. A formulation comprising at least one polymer, oligomer or dendrimer according to claim 3 and at least one solvent.

5. An electronic device comprising at least one polymer, oligomer or dendrimer according to claim 3.

6. A formulation comprising at least one compound according to claim 1 and at least one solvent.

7. A process for the preparation of a compound of the formula (17) according to claim 1, comprising at least one coupling reaction for the linking of the moiety containing the carbazole group to the moiety containing the arylamino group.

8. An electronic device comprising at least one compound according to claim 1.

9. The electronic device according to claim 8, wherein the device is selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

10. An organic electroluminescent device wherein the compound according to claim 1 is employed as hole-transport material in a hole-transport layer or hole-injection layer and/or as matrix material in an emitting layer.

11. The compound according to claim 1, wherein R³ is selected, identically or differently, from straight-chain alkyl groups having 1 to 40 C atoms and branched or cyclic alkyl groups having 3 to 40 C atoms, each of which may be substituted by one or more radicals R¹.

12. The compound according to claim 1, wherein R³ is methyl.

13. The compound according to claim 1, wherein L is C(R³)₂.

14. A compound of the formula (I-A)

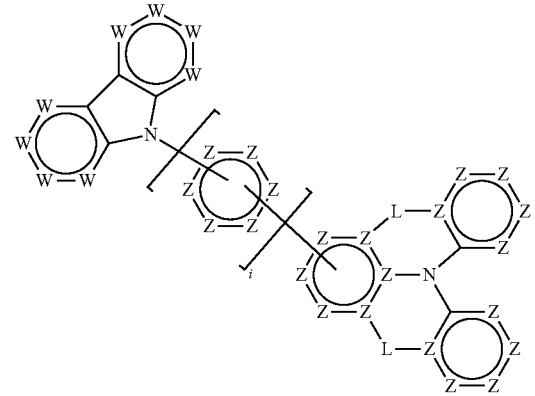

(I-A)

where the following applies to the symbols and indices occurring:

W is on each occurrence equal to Z;

Z is on each occurrence, identically or differently, CR or N, or is equal to C if a substituent is bonded to the group Z;

L is on each occurrence, identically or differently, a divalent group selected from the group consisting of C(R)₂, NR, O, S, S=O and S(=O)₂, where at least one group L is selected from NR, O, S, S=O and S(=O)₂;

R is, identically or differently on each occurrence, H, D, F, Cl, Br, I, CHO, N(R¹)₂, C(=O)R¹, P(=O)(R¹)₂, S(=O)R¹, S(=O)₂R¹, CR¹=C(R¹)₂, CN, NO₂, Si(R¹)₃, B(OR¹)₂, OSO₂R¹, OH, COOR¹, CON(R¹)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $-R^1C=CR^1-$, $-C\equiv C-$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, $-O-$, $-S-$, $-COO-$ or $-CONR^1-$ and where one or more H atoms may be replaced by D, F, Cl, Br, I, CN or $NO_2$, or an aromatic ring system having 6 to 60 aromatic ring atoms or heteroaromatic ring system having 5 to 60 aromatic ring atoms, which may in each case be substituted by one or more radicals $R^1$, or an aryloxy group having 6 to 60 aromatic ring atoms or heteroaryloxy group having 5 to 60 aromatic ring atoms, which may be substituted by one or more radicals $R^1$, or a combination of these systems;

$R^1$ is, identically or differently on each occurrence, H, D, F, Cl, Br, I, CHO, $N(R^2)_2$, $C(=O)R^2$, $P(=O)(R^2)_2$, $S(=O)R^2$, $S(=O)_2R^2$, $CR^2=C(R^2)_2$, CN, $NO_2$, $Si(R^2)_3$, $B(OR^2)_2$, $OSO_2R^2$, OH, $COOR^2$, $CON(R^2)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, $-O-$, $-S-$, $-COO-$ or $-CONR^2-$ and where one or more H atoms may be replaced by D, F, Cl, Br, I, CN or $NO_2$, or an aromatic ring system having 6 to 60 aromatic ring atoms or heteroaromatic ring system having 5 to 60 aromatic ring atoms, which may in each case be substituted by one or more radicals $R^2$, or an aryloxy group having 6 to 60 aromatic ring atoms or heteroaryloxy group having 5 to 60 aromatic ring atoms, which may be substituted by one or more radicals $R^2$, or a combination of these systems;

$R^2$ is, identically or differently on each occurrence, H, D, F or an aliphatic, aromatic and/or heteroaromatic organic radical having 1 to 20 C atoms, in which, in addition, one or more H atoms may be replaced by D or F;

i is equal to 0, 1 or 2, where, for i=0, the two groups which are bonded to the group with the index i are connected directly to one another;

and wherein the compound contains only a single carbazole group.

15. The compound according to claim 14, wherein one group L is $C(R)_2$.

16. The compound according to claim 14, wherein Z is equal to CR or is equal to C if a substituent is bonded to the group Z.

17. The compound according to claim 14, wherein R is on each occurrence, identically or differently, H, D, F, CN, $Si(R^1)_3$, $N(R^1)_2$ or a straight-chain alkyl or alkoxy group having 1 to 20 C atoms or a branched or cyclic alkyl or alkoxy group having 3 to 20 C atoms, each of which may be substituted by one or more radicals $R^1$, where one or more adjacent or non-adjacent $CH_2$ groups may be replaced by $-C\equiv C-$, $-R^1C=CR^1-$, $Si(R^1)_2$, $C=O$, $C=NR^1$, $-NR^1-$, $-O-$, $-S-$, $-COO-$ or $-CONR^1-$, or an aryl or heteroaryl group having 5 to 30 aromatic ring atoms, which may in each case be substituted by one or more radicals $R^1$.

18. A formulation comprising at least one compound according to claim 14 and at least one solvent.

19. An electronic device comprising at least one compound according to claim 14.

20. The electronic device according to claim 19, wherein the device is selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

21. An organic electroluminescent device wherein the compound according to claim 14 is employed as hole-transport material in a hole-transport layer or hole-injection layer and/or as matrix material in an emitting layer.

22. The compound according to claim 14, wherein R in a group $L=C(R)_2$ is selected, identically or differently, from straight-chain alkyl groups having 1 to 40 C atoms and branched or cyclic alkyl groups having 3 to 40 C atoms, each of which may be substituted by one or more radicals $R^1$.

23. The compound according to claim 14, wherein R in a group $L=C(R)_2$ is methyl.

* * * * *